(12) United States Patent
Haurand et al.

(10) Patent No.: US 7,871,999 B2
(45) Date of Patent: *Jan. 18, 2011

(54) SUBSTITUTED THIAZOLES AND THEIR USE FOR PRODUCING DRUGS

(75) Inventors: Michael Haurand, Aachen (DE); Klaus Schiene, Jüchen (DE); Sven Kühnert, Düren (DE); Melanie Reich, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/147,121

(22) Filed: Jun. 26, 2008

(65) Prior Publication Data

US 2009/0176756 A1 Jul. 9, 2009

Related U.S. Application Data

(63) Continuation of application No. PCT/EP2006/012482, filed on Dec. 22, 2006.

(30) Foreign Application Priority Data

Dec. 28, 2005 (DE) .................. 10 2005 062 991

(51) Int. Cl.
```
A61K 31/426    (2006.01)
A61K 31/551    (2006.01)
A61K 31/397    (2006.01)
A61K 31/4535   (2006.01)
A61K 31/4436   (2006.01)
A61K 31/428    (2006.01)
C07D 277/42    (2006.01)
C07D 243/08    (2006.01)
C07D 417/04    (2006.01)
C07D 417/12    (2006.01)
C07D 277/82    (2006.01)
```
(52) U.S. Cl. ............. 514/210.2; 514/218; 514/326; 514/342; 514/367; 514/370; 540/575; 546/209; 546/270.7; 548/161; 548/194

(58) Field of Classification Search .............. None
See application file for complete search history.

(56) References Cited

FOREIGN PATENT DOCUMENTS

| DE | 10 2004 032567 | 3/2006 |
|----|----------------|--------|
| WO | 03093236 | 11/2003 |
| WO | 04 029044 | 4/2004 |
| WO | WO 2004/029044 | * 4/2004 |
| WO | 2005 007641 | 1/2005 |
| WO | 2006 002981 | 1/2006 |
| WO | WO 2006/002981 | * 1/2006 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Regnier et al; "Triphenylpropylpiperazine derivatives as new potent analgetic substances"; Journal of Medicinal Chemistry 1972, 15 (3), pp. 295-301.
Collins, et al: "N-(2-Benzoylphenyl)-L-tyrosine PPARγ agonists 2. structure-activity relationship and optimization of the phenyl alkyl ether moiety"; Journal of Medicinal Chemistry 1998, 41(25), 41(25), pp. 5037-5054.
Greene et al; Protective Groups in Organic Synthesis, 3rd Edition, 1999, Wiley, New York.
Kocienski; Protecting Groups, Georg Thieme Verlag, Stuttgart 2004.
Gennaro edition; Remmington's Pharmaceutical Sciences, 17th Edition, Mack Publishing Company, Easton, PA 1985, in particular in part 8, chapters 76 to 93.
Dubuisson, D et al; "The formalin test: a quantitative study of the analgesic effects of morphine, meperidine, and brain stem stimulation in rats and cats"; Pain, 4, 1977, pp. 161-174.
Gennaro edition; Remmington's Pharmaceutical Sciences, 17th Edition, Mack Publishing Company, Easton, PA 1985, in particular in part 8, chapters 76 to 93.
Dubuisson, D et al; "The formalin test: a quantitative study of the analgesic effects of morphine, meperidine, and brain stem stimulation in rats and cats"; Pain, 4, 1977, pp. 161-174.

* cited by examiner

*Primary Examiner*—Golam M. M. Shameem
*Assistant Examiner*—Alicia L Otton
(74) *Attorney, Agent, or Firm*—Norris McLaughlin & Marcus, P.A.

(57) ABSTRACT

The present invention relates to substituted thiazoles, to methods for the production thereof, to medicaments containing these compounds and to the use thereof for producing medicaments.

30 Claims, No Drawings

SUBSTITUTED THIAZOLES AND THEIR USE FOR PRODUCING DRUGS

This application is a continuation of PCT/EP2006/012482, filed on Dec. 22, 2006, which, in turn, claims priority of German Patent Application No. DE 10 2005 062 991.1, filed on Dec. 28, 2005.

The present invention relates to substituted thiazoles, to methods for the production thereof, to medicaments containing these compounds and to the use thereof for producing medicaments.

Pain is one of the basic clinical symptoms. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Conventional opioids, such as for example morphine, are effective in the treatment of severe to very severe pain, but they often lead to unwanted accompanying symptoms, such as for example respiratory depression, vomiting, sedation, constipation or the development of tolerance. Moreover, they are frequently insufficiently effective in the case of neuropathic pain, suffered in particular by tumour patients.

One object of the present invention was accordingly to provide novel compounds which are suitable in particular as pharmaceutical active ingredients in medicaments, preferably in medicaments for the treatment of pain.

It has now surprisingly been found that the substituted thiazoles of the general formula I stated hereinafter are suitable for mGluR5 receptor regulation and may therefore be used in particular as pharmaceutical active ingredients in medicaments for the prevention and/or treatment of disorders or diseases associated with these receptors or processes.

The present invention accordingly provides substituted thiazoles of the general formula I

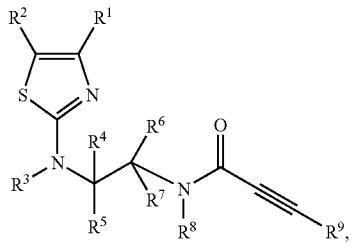

I in which $R^1$ and $R^2$, mutually independently, in each case denote H; F; Cl; Br; I; —$NO_2$; —CN; —$NH_2$; —OH; —SH; —C(=O)—OH; —C(=O)—H; —NH—C(=O)—H; —NH—$R^{55}$; —$NR^{56}R^{57}$; —C(=O)—$R^{58}$; —C(=O)—O—$R^{59}$; —O—C(=O)—$R^{60}$; —NH—C(=O)—$R^{61}$; —$NR^{62}$—C(=O)—$R^{63}$; —C(=O)—$NH_2$; —C(=O)—NH—$R^{64}$; —C(=O)—$NR^{65}R^{66}$; —O—$R^{67}$; —S—$R^{68}$; —S(=O)—$R^{69}$; —S(=O)$_2$—$R^{70}$; —NH—C(=O)—NH—$R^{71}$; —NH—C(=S)—NH—$R^{72}$; —NH—S(=O)$_2$—$R^{73}$; —$NR^{74}$—S(=O)$_2$—$R^{75}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

or $R^1$ and $R^2$ together with the carbon atoms joining them form an unsubstituted or at least monosubstituted phenylene residue;

$R^3$, $R^8$ and $R^{54}$, mutually independently, in each case denote H; —C(=O)—$R^{58}$; —C(=O)—O—$R^{59}$; —C(=O)—$NH_2$; —C(=O)—NH—$R^{64}$; —C(=O)—$NR^{65}R^{66}$; —S(=O)—$R^{69}$; —S(=O)$_2$—$R^{70}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$, mutually independently, in each case denote H; F; Cl; Br; I; —$NO_2$; —CN; —$NH_2$; —OH; —SH; —C(=O)—OH; —C(=O)—H; —NH—C(=O)—H; —NH—$R^{55}$; —$NR^{56}R^{57}$; —C(=O)—$R^{58}$; —C(=O)—O—$R^{59}$; —O—C(=O)—$R^{60}$; —NH—C(=O)—$R^{61}$; —$NR^{62}$—C(=O)—$R^{63}$;

—C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=S)—NH—R$^{72}$; —NH—S(=O)$_2$—R$^{73}$; —NR$^{74}$—S(=O)$_2$—R$^{75}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

or R$^4$ and R$^5$ or R$^6$ and R$^7$ or R$^{10}$ and R$^{11}$ or R$^{12}$ and R$^{13}$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$ or R$^{28}$ and R$^{29}$ or R$^{30}$ and R$^{31}$ or R$^{32}$ and R$^{33}$ or R$^{34}$ and R$^{35}$ or R$^{36}$ and R$^{37}$ or R$^{38}$ and R$^{39}$ or R$^{40}$ and R$^{41}$ or R$^{42}$ and R$^{43}$ or R$^{44}$ and R$^{45}$ or R$^{46}$ and R$^{47}$ or R$^{48}$ and R$^{49}$ or R$^{50}$ and R$^{51}$ or R$^{52}$ and R$^{53}$, mutually independently, together in each case denote a residue selected from the group consisting of an oxo group (=O) and a thioxo group (=S);

or R$^3$ and R$^4$ together with the —N—CR$^5$ group joining them form a residue of the general formula A,

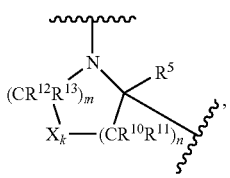

or R$^6$ and R$^8$ together with the —N—CR$^7$ group joining them form a residue of the general formula B,

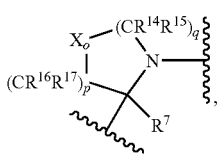

m and q in each case denote 1, 2, 3, 4 or 5;

n and p in each case denote 0, 1, 2, 3 or 4;

k and o in each case denote 0 or 1;

wherein the sum of m, n and k or the sum of p, q and o is in each case equal to 1, 2, 3, 4, 5 or 6;

or R$^3$ and R$^6$ together with the —N—CR$^4$R$^5$—CR$^7$ group joining them form a residue of the general formula C,

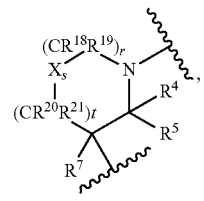

or R$^4$ and R$^8$ together with the —CR$^5$—CR$^6$R$^7$—N group joining them form a residue of the general formula D,

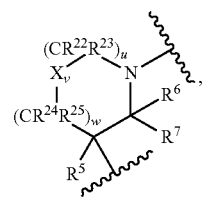

r and u in each case denote 1, 2, 3 or 4;

t and w in each case denote 0, 1, 2 or 3;

s and v in each case denote 0 or 1;

wherein the sum of r, s and t or the sum of u, v and w is in each case equal to 1, 2, 3, 4 or 5;

or R$^3$ and R$^8$ together with the —N—CR$^4$R$^5$—CR$^6$R$^7$—N group joining them form a residue of the general formula E,

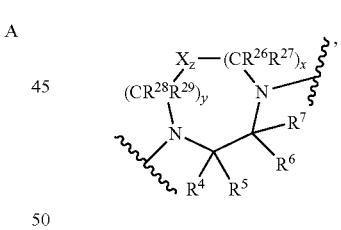

x and y in each case denote 1 or 2;

z denotes 0 or 1;

wherein the sum of x, y and z is equal to 3 or 4;

or R$^4$ and R$^6$ together with the —CR$^5$—CR$^7$ group joining them form a residue of the general formula F,

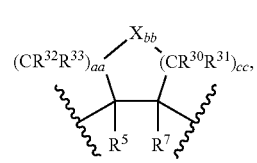

aa and cc, mutually independently, in each case denote 1, 2, 3, 4 or 5;

bb denotes 0 or 1;

wherein the sum of aa, bb and cc is equal to 1, 2, 3, 4, 5 or 6;

or $R^3$ and $R^4$ together with the —N—$CR^5$ group joining them and $R^6$ and $R^8$ together with the —N—$CR^7$ group joining them form a residue of the general formula G,

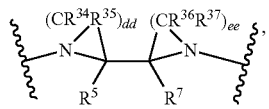

G dd and ee, mutually independently, in each case denote 1, 2, 3 or 4;

or $R^3$ and $R^6$ together with the —N—$CR^4CR^5$—$CR^7$ group joining them and $R^4$ and $R^8$ together with the —$CR^5$—$CR^6R^7$—N group joining them form a residue of the general formula H,

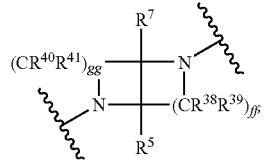

H ff and gg, mutually independently, in each case denote 1, 2 or 3;

or $R^3$ and $R^8$ together with the —N—$CR^4R^5$—$CR^6R^7$—N group joining them and $R^4$ and $R^6$ together with the —$CR^5$—$CR^7$ group joining them form a residue of the general formula K,

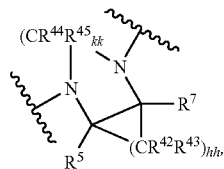

K hh denotes 1, 2, 3 or 4;

kk denotes 1, 2, 3, 4, 5 or 6;

or $R^3$ and $R^8$ together with the —N—$CR^4R^5$—$CR^6R^7$—N group joining them form a bicyclic residue of the general formula L,

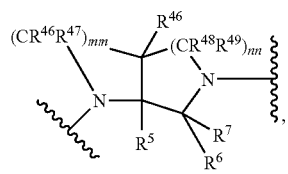

L mm denotes 1, 2 or 3;

nn denotes 1 or 2;

or $R^3$ and $R^8$ together with the —N—$CR^4R^5$—$CR^6R^7$—N group joining them form a bicyclic residue of the general formula M,

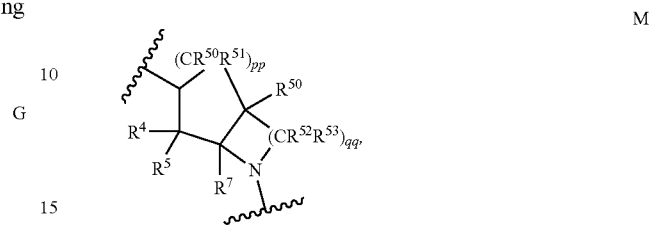

M pp denotes 1 or 2;

qq denotes 1, 2 or 3;

X denotes O, S or N—$R^{54}$;

$R^9$ denotes H; F; Cl; Br; I; —CN; —C(=O)—OH; —C(=O)—H; —C(=O)—$R^{58}$; —C(=O)—O—$R^{59}$; —C(=O)—$NH_2$; —C(=O)—NH—$R^{64}$; —C(=O)—$NR^{65}R^{66}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

and $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{86}$, $R^{69}$, $R^{70}$, $R^{71}$, $R^{72}$, $R^{73}$, $R^{74}$ and $R^{75}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

For the purposes of the present invention, the term "alkyl" covers acyclic saturated hydrocarbon residues, which may be branched or straight-chain and unsubstituted or at least monosubstituted with, as in the case of $C_{1-12}$ alkyl, 1 to 12 (i.e. 1, 2, 3, 4, 5, 6, 7, 8, 9, 10, 11 or 12) C atoms or with, as in the case of $C_{1-6}$ alkyl, 1 to 6 (i.e. 1, 2, 3, 4, 5 or 6) C atoms. If one or more of the substituents denote an alkyl residue or comprise an alkyl residue which is mono- or polysubstituted, this may preferably be substituted with optionally 1, 2, 3, 4 or 5, particularly preferably with 1, 2 or 3, substituents mutually independently selected from the group consisting of F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$- alkyl, —S(=O)$_2$-phenyl, —S(=O)$_2$—$NH_2$ and —$SO_3H$, wherein the above-stated $C_{1-5}$ alkyl residues may in each case be linear or branched and the above-stated phenyl residues may be substituted preferably with 1, 2, 3, 4 or 5 substituents mutually independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert.-butyl. Particularly preferred substituents may mutually independently be selected from the group consisting of F, Cl, Br, I, —$NO_2$, —CN, —OH, —SH, —$NH_2$, —N($CH_3$)$_2$, —N($C_2H_5$)$_2$ and —N($CH_3$)($C_2H_5$).

Examples which may be mentioned of suitable $C_{1-12}$ alkyl residues which may be unsubstituted or mono- or polysubstituted are methyl, ethyl, n-propyl, isopropyl, n-butyl, isobutyl, 2-butyl, tert.-butyl, n-pentyl, 2-pentyl, 3-pentyl, iso-pentyl, neopentyl, n-hexyl, 2-hexyl, 3-hexyl, n-heptyl, n-octyl, —C(H)($C_2H_5$)$_2$, —C(H)(n-$C_3H_7$)$_2$ and —$CH_2$—$CH_2$—C(H)($CH_3$)—($CH_2$)$_3$—$CH_3$. Examples of suitable $C_{1-6}$ alkyl residues which may be mentioned are methyl, ethyl, n-propyl, isopropyl, n-butyl, isobutyl, 2-butyl, tert.-butyl, n-pentyl, 2-pentyl, 3-pentyl, iso-pentyl, neopentyl, n-hexyl, 2-hexyl and 3-hexyl.

Polysubstituted alkyl residues are understood to be those alkyl residues which are polysubstituted, preferably di- or trisubstituted, either on different or on the same C atoms, for example trisubstituted on the same C atom as in the case of —$CF_3$, or at different locations as in the case of —(CHCl)—($CH_2F$). Polysubstitution may proceed with identical or different substituents. Examples of suitable substituted alkyl residues which may be mentioned are —$CF_3$, —$CF_2H$, —$CFH_2$, —($CH_2$)—OH, —($CH_2$)—$NH_2$, —($CH_2$)—CN, —($CH_2$)—($CF_3$), —($CH_2$)—($CHF_2$), —($CH_2$)—($CH_2F$), —($CH_2$)—($CH_2$)—OH, —($CH_2$)—($CH_2$)—$NH_2$, —($CH_2$)—($CH_2$)—CN, —($CF_2$)—($CF_3$), —($CH_2$)—($CF_2$)—($CF_3$) and —($CH_2$)—($CH_2$)—($CH_2$)—OH.

For the purposes of the present invention, the term "alkenyl" covers acyclic unsaturated hydrocarbon residues, which may be branched or straight-chain and unsubstituted or at least monosubstituted and comprise at least one double bond, preferably 1, 2 or 3 double bonds, with, as in the case of $C_{2-12}$ alkenyl, 2 to 12 (i.e. 2, 3, 4, 5, 6, 7, 8, 9, 10, 11 or 12) C atoms or with, as in the case of $C_{2-6}$ alkenyl, 2 to 6 (i.e. 2, 3, 4, 5 or 6) C atoms. If one or more of the substituents denote an alkenyl residue or comprise an alkenyl residue which is mono- or polysubstituted, this may preferably be substituted with optionally 1, 2, 3, 4 or 5, particularly preferably with 1, 2 or 3, substituents mutually independently selected from the group consisting of F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, wherein the above-stated $C_{1-5}$ alkyl residues may in each case be linear or branched and the above-stated phenyl residues may preferably be substituted with 1, 2, 3, 4 or 5 substituents mutually independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert.-butyl. Particularly preferred substituents may mutually independently be selected from the group consisting of F, Cl, Br, I, —$NO_2$, —CN, —OH, —SH, —$NH_2$, —N($CH_3$)$_2$, —N($C_2H_5$)$_2$ and —N($CH_3$)($C_2H_5$).

Examples of suitable $C_{2-12}$ alkenyl residues which may be mentioned are ethenyl, 1-propenyl, 2-propenyl, 1-butenyl, 2-butenyl, 3-butenyl, 1-pentenyl, 2-pentenyl, 3-pentenyl, 4-pentenyl, hexenyl, —CH=CH—CH=CH—$CH_3$ and —$CH_2$—$CH_2$—CH=$CH_2$.

Polysubstituted alkenyl residues are understood to be those alkenyl residues which are polysubstituted, preferably disubstituted, either on different or on the same C atoms, for example disubstituted on the same C atom as in the case of —CH=$CCl_2$, or at different locations as in the case of CCl=CH—($CH_2$)—$NH_2$. Polysubstitution may proceed with identical or different substituents. Examples of suitable substituted alkenyl residues which may be mentioned are —CH=CH—($CH_2$)—OH, —CH=CH—($CH_2$)—$NH_2$ and —CH=CH—CN.

For the purposes of the present invention, the term "alkynyl" covers acyclic unsaturated hydrocarbon residues, which may be branched or straight-chain and unsubstituted or at least monosubstituted and comprise at least one triple bond, preferably 1 or 2 triple bonds, with, as in the case of $C_{2-12}$ alkynyl, 2 to 12 (i.e. 2, 3, 4, 5, 6, 7, 8, 9, 10, 11 or 12) C atoms or with, as in the case of $C_{2-6}$ alkynyl, 2 to 6 (i.e. 2, 3, 4, 5 or 6) C atoms. If one or more of the substituents denote an alkynyl residue or comprise an alkynyl residue which is mono- or polysubstituted, this may preferably be substituted with optionally 1, 2, 3, 4 or 5, particularly preferably with optionally 1 or 2, substituents mutually independently selected from the group consisting of F, Cl, Br, I, —$NO_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated C$_{1-5}$ alkyl residues may in each case be linear or branched and the above-stated phenyl residues may preferably be substituted with 1, 2, 3, 4 or 5 substituents mutually independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert.-butyl. Particularly preferred substituents may mutually independently be selected from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Examples of suitable C$_{2-12}$ alkynyl residues which may be mentioned are ethynyl, 1-propynyl, 2-propynyl, 1-butynyl, 2-butynyl, 3-butynyl, 1-pentynyl, 2-pentynyl, 3-pentynyl, 4-pentynyl and hexynyl.

Polysubstituted alkynyl residues should be taken to mean those alkynyl residues which are either polysubstituted on different C atoms, for example disubstituted on different C atoms as in the case of —CHCl—C≡CCl. Examples of suitable substituted alkynyl residues which may be mentioned are —C≡C—F, —C≡C—Cl and —C≡C—I.

The term "heteroalkyl" denotes an alkyl residue as described above, in which one or more C atoms have in each case been replaced by a heteroatom mutually independently selected from the group consisting of oxygen, sulfur and nitrogen (NH). Heteroalkyl residues preferably comprise 1, 2 or 3 heteroatom(s) mutually independently selected from the group consisting of oxygen, sulfur and nitrogen (NH) as chain link(s). Heteroalkyl residues may preferably be 2- to 12-membered, particularly preferably 2- to 6-membered.

Examples which may be mentioned of suitable heteroalkyl residues which may be unsubstituted or mono- or polysubstituted, are —CH$_2$—O—CH$_3$, —CH$_2$—O—C$_2$H$_5$, —CH$_2$—O—CH(CH$_3$)$_2$, —CH$_2$—O—C(CH$_3$)$_3$, —CH$_2$—S—CH$_3$, —CH$_2$—S—C$_2$H$_5$, —CH$_2$—S—CH(CH$_3$)$_2$, —CH$_2$—S—C(CH$_3$)$_3$, —CH$_2$—NH—CH$_3$, —CH$_2$—NH—C$_2$H$_5$, —CH$_2$—NH—CH(CH$_3$)$_2$, —CH$_2$—NH—C(CH$_3$)$_3$, —CH$_2$—CH$_2$—O—CH$_3$, —CH$_2$—CH$_2$—O—C$_2$H$_5$, —CH$_2$—CH$_2$—O—CH(CH$_3$)$_2$, —CH$_2$—CH$_2$—O—C(CH$_3$)$_3$, —CH$_2$—CH$_2$—S—CH$_3$, —CH$_2$—CH$_2$—S—C$_2$H$_5$, —CH$_2$—CH$_2$—S—CH(CH$_3$)$_2$, —CH$_2$—CH$_2$—S—C(CH$_3$)$_3$, —CH$_2$—CH$_2$—NH—CH$_3$, —CH$_2$—CH$_2$—NH—C$_2$H$_5$, —CH$_2$—CH$_2$—NH—CH(CH$_3$)$_2$, —CH$_2$—CH$_2$—NH—C(CH$_3$)$_3$, —CH$_2$—S—CH$_2$—O—CH$_3$, —CH$_2$—O—CH$_2$—O—C$_2$H$_5$, —CH$_2$—O—CH$_2$—O—CH(CH$_3$)$_2$, —CH$_2$—S—CH$_2$—O—C(CH$_3$)$_3$, —CH$_2$—O—CH$_2$—S—CH$_3$, —CH$_2$—O—CH$_2$—S—C$_2$H$_5$, —CH$_2$—O—CH$_2$—S—CH(CH$_3$)$_2$, —CH$_2$—NH—CH$_2$—S—C(CH$_3$)$_3$, —CH$_2$—O—CH$_2$—NH—CH$_3$, —CH$_2$—O—CH$_2$—NH—C$_2$H$_5$, —CH$_2$—O—CH$_2$—NH—CH(CH$_3$)$_2$, —CH$_2$—S—CH$_2$—NH—C(CH$_3$)$_3$ and —CH$_2$—CH$_2$—C(H)(CH$_3$)—(CH$_2$)$_3$—CH$_3$.

Examples of suitable substituted heteroalkyl residues which may be mentioned are —(CH$_2$)—O—(CF$_3$), —(CH$_2$)—O—(CHF$_2$), —(CH$_2$)—O—(CH$_2$F), —(CH$_2$)—S—(CF$_3$), —(CH$_2$)—S—(CHF$_2$), —(CH$_2$)—S—(CH$_2$F), —(CH$_2$)—(CH$_2$)—O—(CF$_3$), —(CF$_2$)—O—(CF$_3$), —(CH$_2$)—(CH$_2$)—S—(CF$_3$) and —(CH$_2$)—(CH$_2$)—(CH$_2$)—O—(CF$_3$).

The term "heteroalkenyl" denotes an alkenyl residue as described above in which one or more C atoms have in each case been replaced by a heteroatom mutually independently selected from the group consisting of oxygen, sulfur and nitrogen (NH). Heteroalkenyl groups may preferably comprise 1, 2 or 3 heteroatom(s) mutually independently selected from the group consisting of oxygen, sulfur and nitrogen (NH) as chain link(s). Heteroalkenyl groups may preferably be 2- to 12-membered, particularly preferably 2- to 6-membered.

Examples of suitable heteroalkenyl residues which may be mentioned are —CH$_2$—O—CH=CH$_2$, —CH=CH—O—CH=CH—CH$_3$, —CH$_2$—CH$_2$—O—CH=CH$_2$, —CH$_2$—S—CH=CH$_2$, —CH=CH—S—CH=CH—CH$_3$, —CH$_2$—CH$_2$—S—CH=CH$_2$, —CH$_2$—NH—CH=CH$_2$, —CH=CH—NH—CH=CH—CH$_3$ and —CH$_2$—CH$_2$—NH—CH=CH$_2$.

Examples of suitable substituted heteroalkenyl residues which may be mentioned are —CH$_2$—O—CH=CH—(CH$_2$)—OH, —CH$_2$—S—CH=CH—(CH$_2$)—NH$_2$ and —CH$_2$—NH—CH=CH—CN.

The term "heteroalkynyl" denotes an alkynyl residue as described above in which one or more C atoms have in each case been replaced by a heteroatom mutually independently selected from the group consisting of oxygen, sulfur and nitrogen (NH). Heteroalkynyl residues may preferably comprise 1, 2 or 3 heteroatom(s) mutually independently selected from the group consisting of oxygen, sulfur and nitrogen (NH) as chain link(s). Heteroalkynyl residues may preferably be 2- to 12-membered, particularly preferably 2- to 6-membered.

Examples of suitable heteroalkynyl residues which may be mentioned are —CH$_2$—O—C≡CH, —CH$_2$—CH$_2$—O—C≡CH, —CH$_2$—O—C≡C—CH$_3$, —CH$_2$—CH$_2$—O—C≡C—CH$_3$, —CH$_2$—S—C≡CH, —CH$_2$—CH$_2$—S—C≡CH, —CH$_2$—S—C≡C—CH$_3$, —CH$_2$—CH$_2$—S—C≡C—CH$_3$.

Examples of suitable substituted heteroalkynyl residues which may be mentioned are —CH$_2$—O—C≡C—Cl, —CH$_2$—CH$_2$—O—C≡C—I, —CHF—O—C≡C—CH$_3$, —CHF—CH$_2$—O—C≡C—CH$_3$, —CH$_2$—S—C≡C—Cl, —CH$_2$—CH$_2$—S—C≡C—Cl, —CHF—S—C≡C—CH$_3$, —CHF—CH$_2$—S—C≡C—CH$_3$.

For the purposes of the present invention, the term "cycloalkyl" means a cyclic saturated hydrocarbon residue, with preferably 3, 4, 5, 6, 7, 8 or 9 C atoms, particularly preferably with 3, 4, 5, 6 or 7 C atoms, very particularly preferably with 5 or 6 C atoms, wherein the residue may be unsubstituted or monosubstituted or identically or differently polysubstituted.

Examples which may be mentioned of suitable C$_{3-9}$ cycloalkyl residues which may be unsubstituted or mono- or polysubstituted are cyclopropyl, cyclobutyl, cyclopentyl, cyclohexyl, cycloheptyl, cyclooctyl and cyclononyl. Examples of suitable C$_{3-7}$ cycloalkyl residues which may be mentioned are cyclopropyl, cyclobutyl, cyclopentyl, cyclohexyl and cycloheptyl.

For the purposes of the present invention, the term "cycloalkenyl" means a cyclic unsaturated hydrocarbon residue with preferably 3, 4, 5, 6, 7, 8 or 9 C atoms, particularly preferably with 3, 4, 5, 6 or 7 C atoms, very particularly preferably with 5 or 6 C atoms, which comprises at least one double bond, preferably one double bond, and may be unsubstituted or monosubstituted or identically or differently polysubstituted.

Examples which may be mentioned of suitable $C_{3-9}$ cycloalkenyl residues which may be unsubstituted or mono- or polysubstituted are cyclobutenyl, cyclopentenyl, cyclohexenyl, cycloheptenyl, cyclononenyl and cyclooctenyl. Examples of suitable $C_{5-6}$ cycloalkenyl residues which may be mentioned are cyclopentenyl and cyclohexenyl.

For the purposes of the present invention, the term "heterocycloalkyl" means a cyclic saturated hydrocarbon residue with preferably 3, 4, 5, 6, 7, 8 or 9 C atoms, particularly preferably with 3, 4, 5, 6 or 7 C atoms, very particularly preferably with 5 or 6 C atoms, in which one or more C atoms have in each case been replaced by a heteroatom mutually independently selected from the group consisting of oxygen, sulfur and nitrogen (NH). Heterocycloalkyl residues may preferably comprise 1, 2 or 3 heteroatom(s) mutually independently selected from the group consisting of oxygen, sulfur and nitrogen (NH) as ring member(s). A heterocycloalkyl residue may be unsubstituted or monosubstituted or identically or differently polysubstituted. Heterocycloalkyl residues may preferably be 3- to 9-membered, particularly preferably 3- to 7-membered, very particularly preferably 5- to 7-membered.

Examples which may be mentioned of suitable 3- to 9-membered heterocycloalkyl residues which may be unsubstituted or mono- or polysubstituted are imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1,3)-dioxolan-2-yl, isoxazolidinyl, isothioazolidinyl, pyrazolidinyl, oxazolidinyl, (1,2,4)-oxadiazolidinyl, (1,2,4)-thiadiazolidinyl, (1,2,4)-triazolidin-3-yl, (1,3,4)-thiadiazolidin-2-yl, (1,3,4)-triazolidin-1-yl, (1,3,4)-triazolidin-2-yl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,3)-dithian-2-yl and (1,3)-thiazolidinyl. Examples of suitable 5- to 7-membered heterocycloalkyl residues which may be mentioned are imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, diazepanyl and (1,3)-dioxolan-2-yl.

For the purposes of the present invention, the term "heterocycloalkenyl" means a cyclic unsaturated hydrocarbon residue with preferably 4, 5, 6, 7, 8 or 9 C atoms, particularly preferably with 4, 5, 6 or 7 C atoms, very particularly preferably with 5 or 6 C atoms, which comprises at least one double bond, preferably one double bond, and in which one or more C atoms have in each case been replaced by a heteroatom mutually independently selected from the group consisting of oxygen, sulfur and nitrogen (NH). Heterocycloalkenyl residues may preferably comprise 1, 2 or 3 heteroatom(s) mutually independently selected from the group consisting of oxygen, sulfur and nitrogen (NH) as ring member(s). A heterocycloalkenyl residue may be unsubstituted or monosubstituted or identically or differently polysubstituted. Heterocycloalkenyl residues may preferably be 4- to 9-membered, particularly preferably 4- to 7-membered, very particularly preferably 5- to 7-membered.

Examples which may be mentioned of suitable heterocycloalkenyl residues or of suitable 5- to 7-membered heterocycloalkenyl residues which may be unsubstituted or mono- or polysubstituted are (2,3)-dihydrofuranyl, (2,5)-dihydrofuranyl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, (3,4,5,6)-tetrahydropyridin-2-yl, (1,2,5,6)-tetrahydropyridin-1-yl, (1,2)-dihydropyridin-1-yl, (1,4)-dihydropyridin-1-yl, dihydropyranyl and (1,2,3,4)-tetrahydropyridin-1-yl.

The cycloalkyl residues, heterocycloalkyl residues, cycloalkenyl residues or heterocycloalkenyl residues may for the purposes of the present invention be fused (anellated) with an unsubstituted or at least monosubstituted mono- or bicyclic ring system. For the purposes of the present invention, a mono- or bicyclic ring system should be understood to mean mono- or bicyclic hydrocarbon residues which may be saturated, unsaturated or aromatic and optionally comprise one or more heteroatoms as ring members. Preferably, the rings of the above-stated mono- or bicyclic ring systems are in each case 4-, 5- or 6-membered and may in each case preferably optionally comprise 0, 1, 2, 3, 4 or 5 heteroatom(s), particularly preferably optionally 0, 1 or 2 heteroatom(s) as ring member(s), which are mutually independently selected from the group consisting of oxygen, nitrogen and sulfur. If a bicyclic ring system is present, the different rings may, in each case mutually independently, exhibit a different degree of saturation, i.e. be saturated, unsaturated or aromatic.

If one or more of the substituents comprises a monocyclic or bicyclic ring system, which is mono- or polysubstituted, this may preferably be substituted with optionally 1, 2, 3, 4 or 5, particularly preferably with optionally 1, 2 or 3, substituents which may be mutually independently selected from the group consisting of F, Cl, Br, I, —CN, —NO$_2$, —OH, —SH, —NH$_2$, oxo (=O), thioxo (=S), —C(=O)—OH, $C_{1-5}$ alkyl, —C$_{2-5}$ alkenyl, —C$_{2-5}$ alkynyl, —C≡C—Si(CH$_3$)$_3$, —C≡C—Si(C$_2$H$_5$)$_3$, —(CH$_2$)—O—C$_{1-5}$-alkyl, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)$_2$—C$_{1-5}$-alkyl, —NH—C$_{1-5}$-alkyl, N(C$_{1-5}$alkyl)(C$_{1-5}$-alkyl), —C(=O)—O—C$_{1-5}$-alkyl, —C(=O)—H, —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiadiazolyl, thiophenyl (thienyl) and benzyl, wherein the above-stated C$_{1-5}$ alkyl residues may in each case be linear or branched and the cyclic substituents or the cyclic residues of these substituents themselves may in each case be substituted with optionally 1, 2, 3, 4 or 5, preferably with optionally 1, 2, 3 or 4, substituents mutually independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$ alkyl, —C$_{2-5}$ alkenyl, —C$_{2-5}$ alkynyl, —C≡C—Si(CH$_3$)$_3$, —C≡C—Si(C$_2$H$_5$)$_3$, —C(=O)—O—C$_{1-5}$-alkyl and —C(=O)—CF$_3$.

Particularly preferably, the substituents may be in each case mutually independently selected from the group consisting of F, Cl, Br, I, —CN, —NO$_2$, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —NH$_2$, oxo (=O), —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —O—C(CH₃)₃, —CF₃, —CHF₂, —CH₂F, —O—CF₃, —O—CHF₂, —O—CH₂F, —C(=O)—CF₃, —S—CF₃, —S—CHF₂, —S—CH₂F, —S(=O)₂-phenyl, pyrazolyl, phenyl, —N(CH₃)₂, —N(C₂H₅)₂, —NH—CH₃, —NH—C₂H₅, —CH₂—O—C(=O)-phenyl, —NH—S(=O)₂—CH₃, —C(=O)—O—CH₃, —C(=O)—O—C₂H₅, —C(=O)—O—C(CH₃)₃, —C(=O)—H, —C(=O)—CH₃, —C(=O)—C₂H₅, —NH—C(=O)—CH₃, —NH—C(=O)—C₂H₅, —O—C(=O)-phenyl, —C(=O)—NH₂, —C(=O)—NH—CH₃, —C(=O)—N(CH₃)₂, phenyl, furyl (furanyl), thiadiazolyl, thiophenyl (thienyl) and benzyl, wherein the cyclic substituents or the cyclic residues of these substituents themselves may be substituted with optionally 1, 2, 3, 4, or 5, preferably with optionally 1, 2, 3 or 4, substituents mutually independently selected from the group consisting of F, Cl, Br, I, —CN, —CF₃, —OH, —NH₂, —O—CF₃, —SH, —O—CH₃, —O—C₂H₅, —O—C₃H₇, methyl, ethyl, n-propyl, isopropyl, n-butyl, 2-butyl, isobutyl, tert.-butyl, ethenyl, allyl, ethynyl, propynyl, —C≡C—Si(CH₃)₃, —C≡C—Si(C₂H₅)₃, —C(=O)—O—C₁₋₅-alkyl and —C(=O)—CF₃.

Examples which may be mentioned of suitable cycloalkyl residues, heterocycloalkyl residues, cycloalkenyl residues or heterocyclalkenyl residues which may be unsubstituted or mono- or polysubstituted, and are fused with a mono- or bicyclic ring system, are (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1.4]dioxinyl, benzo[1.3]dioxolyl, (3,4)-dihydro-2H-benzo[1.4]oxazinyl and octahydro-pyrrolo[3,4-c]pyrrolyl.

If one or more of the substituents denote a cycloalkyl residue, heterocycloalkyl residue, cycloalkenyl residue or heterocycloalkenyl residue or comprise such a residue, which is mono- or polysubstituted, this may preferably be substituted with optionally 1, 2, 3, 4 or 5, particularly preferably with optionally 1, 2 or 3, substituents mutually independently selected from the group consisting of F, Cl, Br, I, —CN, —CF₃, —OH, —NH₂, —O—CF₃, —SH, —O—C₁₋₅-alkyl, —O-phenyl, —O—CH₂-phenyl, —(CH₂)—O—C₁₋₅-alkyl, —S—C₁₋₅-alkyl, —S-phenyl, —S—CH₂-phenyl, —C₁₋₅ alkyl, —C₂₋₅ alkenyl, —C₂₋₅ alkynyl, —C≡C—Si(CH₃)₃, —C≡C—Si(C₂H₅)₃, —C(=O)—O—C₁₋₅-alkyl, —C(=O)—CF₃, —S(=O)₂—C₁₋₅-alkyl, —S(=O)—C₁₋₅-alkyl, —S(=O)₂-phenyl, oxo (=O), thioxo (=S), —N(C₁₋₅-alkyl)₂, —N(H)(C₁₋₅-alkyl), —NO₂, —S—CF₃, —C(=O)—OH, —NH—S(=O)₂—C₁₋₅-alkyl, —NH—C(=O)—C₁₋₅-alkyl, —C(=O)—H, —C(=O)—C₁₋₅-alkyl, —C(=O)—NH₂, —C(=O)—N(C₁₋₅-alkyl)₂, —C(=O)—N(H)(C₁₋₅-alkyl) and phenyl, wherein the above-stated C₁₋₅ alkyl residues may in each case be linear or branched and the phenyl residue may in each case be unsubstituted or substituted with 1, 2, 3, 4 or 5, preferably with 1, 2, 3 or 4, substituents mutually independently selected from the group consisting of F, Cl, Br, I, —CN, —CF₃, —OH, —NH₂, —O—CF₃, —SH, —O—C₁₋₅-alkyl, —O-phenyl, —O—CH₂-phenyl, —(CH₂)—O—C₁₋₅-alkyl, —S—C₁₋₅-alkyl, —S-phenyl, —S—CH₂-phenyl, —C₁₋₅ alkyl, —C₂₋₅ alkenyl, —C₂₋₅ alkynyl, —C≡C—Si(CH₃)₃, —C≡C—Si(C₂H₅)₃, —C(=O)—O—C₁₋₅-alkyl and —C(=O)—CF₃.

Particularly preferably, the substituents may be in each case mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —C≡C—Si(CH₃)₃, —C≡C—Si(C₂H₅)₃, —OH, oxo, thioxo, —O—CH₃, —O—C₂H₅, —O—C₃H₇, —(CH₂)—O—CH₃, —(CH₂)—O—C₂H₅, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃, —S—C₂H₅, —S(=O)—CH₃, —S(=O)₂—CH₃, —S(=O)—C₂H₅, —S(=O)₂—C₂H₅, —NH—S(=O)₂—CH₃, —C(=O)—OH, —C(=O)—H, —C(=O)—CH₃, —C(=O)—C₂H₅, —C(=O)—N(CH₃)₂, —C(=O)—NH—CH₃, —C(=O)—NH₂, —NH—C(=O)—CH₃, —NH—C(=O)—C₂H₅, —C(=O)—O—CH₃, —C(=O)—O—C₂H₅, —C(=O)—O—C(CH₃)₃ and phenyl, wherein the phenyl residue may be substituted with 1, 2, 3, 4 or 5, preferably 1, 2 or 3, substituents mutually independently selected from the group consisting of F, Cl, Br, I, —CN, —CF₃, —OH, —NH₂, —O—CF₃, —SH, —O—CH₃, —O—C₂H₅, —O—C₃H₇, methyl, ethyl, n-propyl, isopropyl, n-butyl, 2-butyl, isobutyl, tert.-butyl, ethenyl, allyl, ethynyl, propynyl, —C≡C—Si(CH₃)₃, —C≡C—Si(C₂H₅)₃, —C(=O)—O—C₁₋₅-alkyl and —C(=O)—CF₃.

The term "phenylene" denotes a divalent 6-membered aromatic hydrocarbon residue of the following structure:

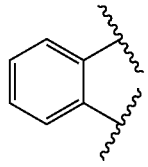

If $R^1$ and $R^2$ together with the carbon atoms joining them form an unsubstituted or at least monosubstituted phenylene residue, there results, together with the thiazolyl residue of the general formula I, an unsubstituted or at least monosubstituted benzothiazolyl residue of the following structure:

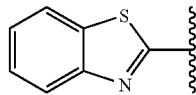

For the purposes of the present invention, the term "aryl" means a mono- or polycyclic, preferably a mono- or bicyclic, aromatic hydrocarbon residue with preferably 6, 10 or 14 C atoms. An aryl residue may be unsubstituted or monosubstituted or identically or differently polysubstituted. Examples of suitable aryl residues which may be mentioned are phenyl, 1-naphthyl, 2-naphthyl and anthracenyl. An aryl residue is particularly preferably a phenyl residue.

For the purposes of the present invention, the term "heteroaryl" means a monocyclic or polycyclic, preferably a mono-, bi- or tricyclic aromatic hydrocarbon residue with preferably 5, 6, 7, 8, 9, 10, 11, 12, 13 or 14 C atoms, particularly preferably with 5, 6, 9, 10, 13 or 14 C atoms, very particularly preferably with 5 or 6 C atoms, in which one or more C atoms have in each case been replaced by a heteroatom mutually independently selected from the group consisting of oxygen, sulfur and nitrogen (NH). Heteroaryl residues may preferably comprise 1, 2, 3, 4 or 5, particularly preferably 1, 2 or 3, heteroatom(s) mutually independently selected from the group consisting of oxygen, sulfur and nitrogen (NH) as ring member(s) A heteroaryl residue may be unsubstituted or monosubstituted or identically or differently polysubstituted.

Examples of suitable heteroaryl residues which may be mentioned are thienyl, furyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, pyrimidinyl, indazolyl, quinoxalinyl, quinazolinyl, quinolinyl, naphthridinyl and isoquinolinyl.

For the purposes of the present invention aryl or heteroaryl residues may be fused (anellated) with a mono- or bicyclic ring system.

Examples which may be mentioned of aryl residues which are fused with a mono- or bicyclic ring system are (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1.4]dioxinyl, benzo[1.3]dioxolyl and (3,4)-dihydro-2H-benzo[1.4]oxazinyl.

If one or more of the substituents denote a phenylene, aryl or heteroaryl residue or comprise an aryl or heteroaryl residue which is mono- or polysubstituted, this may preferably be substituted with optionally 1, 2, 3, 4 or 5, particularly preferably with optionally 1, 2 or 3, substituents mutually independently selected from the group consisting of F, Cl, Br, I, —CN, —NO$_2$, —OH, —SH, —NH$_2$, —C(=O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$alkyl)$_2$, —C(=O)—O—C$_{1-5}$-alkyl, —C(=O)—H; —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiazolyl, thiadiazolyl, thiophenyl (thienyl), benzyl and phenethyl, wherein the above-stated C$_{1-5}$ alkyl residues may in each case be linear or branched and the cyclic substituents or the cyclic residues of these substituents themselves may be substituted with optionally 1, 2, 3, 4 or 5, preferably with optionally 1, 2, 3 or 4, substituents mutually independently selected from the group consisting of F, Cl, Br, I, —CN, —NO$_2$, —OH, —SH, —NH$_2$, —C(=O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

Particularly preferably, the substituents may be in each case mutually independently selected from the group consisting of F, Cl, Br, I, —CN, —NO$_2$, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl, wherein the cyclic substituents or the cyclic residues of these substituents themselves may in each case be substituted with optionally 1, 2, 3, 4, or 5, preferably with optionally 1, 2, 3 or 4, substituents mutually independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

Very particularly preferably, a substituted aryl residue may be selected from the group consisting of 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert.-butylphenyl, 3-tert.-butylphenyl, 4-tert.-butylphenyl, 2-carboxyphenyl, 3-carboxyphenyl, 4-carboxyphenyl, 2-ethenylphenyl, 3-ethenylphenyl, 4-ethenylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethyl ester phenyl, 3-carboxymethyl ester phenyl, 4-carboxymethyl ester phenyl, 2-carboxyethyl ester phenyl, 3-carboxyethyl ester phenyl, 4-carboxyethyl ester phenyl, 2-carboxy-tert.-butyl ester phenyl, 3-carboxy-tert.-butyl ester phenyl, 4-carboxy-tert.-butyl ester phenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, 4-trifluoro-methoxyphenyl, 2-fluoro-3-trifluoromethylphenyl, 2-fluoro-4-methylphenyl, (2,3)-difluorophenyl, (2,3)-dimethylphenyl, (2,3)-dichlorophenyl, 3-fluoro-2-trifluoro-methylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dibromophenyl, (2,4)-dimethylphenyl, 2-fluoro-4-trifluoromethylphenyl, (2,5)-difluorophenyl, 2-fluoro-5-trifluoro-methylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoro-methylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, 3-chloro-5-methylphenyl, (3,4)-dichlorophenyl, (3,4)-dimethylphenyl, 3-methyl-4-methoxyphenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 3-fluoro-4-methylphenyl, 3-fluoro-5-methylphenyl, 2-fluoro-3-methylphenyl, 4-methyl-3-nitrophenyl, (3,5)-dimethoxyphenyl, (3,5)-dimethylphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoro-methylphenyl, (3,5)-dibromophenyl, 5-chloro-4-fluorophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4,5)-trimethoxyphenyl, (2,3,4,5)-tetrafluorophenyl, 4-methoxy-(2,3,6)-trimethylphenyl, 4-methoxy-(2,3,6)-trimethylphenyl, 4-chloro-2,5-dimethylphenyl, 2-chloro-6-fluoro-3-methylphenyl, 6-chloro-2-fluoro-3-methyl, (2,4,6)-trimethylphenyl and (2,3,4,5,6)-pentafluorophenyl.

Very particularly preferably, a substituted heteroaryl residue may be selected from the group consisting of 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, 4-methyloxazol-2-yl, 5-methyloxazol-2-yl, 4-trifluoromethyloxazol-2-yl, 5-trifluoromethyloxazol-2-yl, 4-chlorooxazol-2-yl, 5-chlorooxazol-2-yl, 4-bromooxazol-2-yl, 5-bromooxazol-2-yl, 4-fluorooxazol-2-yl, 5-fluorooxazol-2-yl, 4-cyanooxazol-2-yl, 5-cyanooxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazolyl-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl and 2-cyano-(1,2,4)-oxadiazol-5-yl.

For the purposes of the present invention, the term "alkylene" covers acyclic saturated hydrocarbon chains, which combine an aryl, heteroaryl, cycloalkyl, heterocycloalkyl, cycloalkenyl or heterocycloalkenyl residue with the substituted thiazole of the general formula I or with another substituent. Alkylene chains may be branched or straight-chain and unsubstituted or at least monosubstituted with, as in the case of $C_{1-12}$ alkylene, 1 to 12 (i.e. 1, 2, 3, 4, 5, 6, 7, 8, 9, 10, 11 or 12) C atoms, with, as in the case of $C_{1-6}$ alkylene, 1 to 6 (i.e. 1, 2, 3, 4, 5 or 6) C atoms or with, as in the case of $C_{1-3}$ alkylene, 1 to 3 (i.e. 1, 2 or 3) C atoms. Examples which may be mentioned are $C_{1-6}$ alkylene groups such as —(CH$_2$)—, —(CH$_2$)$_2$—, —C(H)(CH$_3$)—, —(CH$_2$)$_3$—, —(CH$_2$)$_4$—, —(CH$_2$)$_5$—, —C(CH$_3$)$_2$—, —C(H)(CH$_3$)—, —C(H)(C(H)(CH$_3$)$_2$)— and C(C$_2$H$_5$)(H)—. Examples of suitable $C_{1-3}$ alkylene groups are —(CH$_2$)—, —(CH$_2$)$_2$— and —(CH$_2$)$_3$—.

For the purposes of the present invention, the term "alkenylene" covers acyclic unsaturated hydrocarbon chains, which combine an aryl, heteroaryl, cycloalkyl, heterocycloalkyl, cycloalkenyl or heterocycloalkenyl residue with the substituted thiazole of the general formula I or with another substituent. Alkenylene chains comprise at least one double bond, preferably 1, 2 or 3 double bonds, and may be branched or straight-chain and unsubstituted or at least monosubstituted with, as in the case of $C_{2-12}$ alkenylene, 2 to 12 (i.e. 2, 3, 4, 5, 6, 7, 8, 9, 10, 11 or 12) C atoms, with, as in the case of $C_{2-6}$ alkenylene, 2 to 6 (i.e. 2, 3, 4, 5 or 6) C atoms or with, as in the case of $C_{2-3}$ alkenylene, 2 to 3 (i.e. 2 or 3) C atoms. Examples which may be mentioned are $C_{2-3}$ alkenylene groups such as —CH═CH— and —CH$_2$—CH═CH.

For the purposes of the present invention, the term "alkynylene" covers acyclic unsaturated hydrocarbon chains, which combine an aryl, heteroaryl, cycloalkyl, heterocycloalkyl, cycloalkenyl or heterocycloalkenyl residue with the substituted thiazole of the general formula I or with another substituent. Alkynylene chains comprise at least one triple bond, preferably 1 or 2 triple bonds, and may be branched or straight-chain and unsubstituted or at least monosubstituted with, as in the case of $C_{2-12}$ alkynylene, 2 to 12 (i.e. 2, 3, 4, 5, 6, 7, 8, 9, 10, 11 or 12) C atoms, with, as in the case of $C_{2-6}$ alkynylene, 2 to 6 (i.e. 2, 3, 4, 5 or 6) C atoms or with, as in the case of $C_{2-3}$ alkynylene, 2 to 3 (i.e. 2 or 3) C atoms. Examples which may be mentioned are $C_{2-3}$ alkynylene groups such as —C≡C— and —CH$_2$—C≡C—.

The term "heteroalkylene" denotes an alkylene chain as described above in which one or more C atoms have in each case been replaced by a heteroatom mutually independently selected from the group consisting of oxygen, sulfur and nitrogen (NH). Heteroalkylene groups may preferably comprise 1, 2 or 3 heteroatom(s), particularly preferably one heteroatom, selected from the group consisting of oxygen, sulfur and nitrogen (NH) as chain link(s). Heteroalkylene groups may preferably be 2- to 12-membered, particularly preferably 2- to 6-membered, very particularly preferably 2- or 3-membered.

Examples which may be mentioned are heteroalkylene groups such as —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —CH$_2$—NH—CH$_2$—, —CH$_2$—NH— and —CH$_2$—CH$_2$—NH—CH$_2$—CH$_2$.

The term "heteroalkenylene" denotes an alkenylene chain as described above in which one or more C atoms have in each case been replaced by a heteroatom mutually independently selected from the group consisting of oxygen, sulfur and nitrogen (NH). Heteroalkenylene groups may preferably comprise 1, 2 or 3 heteroatom(s), particularly preferably 1 heteroatom, selected from the group consisting of oxygen, sulfur and nitrogen (NH) as chain link(s). Heteroalkenylene groups may preferably be 2- to 12-membered, particularly preferably 2- to 6-membered, very particularly preferably 2- or 3-membered. Examples which may be mentioned are heteroalkenylene groups such as —CH═CH—NH—, —CH═CH—O— and —CH═CH—S.

If one or more of the substituents denote an alkylene, alkenylene, alkynylene, heteroalkylene or heteroalkenylene group or comprise such a group, which is mono- or polysubstituted, this may preferably be substituted with optionally 1, 2, 3, 4 or 5, particularly preferably with optionally 1, 2 or 3, substituents mutually independently selected from the group consisting of phenyl, F, Cl, Br, I, —NO$_2$, —CN, —OH, —O-phenyl, —O—CH$_2$-phenyl, —SH, —S-phenyl, —S—CH$_2$-phenyl, —NH$_2$, —N(C$_{1-5}$-alkyl)$_2$, —NH-phenyl, (phenyl)-N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(═O)—H, —C(═O)—C$_{1-5}$-alkyl, —C(═O)-phenyl, —C(═S)—C$_{1-5}$-alkyl, —C(═S)-phenyl, —C(═O)—OH, —C(═O)—O—C$_{1-5}$-alkyl, —C(═O)—O-phenyl, —C(═O)—NH$_2$, —C(═O)—NH—C$_{1-5}$-alkyl, —C(═O)—N(C$_{1-5}$-alkyl)$_2$, —S(═O)—C$_{1-5}$-alkyl, —S(═O)-phenyl, —S(═O)$_2$—C$_{1-5}$-alkyl, —S(═O)$_2$-phenyl, —S(═O)$_2$—NH$_2$ and —SO$_3$H, wherein the above-stated-C$_{1-5}$ alkyl residues may in each case be linear or branched and the above-stated phenyl residues may be substituted with 1, 2, 3, 4 or 5, preferably with 1, 2, 3 or 4, substituents mutually independently selected from the group consisting of F, Cl, Br, I, —CN, —NO$_2$, —OH, —SH, —NH$_2$, —C(═O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F.

Particularly preferably, alkylene, alkenylene, alkynylene, heteroalkylene or heteroalkenylene groups may be substituted with 1, 2 or 3 substituents mutually independently selected from the group consisting of phenyl, F, Cl, Br, I, —NO$_2$, —CN, —OH, —O-phenyl, —SH, —S-phenyl, —NH$_2$, —N(CH$_3$)$_2$, —N(C$_2$H$_5$)$_2$ and —N(CH$_3$)(C$_2$H$_5$), wherein the phenyl residue may be substituted with 1, 2, 3, 4 or 5 substituents mutually independently selected from the group consisting of F, Cl, Br, I, —OH, —SH, —NO$_2$, —CN, —O—CH$_3$, —O—CF$_3$, and —O—C$_2$H$_5$.

If compounds of the general formula I comprise substituents selected from the group consisting of $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$ with the identical designation, each of these substituents may in each case be selected independently of other substituents with the identical designation of the substituents. For example, the following residue,

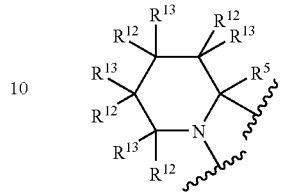

after selection of the appropriate substituents, may denote said residue

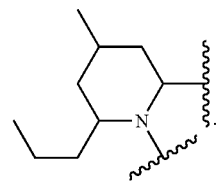

Preferred substituted thiazoles are those of the above-stated general formula I, in which $R^1$ and $R^2$, mutually independently, in each case denote H; F; Cl; Br; I; —NO$_2$; —CN; —NH$_2$; —OH; —SH; —C(═O)—OH; —C(═O)—H; —NH—C(═O)—H; —NH—$R^{55}$; —N$R^{56}$$R^{57}$; —C(═O)—$R^{58}$; —C(═O)—O—$R^{59}$; —O—C(═O)—$R^{60}$; —NH—C(═O)—$R^{61}$; —N$R^{62}$—C(═O)—$R^{63}$; —C(═O)—NH$_2$; —C(═O)—NH—$R^{64}$; —C(═O)—N$R^{65}$$R^{66}$; —O—$R^{67}$; —S—$R^{68}$; —S(═O)—$R^{69}$; —S(═O)$_2$—$R^{70}$; —NH—C(═O)—NH—$R^{71}$; —NH—C(═S)—NH—$R^{72}$; —NH—S(═O)$_2$—$R^{73}$; —N$R^{74}$—S(═O)$_2$—$R^{75}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted- (alkylene)-heteroaryl, -(alkenylene)-heteroaryl, -(alkynylene)-heteroaryl, -(heteroalkylene)-heteroaryl or -(heteroalkenylene)-heteroaryl;

or $R^1$ and $R^2$ together with the carbon atoms joining them form an unsubstituted or at least monosubstituted phenylene residue;

$R^3$, $R^8$ and $R^{54}$, mutually independently, in each case denote H; —C(=O)—$R^{58}$; —C(=O)—O—$R^{59}$; —C(=O)—NH$_2$; —C(=O)—NH—$R^{64}$; —C(=O)—NR$^{65}$R$^{66}$; —S(=O)—R$^{69}$; —S(=O)$_2$—R$^{70}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$, mutually independently, in each case denote H; F; Cl; Br; I; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —O—C(=O)—R$^{60}$; —NH—C(=O)—R$^{61}$; —NR$^{62}$—C(=O)—R$^{63}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=S)—NH—R$^{72}$; —NH—S(=O)$_2$—R$^{73}$; —NR$^{74}$—S(=O)$_2$—R$^{75}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

or $R^4$ and $R^5$ or $R^6$ and $R^7$ or $R^{10}$ and $R^{11}$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{30}$ and $R^{31}$ or $R^{32}$ and $R^{33}$ or $R^{34}$ and $R^{35}$ or $R^{36}$ and $R^{37}$ or $R^{38}$ and $R^{39}$ or $R^{40}$ and $R^{41}$ or $R^{42}$ and $R^{43}$ or $R^{44}$ and $R^{45}$ or $R^{46}$ and $R^{47}$ or $R^{48}$ and $R^{49}$ or $R^{50}$ and $R^{51}$ or $R^{52}$ and $R^{53}$, mutually independently, together in each case denote a residue selected from the group consisting of an oxo group (=O) and a thioxo group (=S);

or $R^3$ and $R^4$ together with the —N—CR$^5$ group joining them form a residue of the general formula A,

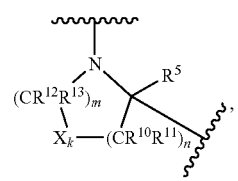

or $R^6$ and $R^8$ together with the —N—CR$^7$ group joining them form a residue of the general formula B,

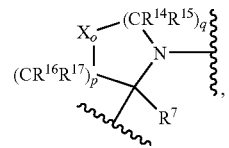

m and q in each case denote 1, 2, 3, 4 or 5;

n and p in each case denote 0, 1, 2, 3 or 4;

k and o in each case denote 0 or 1; wherein the sum of m, n and k or the sum of p, q and o is in each case equal to 1, 2, 3, 4, 5 or 6;

or $R^3$ and $R^6$ together with the —N—CR$^4$R$^5$—CR$^7$ group joining them form a residue of the general formula C,

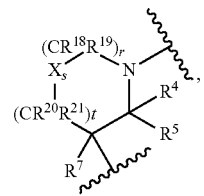

or $R^4$ and $R^8$ together with the —$CR^5$—$CR^6R^7$—N group joining them form a residue of the general formula D,

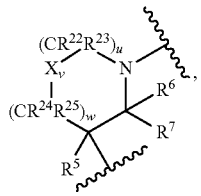

r and u in each case denote 1, 2, 3 or 4;

t and w in each case denote 0, 1, 2 or 3;

s and v in each case denote 0 or 1;

wherein the sum of r, s and t or the sum of u, v and w is in each case equal to 1, 2, 3, 4 or 5;

or $R^3$ and $R^8$ together with the —N—$CR^4R^5$—$CR^6R^7$—N group joining them form a residue of the general formula E,

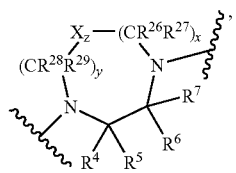

x and y in each case denote 1 or 2;

z denotes 0 or 1;

wherein the sum of x, y and z is equal to 3 or 4;

or $R^4$ and $R^6$ together with the —$CR^5$—$CR^7$ group joining them form a residue of the general formula F,

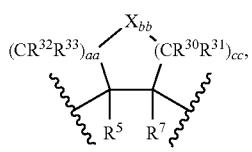

aa and cc, mutually independently, in each case denote 1, 2, 3, 4 or 5;

bb denotes 0 or 1;

wherein the sum of aa, bb and cc is equal to 1, 2, 3, 4, 5 or 6;

or $R^3$ and $R^4$ together with the —N—$CR^5$ group joining them and $R^6$ and $R^8$ together with the —N—$CR^7$ group joining them form a residue of the general formula G,

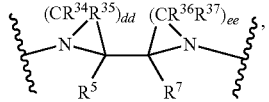

dd and ee, mutually independently, in each case denote 1, 2, 3 or 4;

or $R^3$ and $R^6$ together with the —N—$CR^4CR^5$—$CR^7$ group joining them and $R^4$ and $R^8$ together with the —$CR^5$—$CR^6R^7$—N group joining them form a residue of the general formula H,

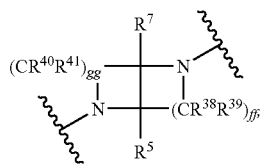

ff and gg, mutually independently, in each case denote 1, 2 or 3;

or $R^3$ and $R^8$ together with the —N—$CR^4R^5$—$CR^6R^7$—N group joining them and $R^4$ and $R^6$ together with the —$CR^5$—$CR^7$ group joining them form a residue of the general formula K,

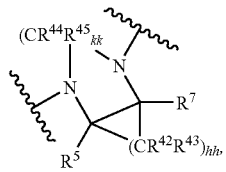

hh denotes 1, 2, 3 or 4;

kk denotes 1, 2, 3, 4, 5 or 6;

or $R^3$ and $R^8$ together with the —N—$CR^4R^5$—$CR^6R^7$—N group joining them form a bicyclic residue of the general formula L,

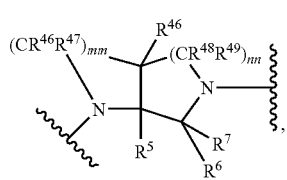

mm denotes 1, 2 or 3;

nn denotes 1 or 2;

or $R^3$ and $R^8$ together with the —N—$CR^4R^5$—$CR^6R^7$—N group joining them form a bicyclic residue of the general formula M,

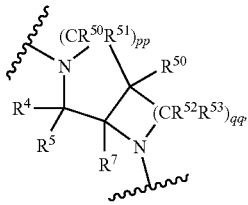

pp denotes 1 or 2;

qq denotes 1, 2 or 3;

X denotes O, S or N—$R^{54}$;

$R^9$ denotes H; F; Cl; Br; I; —CN; —C(=O)—OH; —C(=O)—H; —C(=O)—$R^{58}$; —C(=O)—O—$R^{59}$; —C(=O)—NH$_2$; —C(=O)—NH—$R^{64}$; —C(=O)—N$R^{65}R^{66}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

and $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$ and $R^{75}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

wherein the above-stated alkyl residues are in each case branched or straight-chain and comprise 1, 2, 3, 4, 5, 6, 7, 8, 9, 10, 11 or 12 carbon atoms as chain links;

the above-stated alkenyl residues are in each case branched or straight-chain and comprise 2, 3, 4, 5, 6, 7, 8, 9, 10, 11 or 12 carbon atoms as chain links;

the above-stated alkynyl residues are in each case branched or straight-chain and comprise 2, 3, 4, 5, 6, 7, 8, 9, 10, 11 or 12 carbon atoms as chain links;

the above-stated heteroalkyl residues, heteroalkenyl residues and heteroalkynyl residues are in each case 2-, 3-, 4-, 5-, 6-, 7-, 8-, 9-, 10-, 11- or 12-membered;

the above-stated heteroalkyl residues, heteroalkenyl residues and heteroalkynyl residues in each case optionally comprise 1, 2 or 3 heteroatom(s) mutually independently selected from the group consisting of oxygen, sulfur and nitrogen as chain link(s);

the above-stated alkyl residues, alkenyl residues, alkynyl residues, heteroalkyl residues, heteroalkenyl residues and heteroalkynyl residues may be substituted in each case with optionally 1, 2, 3, 4 or 5 substituents mutually independently selected from the group consisting of F, Cl, Br, I, —NO$_2$, —CN, —OH, —SH, —NH$_2$, —N($C_{1-5}$-alkyl)$_2$, —N($C_{1-5}$-alkyl)(phenyl), —N($C_{1-5}$-alkyl)(CH$_2$-phenyl), —N($C_{1-5}$-alkyl)(CH$_2$—CH$_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—NH$_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—NH$_2$ and —SO$_3$H, wherein the phenyl residues may be substituted with 1, 2, 3, 4 or 5 substituents mutually independently selected from the group consisting of F, Cl, Br, I, —CN, —CF$_3$, —OH, —NH$_2$, —O—CF$_3$, —SH, —O—CH$_3$, —O—$C_2H_5$, —O—$C_3H_7$, methyl, ethyl, n-propyl, isopropyl, n-butyl, 2-butyl, isobutyl and tert.-butyl;

the above-stated cycloalkyl residues in each case comprise 3, 4, 5, 6, 7, 8 or 9 carbon atoms as ring members;

the above-stated cycloalkenyl residues in each case comprise 3, 4, 5, 6, 7, 8 or 9 carbon atoms as ring members;

the above-stated heterocycloalkyl residues are in each case 3-, 4-, 5-, 6-, 7-, 8- or 9-membered;

the above-stated heterocycloalkenyl residues are in each case 4-, 5-, 6-, 7-, 8- or 9-membered;

the above-stated heterocycloalkyl residues and heterocycloalkenyl residues in each case optionally comprise 1, 2 or 3 heteroatom(s) mutually independently selected from the group consisting of oxygen, sulfur and nitrogen (NH) as ring member(s);

the above-stated cycloalkyl residues, heterocycloalkyl residues, cycloalkenyl residues or heterocycloalkenyl residues may be substituted in each case with optionally 1, 2, 3, 4 or 5 substituents mutually independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$ alkyl, —C$_{2-5}$ alkenyl, —C$_{2-5}$ alkynyl, —C≡C—Si(CH$_3$)$_3$, —C≡C—Si(C$_2$H$_5$)$_3$, —C(═O)—O—C$_{1-5}$-alkyl, —C(═O)—CF$_3$, —S(═O)$_2$—C$_{1-5}$-alkyl, —S(═O)—C$_{1-5}$-alkyl, —S(═O)$_2$-phenyl, oxo (═O), thioxo (═S), —N(C$_{1-5}$-alkyl)$_2$, —N(H)(C$_{1-5}$-alkyl), —NO$_2$, —S—CF$_3$, —C(═O)—OH, —NH—S(═O)$_2$—C$_{1-5}$-alkyl, —NH—C(═O)—C$_{1-5}$-alkyl, —C(═O)—H, —C(═O)—C$_{1-5}$-alkyl, —C(═O)—NH$_2$, —C(═O)—N(C$_{1-5}$-alkyl)$_2$, —C(═O)—N(H)(—C$_{1-5}$-alkyl) and phenyl, wherein the phenyl residues may in each case be unsubstituted or substituted with 1, 2, 3, 4 or 5 substituents mutually independently selected from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$ alkyl, —C$_{2-5}$ alkenyl, —C$_{2-5}$ alkynyl, —C≡C—Si(CH$_3$)$_3$, —C≡C—Si(C$_2$H$_5$)$_3$, —C(═O)—O—C$_{1-5}$-alkyl and —C(═O)—CF$_3$, wherein the above-stated phenyl residues may preferably be substituted with 1, 2, 3, 4 or 5 substituents mutually independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert.-butyl;

the above-stated alkylene residues are in each case branched or straight-chain and comprise 1, 2, 3, 4, 5, 6, 7, 8, 9, 10, 11 or 12 carbon atoms as chain links;

the above-stated alkenylene residues are in each case branched or straight-chain and comprise 2, 3, 4, 5, 6, 7, 8, 9, 10, 11 or 12 carbon atoms as chain links;

the above-stated alkynylene residues are in each case branched or straight-chain and comprise 2, 3, 4, 5, 6, 7, 8, 9, 10, 11 or 12 carbon atoms as chain links;

the above-stated heteroalkylene, heteroalkenylene and heteroalkynylene residues are in each case 2-, 3-, 4-, 5-, 6-, 7-, 8-, 9-, 10-, 11- or 12-membered;

the above-stated heteroalkylene, heteroalkenylene and heteroalkynylene groups may in each case optionally comprise 1, 2 or 3 heteroatom(s) mutually independently selected from the group consisting of oxygen, sulfur and nitrogen (NH) as chain link(s);

the above-stated alkylene, alkenylene, alkynylene, heteroalkylene-, heteroalkenylene and heteroalkynylene groups may in each case be unsubstituted or substituted with optionally 1, 2, 3, 4 or 5 substituents mutually independently selected from the group consisting of phenyl, F, Cl, Br, I, —NO$_2$, —CN, —OH, —O-phenyl, —O—CH$_2$-phenyl, —SH, —S-phenyl, —S—CH$_2$-phenyl, NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(═O)—H, —C(═O)—C$_{1-5}$-alkyl, —C(═O)-phenyl, —C(═S)—C$_{1-5}$-alkyl, —C(═S)-phenyl, —C(═O)—OH, —C(═O)—O—C$_{1-5}$-alkyl, —C(═O)—O-phenyl, —C(═O)—NH$_2$, —C(═O)—NH—C$_{1-5}$-alkyl, —C(═O)—N(C$_{1-5}$-alkyl)$_2$, —S(═O)—C$_{1-5}$-alkyl, —S(═O)-phenyl, —S(═O)$_2$—C$_{1-5}$-alkyl, —S(═O)$_2$-phenyl, —S(═O)$_2$—NH$_2$ and —SO$_3$H, wherein the phenyl residues may be substituted with 1, 2, 3, 4 or 5 substituents mutually independently selected from the group consisting of F, Cl, Br, I, —CN, —NO$_2$, —OH, —SH, —NH$_2$, —C(═O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F;

the above-stated aryl residues are mono- or bicyclic and comprise 6, 10 or 14 carbon atoms;

the above-stated heteroaryl residues are mono-, di- or tricyclic and 5-, 6-, 7-, 8-, 9-, 10-, 11-, 12-, 13- or 14-membered;

the above-stated 5- to 14-membered heteroalkyl residues optionally comprise 1, 2, 3, 4 or 5 heteroatom(s) mutually independently selected from the group consisting of oxygen, sulfur and nitrogen (NH) as ring member(s);

and the above-stated phenylene residues, aryl residues or heteroaryl residues may optionally in each case be substituted with 1, 2, 3, 4 or 5 substituents mutually independently selected from the group consisting of F, Cl, Br, I, —CN, —NO$_2$, —OH, —SH, —NH$_2$, —C(═O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, —S(═O)$_2$—C$_{1-5}$-alkyl, —S(═O)—C$_{1-5}$-alkyl, —NH—C$_{1-5}$-alkyl, N(C$_{1-5}$alkyl)$_2$, —C(═O)—O—C$_{1-5}$-alkyl, —C(═O)—H, —C(═O)—C$_{1-5}$-alkyl, —CH$_2$—O—C(═O)-phenyl, —O—C(═O)-phenyl, —NH—S(═O)$_2$—C$_{1-5}$-alkyl, —NH—C(═O)—C$_{1-5}$-alkyl, —C(═O)—NH$_2$, —C(═O)—NH—C$_{1-5}$-alkyl, —C(═O)—N(C$_{1-5}$-alkyl)$_2$, pyrazolyl, phenyl, furyl (furanyl), thiazolyl, thiadiazolyl, thiophenyl (thienyl), benzyl and phenethyl, wherein the cyclic substituents or the cyclic residues of these substituents themselves may be substituted with optionally 1, 2, 3, 4 or 5 substituents mutually independently selected from the group consisting of F, Cl, Br, I, —CN, —NO$_2$, —OH, —SH, —NH$_2$, —C(═O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which R$^1$ denotes H; F; Cl; Br; I; —NO$_2$; —CN; —NH$_2$; —OH; —SH; —C(═O)—OH; —C(═O)—H; —NH—C(═O)—H; —NH—R$^{55}$; —NR$^{56}$R$^{57}$; —C(═O)—R$^{58}$; —C(═O)—O—R$^{59}$; —O—C(═O)—R$^{60}$; —NH—C(═O)—R$^{61}$; —NR$^{62}$—C(═O)—R$^{63}$; —C(═O)—NH$_2$; —C(═O)—NH—R$^{64}$; —C(═O)—NR$^{65}$R$^{66}$; —O—R$^{67}$; —S—R$^{68}$; —S(═O)—R$^{69}$; —S(═O)$_2$—R$^{70}$; —NH—C(═O)—NH—R$^{71}$; —NH—C(═S)—NH—R$^{72}$; —NH—S(═O)$_2$—R$^{73}$; —NR$^{74}$—S(═O)$_2$—R$^{75}$; C$_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —S—$CH_3$ and —S—$C_2H_5$; or denotes a residue selected from the group consisting of phenyl, naphthyl, anthracenyl, thienyl, furyl, pyridinyl, thiazolyl, thiadiazolyl, oxazolyl, oxadiazolyl and isoxazolyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —$CF_3$, —$CHF_2$, —$CH_2F$ and —O—$CF_3$;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^2$ denotes H; F; Cl; Br; I; —$NO_2$; —CN; —$NH_2$; —OH; —SH; —C(=O)—OH; —NH—$R^{55}$; —$NR^{56}R^{57}$; —C(=O)—$R^{58}$; —C(=O)—O—$R^{59}$; —C(=O)—$NH_2$; —C(=O)—NH—$R^{64}$; —C(=O)—$NR^{65}R^{66}$; —O—$R^{67}$; —S—$R^{68}$; —S(=O)—$R^{69}$; —S(=O)$_2$—$R^{70}$; —NH—C(=O)—NH—$R^{71}$; —NH—C(=O)—NH—$R^{72}$; —NH—S(=O)$_2$—$R^{73}$; —$NR^{74}$—S(=O)$_2$—$R^{75}$; $C_{1-6}$ alkyl, which is unsubstituted or substituted with optionally 1, 2, 3, 4 or 5 substituents mutually independently selected from the group consisting of F, Cl, Br, I, —$NO_2$, —CN, —OH, —SH and —$NH_2$; $C_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —S—$CH_3$ and —S—$C_2H_5$; or denotes a residue selected from the group consisting of phenyl, naphthyl, anthracenyl, thienyl, furyl, pyridinyl, thiazolyl, thiadiazolyl, oxazolyl, oxadiazolyl and isoxazolyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —$CF_3$, —$CHF_2$, —$CH_2F$ and —O—$CF_3$;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^1$ and $R^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —$CF_3$, —$CHF_2$, —$CH_2F$ and —O—$CF_3$;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$, $R^8$ and $R^{54}$, mutually independently, in each case denote H; —C(=O)—$R^{67}$; —C(=O)—O—$R^{59}$; —C(=O)—$NH_2$; —C(=O)—NH—$R^{64}$; —C(=O)—$NR^{65}R^{66}$; —S(=O)—$R^{69}$; —S(=O)$_2$—$R^{70}$; $C_{1-6}$ alkyl, which is unsubstituted or substituted with optionally 1, 2, 3, 4 or 5 substituents mutually independently selected from the group consisting of F, Cl, Br, I, —$NO_2$, —CN, —OH, —SH and —$NH_2$; $C_{3-8}$ cycloalkyl, which is unsubstituted or substituted with optionally 1, 2, 3, 4 or 5 substituents mutually independently selected from the group consisting of F, Cl, Br, I, —$NO_2$, —CN, —OH, —SH and —$NH_2$; or denote a phenyl residue, which may be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH—, —O—$CH_3$, —O—$C_2H_5$ and —O—$C_3H_7$;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$, mutually independently, in each case denote H; F; Cl; Br; I; —$NO_2$; —CN; —$NH_2$; —OH; —SH; —C(=O)—OH; —NH—$R^{55}$; —$NR^{56}R^{57}$; —C(=O)—$R^{58}$;

—C(=O)—O—R$^{59}$; —O—R$^{67}$; —S—R$^{68}$; C$_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$ cycloalkyl, C$_{5-6}$ cycloalkenyl, 5- to 7-membered heterocycloalkyl or 5- to 7-membered heterocycloalkenyl, which may in each case be attached via a C$_{1-3}$ alkylene, C$_{2-3}$ alkenylene or C$_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, which may in each case be attached via a C$_{1-3}$ alkylene, C$_{2-3}$ alkenylene or C$_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

or R$^4$ and R$^5$ or R$^6$ and R$^7$ or R$^{10}$ and R$^{11}$ or R$^{12}$ and R$^{13}$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$ or R$^{28}$ and R$^{29}$ or R$^{30}$ and R$^{31}$ or R$^{32}$ and R$^{33}$ or R$^{34}$ and R$^{35}$ or R$^{36}$ and R$^{37}$ or R$^{38}$ and R$^{39}$ or R$^{40}$ and R$^{41}$ or R$^{42}$ and R$^{43}$ or R$^{44}$ and R$^{45}$ or R$^{46}$ and R$^{47}$ or R$^{48}$ and R$^{49}$ or R$^{50}$ and R$^{51}$ or R$^{52}$ and R$^{53}$, mutually independently, together in each case denote a residue selected from the group consisting of an oxo group (=O) and a thioxo group (=S);

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which R$^3$ and R$^4$ together with the —N—CR$^5$ group joining them form a residue selected from the group consisting of

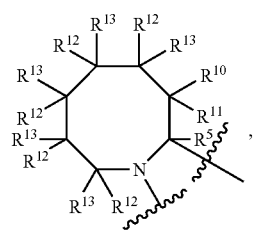, 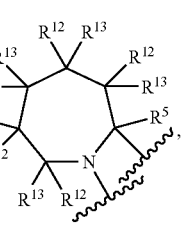

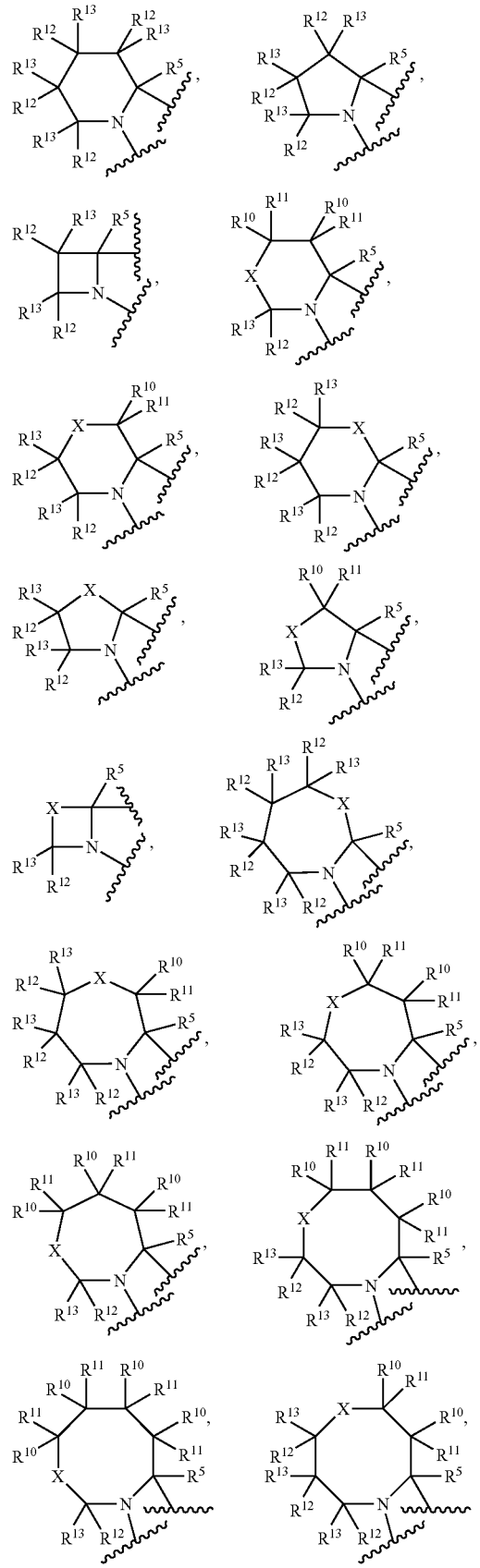

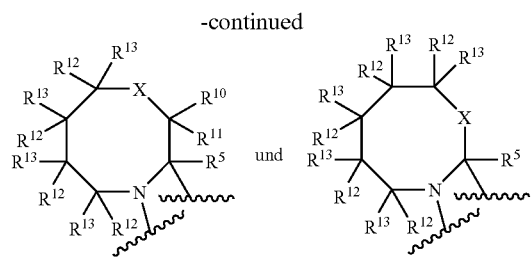

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^6$ and $R^8$ together with the —N—$CR^7$— group joining them form a residue selected from the group consisting of

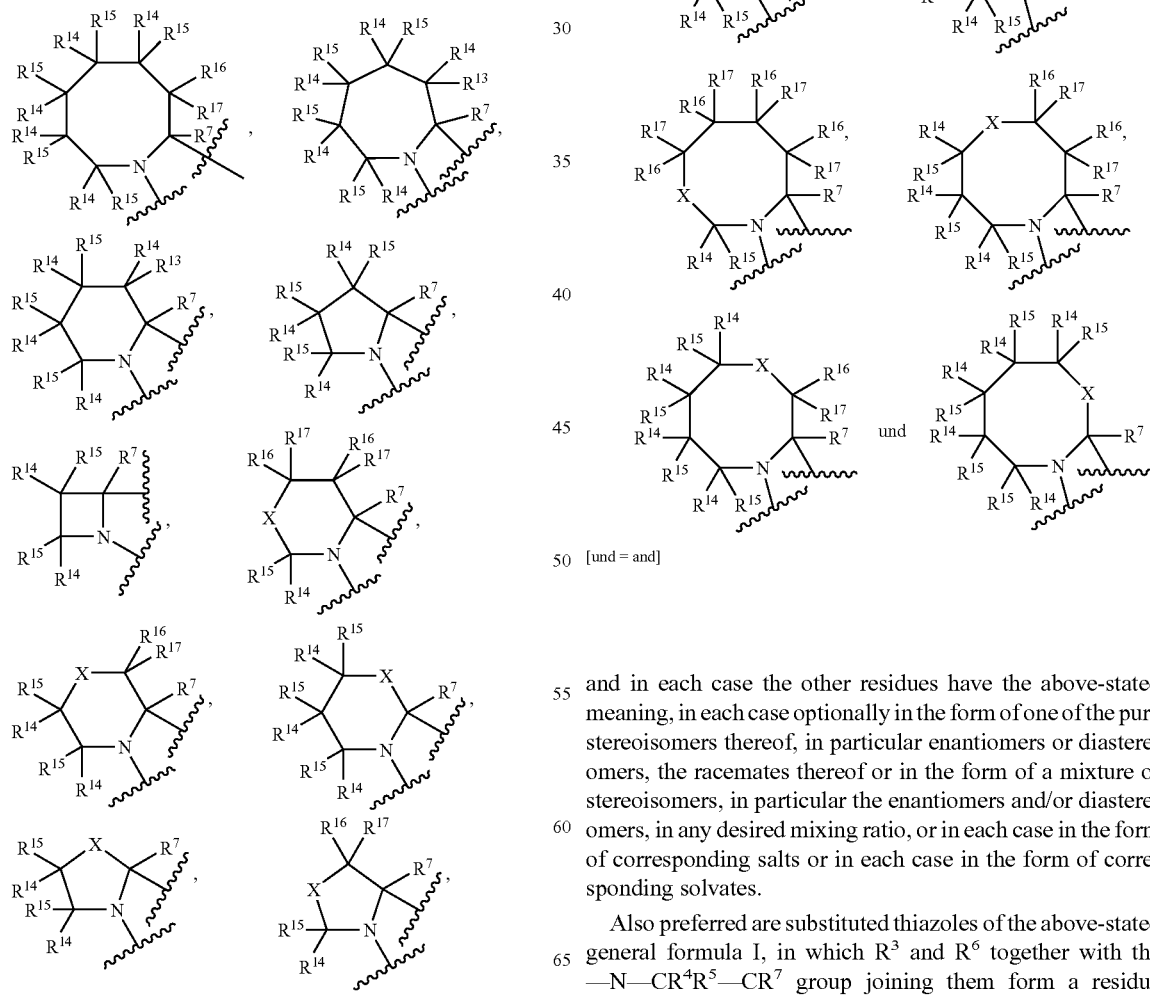

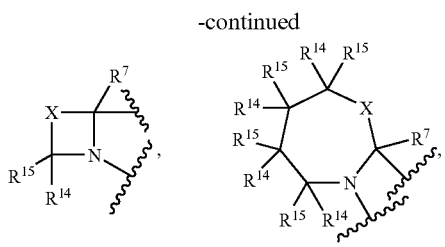

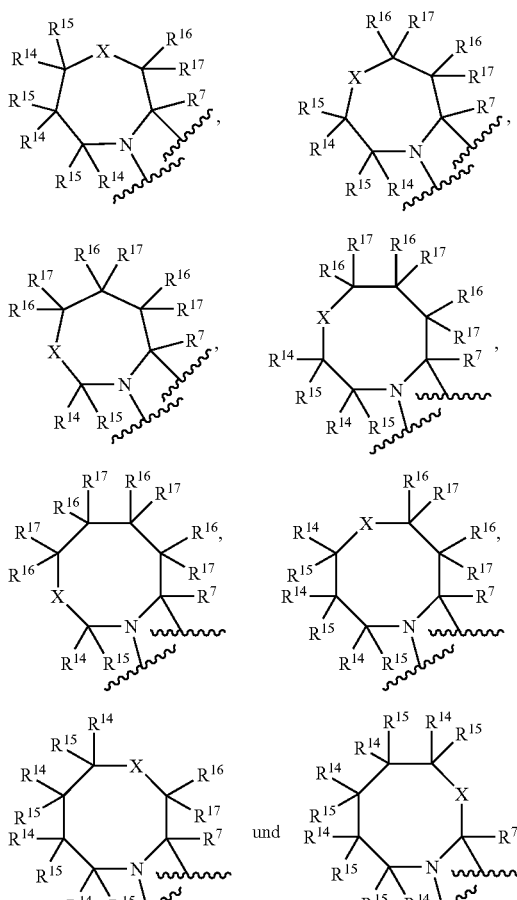

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$ and $R^6$ together with the —N—$CR^4R^5$—$CR^7$ group joining them form a residue selected from the group consisting of

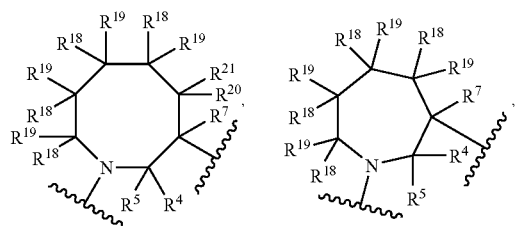
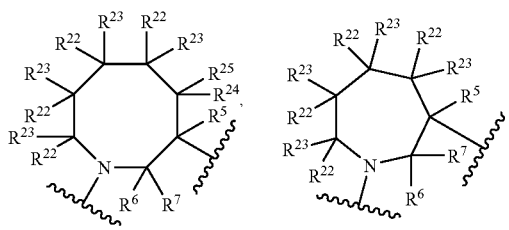
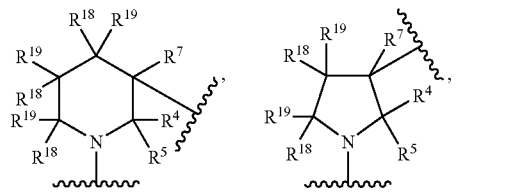
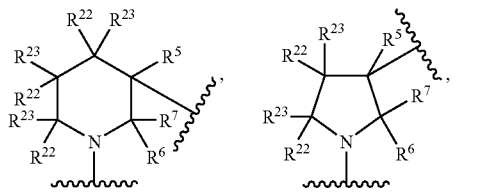
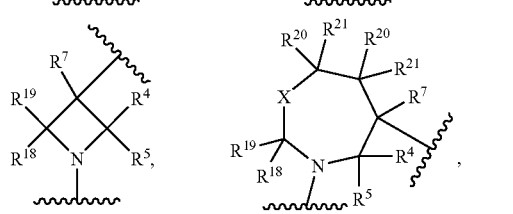
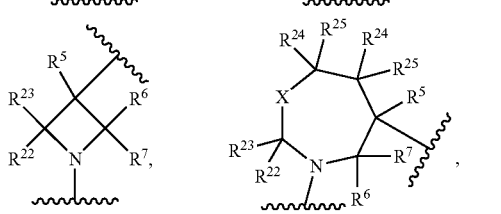
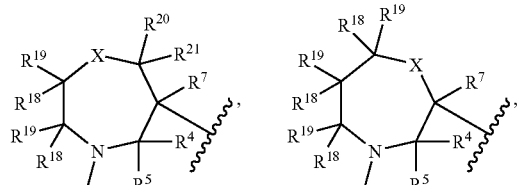
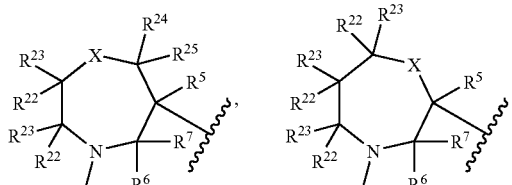
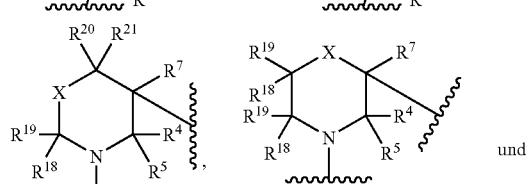
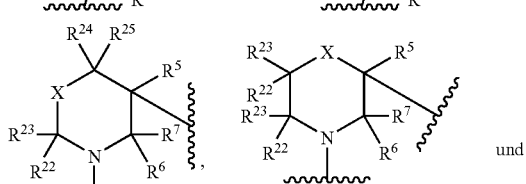
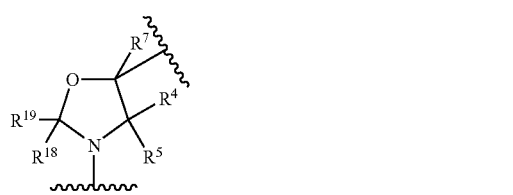 und
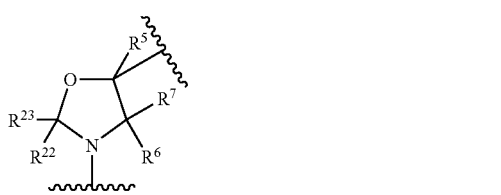 und

[und = and]

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^4$ and $R^8$ together with the —$CR^5$—$CR^6CR^7$—N group joining them form a residue selected from the group consisting of and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$ and $R^8$ together with the —N—$CR^4R^5$—$CR^6CR^7$—N group joining them form a residue selected from the group consisting of

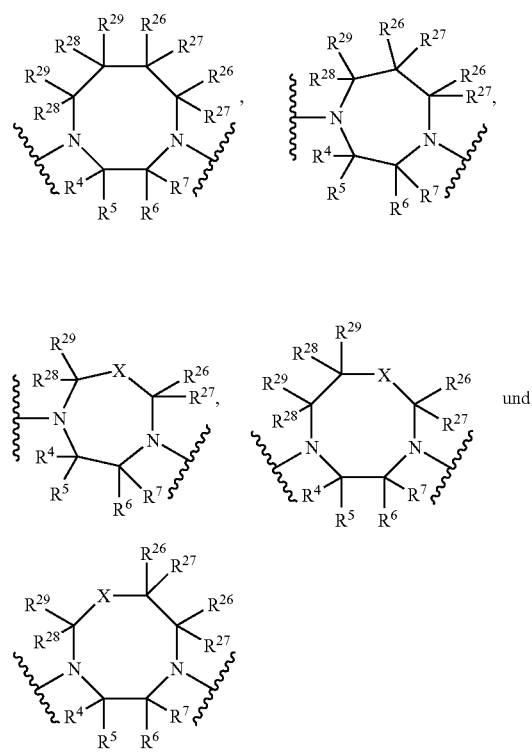

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^4$ and $R^6$ together with the $-CR^5-CR^7$ group joining them form a residue selected from the group consisting of

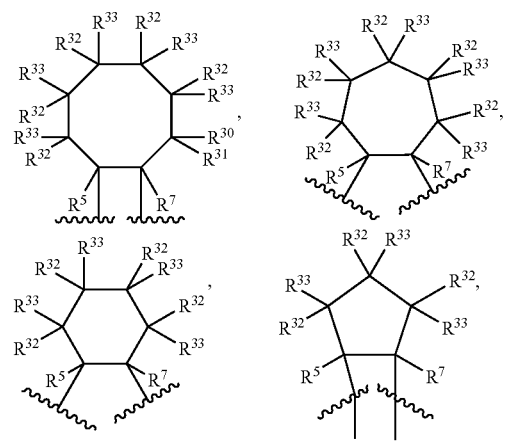

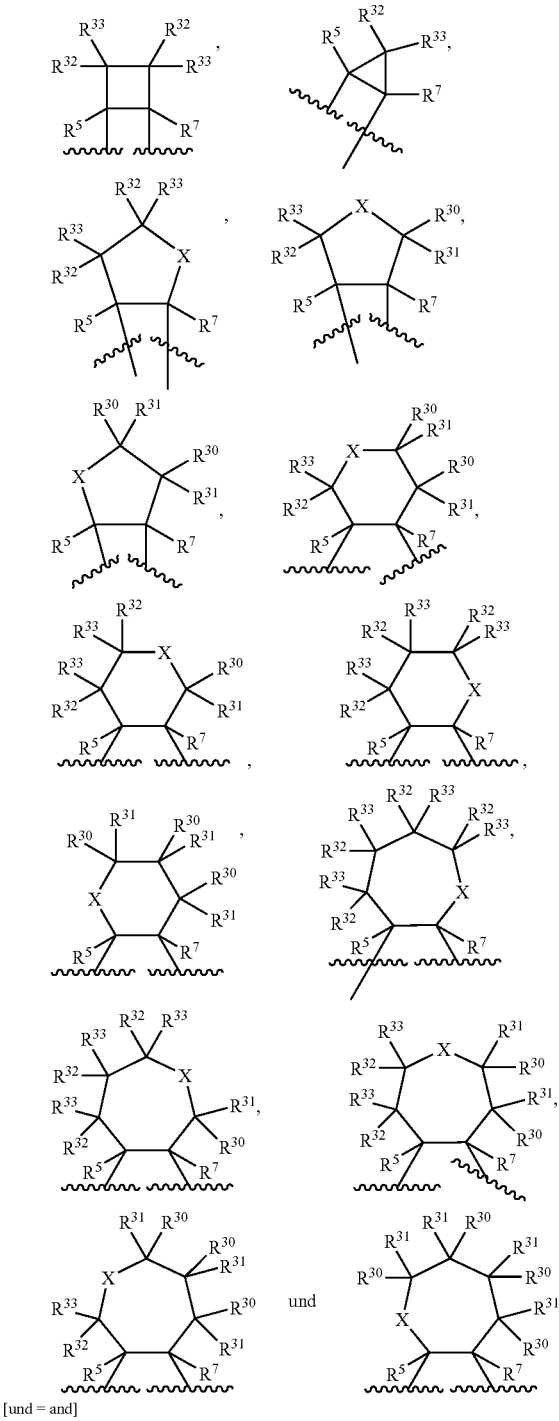

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$ and $R^4$ together with the —N—$CR^5$ group joining them and $R^6$ and $R^8$ together with the —N—$CR^7$ group joining them form a residue selected from the group consisting of

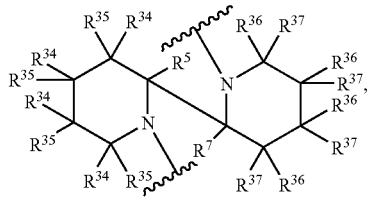

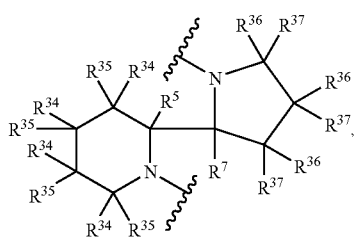

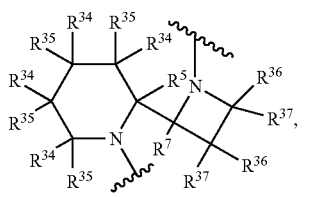

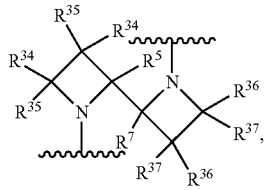

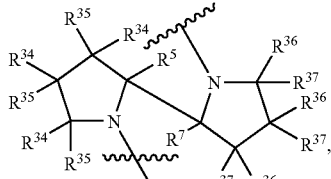

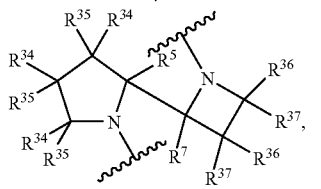

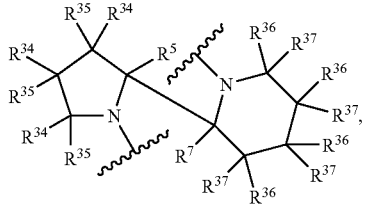

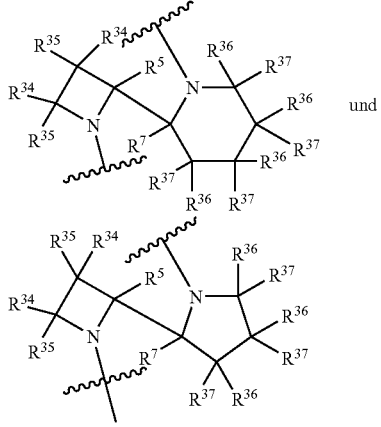

und

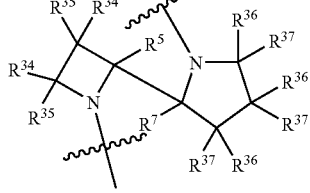

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$ and $R^6$ together with the —N—$CR^4CR^5$—$CR^7$ group joining them and $R^4$ and $R^8$ together with the —$CR^5$—$CR^6R^7$—N group joining them form a residue selected from the group consisting of

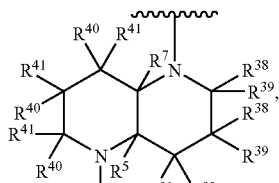

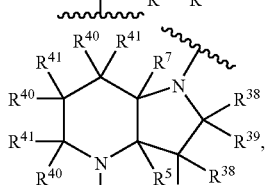

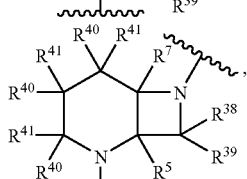

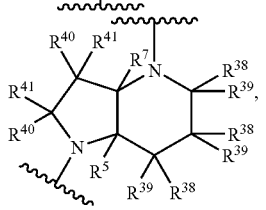

-continued

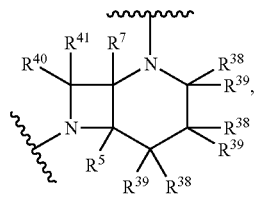

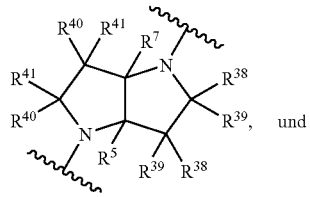, und

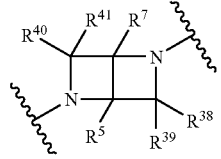

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$ and $R^8$ together with the $-N-CR^4R^5-CR^6R^7-N$ group joining them and $R^4$ and $R^6$ together with the $-CR^5-CR^7$ group joining them form a residue selected from the group consisting of

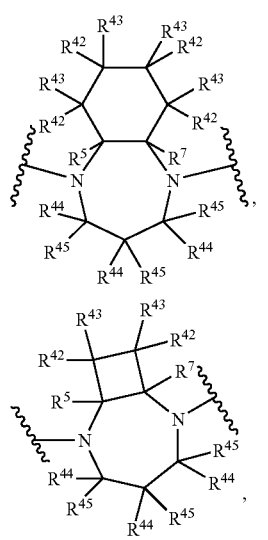

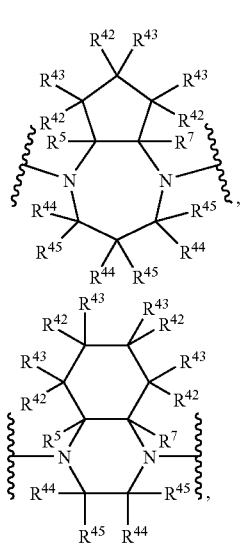

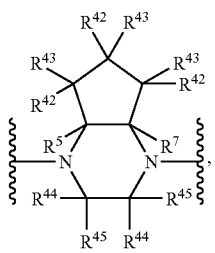 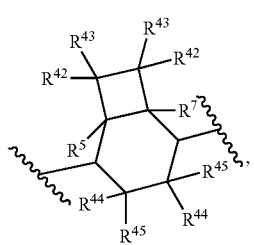

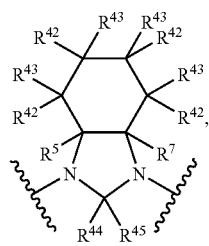 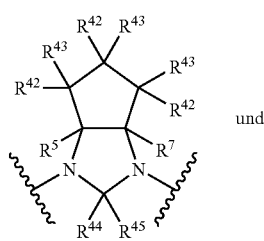 und

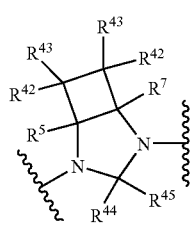

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, preferably in the form of corresponding hydrochlorides, or in each case in the form of corresponding solvates.

Also preferred are substituted thiazoles of the above-stated general formula I, in which $R^3$ and $R^8$ together with the $-N-CR^4R^5-CR^6R^7-N$ group joining them form a bicyclic residue selected from the group consisting of

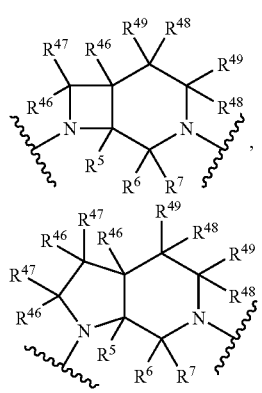 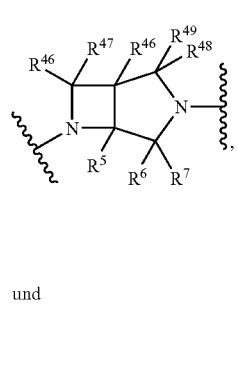 und

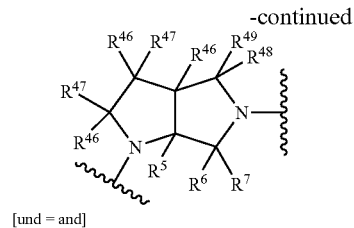

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^3$ and $R^8$ together with the $-N-CR^4R^5-CR^6R^7-N$ group joining them form a bicyclic residue selected from the group

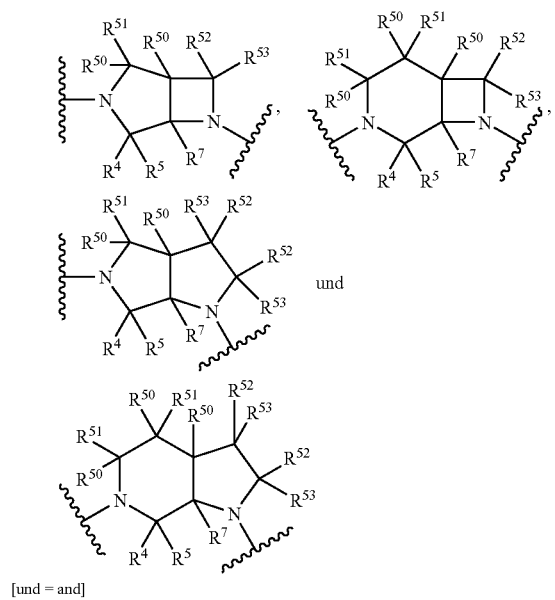

[und = and]

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^9$ denotes H; $-C(=O)-NH_2$; $-C(=O)-NH-R^{64}$; $-C(=O)-NR^{65}R^{66}$; $C_{1-6}$ alkyl, which is unsubstituted or substituted with optionally 1, 2, 3, 4 or 5 substituents mutually independently selected from the group consisting of F, Cl, Br, I, $-NO_2$, $-CN$, $-OH$, $-SH$ and $-NH_2$; $C_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, $-CN$, methyl, ethyl, n-propyl, isopropyl, n-butyl, 2-butyl, isobutyl, tert.-butyl, $-OH$, oxo, thioxo, $-O-CH_3$, $-O-C_2H_5$, $-O-C_3H_7$, $-NH_2$, $-N(CH_3)_2$, $-N(C_2H_5)_2$, $-NH-CH_3$, $-NH-C_2H_5$, $-NO_2$, $-CF_3$, $-O-CF_3$, $-S-CF_3$, $-SH$, $-S-CH_3$ and $-S-C_2H_5$; or denotes a residue selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, $-CN$, methyl, ethyl, n-propyl, isopropyl, n-butyl, 2-butyl, isobutyl, tert.-butyl, ethenyl, allyl, ethynyl, propynyl, $-C\equiv C-Si(CH_3)_3$, $-C\equiv C-Si(C_2H_5)_3$, $-CH_2-O-CH_3$, $-CH_2-O-C_2H_5$, $-OH$, $-O-CH_3$, $-O-C_2H_5$, $-O-C_3H_7$, $-S-CH_3$, $-S-C_2H_5$, $-S(=O)-CH_3$, $-S(=O)_2-CH_3$, $-S(=O)-C_2H_5$, $-S(=O)_2-C_2H_5$, $-NH_2$, $-N(CH_3)_2$, $-N(C_2H_5)_2$, $-NH-CH_3$, $-NH-C_2H_5$, $-NO_2$, $-CF_3$, $-CH_2F$, $-CHF_2$, $-O-CF_3$, $-S-CF_3$, $-SH$, $-NH-S(=O)_2-CH_3$, $-C(=O)-OH$, $-C(=O)-H$; $-C(=O)-CH_3$, $-C(=O)-C_2H_5$, $-C(=O)-NH_2$, $-C(=O)-N(CH_3)_2$, $-C(=O)-NH-CH_3$, $-NH-C(=O)-CH_3$, $-NH-C(=O)-C_2H_5$, $-C(=O)-O-CH_3$, $-C(=O)-O-C_2H_5$, $-C(=O)-O-C(CH_3)_3$ and phenyl;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$ and $R^{75}$, mutually independently, in each case denote $C_{1-6}$ alkyl, which is unsubstituted or substituted with optionally 1, 2, 3, 4 or 5 substituents mutually independently selected from the group consisting of F, Cl, Br, I, $-NO_2$, $-CN$, $-OH$, $-SH$ and $-NH_2$; $C_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, $-CN$, methyl, ethyl, n-propyl, isopropyl, n-butyl, 2-butyl, isobutyl, tert.-butyl, $-OH$, oxo, thioxo, $-O-CH_3$, $-O-C_2H_5$, $-O-C_3H_7$, $-NH_2$, $-N(CH_3)_2$, $-N(C_2H_5)_2$, $-NH-CH_3$, $-NH-C_2H_5$, $-NO_2$, $-CF_3$, $-O-CF_3$, $-S-CF_3$, $-SH$, $-S-CH_3$ and $-S-C_2H_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$ and —C(=O)—O—C$_2$H$_5$;

and in each case the other residues have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted thiazoles of the above-stated general formula I, in which $R^1$ denotes H; F; Cl; Br; I; —CF$_3$; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; unsubstituted $C_{1-6}$ alkyl, or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

$R^2$ denotes H; F; Cl; Br; I; —CF$_3$; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; unsubstituted $C_{1-6}$ alkyl, or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

or $R^1$ and $R^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

$R^3$ and $R^8$, mutually independently, in each case denote H; —C(=O)—R$^{58}$; —C(=O)—O—R$^{59}$; —C(=O)—NH$_2$; —C(=O)—NH—R$^{64}$; —C(=O)—NR$^{65}$R$^{66}$; —S(=O)—R$^{69}$; —S(=O)$_2$—R$^{70}$; $C_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; $C_{3-6}$ cycloalkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

or denote a phenyl residue, which may in each case be attached via a $C_{1-3}$ alkylene, $C_{2-3}$ alkenylene or $C_{2-3}$ alkynylene group and/or is unsubstituted or substituted with 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

$R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$, mutually independently, in each case denote H; F; Cl; Br; I; —NO$_2$; —CN; —NH$_2$; —OH; —SH; —C(=O)—OH; —NH—R$^{55}$; —NR$^{56}$R$^{57}$; —C(=O)—R$^{58}$; —C(=O)—O—R$^{59}$; —O—R$^{67}$; —S—R$^{68}$;

unsubstituted $C_{1-6}$ alkyl; or denote a residue selected from the group consisting of phenyl, benzyl and phenethyl, which is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

or $R^4$ and $R^5$ or $R^6$ and $R^7$ or $R^{10}$ and $R^{11}$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{32}$ and $R^{33}$ or $R^{34}$ and $R^{35}$ or $R^{36}$ and $R^{37}$ or $R^{38}$ and $R^{39}$ or $R^{40}$ and $R^{41}$ or $R^{42}$ and $R^{43}$ or $R^{44}$ and $R^{45}$, mutually independently, in each case together denote a residue selected from the group consisting of an oxo group (=O) and a thioxo group (=S);

or $R^3$ and $R^4$ together with the —N—CR$^5$ group joining them form a residue selected from the group consisting of

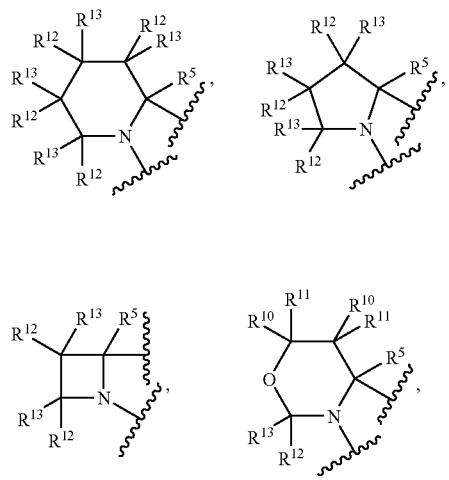

-continued

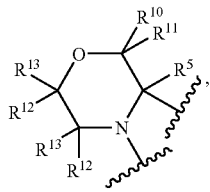 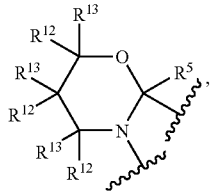

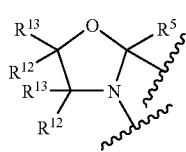 und 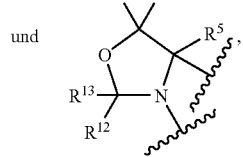

[und = and]

or R⁶ and R⁸ together with the —N—CR⁷ group joining them form a residue selected from the group consisting of

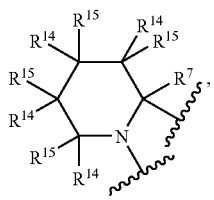 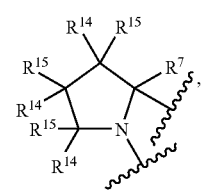

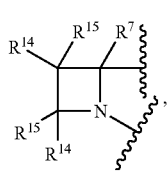 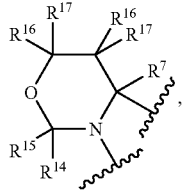

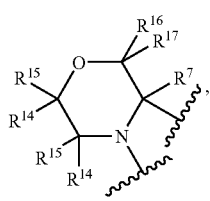 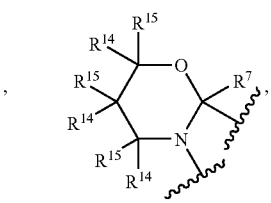

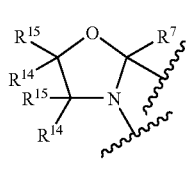 und 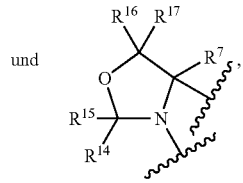

[und = and]

or R³ and R⁶ together with the —N—CR⁴R⁵—CR⁷ group joining them form a residue selected from the group consisting of

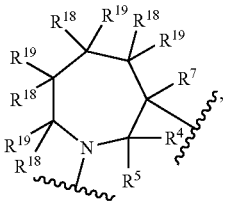 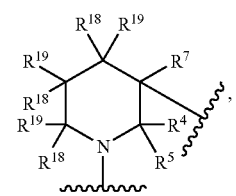

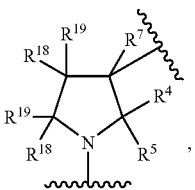 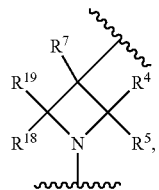

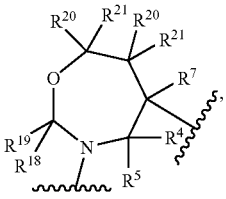 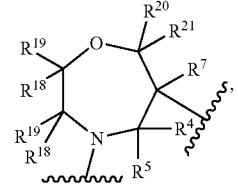

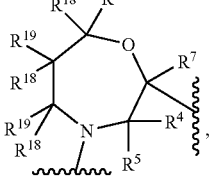 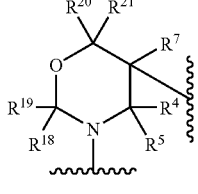

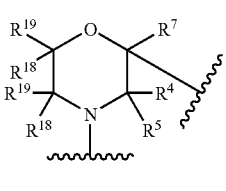 und 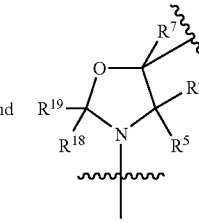

[und = and]

or R⁴ and R⁸ together with the —CR⁵—CR⁶CR⁷—N group joining them form a residue selected from the group consisting of

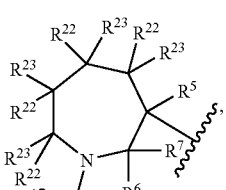 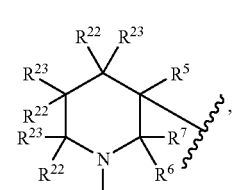

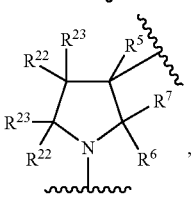 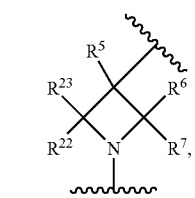

-continued

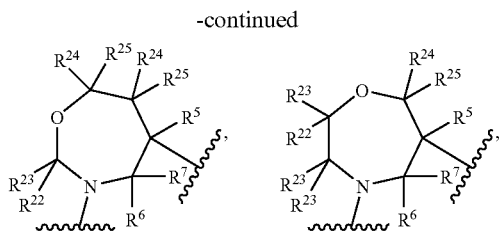

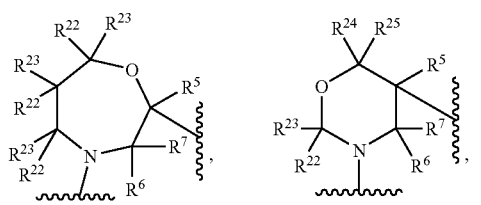

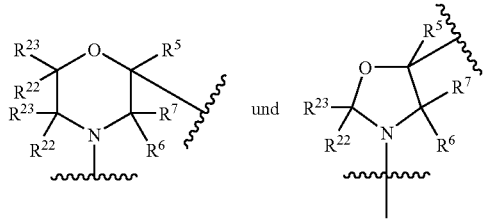
und

[und = and]

or R³ and R⁸ together with the —N—CR⁴R⁵—CR⁶CR⁷—N group joining them form a residue selected from the group consisting of

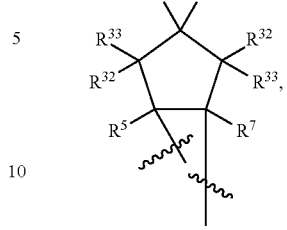 und or R⁴ and R⁶ together with the —CR⁵—CR⁷ group joining them form a residue selected from the group consisting of

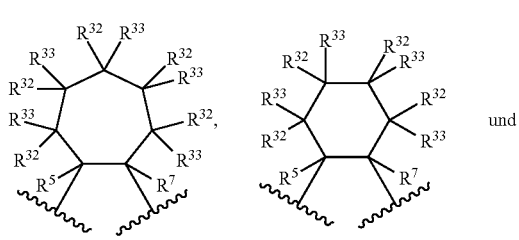 und

-continued

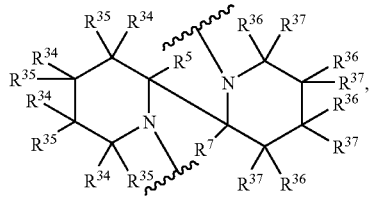

[und = and]

or R³ and R⁴ together with the —N—CR⁵ group joining them and R⁶ and R⁸ together with the —N—CR⁷ group joining them form a residue selected from the group consisting of

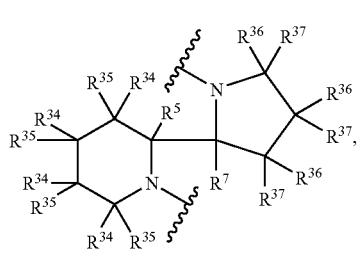

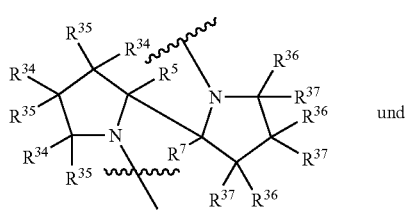

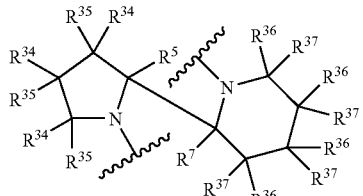 und

[und = and]

or R³ and R⁶ together with the —N—CR⁴CR⁵—CR⁷ group joining them and R⁴ and R⁸ together with the —CR⁵—CR⁶R⁷—N group joining them form a residue selected from the group consisting of

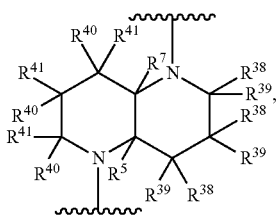

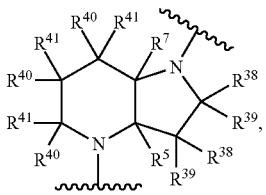

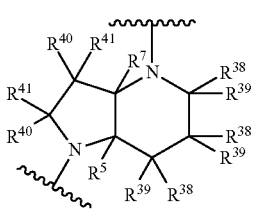 und

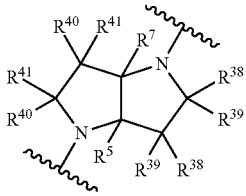

[und = and]

or $R^3$ and $R^8$ together with the $-N-CR^4R^5-CR^6R^7-N$ group joining them and $R^4$ and $R^6$ together with the $-CR^5-CR^7$ group joining them form a residue selected from the group consisting of

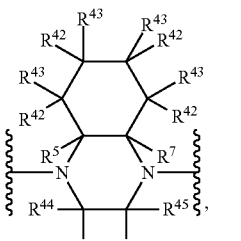 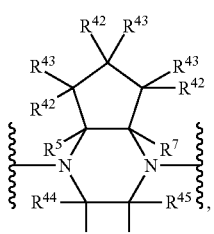

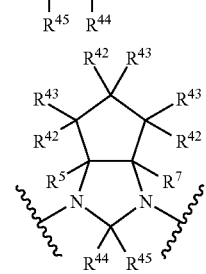 und

[und = and]

$R^9$ denotes H; $-C(=O)-NH_2$; $-C(=O)-NH-R^{64}$; $-C(=O)-NR^{65}R^{66}$;

unsubstituted $C_{1-6}$ alkyl; unsubstituted $C_{3-7}$ cycloalkyl; unsubstituted $C_{5-6}$ cycloalkenyl; unsubstituted 5- to 7-membered heterocycloalkyl and unsubstituted 5- to 7-membered heterocycloalkenyl;

or denotes a residue selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, $-CN$, methyl, ethyl, n-propyl, isopropyl, n-butyl, 2-butyl, isobutyl, tert.-butyl, ethenyl, allyl, ethynyl, propynyl, $-C\equiv C-Si(CH_3)_3$, $-C\equiv C-Si(C_2H_5)_3$, $-CH_2-O-CH_3$, $-CH_2-O-C_2H_5$, $-OH$, $-O-CH_3$, $-O-C_2H_5$, $-O-C_3H_7$, $-S-CH_3$, $-S-C_2H_5$, $-S(=O)-CH_3$, $-S(=O)_2-CH_3$, $-S(=O)-C_2H_5$, $-S(=O)_2-C_2H_5$, $-NH_2$, $-N(CH_3)_2$, $-N(C_2H_5)_2$, $-NH-CH_3$, $-NH-C_2H_5$, $-NO_2$, $-CF_3$, $-CH_2F$, $-CHF_2$, $-O-CF_3$, $-S-CF_3$, $-SH$, $-NH-S(=O)_2-CH_3$, $-C(=O)-OH$, $-C(=O)-H$; $-C(=O)-CH_3$, $-C(=O)-C_2H_5$, $-C(=O)-NH_2$, $-C(=O)-N(CH_3)_2$, $-C(=O)-NH-CH_3$, $-NH-C(=O)-CH_3$, $-NH-C(=O)-C_2H_5$, $-C(=O)-O-CH_3$, $-C(=O)-O-C_2H_5$, $-C(=O)-O-C(CH_3)_3$ and phenyl;

and $R^{55}$, $R^{56}$, $R^{57}$, $R^{58}$, $R^{59}$, $R^{64}$, $R^{65}$, $R^{66}$, $R^{67}$, $R^{68}$, $R^{69}$ and $R^{70}$, mutually independently, in each case denote unsubstituted $C_{1-6}$ alkyl; unsubstituted $C_{3-7}$ cycloalkyl; unsubstituted $C_{5-6}$ cycloalkenyl; unsubstituted 5- to 7-membered heterocycloalkyl and unsubstituted 5- to 7-membered heterocycloalkenyl; or denote a residue selected from the group consisting of phenyl, benzyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, $-CN$, methyl, ethyl, n-propyl, isopropyl, n-butyl, 2-butyl, isobutyl, tert.-butyl, $-OH$, $-O-CH_3$, $-O-C_2H_5$, $-O-C_3H_7$, $-NH_2$, $-N(CH_3)_2$, $-N(C_2H_5)_2$, $-NH-CH_3$, $-NH-C_2H_5$, $-NO_2$, $-CF_3$, $-O-CF_3$, $-S-CF_3$, $-SH$, $-NH-S(=O)_2-CH_3$, $-C(=O)-OH$, $-C(=O)-CH_3$, $-C(=O)-C_2H_5$, $-C(=O)-N(CH_3)_2$, $-C(=O)-NH-CH_3$, $-NH-C(=O)-CH_3$, $-NH-C(=O)-C_2H_5$, $-C(=O)-O-CH_3$ and $-C(=O)-O-C_2H_5$; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred substituted thiazoles are those of the above-stated general formula I, in which $R^1$ denotes H; F; Cl; Br; I; $-CF_3$; $-NO_2$; $-CN$; $-C(=O)-OH$; $-C(=O)-O-R^{59}$; $-C(=O)-NH_2$; $-C(=O)-NH-R^{64}$; $-C(=O)-NR^{65}R^{66}$; $-O-R^{67}$; $-S-R^{68}$; $-S(=O)-R^{69}$; $-S(=O)_2-R^{70}$;

an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

$R^2$ denotes H; F; Cl; Br; I; —$CF_3$; —$NO_2$; —CN; —C(=O)—OH; —C(=O)—O—$R^{59}$; —C(=O)—$NH_2$; —C(=O)—NH—$R^{64}$; —C(=O)—$NR^{65}R^{66}$; —O—$R^{67}$; —S—$R^{68}$; —S(=O)—$R^{69}$; —S(=O)$_2$—$R^{70}$;

an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

or $R^1$ and $R^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —O—$CH_3$, —O—$C_2H_5$, —O—$C_3H_7$, —$CF_3$, —$CHF_2$, —$CH_2F$ and —O—$CF_3$;

$R^3$ and $R^8$, mutually independently, in each case denote H; —C(=O)—$R^{58}$; —C(=O)—O—$R^{59}$; —S(=O)—$R^{69}$; —S(=O)$_2$—$R^{70}$; an alkyl residue selected from the group consisting of methyl, ethyl, n-propyl, isopropyl, n-butyl, 2-butyl, isobutyl, tert.-butyl, n-pentyl and n-hexyl; denote a cycloalkyl residue selected from the group consisting of cyclopropyl, cyclobutyl, cyclopentyl and cyclohexyl; or denote a benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

$R^4$, $R^5$, $R^6$, $R^7$, $R^{12}$, $R^{13}$, $R^{14}$, $R^{15}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{32}$, $R^{33}$, $R^{38}$, $R^{39}$, $R^{40}$, $R^{41}$, $R^{42}$, $R^{43}$, $R^{44}$ and $R^{45}$, mutually independently, in each case denote H; F; Cl; Br; I; —$NO_2$; —CN; —$NH_2$; —OH; —SH; —NH—$R^{55}$; —$NR^{56}R^{57}$; —O—$R^{67}$; —S—$R^{68}$; or denote an alkyl residue selected from the group consisting of methyl, ethyl, n-propyl, isopropyl, n-butyl, 2-butyl, isobutyl, tert.-butyl, n-pentyl and n-hexyl;

or $R^4$ and $R^5$ or $R^6$ and $R^7$ or $R^{12}$ and $R^{13}$ or $R^{14}$ and $R^{15}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{32}$ and $R^{33}$ or $R^{38}$ and $R^{39}$ or $R^{40}$ and $R^{41}$ or $R^{42}$ and $R^{43}$ or $R^{44}$ and $R^{453}$, mutually independently, in each case together denote a residue selected from the group consisting of an oxo group (=O) and a thioxo group (=S);

or $R^3$ and $R^4$ together with the —N—$CR^5$ group joining them form a residue selected from the group consisting of

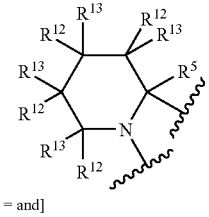 und 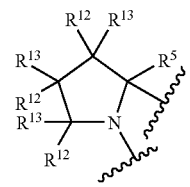

[und = and]

or $R^6$ and $R^8$ together with the —N—$CR^7$ group joining them form a residue selected from the group consisting of

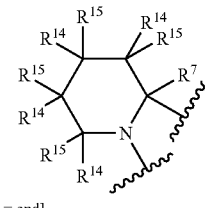 und 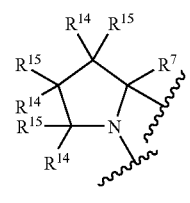

[und = and]

or $R^3$ and $R^6$ together with the —N—$CR^4R^5$—$CR^7$ group joining them form a residue selected from the group consisting of

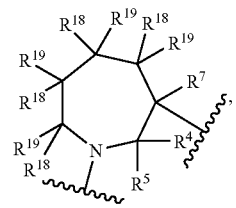 , 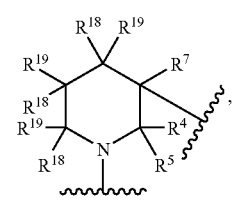 ,

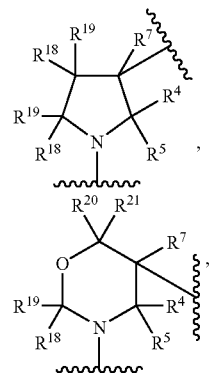 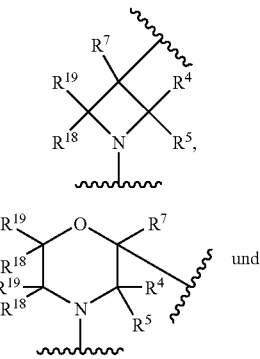 und

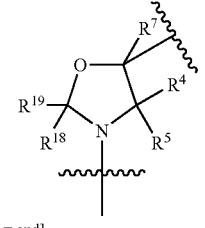

[und = and]

or R$^4$ and R$^8$ together with the —CR$^5$—CR$^6$CR$^7$—N group joining them form a residue selected from the group consisting of

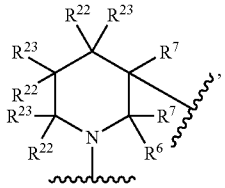 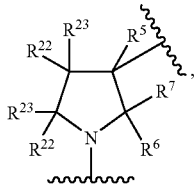

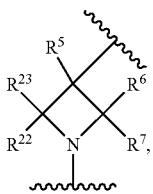 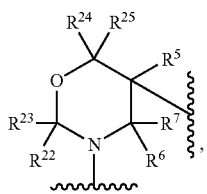

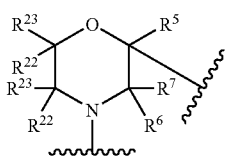 und 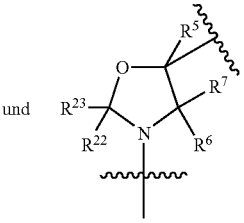

[und = and]

or R$^3$ and R$^8$ together with the —N—CR$^4$R$^5$—CR$^6$CR$^7$—N group joining them form the following residue

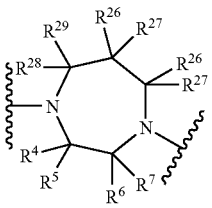

or R$^4$ and R$^6$ together with the —CR$^5$—CR$^7$ group joining them form the following residue

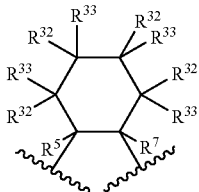

or R$^3$ and R$^6$ together with the —N—CR$^4$CR$^5$—CR$^7$ group joining them and R$^4$ and R$^8$ together with the —CR$^5$—CR$^6$R$^7$—N group joining them form the following residue

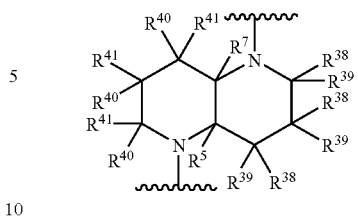

or R$^3$ and R$^8$ together with the —N—CR$^4$R$^5$—CR$^6$R$^7$—N group joining them and R$^4$ and R$^6$ together with the —CR$^5$—CR$^7$ group joining them form the following residue

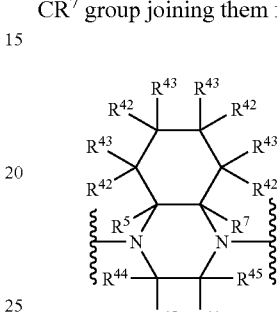

R$^9$ denotes —C(=O)—NH—R$^{64}$; —C(=O)—NR$^{65}$R$^{66}$;

or denotes a residue selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and R$^{55}$, R$^{56}$, R$^{57}$, R$^{58}$, R$^{59}$, R$^{64}$, R$^{65}$, R$^{66}$, R$^{67}$, R$^{68}$, R$^{69}$ and R$^{70}$, mutually independently, in each case denote an alkyl residue selected from the group consisting of methyl, ethyl, n-propyl, isopropyl, n-butyl, 2-butyl, isobutyl, tert.-butyl, n-pentyl and n-hexyl; or denote a phenyl, benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred substituted thiazoles are those of the above-stated general formula I, in which $R^1$ denotes H; F; Cl; Br; I; —$CF_3$; —$NO_2$; —CN; —C(=O)—OH; —C(=O)—O—$R^{59}$; —C(=O)—$NH_2$; —C(=O)—NH—$R^{64}$; —C(=O)—$NR^{65}R^{66}$; —O—$R^{67}$; —S—$R^{68}$; —S(=O)—$R^{69}$; —S(=O)$_2$—$R^{70}$;

an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

$R^2$ denotes H; F; Cl; Br; I; —$CF_3$; —$NO_2$; —CN; —C(=O)—OH; —C(=O)—O—$R^{59}$; —C(=O)—$NH_2$; —C(=O)—NH—$R^{64}$; —C(=O)—$NR^{65}R^{66}$; —O—$R^{67}$; —S—$R^{68}$; —S(=O)—$R^{69}$; —S(=O)$_2$—$R^{70}$;

an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

or $R^1$ and $R^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —O—$CH_3$, —O—$C_2H_5$, —O—$C_3H_7$, —$CF_3$, —$CHF_2$, —$CH_2F$ and —O—$CF_3$;

$R^3$ and $R^8$, mutually independently, in each case denote H; —C(=O)—$R^{58}$; —C(=O)—O—$R^{59}$; —S(=O)—$R^{69}$; —S(=O)$_2$—$R^{70}$; an alkyl residue selected from the group consisting of methyl, ethyl, n-propyl, isopropyl, n-butyl, 2-butyl, isobutyl, tert.-butyl, n-pentyl and n-hexyl; denote a cycloalkyl residue selected from the group consisting of cyclopropyl, cyclobutyl, cyclopentyl and cyclohexyl; or denote a benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

$R^4$, $R^5$, $R^6$ and $R^7$, mutually independently, in each case denote H; F; Cl; Br; I; —$NO_2$; —CN; —$NH_2$; —OH; —SH; —NH—$R^{55}$; —$NR^{56}R^{57}$; —O—$R^{67}$; —S—$R^{68}$; or denote an alkyl residue selected from the group consisting of methyl, ethyl, n-propyl, isopropyl, n-butyl, 2-butyl, isobutyl, tert.-butyl, n-pentyl and n-hexyl;

or $R^4$ and $R^5$ or $R^6$ and $R^7$, mutually independently, together in each case denote a residue selected from the group consisting of an oxo group (=O) and a thioxo group (=S);

or $R^3$ and $R^4$ together with the —N—$CR^5$ group joining them form a residue selected from the group consisting of

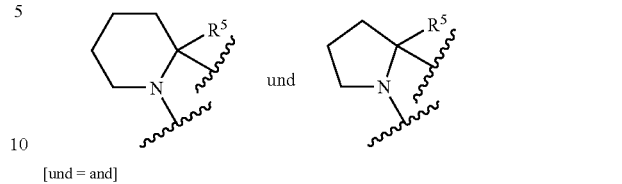

[und = and]

or $R^6$ and $R^8$ together with the —N—$CR^7$ group joining them form a residue selected from the group consisting of

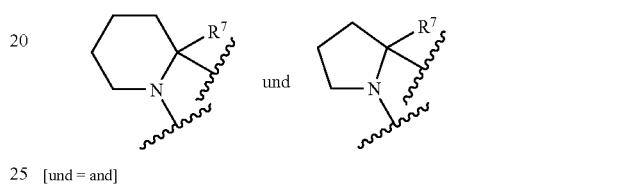

[und = and]

or $R^3$ and $R^6$ together with the —N—$CR^4R^5$—$CR^7$ group joining them form a residue selected from the group consisting of

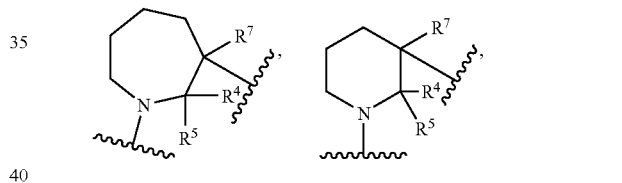

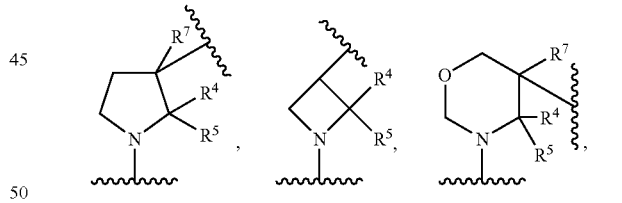

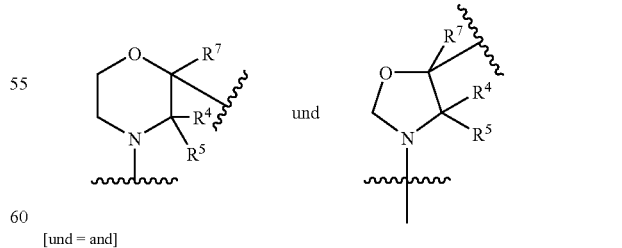

[und = and]

or $R^4$ and $R^8$ together with the —$CR^5$—$CR^6CR^7$—N group joining them form a residue selected from the group consisting of

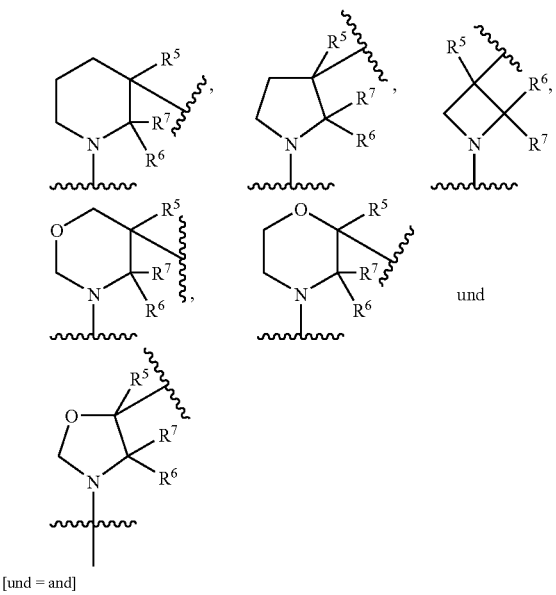

[und = and]

or R³ and R⁸ together with the —N—CR⁴R⁵—CR⁶CR⁷—N group joining them form the following residue

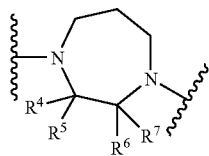

or R⁴ and R⁶ together with the —CR⁵—CR⁷ group joining them form the following residue

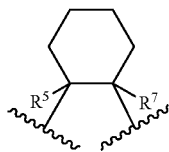

or R³ and R⁶ together with the —N—CR⁴CR⁵—CR⁷ group joining them and R⁴ and R⁸ together with the —CR⁵—CR⁶R⁷—N group joining them form the following residue

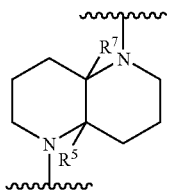

or R³ and R⁸ together with the —N—CR⁴R⁵—CR⁶R⁷—N group joining them and R⁴ and R⁶ together with the —CR⁵—CR⁷ group joining them form the following residue

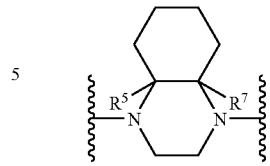

$R^9$ denotes —C(=O)—NH—$R^{64}$; —C(=O)—N$R^{65}R^{66}$; or denotes a residue selected from the group consisting of phenyl, naphthyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —O—CH₃, —O—C₂H₅, —NO₂, —CF₃, —CH₂F, —CHF₂, —O—CF₃ and —S—CF₃;

and $R^{55}$, $R^{56}$, $R^{57}$, $R^{58}$, $R^{59}$, $R^{64}$, $R^{65}$, $R^{66}$, $R^{67}$, $R^{68}$, $R^{69}$ and $R^{70}$, mutually independently, in each case denote an alkyl residue selected from the group consisting of methyl, ethyl, n-propyl, isopropyl, n-butyl, 2-butyl, isobutyl, tert.-butyl, n-pentyl and n-hexyl; or denote a phenyl, benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH₃, —O—C₂H₅ and —O—C₃H₇;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred substituted thiazoles are those of the above-stated general formula I, in which $R^1$ denotes H; F; Cl; Br; I; —CN; —CF₃; —NO₂; —C(=O)—O—$R^{59}$; an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

$R^2$ denotes H; F; Cl; Br; I; —CN; —CF₃; —NO₂; —C(=O)—O—$R^{59}$; an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

or $R^1$ and $R^2$ together with the carbon atoms joining them form a phenylene residue;

$R^3$ and $R^8$, mutually independently, in each case denote H; —C(=O)—$R^{58}$; —C(=O)—O—$R^{59}$; an alkyl residue selected from the group consisting of methyl, ethyl, n-propyl, isopropyl, n-butyl, 2-butyl, isobutyl, tert.-butyl, n-pentyl and n-hexyl; a cycloalkyl residue selected from the group consisting of cyclopropyl, cyclobutyl, cyclopentyl and cyclohexyl; or denote a benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

$R^4$, $R^5$, $R^6$ and $R^7$, mutually independently, in each case denote H; F; Cl; Br; I; —NO$_2$; —CN; —NH$_2$; —OH; —SH; —NH—R$^{55}$; —NR$^{56}$R$^{57}$; —O—R$^{67}$; —S—R$^{68}$; or denote an alkyl residue selected from the group consisting of methyl, ethyl, n-propyl, isopropyl, n-butyl, 2-butyl, isobutyl, tert.-butyl, n-pentyl and n-hexyl;

or $R^4$ and $R^5$ or $R^6$ and $R^7$, mutually independently, together in each case denote a residue selected from the group consisting of an oxo group (=O) and a thioxo group (=S);

or $R^3$ and $R^6$ together with the —N—CR$^4$R$^5$—CR$^7$ group joining them form a residue selected from the group consisting of

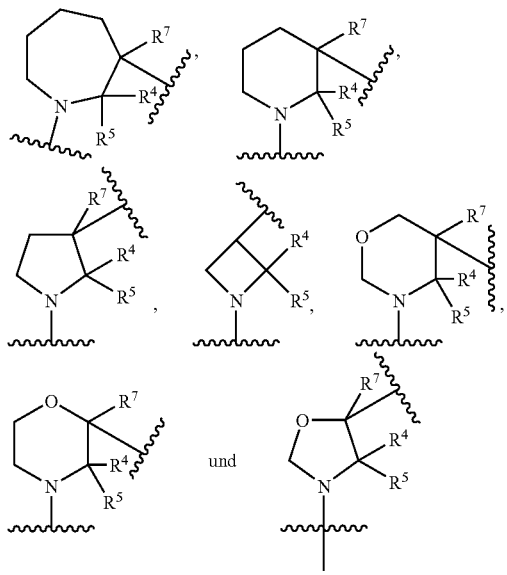

[und = and]

or $R^4$ and $R^8$ together with the —CR$^5$—CR$^6$CR$^7$—N group joining them form a residue selected from the group consisting of

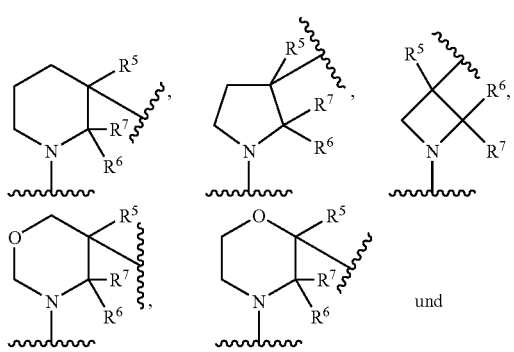

[und = and]

or $R^3$ and $R^8$ together with the —N—CR$^4$R$^5$—CR$^6$CR$^7$—N group joining them form the following residue

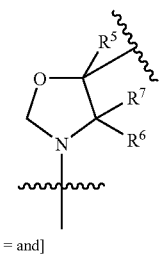

or $R^4$ and $R^6$ together with the —CR$^5$—CR$^7$ group joining them form the following residue

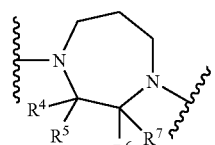

$R^9$ denotes a residue selected from the group consisting of phenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl and imidazolyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —O—CH$_3$, —O—C$_2$H$_5$, —NO$_2$, —CF$_3$, —CH$_2$F, —CHF$_2$, —O—CF$_3$ and —S—CF$_3$;

and R$^{55}$, R$^{56}$, R$^{57}$, R$^{58}$, R$^{59}$, R$^{67}$ and R$^{68}$, mutually independently, in each case denote an alkyl residue selected from the group consisting of methyl, ethyl, n-propyl, isopropyl, n-butyl, 2-butyl, isobutyl, tert.-butyl, n-pentyl and n-hexyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted thiazoles which are still more preferred are those of the above-stated general formula I, in which $R^1$ denotes H, F, Cl, Br, —CN, methyl, ethyl, n-propyl, isobutyl, tert.-butyl, n-butyl, —C(=O)—O—CH$_3$, —C(=O)—O—C$_2$H$_5$ or —C(=O)—O—C(CH$_3$)$_3$;

$R^2$ denotes H, F, Cl, Br, —CN, methyl, ethyl, n-propyl, isobutyl, tert.-butyl, n-butyl, —C(=O)—O—CH$_3$, —C(=O)—O—C$_2$H$_5$ or —C(=O)—O—C(CH$_3$)$_3$;

or $R^1$ and $R^2$ together with the carbon atoms joining them form a phenylene residue;

$R^3$ and $R^8$, mutually independently, in each case denote a residue selected from the group consisting of methyl, ethyl, n-propyl, isopropyl, n-butyl, 2-butyl, isobutyl and tert.-butyl; or denote cyclopropyl;

$R^4$, $R^5$ and $R^7$ in each case denote H;

$R^6$ denotes H or an alkyl residue selected from the group consisting of methyl, ethyl, n-propyl, isopropyl, n-butyl, 2-butyl, isobutyl, tert.-butyl, n-pentyl and n-hexyl;

or $R^4$ and $R^5$ or $R^6$ and $R^7$, mutually independently, together in each case denote an oxo group (=O);

or $R^3$ and $R^6$ together with the —N—CH$_2$—CH group joining them form a residue selected from the group consisting of

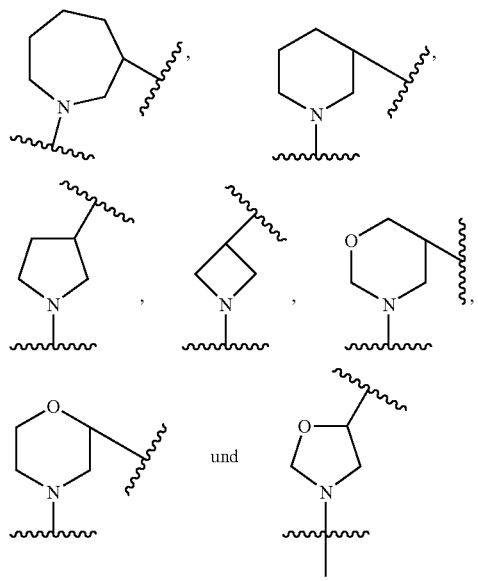

[und = and]

or $R^4$ and $R^8$ together with the —CH—CH$_2$—N group form a residue selected from the group consisting of

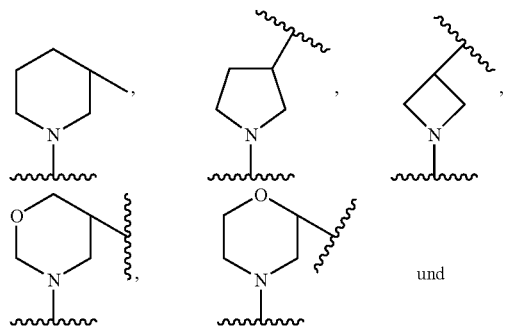

und

-continued

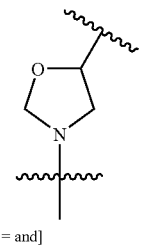

[und = and]

or $R^3$ and $R^8$ together with the —N—CH$_2$—CH$_2$—N group joining them form the following residue

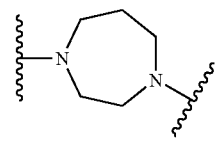

or $R^4$ and $R^6$ together with the —CH—CH group joining them form the following residue

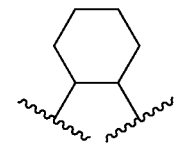

and $R^9$ denotes a residue selected from the group consisting of pyrid-2-yl, pyrid-3-yl, pyrid-4-yl, phenyl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-chlorophenyl, 3-chlorophenyl, 3-chlorophenyl, 2-trifluoromethylphenyl, 3-trifluoro-methylphenyl, 4-trifluoromethylphenyl, 2-methoxyphenyl, 3-methoxyphenyl, 4-methoxyphenyl, (2,4)-difluorophenyl, (2,4)-dichlorophenyl, (3,5)-dichlorophenyl, (3,5)-difluorophenyl, 2-thiophenyl, 2-chloro-5-trifluoromethylphenyl, 3-fluoro-4-methylphenyl, 2-fluoro-3-methylphenyl, 2-difluoromethylphenyl, 3-difluoromethylphenyl, 4-difluoro-methylphenyl, 2-fluoromethylphenyl, 3-fluoromethylphenyl, 4-fluoromethylphenyl, 3-nitrophenyl, 3-ethenylphenyl, 3-ethynylphenyl, 3-allylphenyl, 3-bromophenyl, 2-trifluoro-methoxyphenyl, 3-trifluoromethoxyphenyl and 4-trifluoromethoxyphenyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Substituted thiazoles which are still further preferred are those of the general formula Ia,

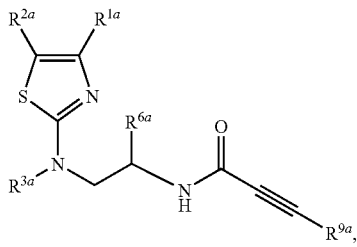

in which

R$^{1a}$ denotes H, F, Cl, Br, —CN, methyl, ethyl, n-propyl, isobutyl, tert.-butyl, n-butyl, —C(=O)—O—CH$_3$, —C(=O)—O—C$_2$H$_5$—C(=O)—O—C(CH$_3$)$_3$;

R$^{2a}$ denotes H, F, Cl, Br, —CN, methyl, ethyl, n-propyl, isobutyl, tert.-butyl, n-butyl, —C(=O)—O—CH$_3$, —C(=O)—O—C$_2$H$_5$—C(=O)—O—C(CH$_3$)$_3$;

or R$^{1a}$ and R$^{2a}$ together with the carbon atoms joining them form a phenylene residue;

R$^{3a}$ denotes H; denotes an alkyl residue selected from the group consisting of methyl, ethyl, n-propyl, isopropyl, n-butyl, 2-butyl, isobutyl and tert.-butyl; or denotes cyclopropyl;

R$^{6a}$ denotes H or denotes an alkyl residue selected from the group consisting of methyl, ethyl, n-propyl, isopropyl, n-butyl, 2-butyl, isobutyl, tert.-butyl, n-pentyl and n-hexyl;

and R$^{9a}$ denotes a residue selected from the group consisting of pyrid-2-yl, pyrid-3-yl, pyrid-4-yl, phenyl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-chlorophenyl, 3-chlorophenyl, 3-chlorophenyl, 2-trifluoromethylphenyl, 3-trifluoro-methylphenyl, 4-trifluoromethylphenyl, 2-methoxyphenyl, 3-methoxyphenyl, 4-methoxyphenyl, (2,4)-difluorophenyl, (2,4)-dichlorophenyl, (3,5)-dichlorophenyl, (3,5)-difluorophenyl, 2-thiophenyl, 2-chloro-5-trifluoromethylphenyl, 3-fluoro-4-methylphenyl, 2-fluoro-3-methylphenyl, 2-difluoromethylphenyl, 3-difluoromethylphenyl, 4-difluoro-methylphenyl, 2-fluoromethylphenyl, 3-fluoromethylphenyl, 4-fluoromethylphenyl, 3-nitrophenyl, 3-ethenylphenyl, 3-ethynylphenyl, 3-allylphenyl, 3-bromophenyl, 2-trifluoro-methoxyphenyl, 3-trifluoromethoxyphenyl and 4-trifluoromethoxyphenyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particular preference is also given to thiazoles of the above-stated general formula I, which after 60 minutes' incubation in 450 µg of protein from pig brain homogenate at a temperature of between 20° C. and 25° C. in a concentration of less than 2000 nM, preferably less than 1000 nM, particularly preferably less than 700 nM, very particularly preferably less than 100 nM, still more preferably less than 30 nM, bring about a 50 percent displacement of [$^3$H]-2-methyl-6-(3-methoxyphenyl)-ethynylpyridine, which is present in a concentration of 5 nM.

The displacement of [$^3$H]-2-methyl-6-(3-methoxyphenyl)-ethynylpyridine is here determined as described in the section Pharmacological Methods, method I for determining the inhibition of [$^3$H]-MPEP-binding in the mGluR5 receptor binding assay.

Substituted thiazoles of the above-stated general formula I which are still more preferred are those selected from the group consisting of

[1] 3-phenyl-N-(1-(thiazol-2-yl)pyrrolidin-3-yl)propiolamide,
[2] N-methyl-3-phenyl-N-(1-(thiazol-2-yl)pyrrolidin-3-yl)propiolamide hydrochloride,
[3] 1-thiazol-2-yl-4-(3-phenylpropioloyl)-1,4-diazepane,
[4] N-methyl-N-(2-(methyl(thiazol-2-yl)amino)ethyl)-3-phenylpropiolamide,
[5] N-(2-((thiazol-2-yl)amino)ethyl)-3-phenylpropiolamide,
[6] 3-phenyl-N-(2-(thiazol-2-ylamino)cyclohexyl)propiolamide,
[7] N-methyl-N-(2-(methyl(thiazol-2-yl)amino)ethyl)-3-(3-methylphenyl)-propiolamide,
[8] 3-phenyl-N-(1-(thiazol-2-yl)azetidin-3-yl)propiolamide,
[9] N-(2-(methyl(thiazol-2-yl)amino)ethyl)-3-phenylpropiolamide,
[10] N-methyl-N-(2-(thiazol-2-yl)amino)ethyl-3-phenylpropiolamide,
[11] 3-(thiazol-2-yl-amino)-1-(3-phenylpropioloyl)pyrrolidine,
[12] N-methyl-N-(2-(methyl(thiazol-2-yl)amino)cyclohexyl)-3-phenylpropiolamide,
[13] N-methyl-N-(2-(methyl(thiazol-2-yl)amino)ethyl)-3-(3-cyanophenyl)-propiolamide,
[14] N-methyl-N-(2-(methyl(thiazol-2-yl)amino)-2-oxoethyl)-3-phenylpropiolamide,
[15] 3-phenyl-N-(1-(thiazol-2-yl)piperidin-3-yl)propiolamide,
[16] N-methyl-N-(1-(thiazol-2-yl)piperidin-3-yl)-3-phenylpropiolamide,
[17] N-methyl-N-(2-(methyl(thiazol-2-yl)amino)ethyl)-3-(pyrid-2-yl)-propiolamide,
[18] N-methyl-N-(2-(methyl(thiazol-2-yl)amino)ethyl)-3-(3-chlorophenyl)-propiolamide,
[19] N-(2-(methyl(thiazol-2-yl)amino)ethyl)-3-(3-chlorophenyl)-propiolamide,
[20] N-methyl-N-(1-(thiazol-2-yl)azetidin-3-yl)-3-phenylpropiolamide,
[21] N-(2-(methyl(thiazol-2-yl)amino)ethyl)-3-(tol-3-yl)-propiolamide,
[22] 3-methyl(thiazol-2-yl)amino)-1-(3-phenylpropioloyl)pyrrolidine,
[23] N-(2-(methyl(thiazol-2-yl)-amino)ethyl)-3-(3-chlorophenyl)-propiolamide hydrochloride,
[24] N-(2-(benzo[d]thiazol-2-yl(methyl)amino)ethyl)-3-(3-chlorophenyl)propiolamide,
[25] N-(2-methyl(5-ethoxycarbonylthiazol-2-yl)amino)ethyl)-3-(3-chlorophenyl)-propiolamide,
[26] N-(2-methyl(4-ethoxycarbonylthiazol-2-yl)amino)ethyl)-3-(3-chlorophenyl)-propiolamide,
[27] 3-(thiazol-2-yl-amino)-1-(3-phenylpropioloyl)piperidine,
[28] 3-(methyl-(thiazol-2-yl)-amino)-1-(3-phenylpropioloyl)piperidine
[29] N-(2-(methyl-(4-methylthiazol-2-yl)amino)ethyl)-3-(3-chlorophenyl)-propiolamide
[30] 3-(3-chlorophenyl)-N-(2-(methyl(5-methylthiazol-2-yl)amino)ethyl)propiolamide
[31] N-(2-((5-bromothiazol-2-yl)(methyl)amino)ethyl)-3-(3-chlorophenyl)propiolamide,

[32] 3-(3-chlorophenyl)-N-(1-(thiazol-2-yl)piperidin-3-yl)propiolamide,
[33] N-(2-((4-bromothiazol-2-yl)(methyl)amino)ethyl)-3-(3-chlorophenyl)propiolamide,
[34] methyl 2-((2-(3-(3-chlorophenyl)propiolamido)ethyl)(methyl)amino)thiazole-5-carboxylate,
[35] 1-(3-(3-chlorophenyl)propioloyl)-3-(methyl(thiazol-2-yl)amino)azetidine,
[36] 3-(3-chlorophenyl)-N-methyl-N-(1-(thiazol-2-yl)piperidin-3-yl)propiolamide,
[37] 3-(3-chlorophenyl)-N-(2-((4-chlorothiazol-2-yl)(methyl)amino)ethyl)propiolamide,
[38] 3-(3-chlorophenyl)-N-(2-((5-chlorothiazol-2-yl)(methyl)amino)ethyl)propiolamide,
[39] 3-(3-chlorophenyl)-N-(1-(thiazol-2-yl)azetidin-3-yl)propiolamide,
[40] 3-(3-chlorophenyl)-N-methyl-N-(1-(thiazol-2-yl)azetidin-3-yl)propiolamide,
[41] 3-(3-chlorophenyl)-N-(2-(ethyl(thiazol-2-yl)amino)ethyl)propiolamide,
[42] 3-(3-chlorophenyl)-N-(2-((5-cyanothiazol-2-yl)(methyl)amino)ethyl)propiolamide,
[43] 1-(3-(3-chlorophenyl)propioloyl)-3-(methyl(5-fluorothiazol-2-yl)amino)azetidine,
[44] 1-(3-(3-chlorophenyl)propioloyl)-3-(methyl(5-fluorothiazol-2-yl)amino)pyrrolidine,
[45] N-(1-(4-methylthiazol-2-yl)pyrrolidin-3-yl)-3-phenylpropiolamide,
[46] 3-(3-methoxyphenyl)-N-(1-(4-methylthiazol-2-yl)pyrrolidin-3-yl)propiolamide,
[47] 3-(2-methoxyphenyl)-N-(1-(4-methylthiazol-2-yl)pyrrolidin-3-yl)propiolamide,
[48] 3-(4-methoxyphenyl)-N-(1-(4-methylthiazol-2-yl)pyrrolidin-3-yl)propiolamide,
[49] 3-(4-fluorophenyl)-N-(1-(4-methylthiazol-2-yl)pyrrolidin-3-yl)propiolamide,
[50] N-(1-(4-methylthiazol-2-yl)pyrrolidin-3-yl)-3-p-tolylpropiolamide,
[51] N-(1-(4,5-dimethylthiazol-2-yl)pyrrolidin-3-yl)-3-phenylpropiolamide,
[52] N-(1-(4,5-dimethylthiazol-2-yl)pyrrolidin-3-yl)-3-(4-methoxyphenyl)propiolamide,
[53] N-(1-(4,5-dimethylthiazol-2-yl)pyrrolidin-3-yl)-3-(4-fluorophenyl)propiolamide,
[54] N-(1-(4,5-dimethylthiazol-2-yl)pyrrolidin-3-yl)-3-(2-methoxyphenyl)propiolamide,
[55] N-(1-(4-tert.-butylthiazol-2-yl)pyrrolidin-3-yl)-3-(4-methoxyphenyl)propiolamide,
[56] N-(1-(4-tert.-butylthiazol-2-yl)pyrrolidin-3-yl)-3-p-tolylpropiolamide,
[57] N-(1-(4-tert.-butylthiazol-2-yl)pyrrolidin-3-yl)-3-(4-fluorophenyl)propiolamide,
[58] N-(1-(4-tert.-butylthiazol-2-yl)pyrrolidin-3-yl)-3-o-tolylpropiolamide,
[59] N-(1-(4-tert.-butylthiazol-2-yl)pyrrolidin-3-yl)-3-(3-fluorophenyl)propiolamide,
[60] N-(1-(4-tert.-butylthiazol-2-yl)pyrrolidin-3-yl)-3-phenylpropiolamide,
[61] N-(1-(4-tert.-butylthiazol-2-yl)pyrrolidin-3-yl)-3-(2-fluorophenyl)propiolamide,
[62] N-(1-(4-tert.-butylthiazol-2-yl)pyrrolidin-3-yl)-3-(3-methoxyphenyl)propiolamide,
[63] N-(1-(4-tert.-butylthiazol-2-yl)pyrrolidin-3-yl)-3-(3-fluoro-4-methylphenyl)-propiolamide,
[64] N-(1-(4-tert.-butylthiazol-2-yl)pyrrolidin-3-yl)-3-(2-methoxyphenyl)propiolamide,
[65] N-(1-(4-methylthiazol-2-yl)pyrrolidin-3-yl)-3-(4-(trifluoromethyl)phenyl)-propiolamide,
[66] N-(1-(4-methylthiazol-2-yl)pyrrolidin-3-yl)-3-o-tolylpropiolamide,
[67] 3-(3-fluorophenyl)-N-(1-(4-methylthiazol-2-yl)pyrrolidin-3-yl)propiolamide,
[68] 3-(3-fluoro-4-methylphenyl)-N-(1-(4-methylthiazol-2-yl)pyrrolidin-3-yl)-propiolamide,
[69] 3-(2,4-difluorophenyl)-N-(1-(4-methylthiazol-2-yl)pyrrolidin-3-yl)propiolamide,
[70] 3-(2-fluorophenyl)-N-(1-(4-methylthiazol-2-yl)pyrrolidin-3-yl)propiolamide,
[71] N-(1-(4-methylthiazol-2-yl)pyrrolidin-3-yl)-3-(3-(trifluoromethyl)phenyl)-propiolamide,
[72] N-(1-(4-methylthiazol-2-yl)pyrrolidin-3-yl)-3-m-tolylpropiolamide,
[73] N-(1-(5-methylthiazol-2-yl)pyrrolidin-3-yl)-3-p-tolylpropiolamide,
[74] N-(1-(5-methylthiazol-2-yl)pyrrolidin-3-yl)-3-m-tolylpropiolamide,
[75] 3-(2-methoxyphenyl)-N-(1-(5-methylthiazol-2-yl)pyrrolidin-3-yl)propiolamide,
[76] N-(1-(5-methylthiazol-2-yl)pyrrolidin-3-yl)-3-phenylpropiolamide,
[77] 3-(2-fluorophenyl)-N-(1-(5-methylthiazol-2-yl)pyrrolidin-3-yl)propiolamide,
[78] 3-(3-methoxyphenyl)-N-(1-(5-methylthiazol-2-yl)pyrrolidin-3-yl)propiolamide,
[79] N-(1-(4,5-dimethylthiazol-2-yl)pyrrolidin-3-yl)-3-(3-fluoro-4-methylphenyl)-propiolamide,
[80] N-(1-(4,5-dimethylthiazol-2-yl)pyrrolidin-3-yl)-3-o-tolylpropiolamide,
[81] 3-(3-fluorophenyl)-N-(1-(5-methylthiazol-2-yl)pyrrolidin-3-yl)propiolamide,
[82] N-(1-(4,5-dimethylthiazol-2-yl)pyrrolidin-3-yl)-3-m-tolylpropiolamide,
[83] N-(1-(5-methylthiazol-2-yl)pyrrolidin-3-yl)-3-o-tolylpropiolamide,
[84] N-(1-(4,5-dimethylthiazol-2-yl)pyrrolidin-3-yl)-3-p-tolylpropiolamide,
[85] N-(1-(4,5-dimethylthiazol-2-yl)pyrrolidin-3-yl)-3-(3-(trifluoromethyl)phenyl)-propiolamide,
[86] 3-(4-methoxyphenyl)-N-(1-(5-methylthiazol-2-yl)pyrrolidin-3-yl)propiolamide,
[87] N-(1-(5-methylthiazol-2-yl)pyrrolidin-3-yl)-3-(3-(trifluoromethyl)phenyl)-propiolamide,
[88] N-(1-(4,5-dimethylthiazol-2-yl)pyrrolidin-3-yl)-3-(4-(trifluoromethyl)phenyl)-propiolamide,
[89] 3-(4-fluorophenyl)-N-(1-(5-methylthiazol-2-yl)pyrrolidin-3-yl)propiolamide,
[90] N-(1-(4,5-dimethylthiazol-2-yl)pyrrolidin-3-yl)-3-(3-methoxyphenyl)propiolamide,
[91] 3-(2,4-difluorophenyl)-N-(1-(4,5-dimethylthiazol-2-yl)pyrrolidin-3-yl)propiolamide,
[92] N-(1-(4,5-dimethylthiazol-2-yl)pyrrolidin-3-yl)-3-(2-fluorophenyl)propiolamide,
[93] N-(1-(5-methylthiazol-2-yl)pyrrolidin-3-yl)-3-(4-(trifluoromethyl)phenyl)-propiolamide,
[94] 3-(3-fluoro-4-methylphenyl)-N-(1-(5-methylthiazol-2-yl)pyrrolidin-3-yl)-propiolamide,
[95] 3-(2,4-difluorophenyl)-N-(1-(5-methylthiazol-2-yl)pyrrolidin-3-yl)propiolamide,
[96] N-(1-(4-tert.-butylthiazol-2-yl)pyrrolidin-3-yl)-3-(2,4-difluorophenyl)propiolamide,
[97] N-(1-(4-tert.-butylthiazol-2-yl)pyrrolidin-3-yl)-3-(4-(trifluoromethyl)phenyl)-propiolamide,

[98] N-(1-(4-tert.-butylthiazol-2-yl)pyrrolidin-3-yl)-3-(3-(trifluoromethyl)phenyl)-propiolamide,
[99] N-(1-(4-tert.-butylthiazol-2-yl)pyrrolidin-3-yl)-3-m-tolylpropiolamide,
[100] N-(1-(4-tert.-butylthiazol-2-yl)pyrrolidin-3-yl)-3-(3-chlorophenyl)propiolamide,
[101] N-(1-(4-tert.-butylthiazol-2-yl)pyrrolidin-3-yl)-3-(thiophen-2-yl)propiolamide,
[102] N-(1-(4-tert.-butylthiazol-2-yl)pyrrolidin-3-yl)-3-(2,4-dichlorophenyl)propiolamide,
[103] N-(1-(4-tert.-butylthiazol-2-yl)pyrrolidin-3-yl)-3-(2-chloro-5-(trifluoromethyl)phenyl)-propiolamide,
[104] N-(1-(4-tert.-butylthiazol-2-yl)pyrrolidin-3-yl)-3-(3,5-dichlorophenyl)propiolamide,
[105] 3-(3-chlorophenyl)-N-(1-(4-methylthiazol-2-yl)pyrrolidin-3-yl)propiolamide,
[106] N-(1-(4-methylthiazol-2-yl)pyrrolidin-3-yl)-3-(thiophen-2-yl)propiolamide,
[107] 3-(2,4-dichlorophenyl)-N-(1-(4-methylthiazol-2-yl)pyrrolidin-3-yl)propiolamide,
[108] 3-(2-chloro-5-(trifluoromethyl)phenyl)-N-(1-(4-methylthiazol-2-yl)pyrrolidin-3-yl)-propiolamide,
[109] 3-(3,5-dichlorophenyl)-N-(1-(4-methylthiazol-2-yl)pyrrolidin-3-yl)propiolamide,
[110] 3-(3-chlorophenyl)-N-(1-(4,5-dimethylthiazol-2-yl)pyrrolidin-3-yl)propiolamide,
[111] 3-(2,4-dichlorophenyl)-N-(1-(4,5-dimethylthiazol-2-yl)pyrrolidin-3-yl)propiolamide,
[112] 3-(3-chlorophenyl)-N-(1-(5-methylthiazol-2-yl)pyrrolidin-3-yl)propiolamide,
[113] N-(1-(5-methylthiazol-2-yl)pyrrolidin-3-yl)-3-(thiophen-2-yl)propiolamide,
[114] 3-(2,4-dichlorophenyl)-N-(1-(5-methylthiazol-2-yl)pyrrolidin-3-yl)propiolamide,
[115] 3-(2-chloro-5-(trifluoromethyl)phenyl)-N-(1-(5-methylthiazol-2-yl)pyrrolidin-3-yl)-propiolamide,
[116] 3-(3,5-dichlorophenyl)-N-(1-(5-methylthiazol-2-yl)pyrrolidin-3-yl)propiolamide,
[117] N-(1-(4,5-dimethylthiazol-2-yl)pyrrolidin-3-yl)-3-(thiophen-2-yl)propiolamide,
[118] 3-(2-chloro-5-(trifluoromethyl)phenyl)-N-(1-(4,5-dimethylthiazol-2-yl)pyrrolidin-3-yl)propiolamide,
[119] N-(1-(5-methylthiazol-2-yl)pyrrolidin-3-yl)-3-(pyridin-2-yl)propiolamide,
[120] N-(1-(5-methylthiazol-2-yl)pyrrolidin-3-yl)-3-(pyridin-3-yl)propiolamide,
[121] N-(1-(5-methylthiazol-2-yl)pyrrolidin-3-yl)-3-(pyridin-4-yl)propiolamide,
[122] N-(1-(4-tert.-butylthiazol-2-yl)pyrrolidin-3-yl)-3-(pyridin-2-yl)propiolamide,
[123] N-(1-(4-tert.-butylthiazol-2-yl)pyrrolidin-3-yl)-3-(pyridin-3-yl)propiolamide, and
[126] 3-(3-chlorophenyl)-N-(2-((5-fluorothiazol-2-yl)(methyl)amino)ethyl)propiolamide;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention also provides a method for producing compounds of the above-stated general formula I, in accordance with which at least one compound of the general formula II,

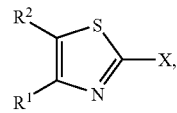

in which the residues $R^1$ and $R^2$ have the above-stated meaning and X denotes a leaving group, preferably a halogen residue or a sulfonic acid ester, particularly preferably a chlorine or bromine residue, is converted with at least one compound of the general formula III,

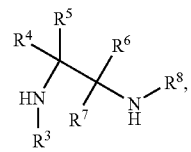

in which $R^3$, $R^4$, $R^5$, $R^6$, $R^7$ and $R^8$ have the above-stated meaning, optionally in a reaction medium, optionally in the presence of at least one base and/or at least one organometallic compound and/or at least one metal hydride reagent or in the presence of at least one copper salt and optionally in the presence of at least one metal, preferably in the presence of copper, preferably at a temperature of −70° C. to 300° C., particularly preferably of −70° C. to 150° C., into at least one corresponding compound of the general formula IV, optionally in the form of a corresponding salt,

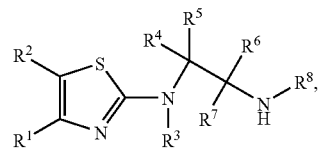

in which $R^1$, $R^2$, $R^3$, $R^4$, $R^5$, $R^6$, $R^7$ and $R^8$ have the above-stated meaning, and the latter is optionally purified and/or isolated;

or at least one compound of the general formula II is converted with at least one compound of the general formula V,

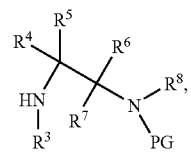

in which $R^3$, $R^4$, $R^5$, $R^6$, $R^7$ and $R^8$ have the above-stated meaning and PG denotes a protective group, preferably a protective group selected from the group consisting of tert.-butyloxycarbonyl, benzyl, benzyloxycarbonyl and 9-fluorenylmethyloxycarbonyl, optionally in a reaction medium, optionally in the presence of at least one base and/or at least one organometallic compound and/or at least one metal hydride reagent, preferably at a temperature of −70° C. to 300° C. into at least one corresponding compound of the general formula VI,

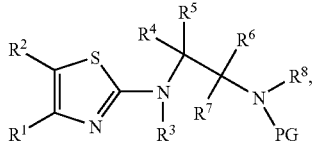

VI in which $R^1$, $R^2$, $R^3$, $R^4$, $R^5$, $R^6$, $R^7$, $R^8$ and PG have the above-stated meaning, and the latter is optionally purified and/or isolated;

and optionally at least one compound of the general formula VI, in which $R^1$, $R^2$, $R^4$, $R^5$, $R^6$, $R^7$, $R^8$ and PG have the above-stated meaning and $R^3$ denotes hydrogen, is converted with at least one compound $R^3$—X, in which $R^3$ has above-stated meaning with the exception of hydrogen and X denotes a leaving group, preferably a halogen residue, optionally in a reaction medium, optionally in the presence of at least one base, preferably in the presence of at least one metal hydride reagent, particularly preferably in the presence of sodium hydride, preferably at a temperature of −70° C. to 300° C. into at least one corresponding compound of the general formula VIa,

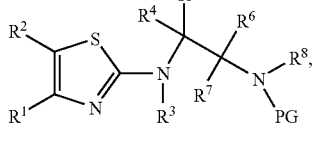

VIa in which $R^1$, $R^2$, $R^3$, $R^4$, $R^5$, $R^6$, $R^7$, $R^8$ and PG have the above-stated meaning and $R^3$ does not denote a hydrogen atom, and the latter is optionally purified and/or isolated;

or at least one compound of the general formula XIII,

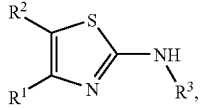

XIII in which $R^1$, $R^2$ and $R^3$ have the above-stated meaning, is converted with at least one compound of the general formula XIV,

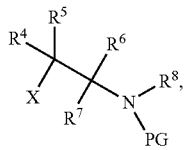

XIV in which $R^4$, $R^5$, $R^6$, $R^7$, $R^8$ and PG have the above-stated meaning and X denotes a leaving group, preferably a halogen residue or denotes a sulfonic acid ester, particularly preferably a chlorine or bromine residue, optionally in a reaction medium, optionally in the presence of at least one base, preferably in the presence of at least one base selected from the group consisting of potassium tert.-butylate, sodium hydroxide, potassium hydroxide, dimethylamine and triethylamine, particularly preferably in the presence of diethylamine, or optionally in the presence of at least one organometallic compound, preferably in the presence of at least one organometallic compound selected from the group consisting of methyllithium and butyllithium or optionally in the presence of at least one metal hydride compound, particularly preferably in the presence of sodium hydride, preferably at a temperature of −70° C. to 300° C., particularly preferably of −70° C. to 150° C., into at least one corresponding compound of the general formula VI and the latter is optionally purified and/or isolated;

or at least one compound of the general formula XIII,

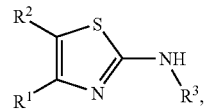

XIII in which $R^1$, $R^2$ and $R^3$ have the meaning according to one or more of claims 1 to 27 is converted with at least one compound of the general formula XIVa,

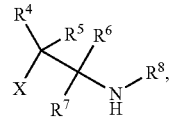

XIVa in which $R^4$, $R^5$, $R^6$, $R^7$ and $R^8$ have the above-stated meaning and X denotes a leaving group, preferably a halogen residue or denotes a sulfonic acid ester, particularly preferably a chlorine or bromine residue, optionally in a reaction medium, optionally in the presence of at least one base, preferably in the presence of at least one base selected from the group consisting of potassium tert.-butylate, sodium hydroxide, potassium hydroxide, dimethylamine and triethylamine, particularly preferably in the presence of diethylamine, or optionally in the presence of at least one organometallic compound, preferably in the presence of at least one organometallic compound selected from the group consisting of methyllithium and butyllithium or optionally in the presence of at least one metal hydride compound, particularly preferably in the presence of sodium hydride, preferably at a temperature of −70° C. to 300° C., particularly preferably of −70° C. to 150° C., into at least one corresponding compound of the general formula IV and the latter is optionally purified and/or isolated;

or at least one compound of the general formula VII,

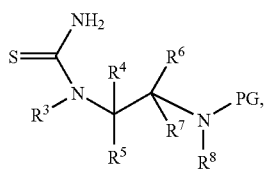

VII in which $R^3$, $R^4$, $R^5$, $R^6$, $R^7$ and $R^8$ have the above-stated meaning and PG denotes a protective group, preferably a protective group selected from the group consisting of tert.-butyloxycarbonyl, benzyl, benzyloxycarbonyl and 9-fluorenylmethyloxycarbonyl, is converted by reaction with at least one compound of the general formula $R^1$—C(=O)—$CH_2$—X or $(C_{1-5}$-alkyl-O$)_2$—CH—$CH_2$—X, in which $R^1$ has the above-stated meaning and X denotes a leaving group, preferably a halogen residue, particularly preferably a bromine atom, in a reaction medium, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid and hydrochloric acid, preferably at a temperature of between −70° C. to 300° C. into at least one corresponding compound of the general formula VI, optionally in the form of a corresponding salt, and the latter is optionally purified and/or isolated;

and at least one compound of the general formula VI or of the general formula VIa, in the event that PG denotes a tert.-butoxycarbonyl residue or 9-fluorenylmethyloxy-carbonyl group, is converted in a reaction medium, in the presence of at least one acid, preferably in the presence of at least one acid selected from the group consisting of hydrochloric acid and trifluoroacetic acid, preferably at a temperature between −70° C. to 100° C. or, in the event that PG denotes a benzyl group or benzyloxycarbonyl group, in a reaction medium, in the presence of hydrogen and in the presence at least one catalyst, preferably in the presence of palladium on carbon, preferably at a temperature between −70° C. to 100° C. into at least one corresponding compound of the general formula IV, optionally in the form of a corresponding salt, and the latter is optionally purified and/or isolated;

and at least one compound of the general formula IV is converted by reaction with at least one compound of the general formula $R^9$—C≡C—C(=O)—OH, in which $R^9$ has the above-stated meaning, in a reaction medium, optionally in the presence of at least one suitable coupling agent, which may be polymer-bound, optionally in the presence of at least one base, preferably at a temperature of −70° C. to 100° C., or by reaction with at least one compound of the general formula $R^9$—C≡C—C(=O)—X, in which $R^9$ has the above-stated meaning and X denotes a leaving group, preferably a halogen residue, particularly preferably a chlorine or bromine residue, in a reaction medium, optionally in the presence of at least one base, preferably at a temperature of −70° C. to 100° C., into at least one corresponding compound of the general formula I, optionally in the form of a corresponding salt,

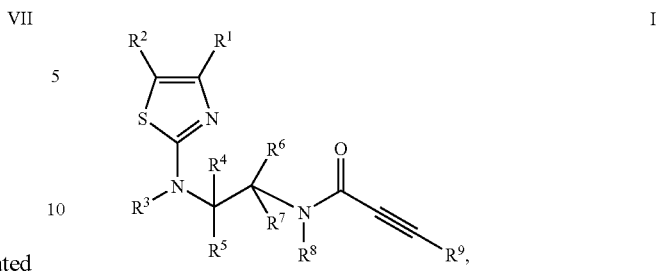

I in which $R^1$, $R^2$, $R^3$, $R^4$, $R^5$, $R^6$, $R^7$, $R^8$ and $R^9$ have the above-stated meaning, and the latter is optionally purified and/or isolated;

or at least one compound of the general formula IV is converted by reaction with propiolic acid [HC≡C—C(=O)—OH] in a reaction medium, optionally in the presence of at least one suitable coupling agent, which may be polymer-bound, optionally in the presence of at least one base, preferably at a temperature of −70° C. to 100° C., or by reaction with at least one compound of the general formula HC≡C—C(=O)—X, in which X denotes a leaving group, preferably a halogen residue, particularly preferably a chlorine residue, in a reaction medium, optionally in the presence of at least one base, preferably at a temperature of −70° C. to 100° C., into at least one corresponding compound of the general formula VIII, optionally in the form of a corresponding salt,

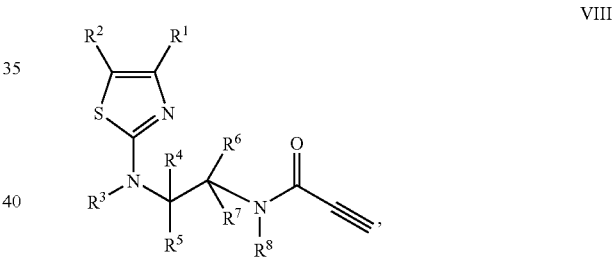

VIII in which $R^1$, $R^2$, $R^3$, $R^4$, $R^5$, $R^6$, $R^7$ and $R^8$ have the above-stated meaning, and the latter is optionally purified and/or isolated, and at least one compound of the general formula VIII is converted by reaction with at least one compound of the general formula $R^9$—X, in which $R^9$ has the above-stated meaning with the exception of hydrogen and X denotes a leaving group, preferably a halogen residue or a sulfonic acid ester, particularly preferably iodine, bromine or triflate, in a reaction medium, optionally in the presence of at least one catalyst, preferably in the presence of at least one palladium catalyst selected from the group consisting of palladium chloride [$PdCl_2$], palladium acetate [$Pd(OAc)_2$], tetrakistriphenylphosphine-palladium [$Pd(PPh_3)_4$], bistriphenylphosphinepalladium dichloride [$Pd(PPh_3)_2Cl_2$] and bistriphenylphosphinepalladium acetate [$Pd(PPh_3)_2(OAc)_2$], optionally in the presence of at least one ligand, preferably in the presence of at least one ligand selected from the group consisting of triphenylphosphine, triphenylarsine and tri-2-furylphosphine, optionally in the presence of at least one inorganic salt, preferably in the presence of at least one inorganic salt selected from the group consisting of lithium chloride and zinc chloride, optionally in the presence of at least one copper salt, preferably in the presence of copper iodide, optionally in the presence of at least one organic or inorganic base, preferably in the presence of at least one base selected from the group consisting of triethylamine, [1,4]-diazabicyclo-[2.2.2]-octane, diisopropylamine, diisopropylethylamine, potassium carbonate and sodium hydrogencarbonate, preferably at a temperature of between −70° C. and 300° C., into at least one corresponding compound of the general formula I, optionally in the form of a corresponding salt, and the latter is optionally purified and/or isolated.

The present invention also provides a method for producing compounds of the general formula I, in accordance with which at least one compound of the general formula III,

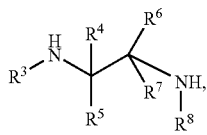

in which $R^3$, $R^4$, $R^5$, $R^6$, $R^7$ and $R^8$ have the above-stated meaning, is converted by reaction with at least one compound of the general formula $R^9$—C≡C—C(═O)—OH, in which $R^9$ has the above-stated meaning, in a reaction medium, optionally in the presence of at least one suitable coupling agent, which may be polymer-bound, optionally in the presence of at least one base, preferably at a temperature of −70° C. to 100° C., or by reaction with at least one compound of the general formula $R^9$—C≡C—C(═O)—X, in which $R^9$ has the above-stated meaning and X denotes a leaving group, preferably a halogen residue, particularly preferably a chlorine or bromine residue, in a reaction medium, optionally in the presence of at least one base, preferably at a temperature of −70° C. to 100° C., into at least one corresponding compound of the general formula IX, optionally in the form of a corresponding salt,

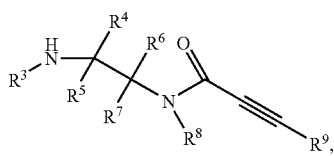

in which $R^3$, $R^4$, $R^5$, $R^6$, $R^7$, $R^8$ and $R^9$ have the above-stated meaning, and the latter is optionally purified and/or isolated;

or at least one compound of the general formula V,

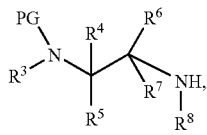

in which $R^3$, $R^4$, $R^5$, $R^6$, $R^7$ and $R^8$ have the above-stated meaning and PG denotes a protective group, preferably a protective group selected from the group consisting of tert.-butyloxycarbonyl, benzyl, benzyloxycarbonyl and 9-fluorenylmethyloxycarbonyl, is converted by reaction with at least one compound of the general formula $R^9$—C≡C—C(═O)—OH, in which $R^9$ has the above-stated meaning, in a reaction medium, optionally in the presence of at least one suitable coupling agent, which may be polymer-bound, optionally in the presence of at least one base, preferably at a temperature of −70° C. to 100° C., or by reaction with at least one compound of the general formula $R^9$—C≡C—C(═O)—X, in which $R^9$ has the above-stated meaning and X denotes a leaving group, preferably a halogen residue, particularly preferably a chlorine or bromine residue, in a reaction medium, optionally in the presence of at least one base, preferably at a temperature of −70° C. to 100° C., into at least one corresponding compound of the general formula XI, optionally in the form of a corresponding salt,

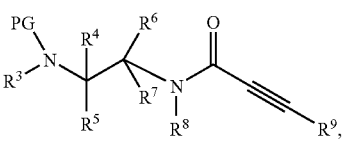

in which $R^3$, $R^4$, $R^5$, $R^6$, $R^7$, $R^8$, $R^9$ and PG have the above-stated meaning, and the latter is optionally purified and/or isolated;

and at least one compound of the general formula XI, in the event that PG denotes a tert.-butoxycarbonyl or 9-fluorenylmethyloxycarbonyl group, is converted in a reaction medium, in the presence of at least one acid, preferably in the presence of at least one acid selected from the group consisting of hydrochloric acid and trifluoroacetic acid, preferably at a temperature of between −70° C. to 100° C. or, in the event that PG denotes a benzyl or benzyloxycarbonyl group, in a reaction medium, in the presence of hydrogen and in the presence of at least one catalyst, preferably in the presence of palladium on carbon, preferably at a temperature of between −70° C. to 100° C. into at least one corresponding compound of the general formula IX, optionally in the form of a corresponding salt, and the latter is optionally purified and/or isolated;

and at least one compound of the general formula IX is converted by reaction with at least one compound of the general formula II,

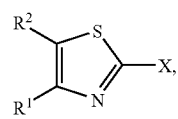

in which the residues $R^1$ and $R^2$ have the above-stated meaning and X denotes a leaving group, preferably a halogen residue or a sulfonic acid ester, particularly preferably a chlorine or bromine residue, in a reaction medium, optionally in the presence of at least one base and/or at least one organometallic compound and/or at least one metal hydride reagent, preferably at a temperature of −70° C. to 300° C. into at least one corresponding compound of the general formula I, optionally in the form of a corresponding salt, in which $R^1$, $R^2$, $R^3$, $R^4$, $R^5$, $R^6$, $R^7$, $R^8$ and $R^9$ have the above-stated meaning, and the latter is optionally purified and/or isolated;

or optionally at least one compound of the general formula IX is converted by reaction with potassium thiocyanate and ethyl chloroformate or ammonium thiocyanate or trimethylsilyl isothiocyanate or thiophosgene and ammonia or cyanogen bromide and hydrogen sulfide in a reaction medium, optionally in the presence of at least one acid, preferably in the presence of at least one acid selected from the group consisting of hydrochloric acid, sulfuric acid, acetic acid and trifluoroacetic acid, particularly preferably in the presence of hydrochloric acid, or optionally in the presence of at least one base, preferably in the presence of at least one base selected from the group consisting of potassium tert.-butylate, sodium hydroxide, potassium hydroxide, dimethylamine and triethylamine, particularly preferably in the presence of diethylamine, or optionally in the presence of at least one organometallic compound, preferably in the presence of at least one organometallic compound selected from the group consisting of methyllithium and butyllithium or optionally in the presence of at least one metal hydride compound, particularly preferably in the presence of sodium hydride, preferably at a temperature of −70° C. to 250° C., into at least one corresponding compound of the general formula XII, optionally in the form of a corresponding salt,

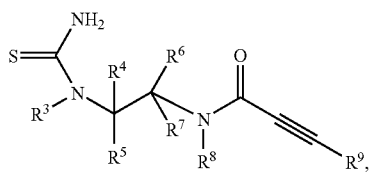

XII in which $R^3$, $R^4$, $R^5$, $R^6$, $R^7$, $R^8$ and $R^9$ have the above-stated meaning, and the latter is optionally purified and/or isolated;

and at least one compound of the general formula XII is converted by reaction with at least one compound of the general formula $R^1$—C(═O)—CH$_2$—X or (C$_{1-5}$-alkyl-O)$_2$—CH—CH$_2$—X, in which $R^1$ has the above-stated meaning and X denotes a leaving group, preferably a halogen residue, particularly preferably a bromine atom, in a reaction medium, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid and hydrochloric acid, preferably at a temperature of between −70° C. to 300° C. into at least one corresponding compound of the general formula I, optionally in the form of a corresponding salt, and the latter is optionally purified and/or isolated.

A method according to the invention for producing substituted thiazoles of the above-stated general formula I is also stated in Scheme 1 below.

Scheme 1.

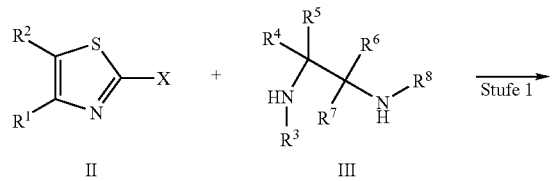

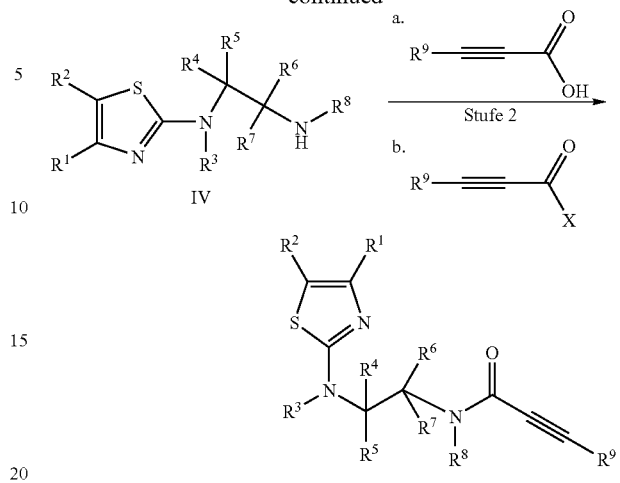

[Stufe = stage]

In stage 1, thiazoles of the above-stated general formula II, in which X denotes a leaving group, preferably a halogen residue or a sulfonic acid ester selected from the group consisting of mesylate, triflate and tosylate, particularly preferably a chlorine or bromine atom, are reacted with compounds of the above-stated general formula III, optionally in a reaction medium, preferably selected from the group consisting of methanol, ethanol, isopropanol, n-butanol, diethyl ether, tetrahydrofuran, dichloromethane, chloroform, dimethylformamide, acetonitrile, pyridine, dioxane, ethyl acetate, dimethyl sulfoxide, toluene and corresponding mixtures, particularly preferably in a reaction medium selected from the group consisting of methanol, ethanol and n-butanol, optionally in the presence of at least one organic or inorganic base, preferably selected from the group consisting of triethylamine, sodium hydrogencarbonate, dimethylaminopyridine, potassium carbonate and sodium hydroxide, and/or optionally in the presence of at least one metal salt, preferably a copper salt, particularly preferably copper(I) iodide and/or copper(I) chloride, and optionally in the presence of at least one metal, preferably in the presence of copper, and/or optionally in the presence of at least one organometallic compound or a metal hydride reagent, preferably selected from the group consisting of n-butyllithium, phenyllithium, sodium hydride, potassium hydride and sodium amide, preferably at temperatures of −70° C. to 300° C., particularly preferably at temperatures of -70° C. to 150° C., to yield compounds of the general formula IV.

In stage 2, compounds of the above-stated general formula IV are reacted with carboxylic acids of the above-stated general formula $R^9$—C≡C—(C═O)—OH, in a reaction medium, preferably selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyl-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonydiimidazole (CDl), N-[(dimethylamino)-1H-1,2,3- triazolo[4,5-b] pyridino-1- ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU) and 1-hydroxy-7-azabenzotriazole (HOAt), preferably in the presence of TBTU as coupling reagent, optionally in the presence of at least one organic base, preferably selected from the group consisting of triethylamine, pyridine, dimethylaminopyridine, N-methylmorpholine and diisopropylethylamine, preferably in the presence of diisopropylethylamine, preferably at temperatures of −70° C. to 100° C. to yield compounds of the general formula I.

Alternatively, compounds of the above-stated general formula IV are reacted with carboxylic acid derivatives of the above-stated general formula $R^9$—C≡C—C(═O)—X, in which X denotes a leaving group, preferably a halogen residue, particularly preferably chlorine or bromine, in a reaction medium, preferably selected from the group consisting of diethyl ether, tetrahydrofuran, acetonitrile, methanol, ethanol, dimethylformamide, dichloromethane and corresponding mixtures, optionally in the presence of an organic base or inorganic base, preferably selected from the group consisting of triethylamine, dimethylaminopyridine, pyridine and diisopropylamine, at temperatures of −70° C. to 100° C. to yield compounds of the general formula I.

A further method according to the invention for producing substituted thiazoles of the above-stated general formula I is also stated in scheme 2 below.

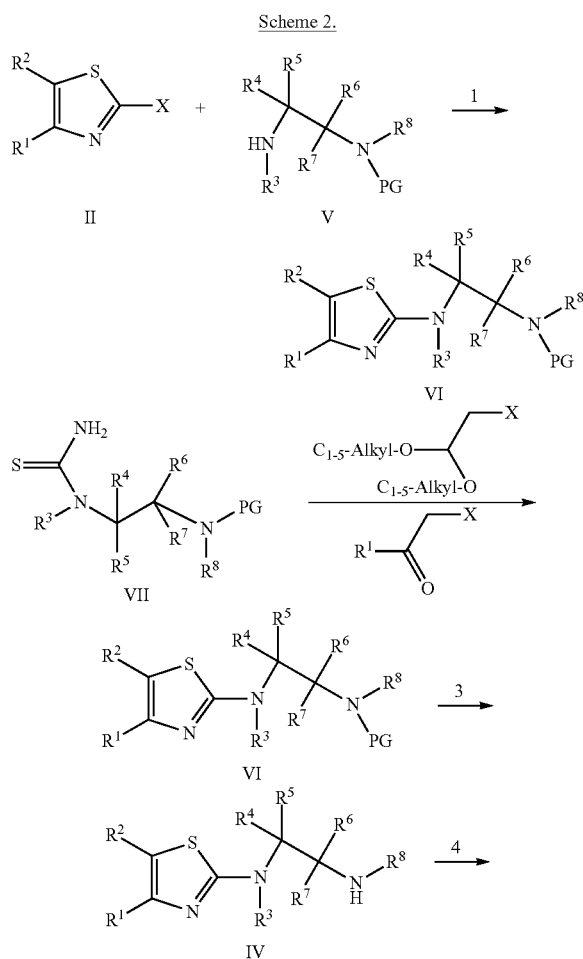

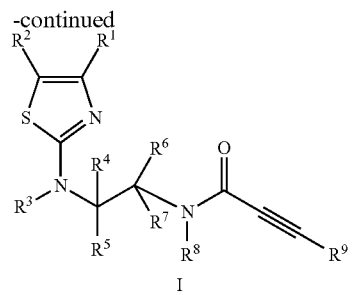

[Stufe = stage]

In stage 1, thiazoles of the above-stated general formula II, in which X denotes a leaving group, preferably a halogen residue or a sulfonic acid ester selected from the group consisting of mesylate, triflate and tosylate, particularly preferably a chlorine or bromine atom, are reacted with compounds of the above-stated general formula V, in which PG denotes a protective group, preferably a protective group selected from the group consisting of tert.-butyloxycarbonyl, benzyloxycarbonyl, benzyl and 9-fluorenylmethyloxycarbonyl to yield compounds of the general formula VI.

Precise conditions may also be obtained from the publication Journal of Medicinal Chemistry 1972, 15(3), pages 295 to 301. The corresponding parts of the publication are hereby deemed to be part of the disclosure.

In stage 2, compounds of the above-stated general formula VII, in which PG denotes a protective group, preferably a protective group selected from the group consisting of tert.-butyloxycarbonyl, benzyl, benzyloxycarbonyl and 9-fluorenylmethyloxycarbonyl, are reacted with at least one compound of the general formula $R^1$—C(═O)—$CH_2$—X or $(C_{1-5}\text{-alkyl-O})_2$—CH—$CH_2$—X, preferably with at least one compound of the general formula $R^1$—C(═O)—$CH_2$—X or $(C_2H_5$—O$)_2$—CH—$CH_2$—X, in which X denotes a leaving group, preferably a halogen residue, particularly preferably a bromine atom, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, toluene and corresponding mixtures, particularly preferably in ethanol and/or dioxane, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid and hydrochloric acid, preferably at a temperature of between −70° C. to 300° C. to yield a corresponding compound of the general formula VI.

Precise conditions may also be obtained from the publication Journal of Medicinal Chemistry 1998, 41 (25), pages 5027 to 5054. The corresponding parts of the publication are hereby deemed to be part of the disclosure.

In stage 3, compounds of the general formula VI, in the event that PG denotes a tert.-butoxycarbonyl or 9-fluorenylmethyloxycarbonyl group, are converted in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, toluene and corresponding mixtures, in the presence of at least one acid, preferably in the presence of at least one acid selected from the group consisting of hydrochloric acid and trifluoroacetic acid, preferably at a temperature of between −70° C. to 100° C. or, in the event that PG denotes a benzyl group or benzyloxycarbonyl group, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, toluene and corresponding mixtures, in the presence of hydrogen and in the presence of at least one catalyst, preferably in the presence of palladium on carbon, preferably at a temperature of between −70° C. to 100° C. into a corresponding compound of the general formula IV.

Suitable methods for removing the above-stated protective groups may be also be obtained from the monographs "Protective Groups in Organic Synthesis", T. W. Greene et al., $3^{rd}$ edition, 1999, Wiley, New York and "Protecting Groups", P. J. Kocienski, $3^{rd}$ edition, 2004, Georg Thieme Verlag, Stuttgart 2004. The corresponding parts of the references are hereby deemed to be part of the disclosure.

In stage 4, compounds of the above-stated general formula IV are reacted with carboxylic acids of the above-stated general formula $R^9$—C≡C—(C=O)—OH, or with carboxylic acid derivatives of the above-stated general formula $R^9$—C≡C—(C=O)—X as described in scheme 1, stage 2, to yield compounds of the general formula I.

A further method according to the invention for producing substituted thiazoles of the above-stated general formula I is also stated in scheme 3 below.

Scheme 3.

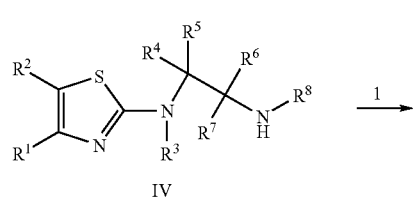

IV

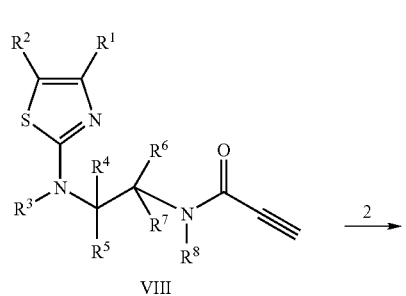

VIII

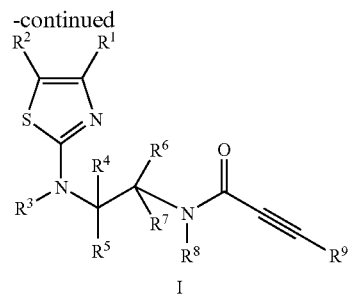

I

In stage 1, compounds of the above-stated general formula IV are reacted with propiolic acid H—C≡C—C(=O)—OH or with carboxylic acid derivatives of the general formula H—C≡C—C(=O)—X, in which X denotes a leaving group, preferably a halogen residue, particularly preferably chlorine or bromine, as described in scheme 1, stage 2, to yield compounds of the general formula VIII.

In stage 2, compounds of the above-stated general formula VIII are reacted with compounds of the general formula $R^9$—X, in which $R^9$ has the above-stated meaning with the exception of hydrogen and X denotes a leaving group, preferably a halogen residue or a sulfonic acid ester, particularly preferably iodine, bromine or triflate, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, water, toluene and corresponding mixtures, preferably in dimethylformamide, water, ethyl acetate, tetrahydrofuran and corresponding mixtures, optionally in the presence of at least one catalyst, preferably in the presence of a palladium catalyst selected from the group consisting of palladium chloride [$PdCl_2$], palladium acetate [$Pd(OAc)_2$], tetrakistriphenylphosphinepalladium [$Pd(PPh_3)_4$], bistriphenylphosphinepalladium dichloride [$Pd(PPh_3)_2Cl_2$] and bistriphenylphosphinepalladium acetate [$Pd(PPh_3)_2(OAc)_2$], preferably in the presence of $Pd(PPh_3)_4$, $Pd(PPh_3)_2Cl_2$ and $Pd(PPh_3)_2(OAc)_2$, optionally in the presence of at least one ligand, preferably in the presence of at least one ligand selected from the group consisting of triphenylphosphine, triphenylarsine and tri-2-furylphosphine, preferably in the presence of triphenylphosphine, optionally in the presence of at least one inorganic salt, preferably in the presence of at least one inorganic salt selected from the group consisting of lithium chloride and zinc chloride, optionally in the presence of at least one copper salt, preferably in the presence of copper iodide, optionally in the presence of at least one organic or inorganic base, preferably in the presence of at least one base selected from the group consisting of triethylamine, [1,4]-diazabicyclo-[2.2.2]-octane, diisopropylamine, diisopropylethylamine, potassium carbonate and sodium hydrogencarbonate, preferably at a temperature of between −70° C. and 300° C. to yield a compound of the general formula I. Particularly preferably, compounds of the general formula $R^9$—I or $R^9$—Br are reacted with compounds of the general formula VIII in dimethylformamide in the presence of $Pd(PPh_3)_2Cl_2$, copper(I) iodide and diisopropylamine or triethylamine.

A further method according to the invention for producing substituted thiazoles of the above-stated general formula I is also stated in scheme 4 below

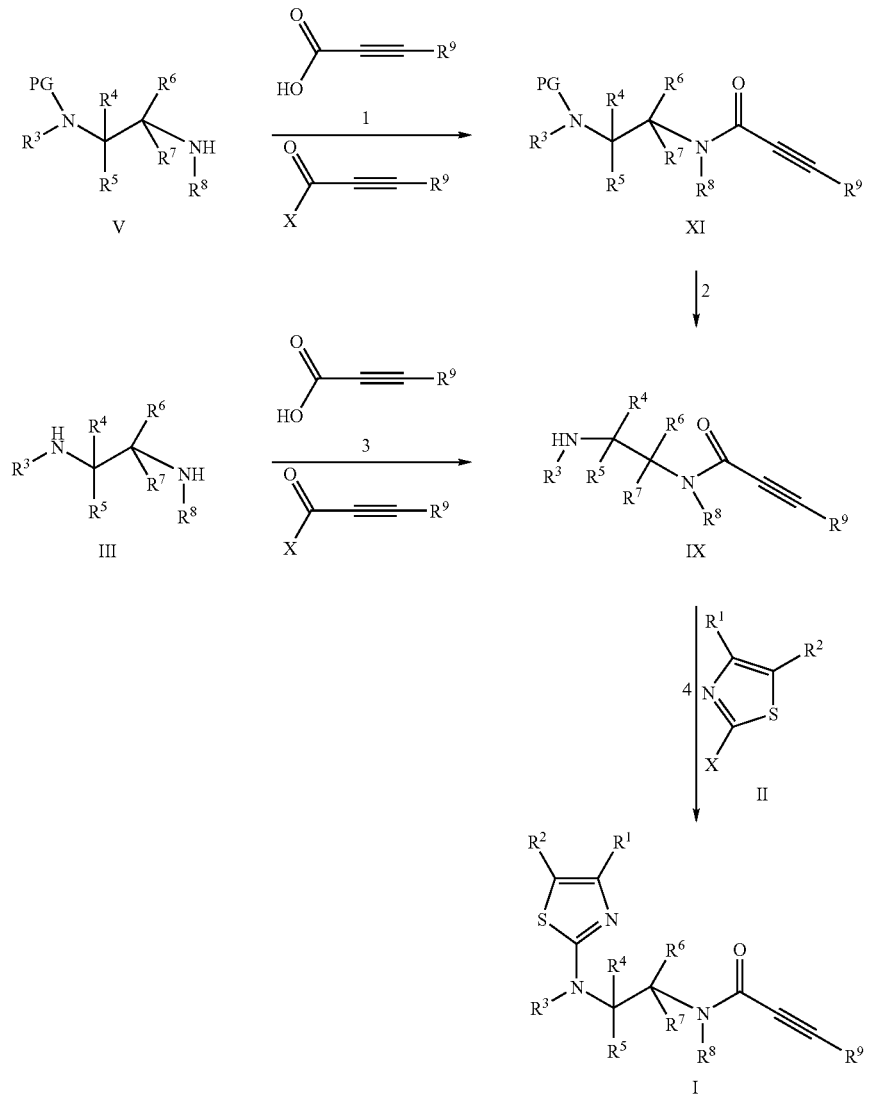

[Stufe = stage]

In stage 1, compounds of the general formula V, in which PG denotes a protective group, preferably a protective group selected from the group consisting of tert.-butyloxycarbonyl, benzyl, benzyloxycarbonyl and 9-fluorenylmethyloxycarbonyl, are reacted with compounds of the general formula $R^9$—C≡C—(C=O)—OH, or $R^9$—C≡C—(C=O)—X, in which X denotes a leaving group, preferably a halogen residue, particularly preferably chlorine or bromine, as in scheme 1, stage 2, to yield compounds of the general formula XI.

In stage 2, compounds of the general formula XI, in which PG denotes a protective group, preferably a protective group selected from the group consisting of tert.-butyloxycarbonyl, benzyl, benzyloxycarbonyl and 9-fluorenylmethyloxycarbonyl, as described in scheme 2, stage 3, to yield compounds of the general formula IX.

In stage 3, compounds of the above-stated general formula III are reacted with propiolic acid H—C≡C—C(=O)—OH or with carboxylic acid derivatives of the general formula H—C≡C—C(=O)—X, in which X denotes a leaving group, preferably a halogen residue, particularly preferably chlorine or bromine, as described in scheme 1, stage 2, to yield compounds of the general formula IX.

In stage 4, compounds of the general formula IX are reacted with compounds of the general formula II as in scheme 1, stage 1, to yield compounds of the general formula I.

Compounds of the general formula I, in which $R^3$ and $R^8$ in each case denote a hydrogen residue, hereinafter designated as compounds of the general formula XV, may be converted into compounds of the general formula I, in which $R^3$ and $R^8$ with the —N—$CR^4R^5$—$CR^6R^7$—N group joining them form a cyclic residue, hereinafter designated as compounds of the general formula XVI.

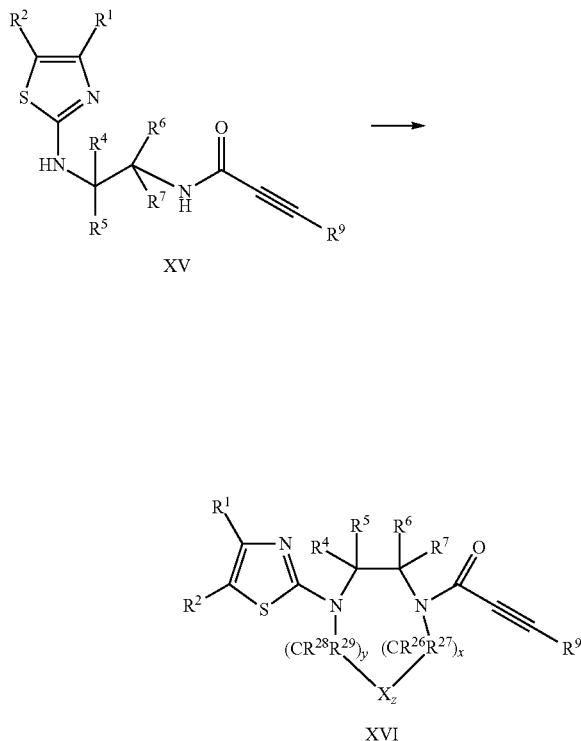

XV

XVI

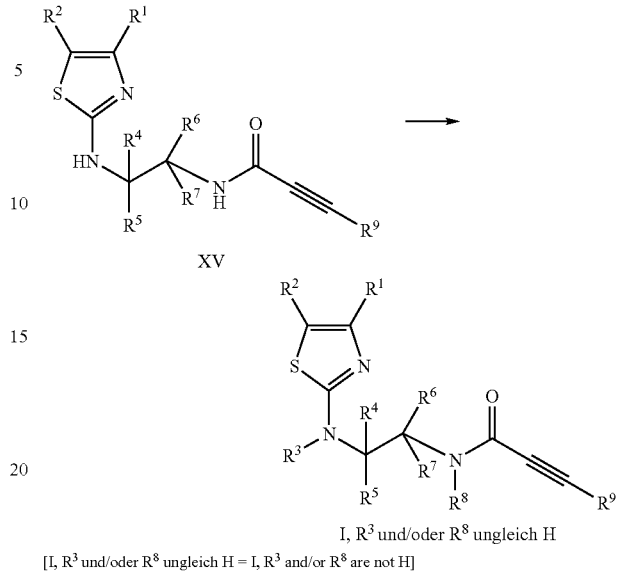

XV

I, R³ und/oder R⁸ ungleich H
[I, R³ und/oder R⁸ ungleich H = I, R³ and/or R⁸ are not H]

Compounds of the general formula XV may be reacted with compounds of the general formula Y—(CR$^{28}$, R$^{29}$)$_y$—X$_z$—(CR$^{26}$R$^{27}$)$_x$—W in which R$^{28}$, R$^{29}$, R$^{26}$, R$^{27}$, X, y, z and x have the above-stated meaning and Y and W mutually independently in each case denote a leaving group, preferably a halogen residue or a sulfonic acid ester selected from the group consisting of mesylate, triflate and tosylate, particularly preferably a chlorine or bromine atom, optionally in a reaction medium, preferably selected from the group consisting of methanol, ethanol, isopropanol, n-butanol, diethyl ether, tetrahydrofuran, dichloromethane, chloroform, dimethylformamide, acetonitrile, pyridine, dioxane, ethyl acetate, dimethyl sulfoxide, toluene and corresponding mixtures, particularly preferably in a reaction medium selected from the group consisting of acetonitrile, dichloroethane, chloroform, dimethylformamide, tetrahydrofuran and diethyl ether, optionally in the presence of at least one organic or inorganic base, preferably selected from the group consisting of triethylamine, sodium hydrogencarbonate, dimethylaminopyridine, potassium carbonate and sodium hydroxide, and/or optionally in the presence of at least one organometallic compound or a metal hydride reagent, preferably selected from the group consisting of n-butyllithium, phenyllithium, sodium hydride, potassium tert.-butanolate, potassium hydride and sodium amide, preferably at temperatures of −70° C. to 300° C., particularly preferably at temperatures of −70° C. to 150° C., to yield compounds of the general formula XVI.

Compounds of the general formula XV may likewise be converted into compounds of the general formula I, in which at least one the residues R³ and R⁸ does not denote a hydrogen residue.

Compounds of the general formula XV may be reacted with compounds of the general formula R³—X or R⁸—X, in which R³ and R⁸ have the above-stated meaning and X denotes a leaving group, preferably a halogen residue or a sulfonic acid ester selected from the group consisting of mesylate, triflate and tosylate, particularly preferably a chlorine or bromine atom, optionally in a reaction medium, preferably selected from the group consisting of methanol, ethanol, isopropanol, n-butanol, diethyl ether, tetrahydrofuran, dichloromethane, chloroform, dimethylformamide, acetonitrile, pyridine, dioxane, ethyl acetate, dimethyl sulfoxide, toluene and corresponding mixtures, particularly preferably in a reaction medium selected from the group consisting of acetonitrile, dichloroethane, chloroform, dimethylformamide, tetrahydrofuran and diethyl ether, optionally in the presence of at least one organic or inorganic base, preferably selected from the group consisting of triethylamine, sodium hydrogencarbonate, dimethylaminopyridine, potassium carbonate and sodium hydroxide, and/or optionally in the presence of at least one organometallic compound or a metal hydride reagent, preferably selected from the group consisting of n-butyllithium, phenyllithium, sodium hydride, potassium tert.-butanolate, potassium hydride and sodium amide, preferably at temperatures of −70° C. to 300° C., particularly preferably at temperatures of −70° C. to 150° C., to yield compounds of the general formula I, in which at least one of the residues R³ and R⁸ does not denote a hydrogen residue.

The compounds the above-stated formulae II, III, V, VII, XIII, XIV, and of the general formulae R⁹—X, Y—(CR$^{28}$R$^{29}$)$_y$—X$_z$—(CR$^{26}$R$^{27}$)$_x$—W, R³—X, R⁸—X, R⁹—C≡C—(C═O)—OH, R⁹—C≡C—(C═O)—X and H—C≡C—C(═O)—X are in each case commercially available and/or may be produced using conventional methods known to a person skilled in the art.

The above-described reactions may in each case be performed under conventional conditions familiar to a person skilled in the art, for example with regard to pressure or the sequence of addition of the components. Optimum control of the method according to the respective conditions may optionally be established by a person skilled in the art by simple preliminary testing.

The intermediate and final products obtained from the above-described reactions may in each case, if desired and/or necessary, be purified and/or isolated using conventional methods known to a person skilled in the art. Suitable purification methods are, for example, extraction methods and chromatographic methods such as column chromatography or preparative chromatography.

All the above-described process steps and in each case also the purification and/or isolation of intermediate or final products may be performed in part or entirely under an inert gas atmosphere, preferably under a nitrogen atmosphere.

If the substituted thiazoles according to the invention of the above-stated general formula I are obtained after the production thereof in the form of the stereoisomers thereof, preferably in the form of the racemates thereof or other mixtures of their various enantiomers and/or diastereomers, these may be separated and optionally isolated by conventional methods known to a person skilled in the art. Examples which may be mentioned are chromatographic separation methods, in particular liquid chromatography methods at standard pressure or at elevated pressure, preferably MPLC and HPLC methods, and fractional crystallisation methods. Individual enantiomers, e.g. diastereomeric salts formed by means of HPLC on a chiral phase or by means of crystallisation with chiral acids, for instance (+)-tartaric acid, (−)-tartaric acid or (+)-10-camphorsulfonic acid, may here in particular be separated from one another.

The substituted thiazoles according to the invention of the above-stated general formula I and optionally in each case corresponding stereoisomers may be obtained using conventional methods known to a person skilled in the art in the form of corresponding salts, preferably in the form of corresponding hydrochlorides, in particular in the form of corresponding physiologically acceptable salts, wherein the medicament according to the invention may comprise one or more salts of one or more of these compounds.

The respective salts of the substituted thiazoles according to the invention of the above-stated general formula I and corresponding stereoisomers may be obtained for example by reaction with one or more inorganic acids and/or one or more organic acids. Suitable acids may preferably be selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, cyclohexanesulfamic acid, aspartame, monomethylsebacic acid, 5-oxo-proline, hexane-1-sulfonic acid, nicotinic acid, 2-aminobenzoic acid, 3-aminobenzoic acid or 4-aminobenzoic acid, 2,4,6-trimethylbenzoic acid, α-lipoic acid, acetylglycine, hippuric acid, phosphoric acid, maleic acid, malonic acid and aspartic acid.

The substituted thiazoles according to the invention of the above-stated general formula I, and optionally corresponding stereoisomers and in each case the physiologically acceptable salts thereof may be obtained using conventional methods known to a person skilled in the art also in the form of the solvates thereof, in particular in the form of the hydrates thereof.

It has surprisingly been found that the above-stated substituted thiazoles of the general formula I are suitable for mGluR5 receptor regulation and may therefore be used in particular as pharmaceutical active ingredients in medicaments for the prevention and/or treatment of disorders or diseases associated with these receptors or processes.

The substituted thiazoles according to the invention of the above-stated general formula I and optionally corresponding stereoisomers and in each case the corresponding salts and solvates appear to be toxicologically safe and are therefore suitable as pharmaceutically active ingredients in pharmaceutical preparations.

The present invention accordingly also provides a medicament containing at least one substituted thiazole according to the invention of the above-stated general formula I in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The medicament according to the invention is suitable for mGluR5 receptor regulation, in particular for inhibiting the mGluR5 receptor.

Preferably, the medicament according to the invention is suitable for the prevention and/or treatment of disorders and/or diseases which are at least partially mediated by mGluR5 receptors.

The medicament according to the invention is therefore particularly preferably suitable for the treatment and/or prevention of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's chorea; cognitive diseases, preferably cognitive deficiency states, particularly preferably attention deficit syndrome (ADS); anxiety states; panic attacks; epilepsy; coughing; urinary incontinence; diarrhea; pruritus; schizophrenia; cerebral ischaemic episodes; muscle spasms; cramps; pulmonary diseases, preferably selected from the group comprising asthma and pseudocroup; regurgitation (vomiting); stroke; dyskinesia; retinopathy; lack of drive; laryngitis; disorders of food intake, preferably selected from the group consisting of bulimia, cachexia, anorexia and obesity; dependency on alcohol; dependency on medicines; dependency on drugs, preferably nicotine and/or cocaine dependency; alcohol abuse; abuse of medicines; drug abuse; preferably nicotine and/or cocaine abuse; withdrawal symptoms associated with dependency on alcohol, medicines and/or drugs (in particular nicotine and/or cocaine dependency); development of tolerance towards medicines, preferably towards natural or synthetic opioids; gastro-oesophageal reflux syndrome; gastro-oesophageal reflux disease; irritable bowel syndrome; for diuresis; for antinatriuresis; for influencing the cardiovascular system; for increasing vigilance; for increasing libido; for modulating locomotor activity or for local anaesthesia.

The medicament according to the invention is very particularly preferably suitable for the prevention of pain, preferably of pain selected from the group consisting of acute pain, chronic pain, neuropathic pain and visceral pain; anxiety states; panic attacks; dependency on alcohol; dependency on medicines; disorders of food intake, preferably selected from the group consisting of bulimia, cachexia, anorexia and obesity; dependency on drugs, preferably nicotine and/or cocaine dependency; alcohol abuse; abuse of medicines; drug abuse; preferably nicotine and/or cocaine abuse; withdrawal symptoms associated with dependency on alcohol, medicines and/or drugs (in particular nicotine and/or cocaine dependency); development of tolerance towards medicines and/or drugs, preferably towards natural or synthetic opioids; gastro-oesophageal reflux syndrome, gastro-oesophageal reflux disease and irritable bowel syndrome.

The medicament according to the invention is still more preferably suitable for the prevention and/or treatment of pain, preferably of pain selected from the group consisting of acute pain, chronic pain, neuropathic pain and visceral pain, anxiety states and panic attacks.

The medicament according to the invention is most preferably suitable for the prevention and/or treatment of pain, preferably acute pain, chronic pain, neuropathic pain or visceral pain.

The present invention also provides the use of at least one substituted thiazole according to the invention of the above-stated general formula I in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for producing a medicament for mGluR5 receptor regulation, preferably for inhibiting the mGluR5 receptor.

It is preferred to use at least one substituted thiazole according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for producing a medicament for the prevention and/or treatment of disorders and/or diseases which are mediated at least in part by mGluR5 receptors.

Particular preference is given to the use of at least one substituted thiazole according to the invention of the above-stated general formula I in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for producing a medicament for the prevention and/or treatment of pain, preferably of pain selected from the group consisting of acute pain, chronic pain, neuropathic pain and visceral pain; migraine; depression; neurodegenerative diseases, preferably selected from the group consisting of multiple sclerosis, Alzheimer's disease, Parkinson's disease and Huntington's chorea; cognitive diseases, preferably cognitive deficiency states, particularly preferably attention deficit syndrome (ADS); anxiety states; panic attacks; epilepsy; coughing; urinary incontinence; diarrhea; pruritus; schizophrenia; cerebral ischaemic episodes; muscle spasms; cramps; pulmonary diseases, preferably selected from the group comprising asthma and pseudocroup; regurgitation (vomiting); stroke; dyskinesia; retinopathy; lack of drive; laryngitis; disorders of food intake, preferably selected from the group consisting of bulimia, cachexia, anorexia and obesity; dependency on alcohol; dependency on medicines; dependency on drugs, preferably nicotine and/or cocaine dependency; alcohol abuse; abuse of medicines; drug abuse; preferably nicotine and/or cocaine abuse; withdrawal symptoms associated with dependency on alcohol, medicines and/or drugs (in particular nicotine and/or cocaine dependency); development of tolerance towards medicines, in particular towards natural or synthetic opioids; gastro-oesophageal reflux syndrome; gastro-oesophageal reflux disease; irritable bowel syndrome; for diuresis; for antinatriuresis; for influencing the cardiovascular system; for increasing vigilance; for increasing libido; for modulating locomotor activity or for local anaesthesia.

Very particular preference is given to the use of at least one substituted thiazole according to the invention of the above-stated general formula I in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for producing a medicament for the prevention and/or treatment of pain, preferably of pain selected from the group consisting of acute pain, chronic pain, neuropathic pain and visceral pain; anxiety states; panic attacks; dependency on alcohol; dependency on medicines; disorders of food intake, preferably selected from the group consisting of bulimia, cachexia, anorexia and obesity; dependency on drugs, preferably nicotine and/or cocaine dependency; alcohol abuse; abuse of medicines; drug abuse; preferably nicotine and/or cocaine abuse; withdrawal symptoms associated with dependency on alcohol, medicines and/or drugs (in particular nicotine and/or cocaine dependency); development of tolerance towards medicines and/or drugs, preferably towards natural or synthetic opioids; gastro-oesophageal reflux syndrome, gastro-oesophageal reflux disease and irritable bowel syndrome.

Still greater preference is given to the use of at least one substituted thiazole according to the invention of the above-stated general formula I in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances for producing a medicament for the prevention and/or treatment of pain, preferably of pain selected from the group consisting of acute pain, chronic pain, neuropathic pain and visceral pain, anxiety states and panic attacks.

The medicament according to the invention is suitable for administration to adults and children including small children and babies.

The medicament according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted thiazole according to the invention of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which may preferably be selected from the group consisting of excipients, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted thiazoles of the above-stated general formula I used in the medicament according to the invention in a depot in dissolved form or in a dressing, optionally with the addition of skin penetration promoters, are suitable percutaneous administration preparations.

Orally or percutaneously administrable preparation forms may also release the respective substituted thiazoles of the above-stated general formula I in delayed manner.

Production of the pharmaceutical preparations according to the invention proceeds with the assistance of conventional means, devices, methods and processes known from the prior art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the particular substituted thiazole of the above-stated general formula I to be administered to the patient may vary and is for example dependent on the weight or age of the patient and on the mode of administration, the indication and the severity of the disease. Conventionally, at least one such compound is administered in a quantity of 0.05 to 100 mg/kg, preferably of 0.05 to 10 mg/kg, of patient body weight.

Pharmacological Methods:

I. Method for Determining the Inhibition of [$^3$H]-MPEP Binding in the mGluR5 Receptor Binding Assay Pig brain homogenate is produced by homogenisation (Polytron Pt 3000, Kinematica AG, 10,000 revolutions per minute for 90 seconds) of pig brain hemispheres without medulla, cerebellum and pons in a buffer of pH 8.0 (30 mM Hepes, Sigma, order number H3375+1 tablet Complete Roche Diagnostics, order number 1836145 made up to 100 ml) in a ratio of 1:20 (brain weight/volume) and differential centrifugation at 900×g and 40,000×g. 450 µg of protein from brain homogenate is incubated in each case in 250 µl incubation batches in 96-well microtitre plates with 5 nM$^3$[H]-MPEP (Tocris, order number R1212) (MPEP=2-methyl-6-(3-methoxyphenyl)-ethylnylpyridine) and the compounds to be investigated (10 µM in the test) in the buffer (as above) at room temperature for 60 min.

The batches are then filtered with the assistance of a Brandel Cell Harvester (Brandel, Robotic 9600 model) on Unifilter plates with glass filter mats (Perkin Elmer, order number 6005177) and then washed 3 times with buffer (as above) using 250 µl per sample. The filter plates are then dried for 60 min at 55° C. Then 30 µl of Ultima Gold™ scintillating material (Packard BioScience, order number 6013159) is added per well and after 3 hours the samples are measured using the β counter (Microbeta, Perkin Elmer). Nonspecific binding is determined by the addition of 10 µM MPEP (Tocris, order number 1212).

II. Method for Determining Ca$^{2+}$ Influx in the mGluR5 Receptor Assay

An agonistic and/or antagonistic substance action on the mGluR5 receptor of the rat species may be determined with the following assay. According to this assay, intracellular Ca$^{2+}$ release is quantified after activation of the mGluR5 receptor with the assistance of a Ca$^{2+}$-sensitive dye (type Fluo-4, Molecular Probes Europe BV, Leiden, Netherlands) in a FlexStation (Molecular Devices, Sunnyvale, USA).

Preparation of Cortical Neurones:

Cortical neurones from postnatal rats (P2-6) are prepared under sterile conditions. To this end, the cortex is removed and transferred directly into collagenase solution (PAA Laboratories GmbH, Cölbe, Germany) and incubated for 45 minutes in a heated agitator (37° C., 300 revolutions per minute). Then the collagenase solution is removed and the tissue combined with culture medium.

Culture Medium (100 ml):

Neurobasal medium (Gibco Invitrogen GmbH, Karlsruhe, Germany)

2 mM L-glutamine (Sigma, Taufkirchen, Germany)

1 vol. % antibiotic/antimycotic solution (PAA Laboratories GmbH, Cölbe, Germany)

15 ng/ml NGF (Gibco Invitrogen GmbH, Karlsruhe, Germany)

1 ml B27 supplement (Gibco Invitrogen GmbH, Karlsruhe, Germany)

1 ml ITS supplement (Sigma, Taufkirchen, Germany)

The cells are isolated by resuspension and centrifuged through a 70 µm filter insert (BD Biosciences, Heidelberg, Germany) after addition of 15 ml of neurobasal medium. The resultant cell pellet is resuspended in culture medium. Then, the cells are plated out onto poly-D-lysine-coated, black 96-well plates with a clear base (BD Biosciences, Heidelberg, Germany), which have previously been additionally coated with laminin (2 µg/cm$^2$, Gibco Invitrogen GmbH, Karlsruhe, Germany). Cell density amounts to 15,000 cells/well. The cells are incubated at 37° C. and 5% CO$_2$ and the medium is changed on the 2nd or 3rd day after preparation. Depending on cell growth, the functional investigation may be performed on the 3rd-7th day after preparation.

Description of the Functional Ca$^{2+}$ Influx Assay 20,000 CHO-hmGluR5 cells/well (Euroscreen, Gosselies, Belgium) are pipetted out into 96 well plates (BD Biosciences, Heidelberg, Germany, Ref. 356640, clear bottom, 96 well, poly-D-lysine) and incubated overnight in HBSS buffer (Gibco No. 14025-050) with the following additives: 10% FCS (GIBCO, 10270-106) and doxycycline (BD Biosciences Clontech 631311 600 ng/ml).

For the purpose of functional investigation, the cells were loaded with 2 µM Fluo-4 and 0.01 vol. % Pluronic F127 (Molecular Probes Europe BV, Leiden, Netherlands) in HBSS buffer (Hank's buffered saline solution, Gibco Invitrogen GmbH, Karlsruhe, Germany) with Probenicid (Sigma P8761, 0.69 mg/ml) for 30 min at 37° C.

The cells are then washed 3 times with washing buffer (HBSS buffer, Gibco No. 14025-050, with Probenicid (Sigma P8761, 0.69 mg/ml) and then resuspended with the same buffer to make up to 100 µl. After 15 min, the plates are transferred for determination of $Ca^{2+}$ measurements in the presence of DHPG ((S)-3,5-dihydroxyphenylglycine, Tocris Biotrend Chemikalien GmbH, Cologne, Germany, final DHPG concentration: 10 µM) and in the presence or absence of test substances into a FLuorometric Imaging Plate Reader (FLIPR, Molecular Devices, Sunnyvale, Calif.).

$Ca^{2+}$-dependent fluorescence is measured before and after addition of test substances. Quantification proceeds by measuring the highest fluorescence intensity over time.

After recording a fluorescence baseline for 10 s, 50 µl of test substance solution (various test substance concentrations in HBSS buffer with 1% DMSO and 0.02% Tween 20, Sigma) are added and the fluorescence signal is measured for 6 min. Then, 50 µl of DHPG solution ((S)-3,5-dihydroxyphenylglycine, Tocris Biotrend Chemikalien GmbH, Cologne, Germany, final DHPG concentration: 10 µM) are added and $Ca^{2+}$ influx is simultaneously measured for 60 s. The final DMSO concentration amounts to 0.25% and the final Tween 20 content amounts to 0.005%. The data are analysed with Microsoft Excel and GraphPad Prism. The dose-response curves are calculated with non-linear regression and $IC_{50}$ values are determined. Each data point is determined in triplicate and $IC_{50}$ values are averaged from a minimum of 2 independent measurements.

Ki values are calculated using the following formula: $Ki=IC50/(1+(AG_{conc.}/EC50))$.

$AG_{conc.}=10$ µM; EC50 corresponds to the DHPG concentration which is necessary for the semimaximal influx of $Ca^{2+}$.

III. Formaldehyde Test in Rats:

The formaldehyde test (Dubuisson, D. and Dennis, S. G., 1977, Pain, 4, 161-174) is a model of both acute and chronic pain. A biphasic nociceptive response is induced in freely mobile test animals by a single formaldehyde injection into the dorsal side of a hind paw, said response being detected by the observation of three clearly distinguishable behaviour patterns. The response is in two phases: phase 1=immediate response (duration up to 10 min; paw shaking, licking), phase 2=late response (after a resting phase; likewise paw shaking, licking; duration up to 60 min). The 1st phase reflects direct stimulation of the peripheral nocisensors with an elevated spinal nociceptive input or glutamate release (acute pain phase); the 2nd phase reflects spinal and peripheral hypersensitisation (chronic pain phase). In the investigations presented here, it was the chronic pain component (phase 2) which was evaluated.

Formaldehyde is administered subcutaneously in a volume of 50 µl and a concentration of 5% into the dorsal side of the right hind paw of each animal. The substances to be tested are administered orally (per os), intravenously (i.v.) or intraperitoneally (i.p.) 30 min before the formaldehyde injection. The specific behavioural changes, such as raising and shaking the paw, changes in weight bearing of the animal and biting and licking responses are observed and recorded over the observation period of 21 to 27 min after the formaldehyde injection. The various behaviours are summarised as a "pain rate" (PR), which is the calculated nociceptive response averaged over 3 min sub-intervals. The PR is calculated on the basis of a numerical weighting (=in each case a factor of 1, 2, 3) of the observed behaviours (corresponding behaviour score 1, 2, 3) and is calculated using the following formula:

$$PR=[(T_0\times0)+(T_1\times1)+(T_2\times2)+(T_3\times3)]/180$$

wherein $T_0$, $T_1$, $T_2$, and $T_3$ correspond to the time in seconds for which the animal exhibited behaviour 0, 1, 2 or 3 respectively. Group size is 10 animals (n=10).

The following Examples serve to explain the invention in more detail and do not restrict the general concept of the invention.

EXAMPLES

The yields of the compounds produced have not been optimised.

All temperatures are uncorrected.

The term "equivalents" means molar equivalents, "RT" room temperature, "conc." concentrated, "d" days, "min" minutes, "h" hours, "M" is a concentration stated in mol/l, "aq." aqueous, "sat." saturated, "soln." solution, "CC" column chromatography Other Abbreviations:

Boc tert.-butoxycarbonyl brine saturated aqueous sodium chloride solution

BuLi butyllithium

CDI 1,1'-carbonyldiimidazole

DCC dicyclohexylcarbodiimide

DCE dichloroethane

DCM dichloromethane

DIC N,N'-diisopropylcarbodiimide

DMF N,N-dimethylformamide

DIPE diisopropyl ether

DIPEA diisopropylethylamine

EDCl N-ethyl-N'-(3-dimethylaminopropyl)-carbodiimide hydrochloride

EA ethyl acetate

EtOH ethanol $H_2O$ water

HOBt 1-hydroxybenzotriazole soln. solution

M molar

MeCN acetonitrile

MeOH methanol

PS-carbodiimide a polymer-bound carbodiimide of the following structure:

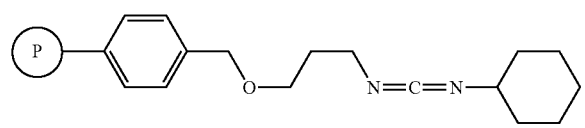

Loading: 0.9-1.4 mmol/g

Particle size: 75-150 µm

TBTU O-(benzotriazol-1-yl)-N,N,N',N'-tetramethyluronium tetrafluoroborate

TFA trifluoroacetic acid

THF tetrahydrofuran

TMSCl trimethylchlorosilane

The chemicals and solvents used were purchased from conventional suppliers (Acros, Avocado, Aldrich, Bachem, Fluka, Lancaster, Maybridge, Merck, Sigma, TCI, etc.) or synthesised using conventional methods familiar to a person skilled in the art.

Silica gel 60 (0.040-0.063 mm) from E. Merck, Darmstadt, was used as the stationary phase for the column chromatography.

Thin-layer chromatography was performed with pre-coated silica gel 60 F 254 HPTLC plates from E. Merck, Darmstadt.

The mixture ratios for solvents, mobile solvents or for chromatographic investigations are always stated in volume/volume.

Analysis was performed by mass spectroscopy and/or NMR.

Synthesis of Exemplary Compound 1

3-Phenyl-N-(1-(thiazol-2-yl)pyrrolidin-3-yl)propiolamide

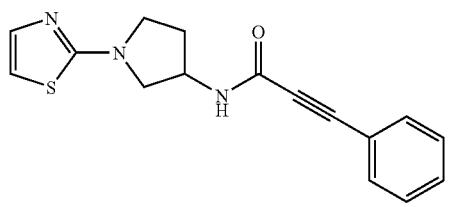

a) Synthesis of tert.-butyl 1-(thiazol-2-yl)pyrrolidin-3-ylcarbamate

A solution of 815 μl (9.1 mmol) of 2-bromothiazole and 1.7 g, (9.1 mmol) of tert.-butyl pyrrolidin-3-ylcarbamate in n-butanol (30 ml) was refluxed for 3 h. The solvent was then removed under a vacuum and the residue redissolved in chloroform. This solution was washed successively with water and sat. aq. NaCl soln., dried over MgSO₄, filtered and evaporated under a vacuum. Column chromatography (SiO₂, EA/hexane 1:1) was carried out with the residue, 900 mg (3.3 mmol, 37%) of tert.-butyl 1-(thiazol-2-yl)pyrrolidin-3-ylcarbamate being obtained.

b) Synthesis of 1-(thiazol-2-yl)pyrrolidin-3-amine hydrochloride

Aq. conc. hydrochloric acid (2 ml) was added to a solution of 890 mg (3.3 mmol) of tert.-butyl 1-(thiazol-2-yl)pyrrolidin-3-ylcarbamate in MeOH (20 ml). The reaction solution was stirred at RT for 16 h and then evaporated under a vacuum. 653 mg (3.2 mmol, 97%) of 1-(thiazol-2-yl)pyrrolidin-3-amine hydrochloride were obtained by crystallising the residue from an ethanol/ether mixture.

c) Synthesis of 3-phenyl-N-(1-(thiazol-2-yl)pyrrolidin-3-yl)propiolamide 323 mg (1.7 mmol) of EDCl, 228 mg (1.7 mmol) of HOBt and 287 μl (1.7 mmol) of diisopropylethylamine were added with cooling (ice bath) to a solution of 206 mg (1.4 mmol) of phenylpropiolic acid in DMF (20 ml). After 30 min stirring at RT, a solution of 319 mg (1.6 mmol) of 1-(thiazol-2-yl)pyrrolidin-3-amine hydrochloride was added thereto with cooling (ice bath). The reaction solution was then stirred for 4 h at 55° C. After removal of the solvent under a vacuum, the residue was redissolved in EA, washed with a sat. aq. NaHCO₃ soln. and dried over MgSO₄. After filtration and evaporation under a vacuum, column chromatography (SiO₂, EA/hexane 1:1) was carried out with the residue, 180 mg (0.6 mmol, 43%) of 3-phenyl-N-(1-(thiazol-2-yl)pyrrolidin-3-yl)-propiolamide being obtained. MS [MH+] 298.1

Synthesis of Exemplary Compound 2

N-Methyl-3-phenyl-N-(1-(thiazol-2-yl)pyrrolidin-3-yl)propiolamide

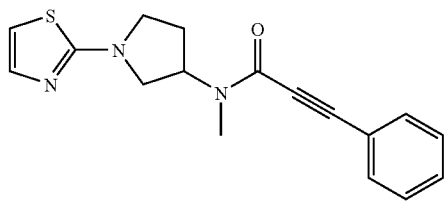

A solution of 180 mg (0.6 mmol) of 3-phenyl-N-(1-(thiazol-2-yl)pyrrolidin-3-yl)-propiolamide (Example 1) in DMF (5 ml) was added dropwise with cooling (ice bath) to a solution of 71 mg (3.0 mmol) of sodium hydride in DMF (5 ml). Stirring was then performed for 60 min at RT and, after cooling to 0° C. (ice bath), 106 μl (1.7 mmol) of iodomethane were added. The reaction solution was stirred at RT for 16 h and thereafter diluted with EA and a sat. aq. NaHCO₃ soln. The phases were separated and the aqueous phase extracted repeatedly with EA. The combined organic phases were dried over MgSO₄, filtered and evaporated under a vacuum. Column chromatography (SiO₂, EA/hexane 1:1) was carried out with the residue, 170 mg (0.55 mmol, 91%) of N-methyl-3-phenyl-N-(1-(thiazol-2-yl)pyrrolidin-3-yl)propiolamide being obtained. MS [MH+] 312.1

The corresponding hydrochloride was obtained from this compound.

Synthesis of Exemplary Compound 3

1-Thiazol-2-yl-4-(3-phenylpropioloyl)-1,4-diazepane

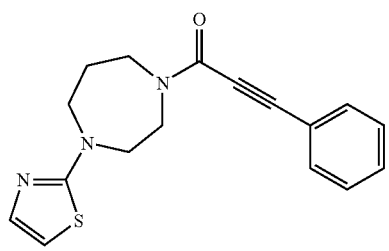

a) Synthesis of 2-(1,4-diazepan-1-yl)thiazole 11.0 g (110 mmol) of homopiperazine and 980 μl (11 mmol) of 2-bromothiazole were heated together to 140° C. for 10 min. The reaction solution was poured into water and this solution was saturated with NaCl and extracted with EA.

The organic phase was washed with water and sat. aq. NaCl soln., dried over MgSO$_4$ and evaporated under a vacuum. 1.54 (8.4 mmol, 76%) of 2-(1,4-diazepan-1-yl)thiazole were obtained by crystallising the residue from ether.

b) Synthesis of 1-thiazol-2-yl-4-(3-phenylpropioloyl)-1,4-diazepane 340 mg (2.1 mmol) of CDI were added to a solution of 292 mg (2.0 mmol) of phenylpropiolic acid in DCE (10 ml) and the reaction mixture was stirred at RT for 100 min. After cooling to 10° C., 366 mg (2.0 mmol) of 2-(1,4-diazepan-1-yl)thiazole were added and stirring was then continued at RT for a further 4 h. The solution was then washed with water and sat. aq. NaCl soln., dried over MgSO$_4$ and evaporated under a vacuum. Column chromatography (SiO$_2$, DCE/EtOH 40:1) was carried out with the residue, 113 mg (0.36 mmol, 18%) of 1-thiazol-2-yl-4-(3-phenylpropioloyl)-1,4-diazepane being obtained. MS [MH+] 312.1

Synthesis of Exemplary Compound 4

N-Methyl-N-(2-(methyl(thiazol-2-yl)amino)ethyl)-3-phenylpropiolamide

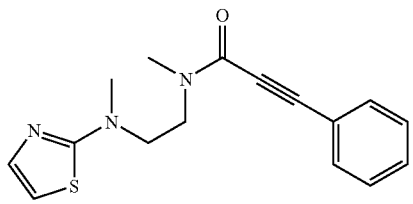

a) Synthesis of N$^1$,N$^2$-dimethyl-N$^1$-(thiazol-2-yl)ethane-1,2-diamine 0.54 ml (6.0 mmol) of 2-bromothiazole were combined with 3.84 ml (36.0 mmol) of N$^1$,N$^2$-dimethylethane-1,2-diamine and heated to 80° C. for 3 h. Column chromatography (SiO$_2$, DCE/EtOH 5:1) was carried out with the residue, 371 mg (2.2 mmol, 36%) of N$^1$,N$^2$-dimethyl-N$^1$-(thiazol-2-yl)ethane-1,2-diamine being obtained.

b) Synthesis of N-methyl-N-(2-(methyl(thiazol-2-yl)amino)ethyl)-3-phenylpropiolamide Synthesis was carried out as above using the method described in Example 3b). MS [MH+] 300.1

Synthesis of Exemplary Compound 8

3-Phenyl-N-(1-(thiazol-2-yl)azetidin-3-yl)propiolamide

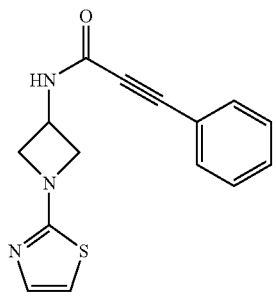

a) Synthesis of tert.-butyl 1-(thiazol-2-yl)azetidin-3-ylcarbamate

Synthesis was carried out as above using the method described in Example 1a).

b) Synthesis of 1-(thiazol-2-yl)azetidin-3-amine hydrochloride 467 mg (1.83 mmol) of tert.-butyl 1-(thiazol-2-yl)azetidin-3-ylcarbamate were dissolved in DCE (10 ml) and with an etheric HCl soln. After stirring at RT for 1 h, the resultant precipitate was filtered out and then washed with ether, 300 mg (1.56 mmol, 86%) of 1-(thiazol-2-yl)azetidin-3-amine hydrochloride being obtained.

c) Synthesis of 3-phenyl-N-(1-(thiazol-2-yl)azetidin-3-yl)propiolamide 2.32 g (corresponding to 3.02 mmol) of PS carbodiimide resin (polystyrene carbodiimide resin) were added to a solution of 290 mg (1.51 mmol) of 1-(thiazol-2-yl)azetidin-3-amine hydrochloride, 221 mg (1.51 mmol) phenylpropiolic acid and 210 µl (1.51 mmol) of NEt$_3$ in DMF (15 ml). The reaction solution was shaken at RT for 3 d. The solution was then filtered and washing performed with DCM and ethanol. The combined filtrates were evaporated under a vacuum and column chromatography (SiO$_2$, DCE/EtOH 20:1) was carried out with the residue, 60 mg (0.21 mmol, 14%) of 3-phenyl-N-(1-(thiazol-2-yl)azetidin-3-yl)propiolamide being obtained. MS [MH+] 284.1

Synthesis of Exemplary Compound 11

3-(Thiazol-2-yl-amino)-1-(3-phenylpropioloyl)pyrrolidine

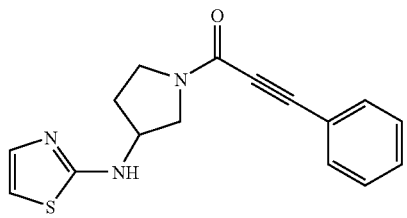

a) Synthesis of tert-butyl 3-(thiazol-2-ylamino)pyrrolidine-1-carboxylate

A mixture of 501 mg (5.0 mmol) of 2-aminothiazole, 926 mg (5.0 mmol) of tert.-butyl 3-aminopyrrolidine-1-carboxylate, 2.1 g of (10.0 mmol) of sodium triacetoxyborohydride and 0.57 ml (10.0 mmol) of acetic acid in DCE (10 ml) was stirred at RT for 16 h. The mixture was then diluted with DCE (50 ml) and washed with a sat. aq. NaHCO$_3$ soln., water and sat. aq. NaCl soln. The organic phase was dried over MgSO$_4$, filtered and evaporated under a vacuum. Column chromatography (SiO$_2$, chloroform/EtOH 10:1) was carried out with the residue, 317 mg (1.2 mmol, 24%) of tert.-butyl 3-(thiazol-2-ylamino)pyrrolidine-1-carboxylate being obtained.

b) Synthesis of N-(pyrrolidin-3-yl)thiazol-2-amine 317 mg (1.18 mmol) of tert.-butyl 3-(thiazol-2-ylamino)pyrrolidine-1-carboxylate were dissolved in ether (15 ml) and combined with an etheric HCl soln. (10 ml). After stirring at RT for 1 h, evaporation under a vacuum was carried out. The residue was with redissolved water and adjusted to pH ~11 with a 10% strength NaOH soln., after which extraction was carried out with chloroform. The organic phase was washed with water and sat. aq. NaCl soln., dried over MgSO$_4$, filtered and evaporated under a vacuum, 97 mg (0.57 mmol, 48%) of N-(pyrrolidin-3-yl)thiazol-2-amine being obtained.

c) Synthesis of 3-(thiazol-2-yl-amino)-1-(3-phenyl-propioloyl)pyrrolidine

100 µl (0.57 mmol) of DIPEA and 183 mg (0.57 mmol) of TBTU were added to a solution of 97 mg (0.57 mmol) of N-(pyrrolidin-3-yl)thiazol-2-amine and 85 mg (0.57 mmol) of phenylpropiolic acid in MeCN (5 ml). The reaction solution was stirred at RT for 16 h. The mixture was then evaporated under a vacuum and the residue redissolved in chloroform. The org. solution was then washed with water and sat. aq. NaCl soln., dried over MgSO$_4$, filtered and evaporated under a vacuum. Column chromatography (SiO$_2$, DCE/EtOH 10:1) was carried out with the residue, 72 mg (0.24 mmol, 42%) of 3-(thiazol-2-yl-amino)-1-(3-phenylpropioloyl)pyrrolidine being obtained. MS [MH+] 298.1

Synthesis of Exemplary Compound 12

N-Methyl-N-(2-(methyl(thiazol-2-yl)amino)cyclohexyl)-3-phenylpropiolamide

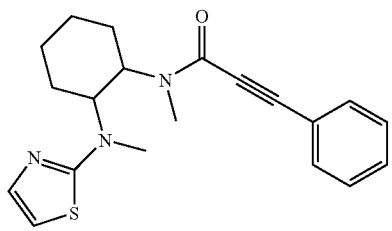

46 mg (1.15 mmol, 60% in mineral oil) of sodium hydride and 1144 µl (2.31 mmol) of iodomethane were added in succession to a solution of 150 mg (0.46 mmol) of 3-phenyl-N-(2-(thiazol-2-ylamino)-cyclohexyl)propiolamide (exemplary compound 6) in MeCN (10 ml). The reaction solution was stirred at RT for 4 h. This procedure was repeated twice more and the mixture was then evaporated under a vacuum. The residue was redissolved with DCM, washed with water, dried over MgSO$_4$, filtered and evaporated under a vacuum, 131 mg (0.37 mmol, 81%) of N-methyl-N-(2-(methyl(thiazol-2-yl)amino)cyclohexyl)-3-phenylpropiolamide being obtained. MS [MH+] 354.2

Synthesis of Exemplary Compound 14

N-Methyl-N-(2-(methyl(thiazol-2-yl)amino)-2-oxo-ethyl)-3-phenylpropiolamide

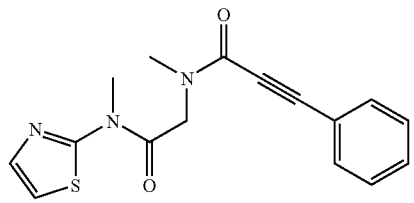

a) Synthesis of N-methylthiazol-2-amine

900 µl (10 mmol) of 2-bromothiazole were heated together with a 33% strength ethanolic methylamine soln. (70 ml) in an autoclave (to approx. 120° C.) until a pressure of 10 bar had developed. The mixture was stirred for 2 h under these conditions. The reaction mixture was then evaporated under a vacuum and the residue was redissolved in a 3% strength aq. HCl soln. and washed with ether, after which the pH was adjusted to 12 with a 20% strength aq. NaOH soln. The solution was saturated with NaCl and extracted with chloroform. The organic phase was dried over MgSO$_4$, filtered and evaporated under a vacuum, 761 mg (6.7 mmol, 67%) of N-methylthiazol-2-amine being obtained.

b) Synthesis of tert.-butyl methyl(2-(methyl(thiazol-2-yl)amino)-2-oxoethyl)carbamate 871 µl (5.0 mmol) of diisopropylethylamine, 571 mg (5.0 mmol) of N-methylthiazol-2-amine and 1.60 g (5.0 mmol) of TBTU were added to a solution of 946 mg (5.0 mmol) of Boc-sarcosine in MeCN (11 ml) and the reaction mixture was stirred at RT for 16 h. A further 284 mg (1.5 mmol) of Boc-sarcosine, 216 µl (1.5 mmol) of diisopropylethylamine, 5 ml of MeCN and 1.60 g (5.0 mmol) of TBTU were added thereto and the reaction mixture was stirred at RT for a further 16 h. After removal of the solvent under a vacuum the residue was redissolved in chloroform, washed with water and sat. aq. NaCl soln. and dried over MgSO$_4$. After filtration and evaporation under a vacuum, column chromatography (SiO$_2$, chloroform) was carried out with the residue, 300 mg (1.05 mmol, 21%) of tert.-butyl methyl(2-(methyl(thiazol-2-yl)amino)-2-oxoethyl)carbamate being obtained.

c) Synthesis of N-methyl-2-(methylamino)-N-(thiazol-2-yl)acetamide 300 mg (1.05 mmol) of tert.-butyl methyl(2-(methyl(thiazol-2-yl)amino)-2-oxoethyl)carbamate were dissolved in DCM (5 ml) and combined with an etheric HCl soln. (5 ml). After 16 h stirring at RT, the solution was evaporated under a vacuum. The residue was dissolved in water and washed with ether. The reaction mixture was then made basic with 20% strength aq. Na$_2$CO$_3$ and extracted with chloroform. The organic phase was dried over MgSO$_4$, filtered and evaporated under a vacuum, 185 mg (1.0 mmol, 95%) of N-methyl-2-(methylamino)-N-(thiazol-2-yl)acetamide being obtained.

d) Synthesis of N-methyl-N-(2-(methyl(thiazol-2-yl) amino)-2-oxoethyl)-3-phenylpropiolamide 1.54 g (corresponding to 2.0 mmol) of PS carbodiimide resin (polystyrene carbodiimide resin) were added to a solution of 185 mg (1.0 mmol) of N-methyl-2-(methylamino)-N-(thiazol-2-yl)acetamide and 146 mg (1.0 mmol) of phenylpropiolic acid in DCM (40 ml). The reaction solution was shaken at RT for 16 h. The solution was then filtered and washing performed with DCM and ethanol. The combined filtrates were wash with a 5% strength aq. potassium carbonate soln., water and sat. aq. NaCl soln., dried over MgSO₄, filtered and evaporated under a vacuum. Column chromatography (SiO₂, DCE/EtOH 10:1) was carried out with the residue, 99 mg (0.32 mmol, 32%) of N-methyl-N-(2-(methyl (thiazol-2-yl)amino)-2-oxoethyl)-3-phenylpropiolamide being obtained. MS [MH+] 314.1

Synthesis of Exemplary Compound 15

3-Phenyl-N-(1-(thiazol-2-yl)piperidin-3-yl)propiolamide

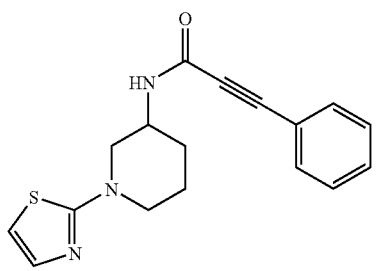

a) Synthesis of 1-(thiazol-2-yl)piperidin-3-ol 2.02 g (20 mmol) of 3-hydroxypiperidine and 1.8 ml (20 mmol) of 2-bromothiazole were together dissolved in n-butanol (29 ml) and stirred for 6 h at 110° C. The mixture was then evaporated under a vacuum and column chromatography (SiO₂, DCM/EtOH 10:1) was carried out with the residue, 1.54 g (8.4 mmol, 42%) of 1-(thiazol-2-yl)piperidin-3-ol being obtained.

b) Synthesis of 1-(thiazol-2-yl)piperidin-3-yl methanesulfonate 1.5 ml (10.8 mmol) of NEt₃ and a catalytic quantity of 4-dimethylaminopyridine were added to a solution of 500 mg (2.7 mmol) of 1-(thiazol-2-yl)piperidin-3-ol in DCE (15 ml). A solution of 376 µl (4.86 mmol) of methanesulfonyl chloride in DCE (2.5 ml) was then added dropwise thereto and the mixture was then stirred for 2 h at RT. The mixture was then washed with water and sat. aq. NaCl soln. and dried over MgSO₄. After filtration and evaporation under a vacuum column chromatography (SiO₂, chloroform/EA 10:1) was carried out with the residue, 502 mg (1.9 mmol, 71%) of 1-(thiazol-2-yl)piperidin-3-yl methanesulfonate being obtained.

c) Synthesis of 1-(thiazol-2-yl)piperidin-3-amine

A solution of 836 mg (3.18 mmol) of 1-(thiazol-2-yl)piperidin-3-yl methanesulfonate in an ethanolic ammonia soln. saturated at 0° C. (25 ml) was stirred in an autoclave for 10 h at 100° C. Evaporation under a vacuum was then carried out and column chromatography (DCE/EtOH/aq.NH₃ 250:50:3) was carried out with the residue, 406 mg (2.2 mmol, 70%) of 1-(thiazol-2-yl)piperidin-3-amine being obtained.

d) Synthesis of 3-phenyl-N-(1-(thiazol-2-yl)piperidin-3-yl)propiolamide

234 µl of NEt₃ were added to a solution of 206 mg (1.12 mmol) of 1-(thiazol-2-yl)piperidin-3-amine in DCE (10 ml) and the solution was cooled to −20° C. At this temperature, 221 mg (1.34 mmol) of phenylpropioloyl chloride dissolved in DCE (2 ml) were added and the reaction mixture was stirred for 2 h at RT. Washing was then carried out with water and sat. aq. NaCl soln. The organic phase was dried over MgSO₄, filtered and evaporated under a vacuum. Column chromatography (SiO₂, DCE/EtOH 10:1, then hexane/EA 1:1) was carried out with the residue, 37 mg (0.12 mmol, 11%) of 3-phenyl-N-(1-(thiazol-2-yl)piperidin-3-yl)propiolamide being obtained. MS [MH+] 312.1

Synthesis of Exemplary Compound 17

N-Methyl-N-(2-(methyl(thiazol-2-yl)amino)ethyl)-3-(pyrid-2-yl)-propiolamide

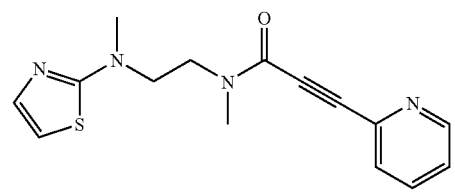

a) Synthesis of N-methyl-N-(2-(methyl(thiazol-2-yl) amino)ethyl)propiolamide

525 µl (3.9 mmol) of diisopropylethylamine and 963 mg (3.0 mmol) of TBTU were added to a solution of 514 mg (3.0 mmol) of $N^1,N^2$-dimethyl-$N^1$-(thiazol-2-yl)ethane-1,2-diamine (see Example 4a)) and 185 µl (3.0 mmol) of propiolic acid in THF (20 ml) and the reaction mixture was stirred for 1 h at RT. The mixture was then evaporated under a vacuum and the residue was redissolved with DCM, washed with water and sat. aq. NaCl soln. and dried over MgSO₄. After filtration and evaporation under a vacuum, column chromatography (SiO₂, hexane/EA 4:1) was carried out with the residue, 484 mg (2.2 mmol, 72%) of N-methyl-N-(2-(methyl (thiazol-2-yl)amino)ethyl)propiolamide being obtained.

b) Synthesis of N-methyl-N-(2-(methyl(thiazol-2-yl) amino)ethyl)-3-(pyrid-2-yl)-propiolamide 484 mg (2.17 mmol) of N-methyl-N-(2-(methyl(thiazol-2-yl)amino)ethyl)propiolamide were dissolved together with 444 mg (2.17 mmol) of 2-iodopyridine, 28 mg of Pd(PPh₃)₂Cl₂, 15 mg of copper(I) iodide and 600 µl of NEt₃ in DMF (10 ml) and stirred for 1 h at 60° C. The reaction solution was largely evaporated under a vacuum and then diluted with water. The mixture was then extracted with DCM and the organic phase washed with water and dried over MgSO₄. After filtration and removal of the solvent under a vacuum, column chromatography (SiO₂, DCM/EtOH 10:1) was carried out with the residue, 134 mg (0.45 mmol, 21%) of N-methyl-N-(2-(methyl(thiazol-2-yl)amino)ethyl)-3-(pyrid-2-yl)-propiolamide being obtained. MS [MH+] 301.1

Synthesis of Exemplary Compound 18

N-Methyl-N-(2-(methyl(thiazol-2-yl)amino)ethyl)-3-(3-chlorophenyl)-propiolamide

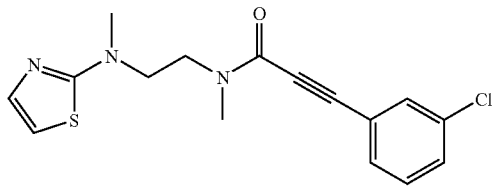

A solution of 514 mg (3.0 mmol) of $N^1,N^2$-dimethyl-$N^1$-(thiazol-2-yl)ethane-1,2-diamine (see Example 4a)) and 542 mg (3.0 mmol) of (3-chlorophenyl)propiolic acid in THF (15 ml) was combined with 546 µl (3.6 mmol) of DIC and stirred for 1 h at RT. The mixture was then evaporated under a vacuum and the residue was redissolved with DCM, washed with water and sat. aq. NaCl soln. and dried over MgSO$_4$. After filtration and removal of the solvent under a vacuum, column chromatography (DCM/EtOH 10:1) was carried out with the residue, 300 mg (0.90 mmol, 30%) of N-methyl-N-(2-(methyl(thiazol-2-yl)amino)ethyl)-3-(3-chlorophenyl)-propiolamide being obtained. MS [MH+] 334.1

Synthesis of Exemplary Compound 19

N-(2-(Methyl(thiazol-2-yl)amino)ethyl)-3-(3-chlorophenyl)-propiolamide

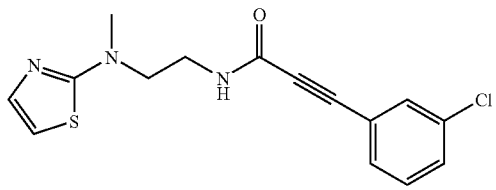

a) Synthesis of $N^1$-methyl-$N^1$-(thiazol-2-yl)ethane-1,2-diamine 159 mg (2.5 mmol) of powdered copper and 642 mg (7.5 mmol) of copper(I) chloride were added to a solution of 4.5 ml (50 mmol) of 2-bromothiazole and 26.4 ml (300 mmol) of N-methylethylene-1,2-diamine in isopropanol (25 ml). The reaction mixture was stirred for 2 h at RT and then evaporated under a vacuum. Column chromatography (SiO$_2$, DCE/EtOH 5:1) was carried out with the residue, 576 mg (3.6 mmol, 7%) of $N^1$-methyl-$N^1$-(thiazol-2-yl)ethane-1,2-diamine being obtained.

b) Synthesis of N-(2-(methyl(thiazol-2-yl)amino)ethyl)-3-(3-chlorophenyl)-propiolamide 314 mg (2.0 mmol) of $N^1$-methyl-$N^1$-(thiazol-2-yl)ethane-1,2-diamine were dissolved together with 361 mg (2.0 mmol) of (3-chlorophenyl)propiolic acid, 348 µl (2.0 mmol) of diisopropylethylamine and 642 mg (2.0 mmol) of TBTU in MeCN (30 ml) and stirred for 16 h at RT. The reaction mixture was evaporated under a vacuum and the residue was redissolved with DCM, washed with water, dried over MgSO$_4$ and evaporated under a vacuum. Column chromatography (SiO$_2$, chloroform/EtOH 40:1) was carried out with the residue, 153 mg (0.48 mmol, 24%) of N-(2-(methyl(thiazol-2-yl)amino)ethyl)-3-(3-chlorophenyl)-propiolamide being obtained. MS [MH+] 320.1

Synthesis of Exemplary Compound 22

3-(Methyl(thiazol-2-yl)amino)-1-(3-phenylpropioloyl)pyrrolidine

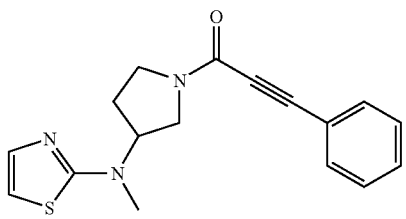

67 mg (1.68 mmol) of sodium hydride (60% suspension in mineral oil) were added to a solution of 334 mg (1.12 mmol) of 3-(thiazol-2-yl-amino)-1-(3-phenylpropioloyl)pyrrolidine (Example 11) in MeCN (15 ml) and the solution was stirred for 1 h at RT. 140 µl (2.24 mmol) of methyl iodide were then added and the mixture was again stirred for 1 h at RT before being combined with a 25% aq. ammonia soln. (2 ml) and concentrated under a vacuum. The residue was extracted with chloroform. The organic phase was washed with water and sat. aq. NaCl soln., dried over MgSO$_4$, filtered and evaporated under a vacuum. Column chromatography (SiO$_2$, chloroform) was carried out with the residue, 99 mg (0.32 mmol, 28%) of 3-(methyl-(thiazol-2-yl)amino)-1-(3-phenylpropioloyl)-pyrrolidine being obtained. MS [MH+] 312.1

Synthesis of Exemplary Compound 23

N-(2-(Methyl(thiazol-2-yl)amino)ethyl)-3-(3-chlorophenyl)-propiolamide hydrochloride

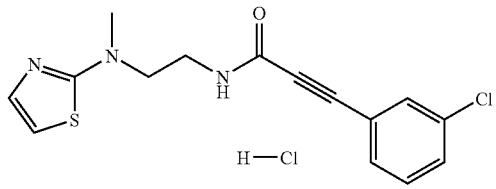

A sat. ethereal HCl soln. (10 ml) was added to a solution of 500 mg (1.56 mmol) of N-(2-(methyl-(thiazol-2-yl)amino)ethyl)-3-(3-chlorophenyl)-propiolamide (Example 19) in ether (50 ml) and the mixture was stirred for 1 h at RT, a precipitate being obtained. This was removed by suction filtration and rewashed with ether, 507 mg (1.42 mmol, 91%) of N-(2-(methyl-(thiazol-2-yl)amino)ethyl)-3-(3-chlorophenyl)-propiolamide hydrochloride being obtained. MS [MH+] 320.1

Exemplary compound 5 N-(2-((thiazol-2-yl)amino)ethyl)-3-phenylpropiolamide (MS [MH+] 272.1) was synthesised by the methods described above for exemplary compounds 19a) and 3b).

Exemplary compounds 6 3-phenyl-N-(2-(thiazol-2-ylamino)cyclohexyl)propiolamide (MS [MH+] 326.1), 9 N-(2-(methyl(thiazol-2-yl)amino)ethyl)-3-phenylpropiolamide, (MS [MH+] 286.1), 10 N-methyl-N-(2-(thiazol-2-yl)amino)ethyl-3-phenylpropiolamide, (MS [MH+] 286.1), 21 N-(2-(methyl(thiazol-2-yl)amino)ethyl)-3-(tol-3-yl)-propiolamide, (MS [MH+] 300.1), 24 N-(2-(benzo[d]thiazol-2-yl(methyl)amino)ethyl)-3-(3-chlorophenyl)-propiolamide, (MS [MH+] 370.1), 25 N-(2-(methyl-(5-ethoxycarbonylthiazol-2-yl)amino)ethyl)-3-(3-chlorophenyl)-propiolamide (MS [MH+] 392.1), 26 N-(2-(methyl-(4-ethoxycarbonylthiazol-2-yl)amino)ethyl)-3-(3-chlorophenyl)-propiolamide (MS [MH+] 392.1) and 29 N-(2-(methyl-(4-methylthiazol-2-yl)amino)ethyl)-3-(3-chlorophenyl)-propiolamide (MS [MH+] 334.1) were synthesised by the method described above for exemplary compound 19.

Exemplary compounds 7 N-methyl-N-(2-(methyl(thiazol-2-yl)amino)ethyl)-3-(3-methylphenyl)-propiolamide (MS [MH+] 314.1) and 13 N-methyl-N-(2-(methyl(thiazol-2-yl)amino)ethyl)-3-(3-cyanophenyl)-propiolamide, (MS [MH+] 325.1) were synthesised in a similar manner to the methods described above for exemplary compounds 4a) and 19b).

Exemplary compounds 16 N-methyl-N-(1-(thiazol-2-yl)piperidin-3-yl)-3-phenylpropiolamide (MS [MH+] 326.1) and 20 N-methyl-N-(1-(thiazol-2-yl)azetidin-3-yl)-3-phenylpropiolamide, (MS [MH+] 298.1) were also produced by the method described above for exemplary compound 2.

Exemplary compound 27 3-(thiazol-2-yl-amino)-1-(3-phenylpropioloyl)piperidine (MS [MH+] 312.1) was produced by the method described above for exemplary compound 11.

Exemplary compound 28 3-(methyl-(thiazol-2-yl)-amino)-1-(3-phenylpropioloyl)piperidine (MS [MH+] 326.1) was also produced by the method described above for exemplary compound 22.

Synthesis of Exemplary Compound 30

3-(3-Chlorophenyl)-N-(2-(methyl(5-methylthiazol-2-yl)amino)ethyl)propiolamide

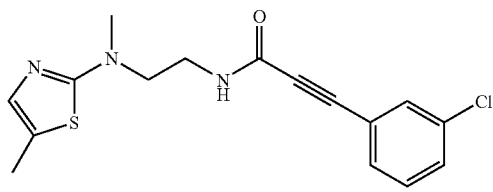

a) Synthesis of N,5-dimethylthiazol-2-amine

A mixture of 21.5 g (188.0 mmol) of 2-amino-5-thiazole, 16.8 ml (225.0 mmol) of 37% strength aq. formaldehyde solution, 22.43 g (188.0 mmol) of benzotriazole and ethanol (150 ml) was refluxed for 2 h and then stirred for 16 h at RT. The resultant precipitate was filtered out and washed with cold ethanol. The residue was then redissolved with MeOH (1000 ml). 3.48 g (92 mmol) of sodium borohydride were added in portions with cooling (ice bath). The mixture was then evaporated under a vacuum. This residue was redissolved with chloroform, washed with water and brine, dried over MgSO$_4$ and evaporated under a vacuum. 4.0 g (31.3 mmol, 17%) of N,5-dimethylthiazol-2-amine were obtained by CC (hexane/EA 1:1) with the residue.

b) Synthesis of N$^1$-methyl-N$^1$-(5-methylthiazol-2-yl)ethane-1,2-diamine

A mixture of 512 mg (4.0 mmol) of N,5-dimethylthiazol-2-amine, 352 mg (8.8 mmol, 60% strength in mineral oil) of sodium hydride and 2-bromoethylamine hydrobromide with DMF (10 ml) was stirred for 2 h at RT. The mixture was then poured into water and extracted with DCM. The organic phase was dried over MgSO$_4$, filtered and evaporated under a vacuum. 232 mg (1.4 mmol, 34%) of N$^1$-methyl-N$^1$-(5-methylthiazol-2-yl)ethane-1,2-diamine were obtained by CC (DCM/EtOH/conc. aq. NH$_4$—OH soln. 5:1:0.06) with the residue.

c) Synthesis of 3-(3-chlorophenyl)-N-(2-(methyl(5-methylthiazol-2-yl)amino)ethyl)-propiolamide 2.19 g (~2.6 mmol) of PS carbodiimide were added to a solution of 232 mg (1.35 mmol) of N$^1$-methyl-N$^1$-(5-methylthiazol-2-yl)ethane-1,2-diamine and 367 mg (2.03 mmol) of (3-chlorophenyl)propiolic acid in DCM (40 ml). The mixture was then shaken for 16 h at RT, after which the resin was filtered out and rinsed with DCM and EtOH. The filtrate was evaporated under a vacuum and CC (DCE/EtOH 5:1) was carried out with the residue, 169 mg (0.51 mmol, 37%) of N-(2-(methyl(thiazol-2-yl)amino)ethyl)-3-(3-chlorophenyl)-propiolamide being obtained. MS [MH+] 334.1

Synthesis of Exemplary Compound 31

N-(2-((5-Bromothiazol-2-yl)(methyl)amino)ethyl)-3-(3-chlorophenyl)propiolamide

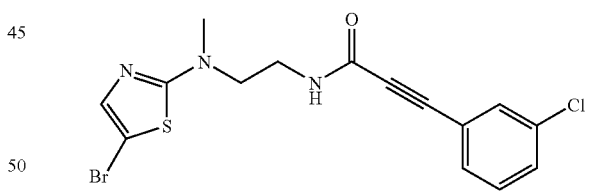

a) Synthesis of N$^1$-(5-bromothiazol-2-yl)-N$^1$-methyl-ethane-1,2-diamine 15 mg (0.24 mmol) of copper and 68 mg (0.69 mmol) of copper(I) chloride were added to a solution of 1.0 g (4.1 mmol) of 2,5-dibromothiazole and 2.2 ml (24.7 mmol) of N-methylethylenediamine in isopropanol (2.3 ml). The mixture was then heated to 70° C. for 1 h. After cooling to RT, filtration through silica gel was carried out and the filtrate was evaporated under a vacuum. 348 mg (1.5 mmol, 36%) of N$^1$-(5-bromothiazol-2-yl)-N$^1$-methylethane-1,2-diamine were obtained by CC (DCE/EtOH/conc. aq. NH$_4$—OH soln. 5:1:0.06) with the residue.

b) Synthesis of N-(2-((5-bromothiazol-2-yl)(methyl) amino)ethyl)-3-(3-chlorophenyl)-propiolamide 2.39 g (~2.9 mmol) of PS carbodiimide were added to a solution of 348 mg (1.47 mmol) of $N^1$-(5-bromothiazol-2-yl)-$N^1$-methylethane-1,2-diamine, 205 µl (1.47 mmol) of triethylamine and 399 mg (2.21 mmol) of (3-chlorophenyl) propiolic acid in DCM (40 ml). The mixture was then shaken for 16 h at RT, after which the resin was filtered out and rinsed with DCM and EtOH. The filtrate was evaporated under a vacuum and CC (DCE/EtOH 10:1) was carried out with the residue, 119 mg (0.30 mmol, 20%) of N-(2-((5-bromothiazol-2-yl)(methyl)amino)ethyl)-3-(3-chlorophenyl)propiolamide being obtained. MS [MH+] 398.0

Synthesis of Exemplary Compound 35

1-(3-(3-Chlorophenyl)propioloyl)-3-(methyl(thiazol-2-yl)amino)azetidine

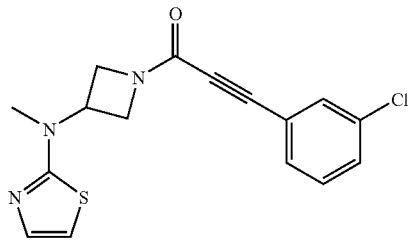

a) Synthesis of 1-Boc-3-(thiazol-2-ylamino)azetidine

A mixture of 5.0 g (29.1 mmol) of 1-Boc-3-aminoazetidine and 2.62 ml (29.1 mmol) of 2-bromothiazole was heated to 140° C. with stirring for 2 h. After cooling to RT, 800 mg (3.14 mmol, 11%) of 1-Boc-3-(thiazol-2-ylamino)azetidine were obtained from the mixture by CC (SiO$_2$, 1 st DCE, 2nd chloroform).

b) Synthesis of 1-Boc-3-(methyl(thiazol-2-yl)amino)azetidine

A suspension of 270 mg (1.05 mmol) of 1-Boc-3-(thiazol-2-ylamino)azetidine in MeCN (5 ml) was combined with 68 mg (1.2 mmol, 60% strength in mineral oil) of sodium hydride and stirred for 30 min at RT. 151 µl (1.73 mmol) of iodomethane were then added and stirring continued for a further 16 h at RT. After addition of MeOH (200 µl), evaporation under a vacuum was carried out. 166 mg (0.62 mmol, 59%) of 1-Boc-3-(methyl(thiazol-2-yl)amino)azetidine were obtained by CC (hexane/EA 3:2) with the residue.

c) Synthesis of 3-(methyl(thiazol-2-yl)amino)azetidine

A solution of 166 mg (0.62 mmol) of 1-Boc-3-(methyl (thiazol-2-yl)amino)azetidine in DCM (5 ml) was combined with 2.5 ml of TFA and stirred for 3 h at RT. The mixture was then evaporated under a vacuum. The residue was redissolved with water and washed with ether. The aqueous phase was adjusted to pH 11 with a 20% strength aq. NaOH soln. and saturated with common salt. The mixture was then extracted with chloroform and the organic phase was dried over MgSO$_4$ and filtered. After removal of the solvents under a vacuum, 102 mg (0.60 mmol, 97%) of 3-(methyl(thiazol-2-yl)amino) azetidine were obtained.

d) Synthesis of 1-(3-(3-chlorophenyl)propioloyl)-3-(methyl(thiazol-2-yl)amino)azetidine 0.78 g (~0.9 mmol) of PS carbodiimide were added to a solution of 100 mg (0.59 mmol) of 3-(methyl(thiazol-2-yl) amino)azetidine and 160 mg (0.89 mmol) of (3-chlorophenyl)-propiolic acid in DCM (15 ml). The mixture was then shaken for 16 h at RT, after which the resin was filtered out and rinsed with DCM and MeOH. The filtrate was evaporated under a vacuum and CC (chloroform) was carried out with the residue, 148 mg (0.45 mmol, 76%) of 1-(3-(3-chlorophenyl) propioloyl)-3-(methyl(thiazol-2-yl)amino)azetidine being obtained. MS [MH+] 332.1

Synthesis of Exemplary Compound 36

3-(3-Chlorophenyl)-N-methyl-N-(1-(thiazol-2-yl) piperidin-3-yl)propiolamide

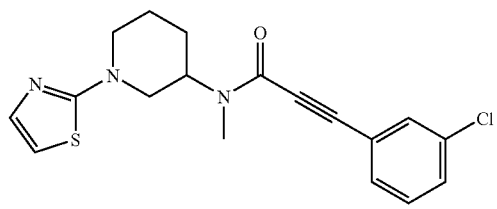

a) Synthesis of N-methyl-1-(thiazol-2-yl)piperidin-3-amine

A mixture of 502 mg (1.92 mmol) of 1-(thiazol-2-yl)piperidin-3-yl methanesulfonate (synthesis described in Example 15) in a 33% strength ethanolic methylamine soln. was heated to 140° C. for 10 min in a pressure vessel in a microwave oven (CEM Explorer, max. 300 W). The mixture was then evaporated under a vacuum.

The residue was redissolved with DCM, washed with water and brine, dried over MgSO$_4$, filtered and again evaporated under a vacuum. 276 mg (1.40 mmol, 73%) of N-methyl-1-(thiazol-2-yl)piperidin-3-amine were obtained by CC (DCE/EtOH/aq.NH$_4$OH 5:1:0.06) of this residue.

b) Synthesis of 3-(3-chlorophenyl)-N-methyl-N-(1-(thiazol-2-yl)piperidin-3-yl)-propiolamide 2.1 g (~2.52 mmol) of PS carbodiimide were added to a solution of 258 mg (1.31 mmol) of N-methyl-1-(thiazol-2-yl) piperidin-3-amine and 354 mg (1.96 mmol) of (3-chlorophenyl)propiolic acid in DCM (40 ml). The mixture was then shaken for 16 h at RT, after which the resin was filtered out and rinsed with DCM and MeOH. The filtrate was evaporated under a vacuum and CC (hexane/EA 1:3) was carried out with the residue, 243 mg (0.67 mmol, 52%) of 3-(3-chlorophenyl)-N-methyl-N-(1-(thiazol-2-yl)piperidin-3-yl)propiolamide being obtained. MS [MH+] 360.1

Synthesis of Exemplary Compound 41

3-(3-Chlorophenyl)-N-(2-(ethyl(thiazol-2-yl)amino)ethyl)propiolamide

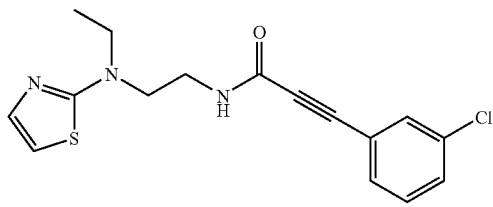

a) Synthesis of N¹-ethyl-N¹-(thiazol-2-yl)ethane-1,2-diamine 47 mg (0.74 mmol) of copper and 225 mg (2.27 mmol) of copper(I) chloride were added to a solution of 1.35 g (15.0 mmol) of 2-bromothiazole and 9.48 ml (90.0 mmol) of N-ethylethylenediamine in isopropanol (7.5 ml). The mixture was then heated to 70° C. for 1 h. After cooling to RT, the reaction solution was poured into water and extracted with EA. The organic phase was dried over MgSO₄, filtered and evaporated under a vacuum. 200 mg (1.2 mmol, 8%) of N¹-ethyl-N¹-(thiazol-2-yl)ethane-1,2-diamine were obtained by carrying out CC twice (i. DCE/EtOH 5:1; ii. DCE/EtOH/conc. aq. NH₄OH soln. 5:1:0.06) with the residue.

b) Synthesis of 3-(3-chlorophenyl)-N-(2-(ethyl(thiazol-2-yl)amino)ethyl)-propiolamide 1.9 g (~2.28 mmol) of PS carbodiimide were added to a solution of 200 mg (1.17 mmol) of N¹-ethyl-N¹-(thiazol-2-yl)ethane-1,2-diamine and 316 mg (1.75 mmol) of (3-chlorophenyl)propiolic acid in DCM (30 ml). The mixture was then shaken for 1 h at RT, after which the resin was filtered out and rinsed with DCM and MeOH. The filtrate was evaporated under a vacuum and CC (chloroform) was carried out with the residue, 181 mg (0.54 mmol, 46%) of 3-(3-chlorophenyl)-N-(2-(ethyl(thiazol-2-yl)amino)ethyl)-propiolamide being obtained. MS [MH+] 334.1

Synthesis of Exemplary Compound 43

1-(3-(3-Chlorophenyl)propioloyl)-3-(methyl(5-fluorothiazol-2-yl)amino)azetidine

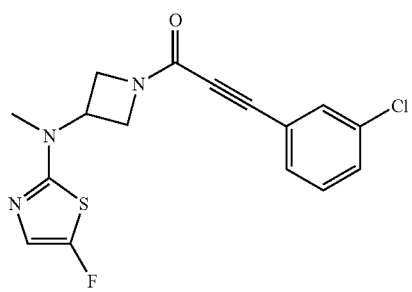

a) Synthesis of 1-Boc-3-(methyl(5-fluorothiazol-2-yl)amino)azetidine 7.5 ml (12.8 mmol, 1.7 M in hexane) of tert.-butyllithium were added dropwise at −50° C. within 30 min to a solution of 1.72 g (6.4 mmol) of 1-Boc-3-(methyl(thiazol-2-yl)amino)azetidine (synthesis described in Example 35) in THF (24 ml). After 30 min stirring at −50° C., a solution of 2.1 g (6.7 mmol) of N-fluorobenzenesulfonimide in THF (6 ml) was added dropwise within 30 min. Once the reaction solution had warmed up to 10° C., a 10% strength aq. ammonium chloride soln. was added and stirring continued for a further 15 min at RT. The phases were then separated and the aqueous phase was repeatedly extracted with ether. The collected organic phases were dried over MgSO₄, filtered and evaporated under a vacuum. CC (hexane/EA 3:2) was carried out with the residue, 170 mg (0.59 mmol, 9%) of 1-Boc-3-(methyl(5-fluorothiazol-2-yl)amino)azetidine being obtained.

b) Synthesis of 3-(methyl(5-fluorothiazol-2-yl)amino)azetidine trifluoroacetate A solution of 170 mg (0.59 mmol) of 1-Boc-3-(methyl(5-fluorothiazol-2-yl)amino)-azetidine in DCM (5 ml) was combined with 2.5 ml of TFA and stirred for 1 h at RT. The mixture was then evaporated under a vacuum, 145 mg (0.48 mmol, 82%) of 3-(methyl(5-fluorothiazol-2-yl)amino)azetidine trifluoroacetate being obtained which were further reacted without being purified.

c) Synthesis of 1-(3-(3-chlorophenyl)propioloyl)-3-(methyl(5-fluorothiazol-2-yl)amino)azetidine 0.76 g (~0.9 mmol) of PS carbodiimide were added to a solution of 135 mg (0.45 mmol) of 3-(methyl(5-fluorothiazol-2-yl)amino)azetidine trifluoroacetate, 69 μl (0.5 mmol) of triethylamine and 121 mg (0.67 mmol) of (3-chlorophenyl)propiolic acid in DCM (15 ml). The mixture was then shaken for 1 h at RT, after which the resin was filtered out and rinsed with DCM and MeOH. The filtrate was evaporated under a vacuum and CC (hexane/EA 3:2) was carried out with the residue, 60 mg (0.17 mmol, 38%) of 1-(3-(3-chlorophenyl)propioloyl)-3-(methyl(5-fluorothiazol-2-yl)amino)azetidine being obtained. MS [MH+] 350.0

Synthesis of Exemplary Compound 44

1-(3-(3-Chlorophenyl)propioloyl)-3-(methyl(5-fluorothiazol-2-yl)amino)pyrrolidine

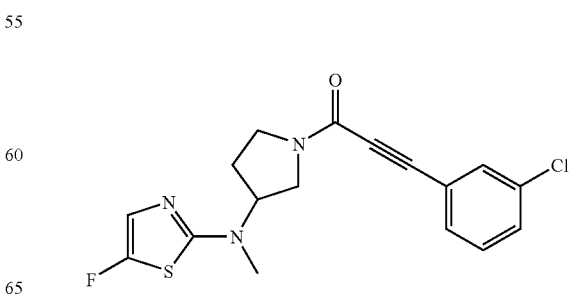

a) Synthesis of tert.-butyl 3-(methyl(thiazol-2-yl)amino)pyrrolidine-1-carboxylate A solution of 8.73 g (32.4 mmol) of tert.-butyl 3-(thiazol-2-ylamino)pyrrolidine-1-carboxylate (synthesis described in Example 11) in MeCN (120 ml) was combined with 1.56 g (38.9 mmol, 60% strength in mineral oil) of sodium hydride and stirred for 30 min at RT. 4.04 ml (64.8 mmol) of iodomethane were then added and stirring was continued for a further 3 h at RT. After addition of a conc. aq. NH$_4$OH soln. (30 ml), the phases were separated and the aqueous phase was extracted with EA. The collected organic phases were dried over MgSO$_4$, filtered and evaporated under a vacuum. 3.16 g (11.2 mmol, 34%) of tert.-butyl 3-(methyl(thiazol-2-yl)amino)pyrrolidine-1-carboxylate were obtained by CC (chloroform/EA 20:1) with the residue.

b) Synthesis of tert.-butyl 3-((5-fluorothiazol-2-yl)(methyl)amino)pyrrolidine-1-carboxylate 5.3 ml (7.8 mmol, 1.7 M in hexane) of tert.-butyllithium were added dropwise at −50° C. within 30 min to a solution of 1.70 g (6.0 mmol) of tert.-butyl 3-(methyl(thiazol-2-yl)amino)-pyrrolidine-1-carboxylate in THF (24 ml). After 30 min stirring at −50° C., a solution of 2.0 g (6.3 mmol) of N-fluorobenzenesulfonimide in THF (6 ml) was added dropwise within 20 min. Once the reaction solution had warmed up to 10° C., a 10% strength aq. ammonium chloride soln. was added and stirring continued for a further 15 min at RT. The phases were then separated and the aqueous phase was repeatedly extracted with ether. The collected organic phases were dried over MgSO$_4$, filtered and evaporated under a vacuum. CC (hexane/EA 4:1) was carried out with the residue, 590 mg (2.0 mmol, 33%) of tert.-butyl 3-((5-fluorothiazol-2-yl)(methyl)amino)pyrrolidine-1-carboxylate being obtained.

c) Synthesis of 5-fluoro-N-methyl-N-(pyrrolidin-3-yl)thiazol-2-amine trifluoroacetate A solution of 590 mg (1.96 mmol) tert.-butyl 3-((5-fluorothiazol-2-yl)(methyl)amino)-pyrrolidine-1-carboxylate in DCM (10 ml) was combined with 5 ml of TFA and stirred for 1 h at RT. The mixture was then evaporated under a vacuum, redissolved with MeOH and again evaporated, 611 mg (1.94 mmol, 99%) of 5-fluoro-N-methyl-N-(pyrrolidin-3-yl)thiazol-2-amine trifluoroacetate being obtained which were further reacted without being purified.

d) Synthesis of 1-(3-(3-chlorophenyl)propioloyl)-3-(methyl(5-fluorothiazol-2-yl)amino)pyrrolidine A solution of 611 mg (1.94 mmol) of 5-fluoro-N-methyl-N-(pyrrolidin-3-yl)thiazol-2-amine trifluoroacetate in DCM (50 ml) was combined with brine (10 ml) and a 5% strength aq. NaOH soln and stirred for 1 h at RT. The phases were then separated and the organic phase was dried over MgSO$_4$ and filtered. 530 mg (2.94 mmol) of (3-chlorophenyl)-propiolic acid and 3.39 g (~4.1 mmol) of PS carbodiimide were added to the filtrate. The mixture was then shaken for 2 h at RT, after which the resin was filtered out and rinsed with DCM and MeOH. The filtrate was evaporated under a vacuum and CC (chloroform/EA 3:2) was carried out with the residue, 148 mg (0.41 mmol, 21%) of 1-(3-(3-chlorophenyl)propioloyl)-3-(methyl(5-fluorothiazol-2-yl)amino)pyrrolidine being obtained. MS [MH+] 364.1

Synthesis of Exemplary Compound 126

3-(3-Chlorophenyl)-N-(2-((5-fluorothiazol-2-yl)(methyl)amino)ethyl)propiolamide

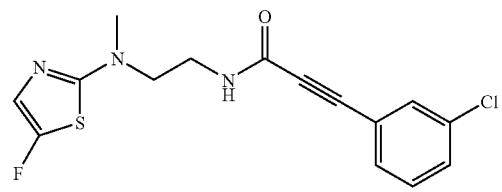

2.9 ml (7.3 mmol, 2.5 M in hexane) of n-BuLi were added dropwise at −78° C. to a solution of 540 mg (3.4 mmol) of N$^1$-methyl-N$^1$-(thiazol-2-yl)ethane-1,2-diamine (synthesis described in Example 19, section a)) in THF (20 ml). Stirring was then continued for 15 min at −40° C., after which the temperature was again lowered to −78° C. At this temperature, a solution of 754 mg (3.5 mmol) of 1,2-bis-(chlorodimethylsilyl)ethane in THF (12 ml) was added slowly. After warming up to RT, the reaction solution was stirred for a further 45 min, then cooled to −50° C. and combined dropwise with 3.0 ml (5.1 mmol, 1.7 M in hexane) of t-BuLi. After a further 30 min stirring at −50° C., a solution of 1.1 g (3.5 mmol) of N-fluorobenzenesulfonimide in THF (12 ml) was added dropwise at this temperature. Once addition was complete, the temperature was raised to RT, stirring continued for 60 min and the mixture quenched with a sat. ammonium chloride soln. (20 ml). The pH was then adjusted to 2 with 6N hydrochloric acid and the mixture stirred for 20 min at RT. The phases were separated and the aqueous phase was made basic an aq. NH$_3$ soln. and extracted with DCM.

This organic phase was dried over MgSO$_4$ and filtered. 921 mg (5.1 mmol) of (3-chlorophenyl)propiolic acid and 5.54 g of PS carbodiimide were added to the filtrate and the reaction solution was stirred for 60 min at RT, after which filtration was carried out and the filtrate evaporated under a vacuum. CC (DCE/EtOH 100:1) was carried out with the residue, 108 mg of 3-(3-chlorophenyl)-N-(2-((5-fluorothiazol-2-yl)(methyl)amino)-ethyl)propiolamide being obtained. MS [MH+] 338.0.

Exemplary compounds 32 3-(3-chlorophenyl)-N-(1-(thiazol-2-yl)piperidin-3-yl)-propiolamide MS [MH+] 346.1, 33 N-(2-((4-bromothiazol-2-yl)(methyl)amino)ethyl)-3-(3-chlorophenyl)propiolamide, MS [MH+] 398.0, 34 methyl 2-((2-(3-(3-chlorophenyl)-propiolamido)ethyl)(methyl)amino)thiazole-5-carboxylate, MS [MH+] 378.1, 37 3-(3-chlorophenyl)-N-(2-((4-chlorothiazol-2-yl)(methyl)amino)ethyl)propiolamide MS [MH+] 354.0, 38 3-(3-chlorophenyl)-N-(2-((5-chlorothiazol-2-yl)(methyl)amino)ethyl)-propiolamide MS [MH+] 354.0 and 42 3-(3-chlorophenyl)-N-(2-((5-cyanothiazol-2-yl)(methyl)amino)ethyl)propiolamide MS [MH+] 345.0 were synthesised by the method described above for exemplary compound 31.

Exemplary compound 39 3-(3-chlorophenyl)-N-(1-(thiazol-2-yl)azetidin-3-yl)-propiolamide MS [MH+] 318.0 was synthesised by the method described above for exemplary compound 1.

Exemplary compound 40 3-(3-chlorophenyl)-N-methyl-N-(1-(thiazol-2-yl)azetidin-3-yl)-propiolamide MS [MH+] 332.1 was produced by the method described above for exemplary compound 2.

General Synthesis Method for the Reaction of Primary and Secondary Amines of the General Formula IV with Aromatically Substituted Propiolic Acids of the General Formula R$^9$—C≡C—C(=O)—OH A solution of CDI (105 µmol, 1.05 equivalents) in DCM (1.05 ml) was added to a solution of the respective aromatically substituted propiolic acid of the general formula R$^9$—C≡C—C(=O)—OH (100 µmol) in DCM (2 ml). The reaction solution was stirred for 1 h at 20° C. and then combined with a solution of the respective primary or secondary amine of the general formula IV (100 µmol, 1.0 equivalent) in DCM (1 ml) after which stirring was performed for a further 16 h at RT. The reaction mixture was then combined with water (3 ml) and the phases were separated. The organic phase was washed with water (3 ml) and with brine (3 ml), dried over MgSO$_4$ and filtered. After removal of the solvent under a vacuum the respective target compound was isolated from the residue by means of preparative HPLC.

Synthesis of Examples 45 to 123 (Table 1) was carried out using the described general method for reacting primary and secondary amines with aromatically substituted propiolic acids. Analysis was carried out by HPLC-MS, purity in all cases being >85%. It is apparent to a person skilled in the art which starting compounds and intermediates were used in each case.

TABLE 1

| Ex. | Name | [MH+] |
|---|---|---|
| [45] | N-(1-(4-methylthiazol-2-yl)pyrrolidin-3-yl)-3-phenylpropiolamide | 312.1 |
| [46] | 3-(3-methoxyphenyl)-N-(1-(4-methylthiazol-2-yl)pyrrolidin-3-yl)-propiolamide | 342.1 |
| [47] | 3-(2-methoxyphenyl)-N-(1-(4-methylthiazol-2-yl)pyrrolidin-3-yl)-propiolamide | 342.1 |
| [48] | 3-(4-methoxyphenyl)-N-(1-(4-methylthiazol-2-yl)pyrrolidin-3-yl)-propiolamide | 342.1 |
| [49] | 3-(4-fluorophenyl)-N-(1-(4-methylthiazol-2-yl)pyrrolidin-3-yl)-propiolamide | 330.1 |
| [50] | N-(1-(4-methylthiazol-2-yl)pyrrolidin-3-yl)-3-p-tolylpropiolamide | 326.1 |
| [51] | N-(1-(4,5-dimethylthiazol-2-yl)pyrrolidin-3-yl)-3-phenylpropiolamide | 326.1 |
| [52] | N-(1-(4,5-dimethylthiazol-2-yl)pyrrolidin-3-yl)-3-(4-methoxyphenyl)-propiolamide | 356.1 |
| [53] | N-(1-(4,5-dimethylthiazol-2-yl)pyrrolidin-3-yl)-3-(4-fluorophenyl)-propiolamide | 344.1 |
| [54] | N-(1-(4,5-dimethylthiazol-2-yl)pyrrolidin-3-yl)-3-(2-methoxyphenyl)-propiolamide | 356.1 |
| [55] | N-(1-(4-tert.-butylthiazol-2-yl)pyrrolidin-3-yl)-3-(4-methoxyphenyl)-propiolamide | 384.2 |
| [56] | N-(1-(4-tert.-butylthiazol-2-yl)pyrrolidin-3-yl)-3-p-tolylpropiolamide | 368.2 |
| [57] | N-(1-(4-tert.-butylthiazol-2-yl)pyrrolidin-3-yl)-3-(4-fluorophenyl)-propiolamide | 372.1 |
| [58] | N-(1-(4-tert.-butylthiazol-2-yl)pyrrolidin-3-yl)-3-o-tolylpropiolamide | 368.2 |
| [59] | N-(1-(4-tert.-butylthiazol-2-yl)pyrrolidin-3-yl)-3-(3-fluorophenyl)-propiolamide | 372.1 |
| [60] | N-(1-(4-tert.-butylthiazol-2-yl)pyrrolidin-3-yl)-3-phenylpropiolamide | 354.2 |
| [61] | N-(1-(4-tert.-butylthiazol-2-yl)pyrrolidin-3-yl)-3-(2-fluorophenyl)-propiolamide | 372.1 |
| [62] | N-(1-(4-tert.-butylthiazol-2-yl)pyrrolidin-3-yl)-3-(3-methoxyphenyl)-propiolamide | 384.2 |
| [63] | N-(1-(4-tert.-butylthiazol-2-yl)pyrrolidin-3-yl)-3-(3-fluoro-4-methylphenyl)propiolamide | 386.2 |
| [64] | N-(1-(4-tert.-butylthiazol-2-yl)pyrrolidin-3-yl)-3-(2-methoxyphenyl)-propiolamide | 384.2 |
| [65] | N-(1-(4-methylthiazol-2-yl)pyrrolidin-3-yl)-3-(4-(trifluoromethyl)phenyl)-propiolamide | 380.1 |
| [66] | N-(1-(4-methylthiazol-2-yl)pyrrolidin-3-yl)-3-o-tolylpropiolamide | 326.1 |
| [67] | 3-(3-fluorophenyl)-N-(1-(4-methylthiazol-2-yl)pyrrolidin-3-yl)-propiolamide | 330.1 |
| [68] | 3-(3-fluoro-4-methylphenyl)-N-(1-(4-methylthiazol-2-yl)pyrrolidin-3-yl)-propiolamide | 344.1 |
| [69] | 3-(2,4-difluorophenyl)-N-(1-(4-methylthiazol-2-yl)pyrrolidin-3-yl)-propiolamide | 348.1 |
| [70] | 3-(2-fluorophenyl)-N-(1-(4-methylthiazol-2-yl)pyrrolidin-3-yl)-propiolamide | 330.1 |
| [71] | N-(1-(4-methylthiazol-2-yl)pyrrolidin-3-yl)-3-(3-(trifluoromethyl)phenyl)-propiolamide | 380.1 |
| [72] | N-(1-(4-methylthiazol-2-yl)pyrrolidin-3-yl)-3-m-tolylpropiolamide | 326.1 |
| [73] | N-(1-(5-methylthiazol-2-yl)pyrrolidin-3-yl)-3-p-tolylpropiolamide | 326.1 |
| [74] | N-(1-(5-methylthiazol-2-yl)pyrrolidin-3-yl)-3-m-tolylpropiolamide | 326.1 |
| [75] | 3-(2-methoxyphenyl)-N-(1-(5-methylthiazol-2-yl)pyrrolidin-3-yl)-propiolamide | 342.1 |
| [76] | N-(1-(5-methylthiazol-2-yl)pyrrolidin-3-yl)-3-phenylpropiolamide | 312.1 |
| [77] | 3-(2-fluorophenyl)-N-(1-(5-methylthiazol-2-yl)pyrrolidin-3-yl)-propiolamide | 330.1 |

TABLE 1-continued

| Ex. | Name | [MH+] |
|---|---|---|
| [78] | 3-(3-methoxyphenyl)-N-(1-(5-methylthiazol-2-yl)pyrrolidin-3-yl)-propiolamide | 342.1 |
| [79] | N-(1-(4,5-dimethylthiazol-2-yl)pyrrolidin-3-yl)-3-(3-fluoro-4-methylphenyl)propiolamide | 358.1 |
| [80] | N-(1-(4,5-dimethylthiazol-2-yl)pyrrolidin-3-yl)-3-o-tolylpropiolamide | 340.1 |
| [81] | 3-(3-fluorophenyl)-N-(1-(5-methylthiazol-2-yl)pyrrolidin-3-yl)-propiolamide | 330.1 |
| [82] | N-(1-(4,5-dimethylthiazol-2-yl)pyrrolidin-3-yl)-3-m-tolylpropiolamide | 340.1 |
| [83] | N-(1-(5-methylthiazol-2-yl)pyrrolidin-3-yl)-3-o-tolylpropiolamide | 326.1 |
| [84] | N-(1-(4,5-dimethylthiazol-2-yl)pyrrolidin-3-yl)-3-p-tolylpropiolamide | 340.1 |
| [85] | N-(1-(4,5-dimethylthiazol-2-yl)pyrrolidin-3-yl)-3-(3-(trifluoromethyl)-phenyl)propiolamide | 394.1 |
| [86] | 3-(4-methoxyphenyl)-N-(1-(5-methylthiazol-2-yl)pyrrolidin-3-yl)-propiolamide | 342.1 |
| [87] | N-(1-(5-methylthiazol-2-yl)pyrrolidin-3-yl)-3-(3-(trifluoromethyl)phenyl)-propiolamide, | 380.1 |
| [88] | N-(1-(4,5-dimethylthiazol-2-yl)pyrrolidin-3-yl)-3-(4-(trifluoromethyl)-phenyl)propiolamide | 394.1 |
| [89] | 3-(4-fluorophenyl)-N-(1-(5-methylthiazol-2-yl)pyrrolidin-3-yl)-propiolamide | 330.1 |
| [90] | N-(1-(4,5-dimethylthiazol-2-yl)pyrrolidin-3-yl)-3-(3-methoxyphenyl)-propiolamide | 356.1 |
| [91] | 3-(2,4-difluorophenyl)-N-(1-(4,5-dimethylthiazol-2-yl)pyrrolidin-3-yl)-propiolamide | 362.1 |
| [92] | N-(1-(4,5-dimethylthiazol-2-yl)pyrrolidin-3-yl)-3-(2-fluorophenyl)-propiolamide | 344.1 |
| [93] | N-(1-(5-methylthiazol-2-yl)pyrrolidin-3-yl)-3-(4-(trifluoromethyl)phenyl)-propiolamide | 380.1 |
| [94] | 3-(3-fluoro-4-methylphenyl)-N-(1-(5-methylthiazol-2-yl)pyrrolidin-3-yl)-propiolamide | 344.1 |
| [95] | 3-(2,4-difluorophenyl)-N-(1-(5-methylthiazol-2-yl)pyrrolidin-3-yl)-propiolamide | 348.1 |
| [96] | N-(1-(4-tert.-butylthiazol-2-yl)pyrrolidin-3-yl)-3-(2,4-difluorophenyl)-propiolamide | 390.1 |
| [97] | N-(1-(4-tert.-butylthiazol-2-yl)pyrrolidin-3-yl)-3-(4-(trifluoromethyl)-phenyl)propiolamide | 422.1 |
| [98] | N-(1-(4-tert.-butylthiazol-2-yl)pyrrolidin-3-yl)-3-(3-(trifluoromethyl)-phenyl)propiolamide | 422.1 |
| [99] | N-(1-(4-tert.-butylthiazol-2-yl)pyrrolidin-3-yl)-3-m-tolylpropiolamide | 368.2 |
| [100] | N-(1-(4-tert.-butylthiazol-2-yl)pyrrolidin-3-yl)-3-(3-chlorophenyl)-propiolamide | 388.1 |
| [101] | N-(1-(4-tert.-butylthiazol-2-yl)pyrrolidin-3-yl)-3-(thiophen-2-yl)-propiolamide | 360.1 |
| [102] | N-(1-(4-tert.-butylthiazol-2-yl)pyrrolidin-3-yl)-3-(2,4-dichlorophenyl)-propiolamide, | 422.1 |
| [103] | N-(1-(4-tert.-butylthiazol-2-yl)pyrrolidin-3-yl)-3-(2-chloro-5-(trifluoro-methyl)phenyl)propiolamide | 456.1 |
| [104] | N-(1-(4-tert.-butylthiazol-2-yl)pyrrolidin-3-yl)-3-(3,5-dichlorophenyl)-propiolamide | 422.1 |
| [105] | 3-(3-chlorophenyl)-N-(1-(4-methylthiazol-2-yl)pyrrolidin-3-yl)-propiolamide | 346.1 |
| [106] | N-(1-(4-methylthiazol-2-yl)pyrrolidin-3-yl)-3-(thiophen-2-yl)propiolamide | 318.1 |
| [107] | 3-(2,4-dichlorophenyl)-N-(1-(4-methylthiazol-2-yl)pyrrolidin-3-yl)-propiolamide | 380.0 |
| [108] | 3-(2-chloro-5-(trifluoromethyl)phenyl)-N-(1-(4-methylthiazol-2-yl)pyrrolidin-3-yl)propiolamide | 414.1 |
| [109] | 3-(3,5-dichlorophenyl)-N-(1-(4-methylthiazol-2-yl)pyrrolidin-3-yl)-propiolamide | 380.0 |
| [110] | 3-(3-chlorophenyl)-N-(1-(4,5-dimethylthiazol-2-yl)pyrrolidin-3-yl)-propiolamide | 360.1 |
| [111] | 3-(2,4-dichlorophenyl)-N-(1-(4,5-dimethylthiazol-2-yl)pyrrolidin-3-yl)-propiolamide | 394.0 |
| [112] | 3-(3-chlorophenyl)-N-(1-(5-methylthiazol-2-yl)pyrrolidin-3-yl)-propiolamide | 346.1 |
| [113] | N-(1-(5-methylthiazol-2-yl)pyrrolidin-3-yl)-3-(thiophen-2-yl)propiolamide | 318.1 |
| [114] | 3-(2,4-dichlorophenyl)-N-(1-(5-methylthiazol-2-yl)pyrrolidin-3-yl)-propiolamide | 380.0 |
| [115] | 3-(2-chloro-5-(trifluoromethyl)phenyl)-N-(1-(5-methylthiazol-2-yl)pyrrolidin-3-yl)propiolamide | 414.1 |
| [116] | 3-(3,5-dichlorophenyl)-N-(1-(5-methylthiazol-2-yl)pyrrolidin-3-yl)-propiolamide | 380.0 |
| [117] | N-(1-(4,5-dimethylthiazol-2-yl)pyrrolidin-3-yl)-3-(thiophen-2-yl)-propiolamide | 332.1 |
| [118] | 3-(2-chloro-5-(trifluoromethyl)phenyl)-N-(1-(4,5-dimethylthiazol-2-yl)pyrrolidin-3-yl)propiolamide | 428.1 |
| [119] | N-(1-(5-methylthiazol-2-yl)pyrrolidin-3-yl)-3-(pyridin-2-yl)propiolamide | 313.1 |
| [120] | N-(1-(5-methylthiazol-2-yl)pyrrolidin-3-yl)-3-(pyridin-3-yl)propiolamide | 313.1 |

TABLE 1-continued

| Ex. | Name | [MH+] |
| --- | --- | --- |
| [121] | N-(1-(5-methylthiazol-2-yl)pyrrolidin-3-yl)-3-(pyridin-4-yl)propiolamide | 313.1 |
| [122] | N-(1-(4-tert.-butylthiazol-2-yl)pyrrolidin-3-yl)-3-(pyridin-2-yl)-propiolamide | 355.2 |
| [123] | N-(1-(4-tert.-butylthiazol-2-yl)pyrrolidin-3-yl)-3-(pyridin-3-yl)-propiolamide | 355.2 |
| [126] | 3-(3-chlorophenyl)-N-(2-((5-fluorothiazol-2-yl)(methyl)amino)ethyl)-propiolamide | 338.0 |

Pharmacological Data:

1. The affinity of the substituted thiazoles according to the invention of the general formula I for the mGluR5 receptor was determined as described above in pharmacological methods I. and II.

The substituted thiazoles according to the invention exhibit an excellent affinity for the mGluR5 receptor.

Table 2 below reproduces the pharmacological data for the substituted thiazoles:

TABLE 2

| Ex. | % inhibition mGluR5 receptor (pig) [$^3$H]-MPEP binding at 1 µM | %-inhibition mGluR5 receptor (pig) [$^3$H]-MPEP binding at 10 µM | $IC_{50}$ mGluR5 receptor (pig) [$^3$H]-MPEP-binding [µM] | $K_i$ mGluR5 receptor (human) $Ca^{2+}$ influx [nM] |
| --- | --- | --- | --- | --- |
| 1 | | 66 | | |
| 2 | | | 1.3200 | |
| 3 | | | 0.5900 | |
| 4 | | | 0.0570 | 5.2 |
| 5 | | | 1.5800 | |
| 6 | | 57 | | |
| 7 | | | 0.0260 | 4.8 |
| 8 | | | 10.2100 | |
| 9 | | | 0.0380 | 1.0 |
| 10 | | | 1.8600 | |
| 11 | | | 2.1800 | |
| 12 | | 41 | | |
| 13 | | | 0.0870 | 20.8 |
| 14 | | | 4.9700 | |
| 15 | | | 0.0860 | 14.4 |
| 16 | | | 0.1400 | |
| 17 | | | 1.2500 | |
| 18 | | | 0.0200 | 4.9 |
| 19 | | | 0.0019 | 0.4 |
| 20 | | | 0.2800 | |
| 21 | | | 0.0083 | 0.8 |
| 22 | | | 0.3500 | |
| 23 | | | 0.0056 | |
| 24 | | | 2.7800 | |
| 25 | | | 0.1500 | |
| 26 | | | 0.0860 | 3.6 |
| 27 | | 19 | | |
| 28 | | | 1.1500 | |
| 29 | | | 0.0270 | |
| 30 | | | 0.0770 | |
| 31 | | | 0.0130 | |
| 32 | | | 0.0050 | 4.0 |
| 33 | | | 0.0130 | 10.0 |
| 34 | | | 0.0200 | |
| 35 | | | 0.0022 | 6.5 |
| 36 | | | 0.0220 | |
| 37 | | | 0.0095 | |
| 38 | | | 0.1600 | |
| 39 | | | 0.3900 | |
| 40 | | | 0.0170 | |
| 41 | | | 0.0041 | |
| 42 | | | 0.2200 | |
| 43 | | | 0.0740 | |
| 44 | | | 0.0710 | |
| 45 | 59 | | | |
| 46 | 48 | | | |
| 51 | 48 | | | |
| 55 | 26 | | | |
| 56 | 37 | | | |
| 57 | 26 | | | |
| 59 | 34 | | | |

TABLE 2-continued

| Ex. | % inhibition mGluR5 receptor (pig) [³H]-MPEP binding at 1 μM | %-inhibition mGluR5 receptor (pig) [³H]-MPEP binding at 10 μM | IC$_{50}$ mGluR5 receptor (pig) [³H]-MPEP-binding [μM] | K$_i$ mGluR5 receptor (human) Ca$^{2+}$ influx [nM] |
|---|---|---|---|---|
| 60 | 30 | | | |
| 61 | 28 | | | |
| 67 | 76 | | | |
| 70 | 50 | | | |
| 71 | 59 | | | |
| 72 | 87 | | | |
| 73 | 18 | | | |
| 74 | 89 | | | |
| 76 | 56 | | | |
| 77 | 21 | | | |
| 78 | 26 | | | |
| 81 | 57 | | | |
| 82 | 81 | | | |
| 85 | 41 | | | |
| 87 | 23 | | | |
| 90 | 34 | | | |
| 99 | 46 | | | |
| 100 | 38 | | | |
| 105 | | 83 | | |
| 106 | | 38 | | |
| 110 | | 63 | | |
| 112 | 24 | | | |
| 113 | | 22 | | |
| 119 | | 20 | | |
| 123 | 20 | | | |
| 126 | | | 0.0160 | |

2. The substituted thiazoles of the general formula I according to the invention likewise exhibit an excellent action in the formaldehyde test in rats, as demonstrated by Example 23 N-(2-(methyl(thiazol-2-yl)amino)ethyl)-3-(3-chlorophenyl)-propiolamide hydrochloride with an ED$_{50}$ value of 1.0 mg/kg after i.v. administration. After oral administration of 10 mg/kg, this compound exhibits inhibition of 38% in the formaldehyde test.

The invention claimed is:
1. A substituted thiazole of the formula I,

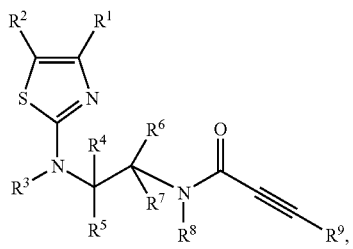

I in which

R$^1$ and R$^2$, mutually independently, in each case denote H; F; Cl; Br; I; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —O—C(=O)—R$^{60}$; —NH—C(=O)—R$^{61}$; —NR$^{62}$—C(=O)—R$^{63}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=S)—NH—R$^{72}$; —NH—S(=O)$_2$—R$^{73}$; —NR$^{74}$—S(=O)$_2$—R$^{75}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

or R$^1$ and R$^2$ together with the carbon atoms joining them form an unsubstituted or at least monosubstituted phenylene residue;

R$^3$, R$^8$ and R$^{54}$, mutually independently, in each case denote H; —C(=O)—R$^{58}$; —C(=O)—O—R$^{59}$; —C(=O)—NH$_2$; —C(=O)—NH—R$^{64}$; —C(=O)—NR$^{65}$R$^{66}$; —S(=O)—R$^{69}$; —S(=O)$_2$—R$^{70}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^4, R^5, R^6, R^7, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}, R^{46}, R^{47}, R^{48}, R^{49}, R^{50}, R^{51}, R^{52}$ and $R^{53}$, mutually independently, in each case denote H; F; Cl; Br; I; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —O—C(=O)—R$^{60}$; —NH—C(=O)—R$^{61}$; —NR$^{62}$—C(=O)—R$^{63}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=S)—NH—R$^{72}$; —NH—S(=O)$_2$—R$^{73}$; —NR$^{74}$—S(=O)$_2$—R$^{75}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

or $R^4$ and $R^5$ or $R^6$ and $R^7$ or $R^{10}$ and $R^{11}$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{30}$ and $R^{31}$ or $R^{32}$ and $R^{33}$ or $R^{34}$ and $R^{35}$ or $R^{36}$ and $R^{37}$ or $R^{38}$ and $R^{39}$ or $R^{40}$ and $R^{41}$ or $R^{42}$ and $R^{43}$ or $R^{44}$ and $R^{45}$ or $R^{46}$ and $R^{47}$ or $R^{48}$ and $R^{49}$ or $R^{50}$ and $R^{51}$ or $R^{52}$ and $R^{53}$, mutually independently, together in each case denote a residue selected from the group consisting of an oxo group (=O) and a thioxo group (=S);

or $R^3$ and $R^4$ together with the —N—CR$^5$ group joining them form a residue of the formula A,

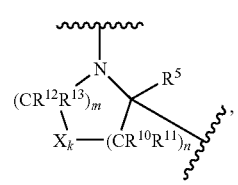

A or $R^6$ and $R^8$ together with the —N—CR$^7$ group joining them form a residue of the formula B,

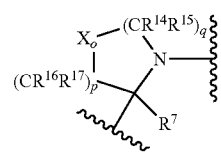

B m and q in each case denote 1, 2, 3, 4 or 5;
n and p in each case denote 0, 1, 2, 3 or 4;
k and o in each case denote 0 or 1;
wherein the sum of m, n and k or the sum of p, q and o is in each case equal to 1, 2, 3, 4, 5 or 6;
or $R^3$ and $R^6$ together with the —N—CR$^4$R$^5$—CR$^7$ group joining them form a residue of the formula C,

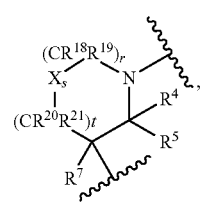

C or $R^4$ and $R^8$ together with the —CR$^5$—CR$^6$R$^7$—N group joining them form a residue of the formula D,

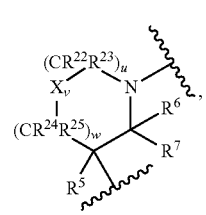

D r and u in each case denote 1, 2, 3 or 4;
t and w in each case denote 0, 1, 2 or 3;
s and v in each case denote 0 or 1;

wherein the sum of r, s and t or the sum of u, v and w is in each case equal to 1, 2, 3, 4 or 5;

or $R^3$ and $R^8$ together with the —N—$CR^4R^5$—$CR^6R^7$—N group joining them form a residue of the formula E,

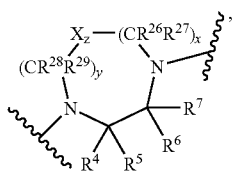

E x and y in each case denote 1 or 2;
z denotes 0 or 1;
wherein the sum of x, y and z is equal to 3 or 4;
or $R^4$ and $R^6$ together with the —$CR^5$—$CR^7$ group joining them form a residue of the formula F,

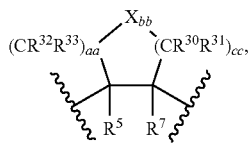

F aa and cc, mutually independently, in each case denote 1, 2, 3, 4 or 5;
bb denotes 0 or 1;
wherein the sum of aa, bb and cc is equal to 1, 2, 3, 4, 5 or 6;
or $R^3$ and $R^4$ together with the —N—$CR^5$ group joining them and $R^6$ and $R^8$ together with the —N—$CR^7$ group joining them form a residue of the formula G,

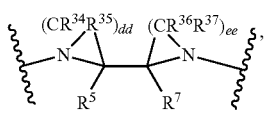

G dd and ee, mutually independently, in each case denote 1, 2, 3 or 4;
or $R^3$ and $R^6$ together with the —N—$CR^4CR^5$—$CR^7$ group joining them and $R^4$ and $R^8$ together with the —$CR^5$—$CR^6R^7$—N group joining them form a residue of the formula H,

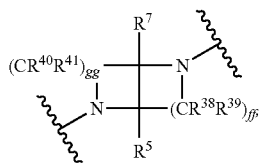

H ff and gg, mutually independently, in each case denote 1, 2 or 3;
or $R^3$ and $R^8$ together with the —N—$CR^4R^5$—$CR^6R^7$—N group joining them and $R^4$ and $R^6$ together with the —$CR^5$—$CR^7$ group joining them form a residue of the formula K,

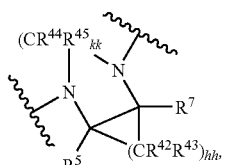

K hh denotes 1, 2, 3 or 4;
kk denotes 1, 2, 3, 4, 5 or 6;
or $R^3$ and $R^8$ together with the —N—$CR^4R^5$—$CR^6R^7$—N group joining them form a bicyclic residue of the formula L,

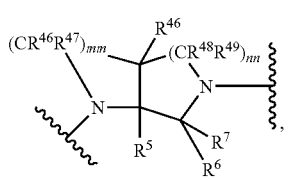

L mm denotes 1, 2 or 3;
nn denotes 1 or 2;
or $R^3$ and $R^8$ together with the —N—$CR^4R^5$—$CR^6R^7$—N group joining them form a bicyclic residue of the formula M,

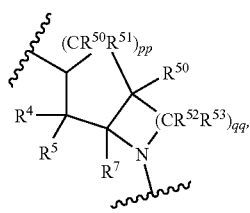

M pp denotes 1 or 2;
qq denotes 1, 2 or 3;
X denotes O, S or N—$R^{54}$;
$R^9$ denotes H; F; Cl; Br; I; —CN; —C(=O)—OH; —C(=O)—H; —C(=O)—$R^{58}$; —C(=O)—O—$R^{59}$; —C(=O)—$NH_2$; —C(=O)—NH—$R^{64}$; —C(=O)—$NR^{65}R^{66}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkynylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

and $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$ and $R^{75}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

in each case optionally in the form of one of the pure stereoisomers thereof, the racemate thereof or in the form of a mixture of stereoisomers in any desired mixing ratio, or in each case in the form of a corresponding salt.

2. A compound according to claim 1, wherein $R^1$ and $R^2$, mutually independently, in each case denote H; F; Cl; Br; I; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —O—C(=O)—R$^{60}$; —NH—C(=O)—R$^{61}$; —NR$^{62}$—C(=O)—R$^{63}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=S)—NH—R$^{72}$; —NH—S(=O)$_2$—R$^{73}$; —NR$^{74}$—S(=O)$_2$—R$^{75}$; unsubstituted or at least monosubstituted alkyl, alkenyl or alkynyl; unsubstituted or at least monosubstituted heteroalkyl, heteroalkenyl or heteroalkynyl; unsubstituted or at least monosubstituted cycloalkyl or cycloalkenyl; unsubstituted or at least monosubstituted heterocycloalkyl or heterocycloalkenyl; unsubstituted or at least monosubstituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or at least monosubstituted-(heteroalkylene)-cycloalkyl, -(heteroalkenylene)-cycloalkyl, -(heteroalkylene)-cycloalkenyl or -(heteroalkenylene)-cycloalkenyl; unsubstituted or at least monosubstituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or at least monosubstituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or at least monosubstituted aryl; unsubstituted or at least monosubstituted heteroaryl; unsubstituted or at least monosubstituted-(alkylene)-aryl, -(alkenylene)-aryl, -(alkynylene)-aryl, -(heteroalkylene)-aryl or -(heteroalkenylene)-aryl; or unsubstituted or at least monosubstituted-(alkylene)-heteroaryl, -(alkenylene)-heteroaryl, -(alkynylene)-heteroaryl, -(heteroalkylene)-heteroaryl or -(heteroalkenylene)-heteroaryl;

or $R^1$ and $R^2$ together with the carbon atoms joining them form an unsubstituted or at least monosubstituted phenylene residue;

$R^3$, $R^8$ and $R^{54}$, mutually independently, in each case denote H; —C(=O)—R$^{58}$; —C(=O)—O—R$^{59}$; —C(=O)—NH$_2$; —C(=O)—NH—R$^{64}$; —C(=O)—NR$^{65}$R$^{66}$; —S(=O)—R$^{69}$; —S(=O)$_2$—R$^{70}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

$R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$, mutually independently, in each case denote H; F; Cl; Br; I; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —O—C(=O)—R$^{60}$; —NH—C(=O)—R$^{61}$; —NR$^{62}$—C(=O)—R$^{63}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—

$R^{70}$; —NH—C(=O)—NH—$R^{71}$; —NH—C(=S)—NH—$R^{72}$; —NH—S(=O)$_2$—$R^{73}$; —N$R^{74}$—S(=O)$_2$—$R^{75}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted-(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted-(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

or $R^4$ and $R^5$ or $R^6$ and $R^7$ or $R^{10}$ and $R^{11}$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{30}$ and $R^{31}$ or $R^{32}$ and $R^{33}$ or $R^{34}$ and $R^{35}$ or $R^{36}$ and $R^{37}$ or $R^{38}$ and $R^{39}$ or $R^{40}$ and $R^{41}$ or $R^{42}$ and $R^{43}$ or $R^{44}$ and $R^{45}$ or $R^{46}$ and $R^{47}$ or $R^{48}$ and $R^{49}$ or $R^{50}$ and $R^{51}$ or $R^{52}$ and $R^{53}$, mutually independently, together in each case denote a residue selected from the group consisting of an oxo group (=O) and a thioxo group (=S);

or $R^3$ and $R^4$ together with the —N—C$R^5$ group joining them form a residue of the formula A,

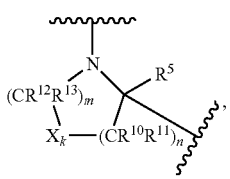

A or $R^6$ and $R^8$ together with the —N—C$R^7$ group joining them form a residue of the formula B,

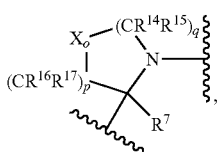

B m and q in each case denote 1, 2, 3, 4 or 5;
n and p in each case denote 0, 1, 2, 3 or 4;
k and o in each case denote 0 or 1;
wherein the sum of m, n and k or the sum of p, q and o is in each case equal to 1, 2, 3, 4, 5 or 6;

or $R^3$ and $R^6$ together with the —N—C$R^4R^5$—C$R^7$ group joining them form a residue of the formula C,

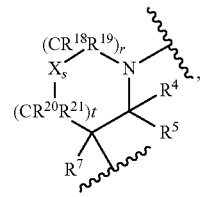

C or $R^4$ and $R^8$ together with the —C$R^5$—C$R^6R^7$—N group joining them form a residue of the formula D,

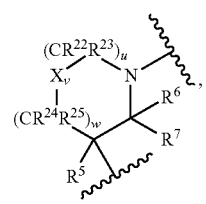

D r and u in each case denote 1, 2, 3 or 4;
t and w in each case denote 0, 1, 2 or 3;
s and v in each case denote 0 or 1;
wherein the sum of r, s and t or the sum of u, v and w is in each case equal to 1, 2, 3, 4 or 5;

or $R^3$ and $R^8$ together with the —N—C$R^4R^5$—C$R^6R^7$—N group joining them form a residue of the formula E,

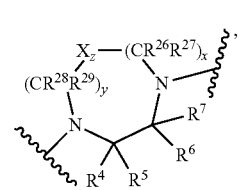

E x and y in each case denote 1 or 2;
z denotes 0 or 1;
wherein the sum of x, y and z is equal to 3 or 4;
or $R^4$ and $R^6$ together with the —C$R^5$—C$R^7$ group joining them form a residue of the formula F,

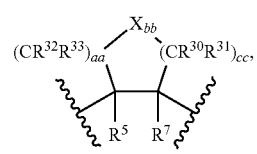

F aa and cc, mutually independently, in each case denote 1, 2, 3, 4 or 5;
bb denotes 0 or 1;
wherein the sum of aa, bb and cc is equal to 1, 2, 3, 4, 5 or 6;

or $R^3$ and $R^4$ together with the —N—$CR^5$ group joining them and $R^6$ and $R^8$ together with the —N—$CR^7$ group joining them form a residue of the formula G,

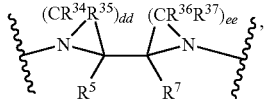

G dd and ee, mutually independently, in each case denote 1, 2, 3 or 4;

or $R^3$ and $R^6$ together with the —N—$CR^4R^5$—$CR^7$ group joining them and $R^4$ and $R^8$ together with the —$CR^5$—$CR^6R^7$—N group joining them form a residue of the formula H,

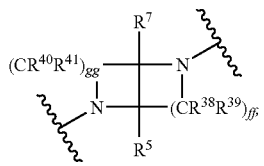

H ff and gg, mutually independently, in each case denote 1, 2 or 3;

or $R^3$ and $R^8$ together with the —N—$CR^4R^5$—$CR^6R^7$—N group joining them and $R^4$ and $R^6$ together with the —$CR^5$—$CR^7$ group joining them form a residue of the formula K,

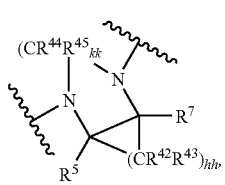

K hh denotes 1, 2, 3 or 4;
kk denotes 1, 2, 3, 4, 5 or 6;
or $R^3$ and $R^8$ together with the —N—$CR^4R^5$—$CR^6R^7$—N group joining them form a bicyclic residue of the formula L,

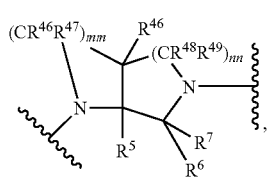

L mm denotes 1, 2 or 3;
nn denotes 1 or 2;

or $R^3$ and $R^8$ together with the —N—$CR^4R^5$—$CR^6R^7$—N group joining them form a bicyclic residue of the formula M,

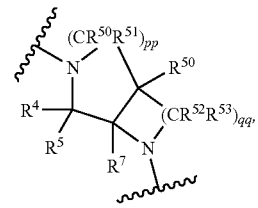

M pp denotes 1 or 2;
qq denotes 1, 2 or 3;
X denotes O, S or N—$R^{54}$;
$R^9$ denotes H; F; Cl; Br; I; —CN; —C(=O)—OH; —C(=O)—H; —C(=O)—$R^{58}$; —C(=O)—O—$R^{59}$; —C(=O)—$NH_2$; —C(=O)—NH—$R^{64}$; —C(=O)—$NR^{65}R^{66}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

and $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$ and $R^{75}$, mutually independently, in each case denote unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted-(heteroalkylene)-cycloalkyl, -(heteroalkenylene)-cycloalkyl, -(heteroalkylene)-cycloalkenyl or -(heteroalkenylene)-cycloalkenyl; unsubstituted or substituted-(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted-(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted-(alkylene)-heteroaryl, -(alkenylene)-heteroaryl, -(alkynylene)-heteroaryl, -(heteroalkylene)-heteroaryl or -(heteroalkenylene)-heteroaryl;

wherein the above-stated alkyl residues are in each case branched or straight-chain and have 1, 2, 3, 4, 5, 6, 7, 8, 9, 10, 11 or 12 carbon atoms as chain links;

the above-stated alkenyl residues are in each case branched or straight-chain and have 2, 3, 4, 5, 6, 7, 8, 9, 10, 11 or 12 carbon atoms as chain links;

the above-stated alkynyl residues are in each case branched or straight-chain and have 2, 3, 4, 5, 6, 7, 8, 9, 10, 11 or 12 carbon atoms as chain links;

the above-stated heteroalkyl residues, heteroalkenyl residues and heteroalkynyl residues are in each case 2-, 3-, 4-, 5-, 6-, 7-, 8-, 9-, 10-, 11- or 12-membered;

the above-stated heteroalkyl residues, heteroalkenyl residues and heteroalkynyl residues in each case optionally have 1, 2 or 3 heteroatom(s) mutually independently selected from the group consisting of oxygen, sulfur and nitrogen (NH) as chain link(s);

the above-stated alkyl residues, alkenyl residues, alkynyl residues, heteroalkyl residues, heteroalkenyl residues and heteroalkynyl residues may be substituted in each case with optionally 1, 2, 3, 4 or 5 substituents mutually independently selected from the group consisting of F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, wherein the phenyl residues may be substituted with 1, 2, 3, 4 or 5 substituents mutually independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert.-butyl;

the above-stated cycloalkyl residues in each case have 3, 4, 5, 6, 7, 8 or 9 carbon atoms as ring members;

the above-stated cycloalkenyl residues in each case have 3, 4, 5, 6, 7, 8 or 9 carbon atoms as ring members;

the above-stated heterocycloalkyl residues are in each case 3-, 4-, 5-, 6-, 7-, 8- or 9-membered;

the above-stated heterocycloalkenyl residues are in each case 4-, 5-, 6-, 7-, 8- or 9-membered;

the above-stated heterocycloalkyl residues and heterocycloalkenyl residues in each case optionally have 1, 2 or 3 heteroatom(s) mutually independently selected from the group consisting of oxygen, sulfur and nitrogen (NH) as ring member(s);

the above-stated cycloalkyl residues, heterocycloalkyl residues, cycloalkenyl residues or heterocycloalkenyl residues may be substituted in each case with optionally 1, 2, 3, 4 or 5 substituents mutually independently selected from the group consisting of F, Cl, Br, I, —CN, —OH, —$NH_2$, —O—$CF_3$, —SH, —O—$C_{1-5}$-alkyl, —O-phenyl, —O—$CH_2$-phenyl, —($CH_2$)—O—$C_{1-5}$-alkyl, —S—$C_{1-5}$-alkyl, —S-phenyl, —S—$CH_2$-phenyl, —$C_{1-5}$ alkyl, —$C_{2-5}$ alkenyl, —$C_{2-5}$ alkynyl, —C≡C—Si($CH_3$)$_3$, —C≡C—Si($C_2H_5$)$_3$, —C(=O)—O—$C_{1-5}$-alkyl, —C(=O)—$CF_3$, —S(=O)$_2$—$C_{1-5}$-alkyl, —S(=O)—$C_{1-5}$-alkyl, —S(=O)$_2$-phenyl, oxo (=O), thioxo (=S), —N($C_{1-5}$-alkyl)$_2$, —N(H)($C_{1-5}$-alkyl), —$NO_2$, —C(=O)—OH, —NH—S(=O)$_2$—$C_{1-5}$-alkyl, —NH—C(=O)—$C_{1-5}$-alkyl, —C(=O)—H, —C(=O)—$C_{1-5}$-alkyl, —C(=O)—$NH_2$, —C(=O)—N($C_{1-5}$-alkyl)$_2$, —C(=O)—N(H)(—$C_{1-5}$-alkyl) and phenyl, wherein the phenyl residues may in each case be unsubstituted or substituted with 1, 2, 3, 4 or 5 substituents mutually independently selected from the group consisting of F, Cl, Br, I, —CN, —OH, —$NH_2$, —O—$CF_3$, —SH, —O—$C_{1-5}$-alkyl, —O-phenyl, —O—$CH_2$-phenyl, —($CH_2$)—O—$C_{1-5}$-alkyl, —S—$C_{1-5}$-alkyl, —S-phenyl, —S—$CH_2$-phenyl, —$C_{1-5}$ alkyl, —$C_{2-5}$ alkenyl, —$C_{2-5}$ alkynyl, —C≡C—Si($CH_3$)$_3$, —C≡C—Si($C_2H_5$)$_3$, —C(=O)—O—$C_{1-5}$-alkyl and —C(=O)—$CF_3$, wherein the above-stated phenyl residues may preferably be substituted with 1, 2, 3, 4 or 5 substituents mutually independently selected from the group consisting of F, Cl, Br, I, —CN, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert.-butyl;

the above-stated alkylene residues are in each case branched or straight-chain and have 1, 2, 3, 4, 5, 6, 7, 8, 9, 10, 11 or 12 carbon atoms as chain links;

the above-stated alkenylene residues are in each case branched or straight-chain and have 2, 3, 4, 5, 6, 7, 8, 9, 10, 11 or 12 carbon atoms as chain links;

the above-stated alkynylene residues are in each case branched or straight-chain and have 2, 3, 4, 5, 6, 7, 8, 9, 10, 11 or 12 carbon atoms as chain links;

the above-stated heteroalkylene, heteroalkenylene and heteroalkynylene residues are in each case 2-, 3-, 4-, 5-, 6-, 7-, 8-, 9-, 10-, 11- or 12-membered;

the above-stated heteroalkylene, heteroalkenylene and heteroalkynylene groups may in each case optionally have 1, 2 or 3 heteroatom(s) mutually independently selected from the group consisting of oxygen, sulfur and nitrogen (NH) as chain link(s);

the above-stated alkylene, alkenylene, alkynylene, heteroalkylene or heteroalkenylene group may in each case be unsubstituted or substituted with optionally 1, 2, 3, 4 or 5 substituents mutually independently selected from the group consisting of phenyl, F, Cl, Br, I, —$NO_2$, —CN, —OH, —O-phenyl, —O—$CH_2$-phenyl, —SH, —S-phenyl, —S—$CH_2$-phenyl, —$NH_2$, —N($C_{1-5}$-alkyl)$_2$, —NH-phenyl, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, wherein the phenyl residues may be substituted with 1, 2, 3, 4 or 5 substituents mutually independently selected from the group consisting of F, Cl, Br, I, —CN, —$NO_2$, —OH, —SH, —$NH_2$, —C(=O)—OH, —$C_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the above-stated aryl residues are mono- or bicyclic and have 6, 10 or 14 carbon atoms;

the above-stated heteroaryl residues are mono-, di- or tricyclic and 5-, 6-, 7-, 8-, 9-, 10-, 11-, 12-, 13- or 14-membered;

the above-stated 5- to 14-membered heteroalkyl residues optionally have 1, 2, 3, 4 or 5 heteroatom(s) mutually independently selected from the group consisting of oxygen, sulfur and nitrogen (NH) as ring member(s);

and the above-stated phenylene residues, aryl residues or heteroaryl residues may optionally in each case be substituted with 1, 2, 3, 4 or 5 substituents mutually independently selected from the group consisting of F, Cl, Br, I, —CN, —NO$_2$, —OH, —SH, —NH$_2$, —C(=O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, NH—C$_{1-5}$ alkyl, N(C$_{1-5}$alkyl)$_2$, —C(=O)—O—C$_{1-5}$-alkyl, —C(=O)—H, —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiazolyl, thiadiazolyl, thiophenyl (thienyl), benzyl and phenethyl, wherein the cyclic substituents or the cyclic residues of these substituents themselves may be substituted with optionally 1, 2, 3, 4 or 5 substituents mutually independently selected from the group consisting of F, Cl, Br, I, —CN, —NO$_2$, —OH, —SH, —NH$_2$, —C(=O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CHF$_2$, —O—CH$_2$F, —C(=O)—CF$_3$, —S—CHF$_2$ and —S—CH$_2$F;

in each case optionally in the form of one of the pure stereoisomers thereof, the racemate thereof or in the form of a mixture of stereoisomers in any desired mixing ratio, or in each case in the form of a corresponding salt.

3. A compound according to claim 1, wherein

R$^1$ denotes H; F; Cl; Br; I; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —O—C(=O)—R$^{60}$; —NH—C(=O)—R$^{61}$; —NR$^{62}$—C(=O)—R$^{63}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=S)—NH—R$^{72}$; —NH—S(=O)$_2$—R$^{73}$; —NR$^{74}$—S(=O)$_2$—R$^{75}$; C$_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$ cycloalkyl, C$_{5-6}$ cycloalkenyl, 5- to 7-membered heterocycloalkyl or 5- to 7-membered heterocycloalkenyl, which may in each case be attached via a C$_{1-3}$ alkylene, C$_{2-3}$ alkenylene or C$_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denotes a residue selected from the group consisting of phenyl, naphthyl, anthracenyl, thienyl, furyl, pyridinyl, thiazolyl, thiadiazolyl, oxazolyl, oxadiazolyl and isoxazolyl, which may in each case be attached via a C$_{1-3}$ alkylene, C$_{2-3}$ alkenylene or C$_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

4. A compound according to claim 1, wherein

R$^2$ denotes H; F; Cl; Br; I; —NO$_2$; —CN; —NH$_2$; —OH; —SH; —C(=O)—OH; —NH—R$^{55}$; —NR$^{56}$R$^{57}$; —C(=O)—R$^{58}$; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; —NH—C(=O)—NH—R$^{71}$; —NH—C(=O)—NH—R$^{72}$; —NH—S(=O)$_2$—R$^{73}$; —NR$^{74}$—S(=O)$_2$—R$^{75}$; C$_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; C$_{3-7}$ cycloalkyl, C$_{5-6}$ cycloalkenyl, 5- to 7-membered heterocycloalkyl or 5- to 7-membered heterocycloalkenyl, which may in each case be attached via a C$_{1-3}$ alkylene, C$_{2-3}$ alkenylene or C$_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denotes a residue selected from the group consisting of phenyl, naphthyl, anthracenyl, thienyl, furyl, pyridinyl, thiazolyl, thiadiazolyl, oxazolyl, oxadiazolyl and isoxazolyl, which may in each case be attached via a C$_{1-3}$ alkylene, C$_{2-3}$ alkenylene or C$_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

5. A compound according to claim 1, wherein

R$^1$ and R$^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—C$_2$H$_5$, —O—C$_3$H$_7$, —CF$_3$, —CHF$_2$, —CH$_2$F and —O—CF$_3$.

6. A compound according to claim 1, wherein $R^3$, $R^8$ and $R^{54}$, mutually independently, in each case denote H; —C(=O)—$R^{67}$; —C(=O)—O—$R^{59}$; —C(=O)—NH$_2$; —C(=O)—NH—$R^{64}$; —C(=O)—NR$^{65}$R$^{66}$; —S(=O)—$R^{69}$; —S(=O)$_2$—$R^{70}$;

$C_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

$C_{3-8}$ cycloalkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

or denote a phenyl residue, which may in each case be attached via a $C_{1-3}$ alkylene, $C_{2-3}$ alkenylene or $C_{2-3}$ alkynylene group and/or is unsubstituted or substituted with 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$.

7. A compound according to claim 1, wherein $R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$, mutually independently, in each case denote H; F; Cl; Br; I; —NO$_2$; —CN; —NH$_2$; —OH; —SH; —C(=O)—OH; —NH—$R^{55}$; —NR$^{56}$R$^{57}$; —C(=O)—$R^{58}$; —C(=O)—O—$R^{59}$; —O—$R^{67}$; —S—$R^{68}$; $C_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; $C_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denote a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

or $R^4$ and $R^5$ or $R^6$ and $R^7$ or $R^{10}$ and $R^{11}$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{30}$ and $R^{31}$ or $R^{32}$ and $R^{33}$ or $R^{34}$ and $R^{35}$ or $R^{36}$ and $R^{37}$ or $R^{38}$ and $R^{39}$ or $R^{40}$ and $R^{41}$ or $R^{42}$ and $R^{43}$ or $R^{44}$ and $R^{45}$ or $R^{46}$ and $R^{47}$ or $R^{48}$ and $R^{49}$ or $R^{50}$ and $R^{51}$ or $R^{52}$ and $R^{53}$, mutually independently, together in each case denote a residue selected from the group consisting of an oxo group (=O) and a thioxo group (=S).

8. A compound according to claim 1, wherein $R^3$ and $R^4$ together with the —N—CR$^5$ group joining them form a residue selected from the group consisting of

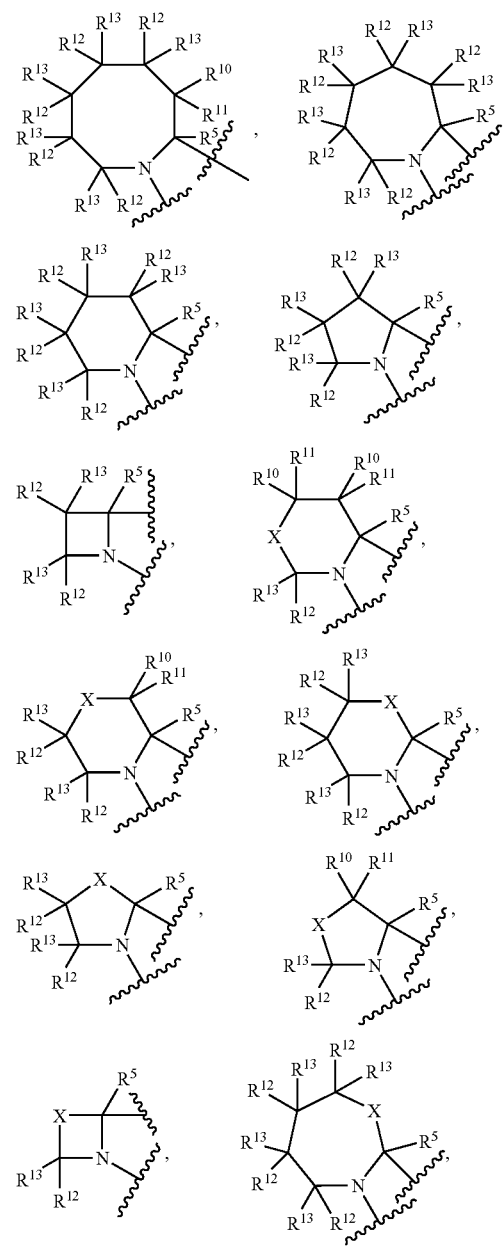

-continued
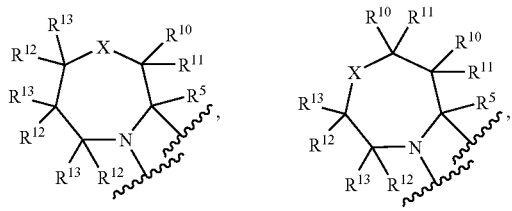 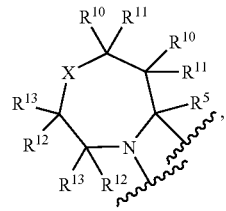
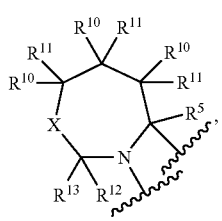 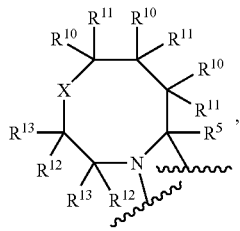
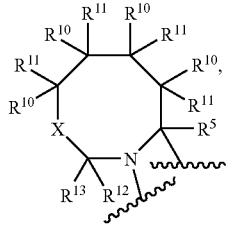 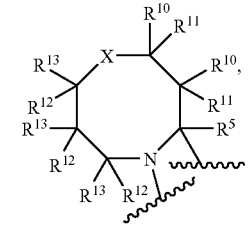
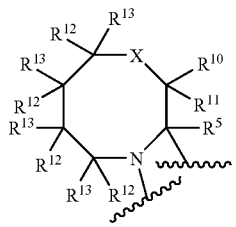 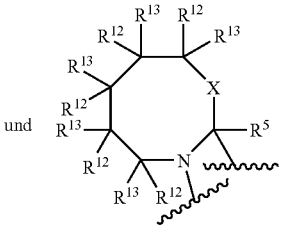 und
[und = and].
9. A compound according to claim 1, wherein R$^6$ and R$^8$ together with the —N—CR$^7$ group joining them form a residue selected from the group consisting of
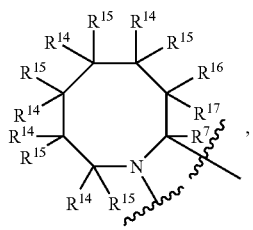 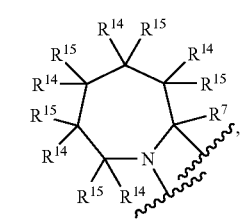
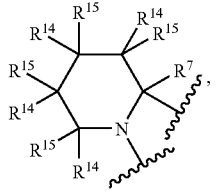 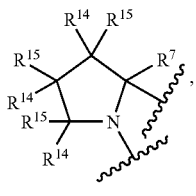
-continued
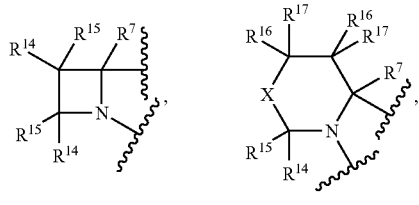 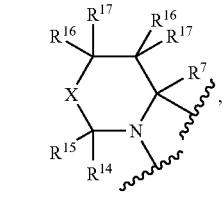
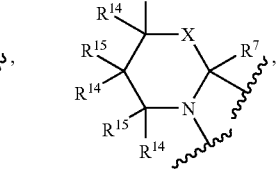
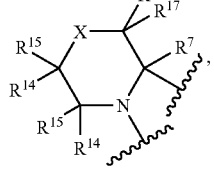
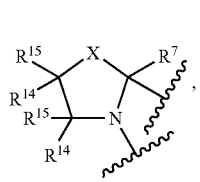 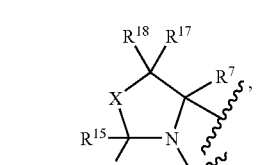
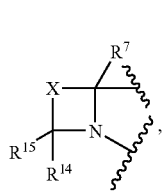 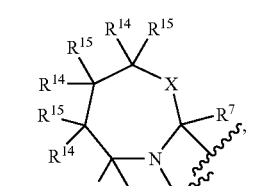
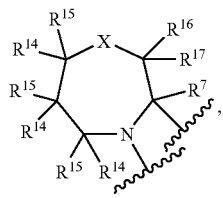 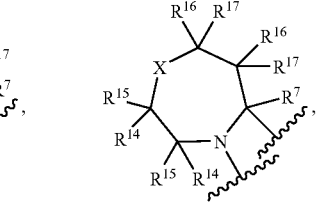
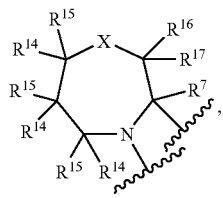 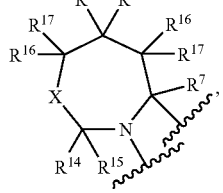
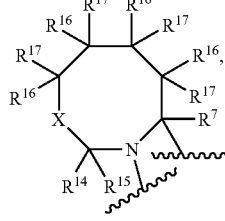 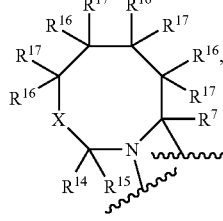

-continued
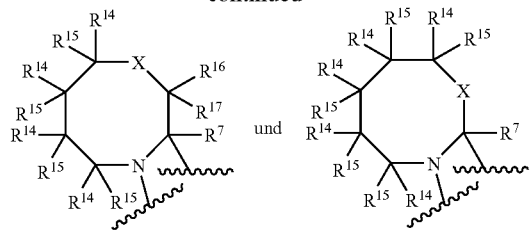 und 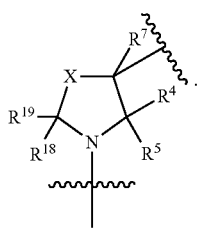
[und = and].
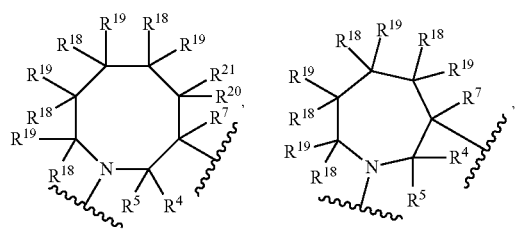
[und = and]
10. A compound according to claim 1, wherein
R³ and R⁶ together with the —N—CR⁴R⁵—CR⁷ group joining them form a residue selected from the group consisting of
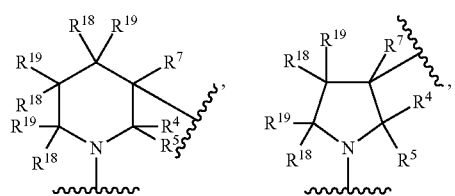
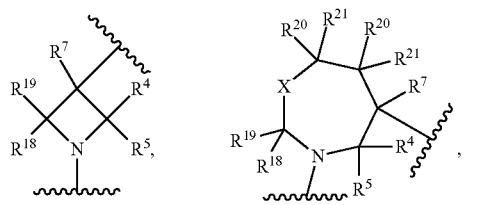
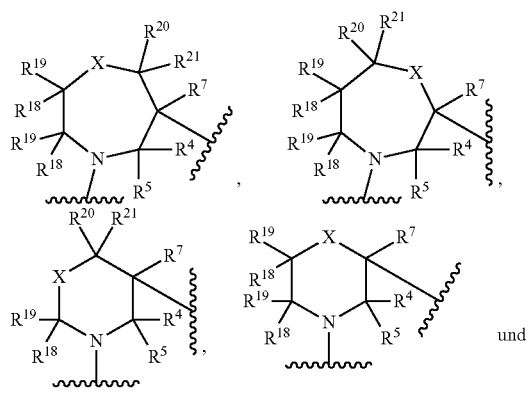
11. A compound according to claim 1, wherein
R⁴ and R⁸ together with the —CR⁵—CR⁶CR⁷—N group joining them form a residue selected from the group consisting of
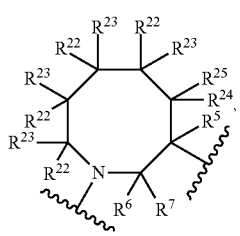 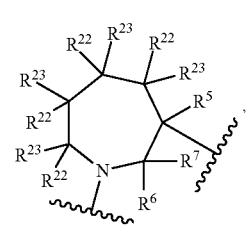
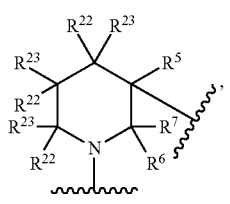 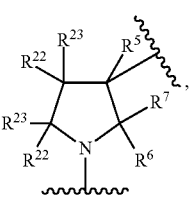
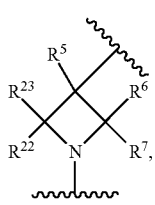 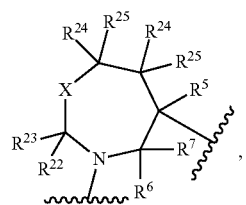
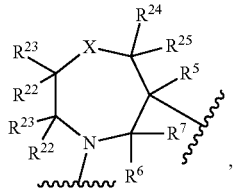 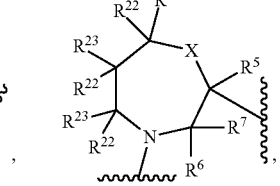
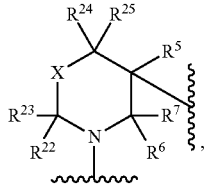 und 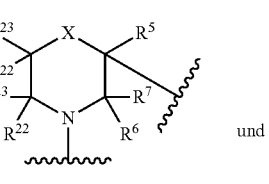

-continued
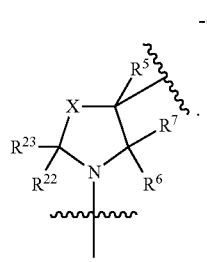
[und = and]
12. A compound according to claim 1, wherein
R³ and R⁸ together with the —N—CR⁴R⁵—CR⁶CR⁷—N group joining them form a residue selected from the group consisting of
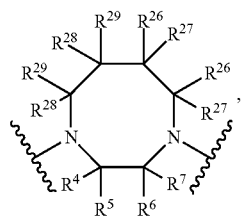 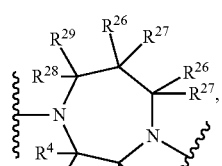
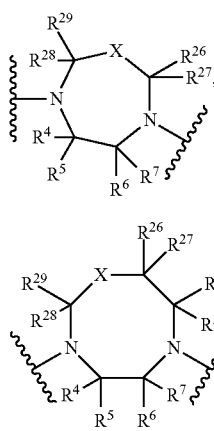 und
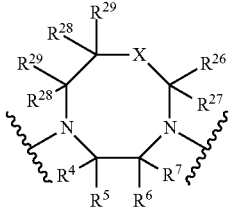
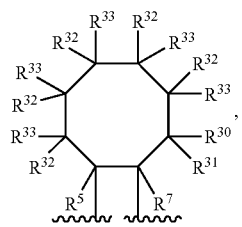 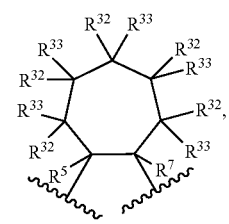
[und = and]
13. A compound according to claim 1, wherein
R⁴ and R⁶ together with the —CR⁵—CR⁷ group joining them form a residue selected from the group consisting of
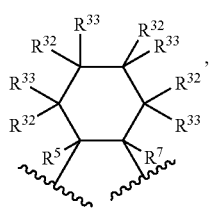 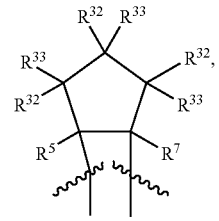
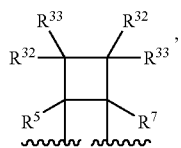 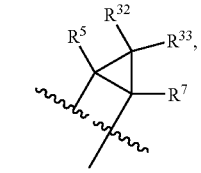
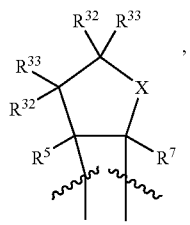
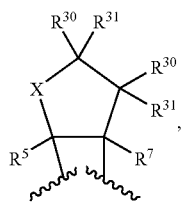 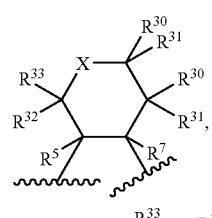
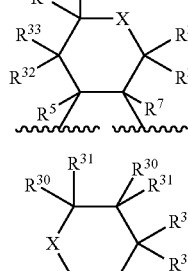 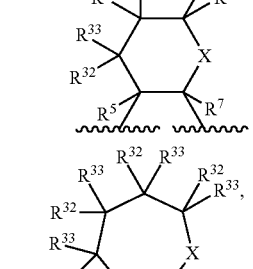
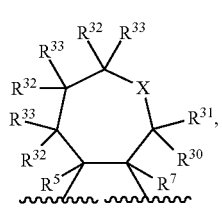
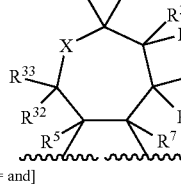 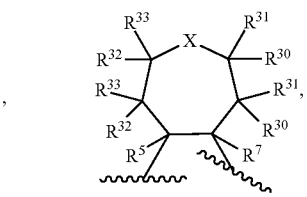
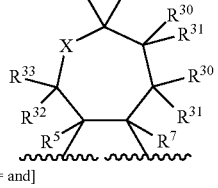 und
[und = and]

14. A compound according to claim 1, wherein R³ and R⁴ together with the —N—CR⁵ group joining them and R⁶ and R⁸ together with the —N—CR⁷ group joining them form a residue selected from the group consisting of

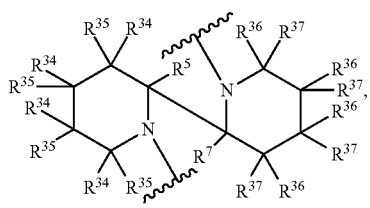

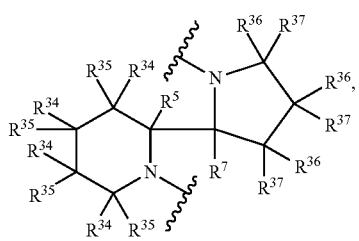

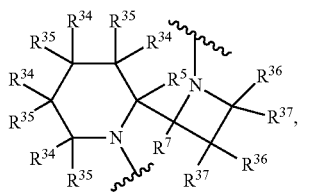

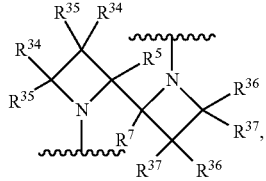

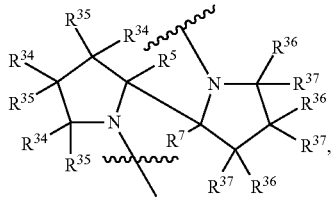

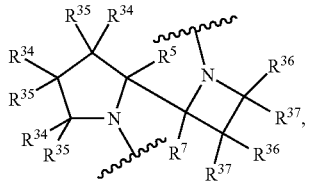

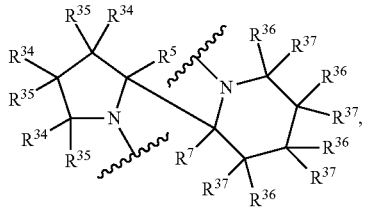

-continued

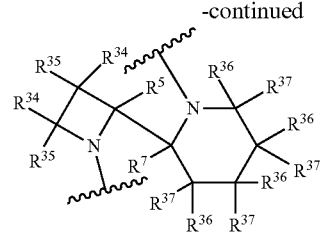 und

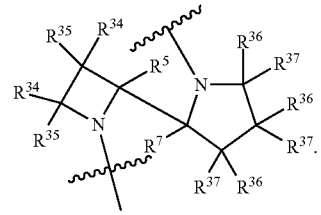

[und = and]

15. A compound according to claim 1, wherein R³ and R⁶ together with the —N—CR⁴CR⁵—CR⁷ group joining them and R⁴ and R⁸ together with the —CR⁵—CR⁶R⁷—N group joining them form a residue selected from the group consisting of

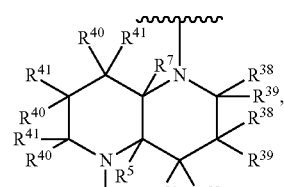

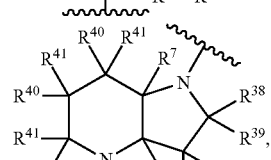

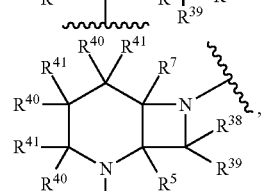

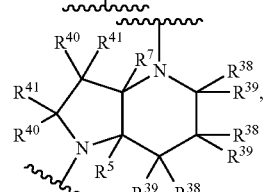

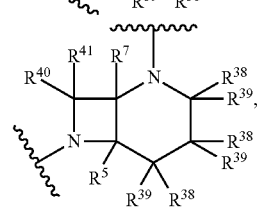

-continued

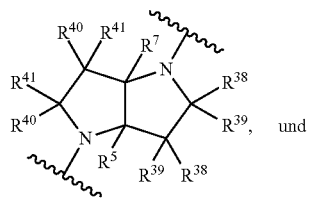

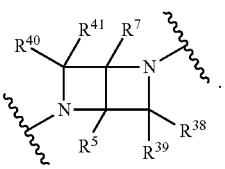

[und = and]

16. A compound according to claim 1, wherein
$R^3$ and $R^8$ together with the $-N-CR^4R^5-CR^6R^7-N$ group joining them and $R^4$ and $R^6$ together with the $-CR^5-CR^7$ group joining them form a residue selected from the group consisting of

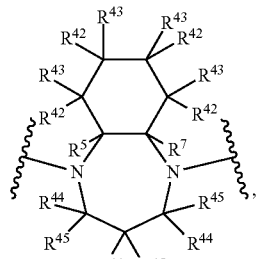 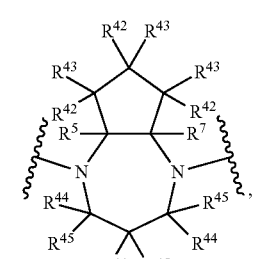

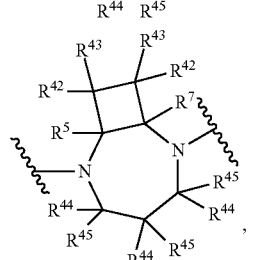 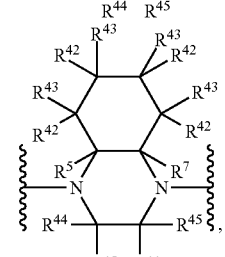

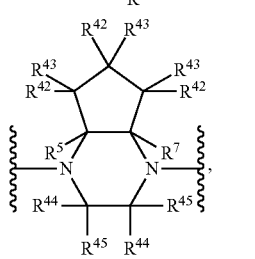 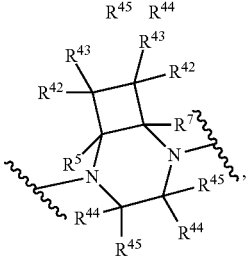

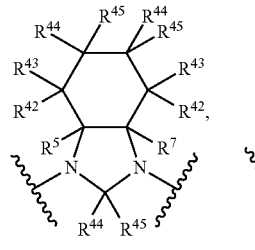 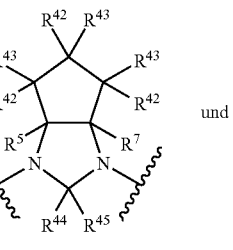

-continued

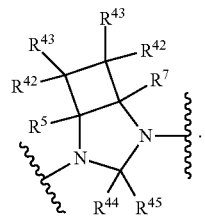

[und = and]

17. A compound according to claim 1, wherein
$R^3$ and $R^8$ together with the $-N-CR^4R^5-CR^6R^7-N$ group joining them form a bicyclic residue selected from the group consisting of

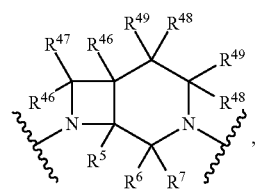 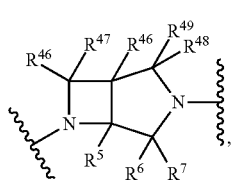

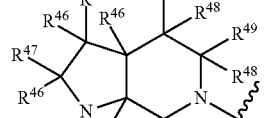 und

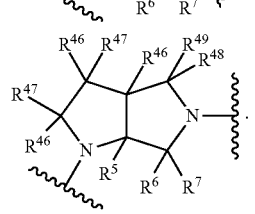

[und = and]

18. A compound according to claim 1, wherein
$R^3$ and $R^8$ together with the $-N-CR^4R^5-CR^6R^7-N$ group joining them form a bicyclic residue selected from the group

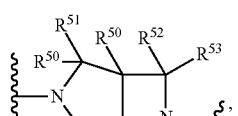 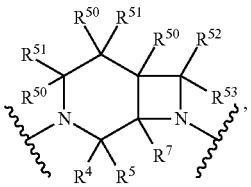

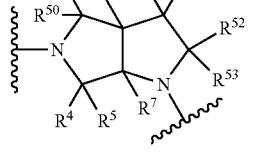 und

-continued

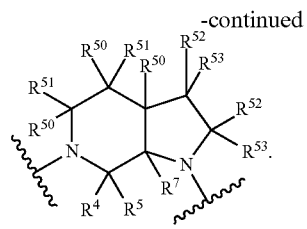

[und = and]

19. A compound according to claim 1, wherein
$R^9$ denotes H; —C(=O)—NH$_2$; —C(=O)—NH—R$^{64}$; —C(=O)—NR$^{65}$R$^{66}$;
$C_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; $C_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or denotes a residue selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl.

20. A compound according to claim 1, wherein
$R^{55}$, $R^{56}$, $R^{57}$, $R^{58}$, R59, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$ and $R^{75}$, mutually independently, in each case denote $C_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$; $C_{3-7}$ cycloalkyl, $C_{5-6}$ cycloalkenyl, 5- to 7-membered heterocycloalkyl or 5- to 7-membered heterocycloalkenyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$;
or denotes a residue selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, which may in each case be attached via a $C_{1-3}$ alkylene, $C_{2-3}$ alkenylene or $C_{2-3}$ alkynylene group and/or is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$ and —C(=O)—O—C$_2$H$_5$.

21. A compound according to claim 1, wherein
$R^1$ denotes H; F; Cl; Br; I; —CF$_3$; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; unsubstituted $C_{1-6}$ alkyl or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;
$R^2$ denotes H; F; Cl; Br; I; —CF$_3$; —NO$_2$; —CN; —NH$_2$; —OH; —SH; —C(=O)—OH; —C(=O)—H; —NH—C(=O)—H; —NH—R$^{55}$; —NR$^{56}$R$^{57}$; —C(=O)—R$^{58}$; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$; unsubstituted $C_{1-6}$ alkyl or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;
or $R^1$ and $R^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

$R^3$ and $R^8$, mutually independently, in each case denote H; —C(=O)—R$^{58}$; —C(=O)—O—R$^{59}$; —C(=O)—NH$_2$; —C(=O)—NH—R$^{64}$; —C(=O)—NR$^{65}$R$^{66}$; —S(=O)—R$^{69}$; —S(=O)$_2$—R$^{70}$; C$_{1-6}$ alkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

C$_{3-6}$ cycloalkyl, which is unsubstituted or substituted with optionally 1, 2, 3, 4 or 5 substituents mutually independently selected from the group consisting of F, Cl, Br, I, —NO$_2$, —CN, —OH, —SH and —NH$_2$;

or denote a phenyl residue, which may in each case be attached via a C$_{1-3}$ alkylene, C$_{2-3}$ alkenylene or C$_{2-3}$ alkynylene group and/or is unsubstituted or substituted with 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

$R^4$, $R^5$, $R^6$, $R^7$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$, mutually independently, in each case denote H; F; Cl; Br; I; —NO$_2$; —CN; —NH$_2$; —OH; —SH; —C(=O)—OH; —NH—R$^{55}$; —NR$^{56}$R$^{57}$; —C(=O)—R$^{58}$; —C(=O)—O—R$^{59}$; —O—R$^{67}$; —S—R$^{68}$; unsubstituted C$_{1-6}$ alkyl; or denote a residue selected from the group consisting of phenyl, benzyl and phenethyl, which is unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

or $R^4$ and $R^5$ or $R^6$ and $R^7$ or $R^{10}$ and $R^{11}$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{32}$ and $R^{33}$ or $R^{34}$ and $R^{35}$ or $R^{36}$ and $R^{37}$ or $R^{38}$ and $R^{39}$ or $R^{40}$ and $R^{41}$ or $R^{42}$ and $R^{43}$ or $R^{44}$ and $R^{45}$, mutually independently, in each case together denote a residue selected from the group consisting of an oxo group (=O) and a thioxo group (=S);

or $R^3$ and $R^4$ together with the —N—CR$^5$ group joining them form a residue selected from the group consisting of

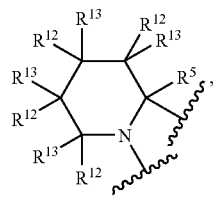 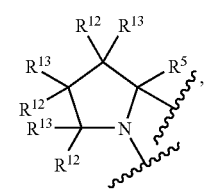

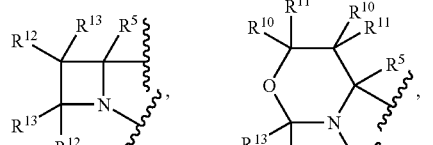

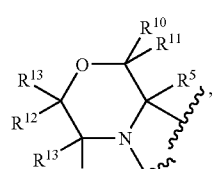

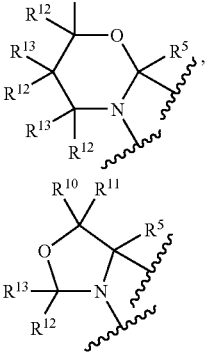

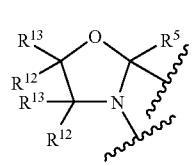

[und = and]

or $R^6$ and $R^8$ together with the —N—CR$^7$ group joining them form a residue selected from the group consisting of

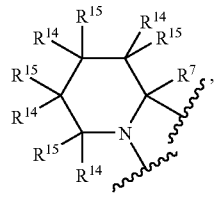 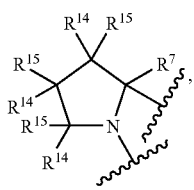

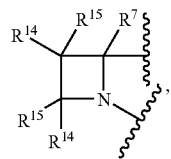 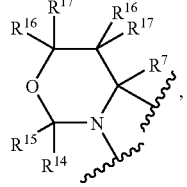

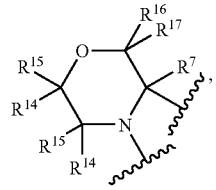

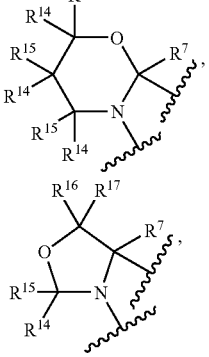

[und = and]

or $R^3$ and $R^6$ together with the —N—CR$^4$R$^5$—CR$^7$ group joining them form a residue selected from the group consisting of

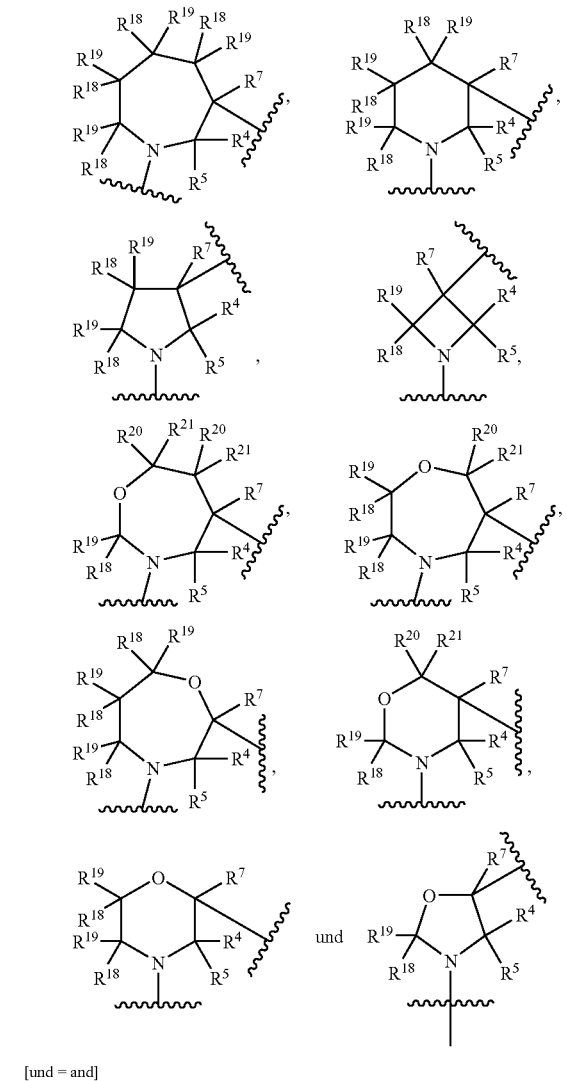

[und = and]

or $R^4$ and $R^8$ together with the —$CR^5$—$CR^6CR^7$—N group joining them form a residue selected from the group consisting of

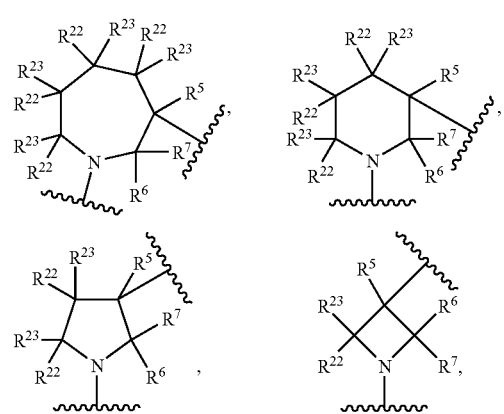

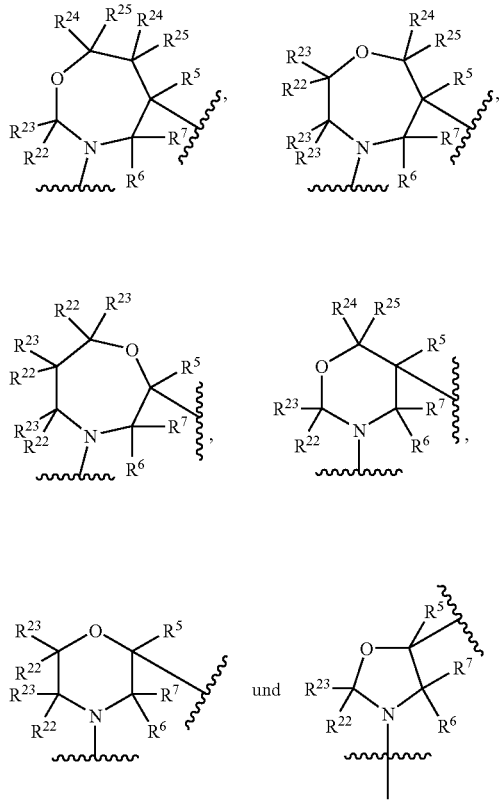

[und = and]

or $R^3$ and $R^8$ together with the —N—$CR^4R^5$—$CR^6CR^7$—N group joining them form a residue selected from the group consisting of

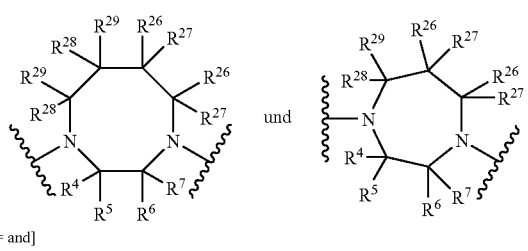

[und = and]

or $R^4$ and $R^6$ together with the —$CR^5$—$CR^7$ group joining them form a residue selected from the group consisting of

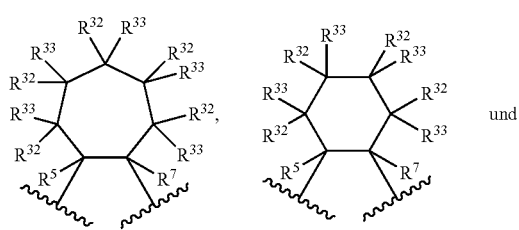

-continued

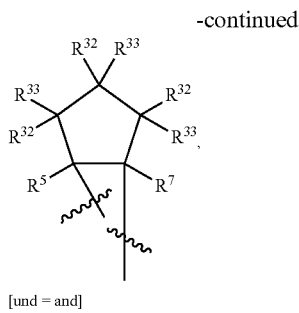

[und = and]

or $R^3$ and $R^4$ together with the —N—$CR^5$ group joining them and $R^6$ and $R^8$ together with the —N—$CR^7$ group joining them form a residue selected from the group consisting of

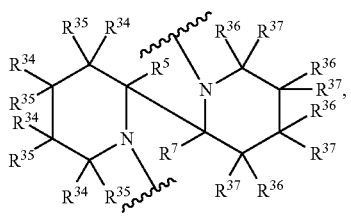

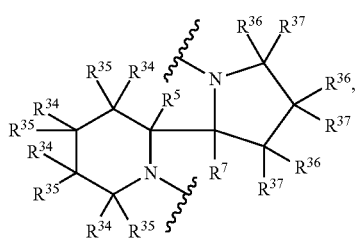

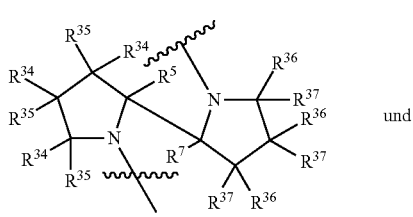

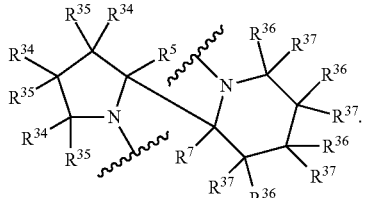

[und = and]

or $R^3$ and $R^6$ together with the —N—$CR^4CR^5$—$CR^7$ group joining them and $R^4$ and $R^8$ together with the —$CR^5$—$CR^6R^7$—N group joining them form a residue selected from the group consisting of

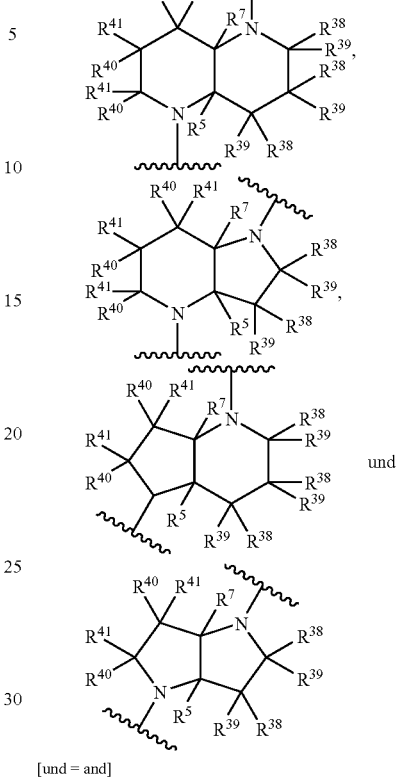

und

[und = and]

or $R^3$ and $R^8$ together with the —N—$CR^4R^5$—$CR^6R^7$—N group joining them and $R^4$ and $R^6$ together with the —$CR^5$—$CR^7$ group joining them form a residue selected from the group consisting of

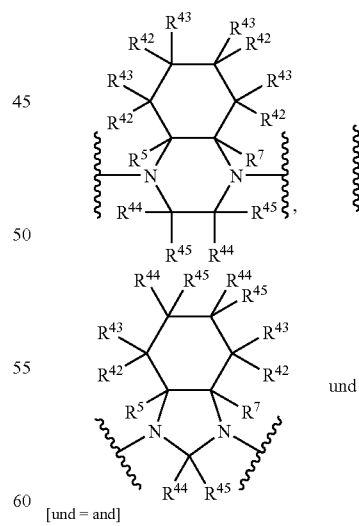

und

[und = and]

$R^9$ denotes H; —C(=O)—$NH_2$; —C(=O)—NH—$R^{64}$; —C(=O)—$NR^{65}R^{66}$;

unsubstituted $C_{1-6}$ alkyl; unsubstituted $C_{3-7}$ cycloalkyl; unsubstituted $C_{5-6}$ cycloalkenyl;

unsubstituted 5- to 7-membered heterocycloalkyl and unsubstituted 5- to 7-membered heterocycloalkenyl; or denotes a residue selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and R$^{55}$, R$^{56}$, R$^{57}$, R$^{58}$, R$^{59}$, R$^{64}$, R$^{65}$, R$^{66}$, R$^{67}$, R$^{68}$, R$^{69}$ and R$^{70}$, mutually independently, in each case denote unsubstituted C$_{1-6}$ alkyl; unsubstituted C$_{3-7}$ cycloalkyl; unsubstituted C$_{5-6}$ cycloalkenyl; unsubstituted 5- to 7-membered heterocycloalkyl and unsubstituted 5- to 7-membered heterocycloalkenyl; or denote a residue selected from the group consisting of phenyl, benzyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$ and —C(=O)—O—C$_2$H$_5$;

in each case optionally in the form of one of the pure stereoisomers thereof, the racemate thereof or in the form of a mixture of stereoisomers in any desired mixing ratio, or in each case in the form of a corresponding salt.

22. A compound according to claim 1, wherein

R$^1$ denotes H; F; Cl; Br; I; —CF$_3$; —NO$_2$; —CN; —C(=O)—OH; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$;

an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

R$^2$ denotes H; F; Cl; Br; I; —CF$_3$; —NO$_2$; —CN; —C(=O)—OH; —C(=O)—O—R$^{59}$; —C(=O)—NH$_2$; —C(=O)—NH—R$^{64}$; —C(=O)—NR$^{65}$R$^{66}$; —O—R$^{67}$; —S—R$^{68}$; —S(=O)—R$^{69}$; —S(=O)$_2$—R$^{70}$;

an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

or R$^1$ and R$^2$ together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —O—CH$_3$, —O—C$_2$H$_5$, —O—C$_3$H$_7$, —CF$_3$, —CHF$_2$, —CH$_2$F and —O—CF$_3$;

R$^3$ and R$^8$, mutually independently, in each case denote H; —C(=O)—R$^{58}$; —C(=O)—O—R$^{59}$; —S(=O)—R$^{69}$; —S(=O)$_2$—R$^{70}$; an alkyl residue selected from the group consisting of methyl, ethyl, n-propyl, isopropyl, n-butyl, 2-butyl, isobutyl, tert.-butyl, n-pentyl and n-hexyl; denote a cycloalkyl residue selected from the group consisting of cyclopropyl, cyclobutyl, cyclopentyl and cyclohexyl; or denote a benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH$_3$, —O—C$_2$H$_5$ and —O—C$_3$H$_7$;

R$^4$, R$^5$, R$^6$, R$^7$, R$^{12}$, R$^{13}$, R$^{14}$, R$^{15}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{32}$, R$^{33}$, R$^{38}$, R$^{39}$, R$^{40}$, R$^{41}$, R$^{42}$, R$^{43}$, R$^{44}$ and R$^{45}$, mutually independently, in each case denote H; F; Cl; Br; I; —NO$_2$; —CN; —NH$_2$; —OH; —SH; —NH—R$^{55}$; —NR$^{56}$R$^{57}$; —O—R$^{67}$; —S—R$^{68}$; or denote an alkyl residue selected from the group consisting of methyl, ethyl, n-propyl, isopropyl, n-butyl, 2-butyl, isobutyl, tert.-butyl, n-pentyl and n-hexyl;

or R$^4$ and R$^5$ or R$^6$ and R$^7$ or R$^{12}$ and R$^{13}$ or R$^{14}$ and R$^{15}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$ or R$^{28}$ and R$^{29}$ or R$^{32}$ and R$^{33}$ or R$^{38}$ and R$^{39}$ or R$^{40}$ and R$^{41}$ or R$^{42}$ and R$^{43}$ or R$^{44}$ and R$^{45}$, mutually independently, in each case together denote a residue selected from the group consisting of an oxo group (=O) and a thioxo group (=S);

or R$^3$ and R$^4$ together with the —N—CR$^5$ group joining them form a residue selected from the group consisting of

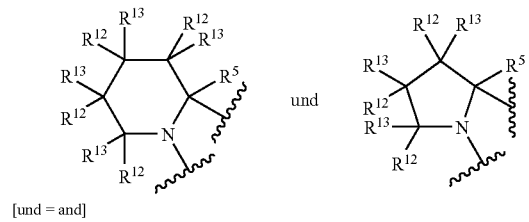

[und = and]

or $R^6$ and $R^8$ together with the —N—$CR^7$ group joining them form a residue selected from the group consisting of

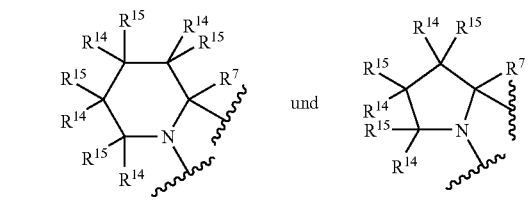

[und = and]

or $R^3$ and $R^6$ together with the —N—$CR^4R^5$—$CR^7$ group joining them form a residue selected from the group consisting of

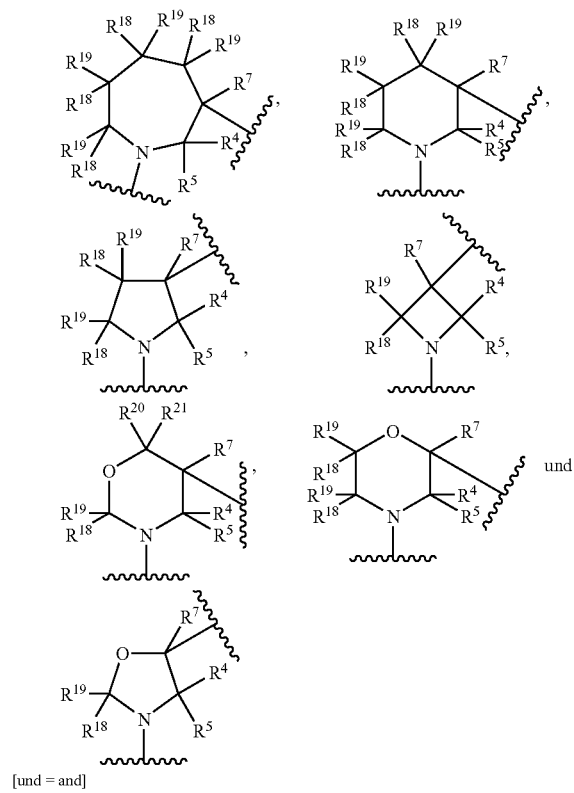

[und = and]

or $R^4$ and $R^8$ together with the —$CR^5$—$CR^6CR^7$—N group joining them form a residue selected from the group consisting of

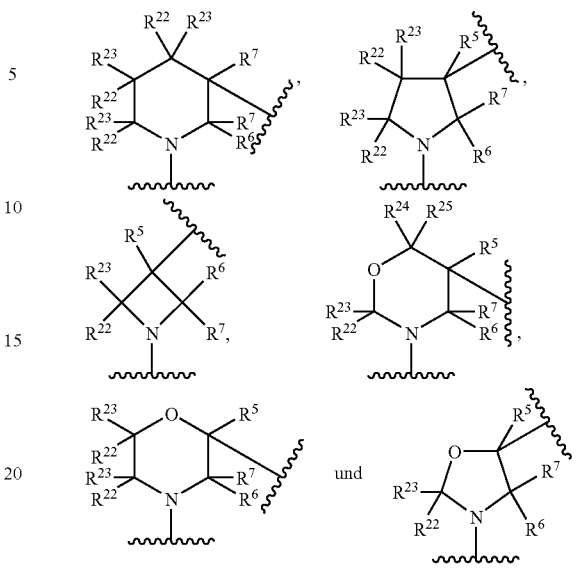

[und = and]

or $R^3$ and $R^8$ together with the —N—$CR^4R^5$—$CR^6CR^7$—N group joining them form the following residue

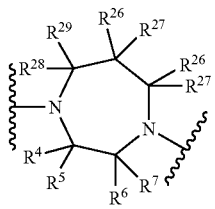

or $R^4$ and $R^6$ together with the —$CR^5$—$CR^7$ group joining them form the following residue

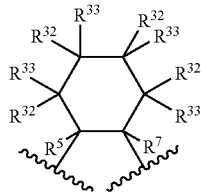

or $R^3$ and $R^6$ together with the —N—$CR^4CR^5$—$CR^7$ group joining them and $R^4$ and $R^8$ together with the —$CR^5$—$CR^6R^7$—N group joining them form the following residue

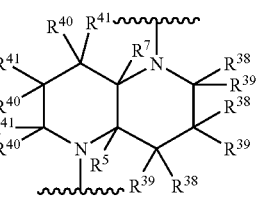

or R³ and R⁸ together with the —N—CR⁴R⁵—CR⁶R⁷—N group joining them and R⁴ and R⁶ together with the —CR⁵—CR⁷ group joining them form the following residue

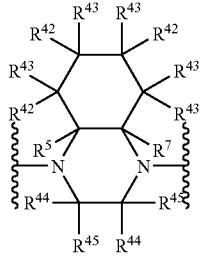

R⁹ denotes —C(=O)—NH—R⁶⁴; —C(=O)—NR⁶⁵R⁶⁶;
or denotes a residue selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —C≡C—Si(CH₃)₃, —C≡C—Si(C₂H₅)₃, —CH₂—O—CH₃, —CH₂—O—C₂H₅, —OH, —O—CH₃, —O—C₂H₅, —O—C₃H₇, —S—CH₃, —S—C₂H₅, —S(=O)—CH₃, —S(=O)₂—CH₃, —S(=O)—C₂H₅, —S(=O)₂—C₂H₅, —NH₂, —N(CH₃)₂, —N(C₂H₅)₂, —NH—CH₃, —NH—C₂H₅, —NO₂, —CF₃, —CH₂F, —CHF₂, —O—CF₃, —S—CF₃, —SH, —NH—S(=O)₂—CH₃, —C(=O)—OH, —C(=O)—H; —C(=O)—CH₃, —C(=O)—C₂H₅, —C(=O)—NH₂, —C(=O)—N(CH₃)₂, —C(=O)—NH—CH₃, —NH—C(=O)—CH₃, —NH—C(=O)—C₂H₅, —C(=O)—O—CH₃, —C(=O)—O—C₂H₅, —C(=O)—O—C(CH₃)₃ and phenyl;
and R⁵⁵, R⁵⁶, R⁵⁷, R⁵⁸, R⁵⁹, R⁶⁴, R⁶⁵, R⁶⁶, R⁶⁷, R⁶⁸, R⁶⁹ and R⁷⁰, mutually independently, in each case denote an alkyl residue selected from the group consisting of methyl, ethyl, n-propyl, isopropyl, n-butyl, 2-butyl, isobutyl, tert.-butyl, n-pentyl and n-hexyl; or denote a phenyl, benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH₃, —O—C₂H₅ and —O—C₃H₇;
in each case optionally in the form of one of the pure stereoisomers thereof, the racemate thereof or in the form of a mixture of stereoisomers in any desired mixing ratio, or in each case in the form of a corresponding salt.

23. A compound according to claim 1, wherein
R¹ denotes H; F; Cl; Br; I; —CF₃; —NO₂; —CN; —C(=O)—OH; —C(=O)—O—R⁵⁹; —C(=O)—NH₂; —C(=O)—NH—R⁶⁴; —C(=O)—NR⁶⁵R⁶⁶; —O—R⁶⁷; —S—R⁶⁸; —S(=O)—R⁶⁹; —S(=O)₂—R⁷⁰;
an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH₃, —O—C₂H₅ and —O—C₃H₇;

R² denotes H; F; Cl; Br; I; —CF₃; —NO₂; —CN; —C(=O)—OH; —C(=O)—O—R⁵⁹; —C(=O)—NH₂; —C(=O)—NH—R⁶⁴; —C(=O)—NR⁶⁵R⁶⁶; —O—R⁶⁷; —S—R⁶⁸; —S(=O)—R⁶⁹; —S(=O)₂—R⁷⁰;
an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, which is in each case unsubstituted or substituted with optionally 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH₃, —O—C₂H₅ and —O—C₃H₇; or R¹ and R² together with the carbon atoms joining them form a phenylene residue, which is unsubstituted or substituted with 1, 2, 3 or 4 substituents mutually independently selected from the group consisting of F, Cl, Br, I, —CN, methyl, ethyl, n-propyl, isopropyl, n-butyl, isobutyl, 2-butyl, tert.-butyl, —O—CH₃, —O—C₂H₅, —O—C₃H₇, —CF₃, —CHF₂, —CH₂F and —O—CF₃;

R³ and R⁸, mutually independently, in each case denote H; —C(=O)—R⁵⁸; —C(=O)—O—R⁵⁹; —S(=O)—R⁶⁹; —S(=O)₂—R⁷⁰; an alkyl residue selected from the group consisting of methyl, ethyl, n-propyl, isopropyl, n-butyl, 2-butyl, isobutyl, tert.-butyl, n-pentyl and n-hexyl; denote a cycloalkyl residue selected from the group consisting of cyclopropyl, cyclobutyl, cyclopentyl and cyclohexyl; or denote a benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—CH₃, —O—C₂H₅ and —O—C₃H₇;

R⁴, R⁵, R⁶ and R⁷, mutually independently, in each case denote H; F; Cl; Br; I; —NO₂; —CN; —NH₂; —OH; —SH; —NH—R⁵⁵; —NR⁵⁶R⁵⁷; —O—R⁶⁷; —S—R⁶⁸; or denote an alkyl residue selected from the group consisting of methyl, ethyl, n-propyl, isopropyl, n-butyl, 2-butyl, isobutyl, tert.-butyl, n-pentyl and n-hexyl;
or R⁴ and R⁵ or R⁶ and R⁷, mutually independently, together in each case denote a residue selected from the group consisting of an oxo group (=O) and a thioxo group (=S);
or R³ and R⁴ together with the —N—CR⁵ group joining them form a residue selected from the group consisting of

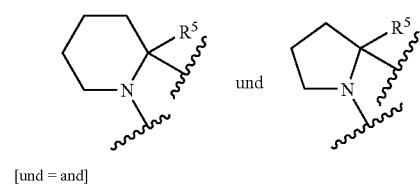

[und = and]

or $R^6$ and $R^8$ together with the —N—$CR^7$ group joining them form a residue selected from the group consisting of

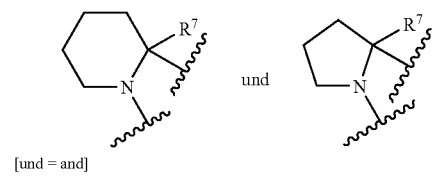

[und = and]

or $R^3$ and $R^6$ together with the —N—$CR^4R^5$—$CR^7$ group joining them form a residue selected from the group consisting of

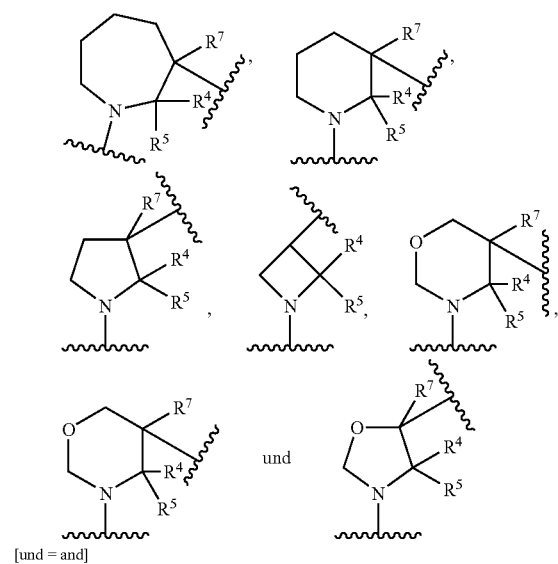

[und = and]

or $R^4$ and $R^8$ together with the —$CR^5$—$CR^6CR^7$—N group joining them form a residue selected from the group consisting of

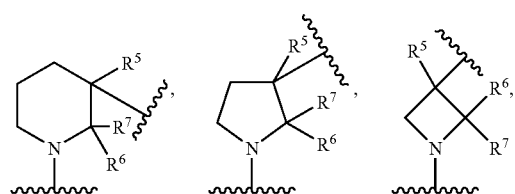

-continued

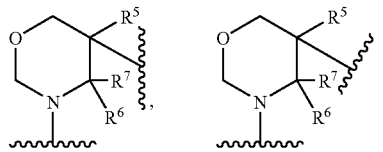
und

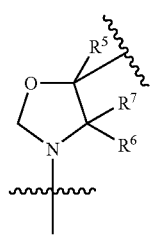

[und = and]

or $R^3$ and $R^8$ together with the —N—$CR^4R^5$—$CR^6CR^7$—N group joining them form the following residue

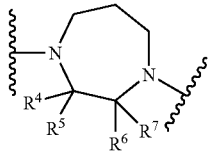

or $R^4$ and $R^6$ together with the —$CR^5$—$CR^7$ group joining them form the following residue

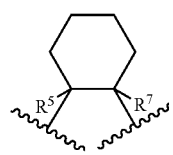

or $R^3$ and $R^6$ together with the —N—$CR^4CR^5$—$CR^7$ group joining them and $R^4$ and $R^8$ together with the —$CR^5$—$CR^6R^7$—N group joining them form the following residue

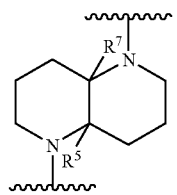

or $R^3$ and $R^8$ together with the —N—$CR^4R^5$—$CR^6R^7$—N group joining them and $R^4$ and $R^6$ together with the —$CR^5$—$CR^7$ group joining them form the following residue

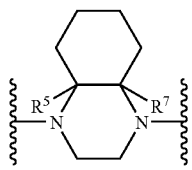

$R^9$ denotes —C(=O)—NH—$R^{64}$; —C(=O)—N$R^{65}R^{66}$; or denotes a residue selected from the group consisting of phenyl, naphthyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —O—$CH_3$, —O—$C_2H_5$, —$NO_2$, —$CF_3$, —$CH_2F$, —$CHF_2$, —O—$CF_3$ and —S—$CF_3$;

and $R^{55}$, $R^{56}$, $R^{57}$, $R^{58}$, $R^{59}$, $R^{64}$, $R^{65}$, $R^{66}$, $R^{67}$, $R^{68}$, $R^{69}$ and $R^{70}$, mutually independently, in each case denote an alkyl residue selected from the group consisting of methyl, ethyl, n-propyl, isopropyl, n-butyl, 2-butyl, isobutyl, tert.-butyl, n-pentyl and n-hexyl; or denote a phenyl, benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

in each case optionally in the form of one of the pure stereoisomers thereof, the racemate thereof or in the form of a mixture of stereoisomers in any desired mixing ratio, or in each case in the form of a corresponding salt.

24. A compound according to claim 1, wherein $R^1$ denotes H; F; Cl; Br; I; —$CF_3$; —$NO_2$; —CN; —C(=O)—O—$R^{59}$; an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

$R^2$ denotes H; F; Cl; Br; I; —$CF_3$; —$NO_2$; —CN; —C(=O)—O—$R^{59}$; an alkyl residue selected from the group consisting of methyl, ethyl, n-propyl, isopropyl, n-butyl, 2-butyl, isobutyl and tert.-butyl; or denotes a residue selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

or $R^1$ and $R^2$ together with the carbon atoms joining them form a phenylene residue;

$R^3$ and $R^8$, mutually independently, in each case denote H; —C(=O)—$R^{58}$; —C(=O)—O—$R^{59}$; an alkyl residue selected from the group consisting of methyl, ethyl, n-propyl, isopropyl, n-butyl, 2-butyl, isobutyl, tert.-butyl, n-pentyl and n-hexyl; denote a cycloalkyl residue selected from the group consisting of cyclopropyl, cyclobutyl, cyclopentyl and cyclohexyl; or denote a benzyl or phenethyl residue, which is unsubstituted or substituted with 1, 2, 3, 4 or 5 substituents mutually independently selected from the group consisting of F, Cl, Br, methyl, ethyl, n-propyl, isopropyl, n-butyl, 2-butyl, isobutyl, tert.-butyl, —OH, —O—$CH_3$, —O—$C_2H_5$ and —O—$C_3H_7$;

$R^4$, $R^5$, $R^6$ and $R^7$, mutually independently, in each case denote H; F; Cl; Br; I; —$NO_2$; —CN; —$NH_2$; —OH; —SH; —NH—$R^{55}$; —N$R^{56}R^{57}$; —O—$R^{67}$; —S—$R^{68}$; or denote an alkyl residue selected from the group consisting of methyl, ethyl, n-propyl, isopropyl, n-butyl, 2-butyl, isobutyl, tert.-butyl, n-pentyl and n-hexyl;

or $R^4$ and $R^5$ or $R^6$ and $R^7$, mutually independently, together in each case denote a residue selected from the group consisting of an oxo group (=O) and a thioxo group (=S);

or $R^3$ and $R^6$ together with the —N—$CR^4R^5$—$CR^7$ group joining them form a residue selected from the group consisting of

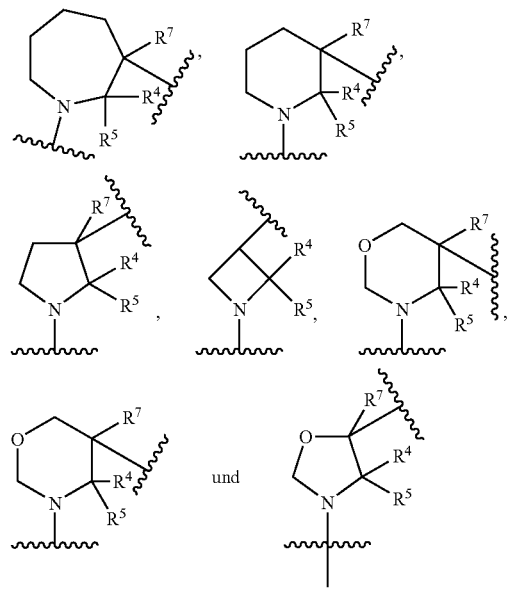

[und = and]

or $R^4$ and $R^8$ together with the —$CR^5$—$CR^6CR^7$—N group joining them form a residue selected from the group consisting of

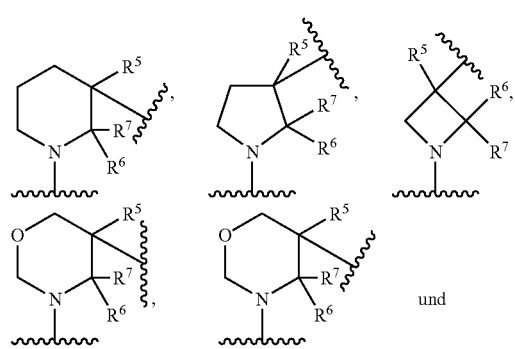

-continued

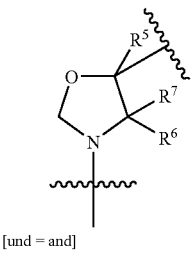

[und = and]

or R³ and R⁸ together with the —N—CR⁴R⁵—CR⁶CR⁷—N group joining them form the following residue

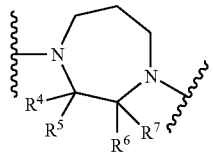

or R⁴ and R⁶ together with the —CR⁵—CR⁷ group joining them form the following residue

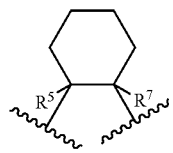

R⁹ denotes a residue selected from the group consisting of phenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl and imidazolyl, which is in each case unsubstituted or substituted with optionally 1, 2, 3, 4 or 5 substituents mutually independently selected from the group consisting of F, Cl, Br, I, —CN, methyl, ethyl, n-propyl, isopropyl, n-butyl, 2-butyl, isobutyl, tert.-butyl, ethenyl, allyl, ethynyl, propynyl, —O—CH₃, —O—C₂H₅, —NO₂, —CF₃, —CH₂F, —CHF₂, —O—CF₃ and —S—CF₃;

and R⁵⁵, R⁵⁶, R⁵⁷, R⁵⁸, R⁵⁹, R⁶⁷ and R⁶⁸, mutually independently, in each case denote an alkyl residue selected from the group consisting of methyl, ethyl, n-propyl, isopropyl, n-butyl, 2-butyl, isobutyl, tert.-butyl, n-pentyl and n-hexyl;

in each case optionally in the form of one of the pure stereoisomers thereof, the racemate thereof or in the form of a mixture of stereoisomers in any desired mixing ratio, or in each case in the form of a corresponding salt.

25. A compound according to claim 1, wherein

R¹ denotes H, CN, Cl, Br, F, methyl, ethyl, n-propyl, isobutyl, n-butyl, tert.-butyl, —C(=O)—O—CH₃, —C(=O)—O—C₂H₅ or —C(=O)—O—C(CH₃)₃;

R² denotes H, CN, Cl, Br, F, methyl, ethyl, n-propyl, isobutyl, n-butyl, tert.-butyl, —C(=O)—O—CH₃, —C(=O)—O—C₂H₅ or —C(=O)—O—C(CH₃)₃;

or R¹ and R² together with the carbon atoms joining them form a phenylene residue;

R³ and R⁸, mutually independently, in each case denote a residue selected from the group consisting of methyl, ethyl, n-propyl, isopropyl, n-butyl, 2-butyl, isobutyl and tert.-butyl; or denote cyclopropyl;

R⁴, R⁵ and R⁷ in each case denote H;

R⁶ denotes H or denotes an alkyl residue selected from the group consisting of methyl, ethyl, n-propyl, isopropyl, n-butyl, 2-butyl, isobutyl, tert.-butyl, n-pentyl and n-hexyl;

or R⁴ and R⁵ or R⁶ and R⁷, mutually independently, together in each case denote an oxo group (=O);

or R³ and R⁶ together with the —N—CH₂—CH group joining them form a residue selected from the group consisting of

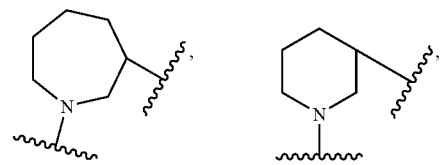

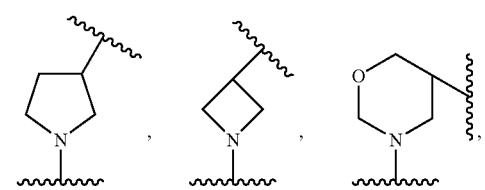

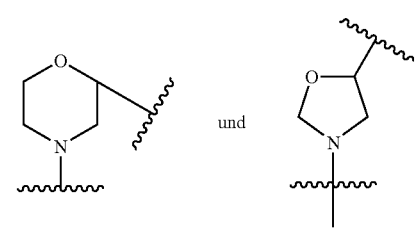

[und = and]

or R⁴ and R⁸ together with the —CH—CH₂—N group form a residue selected from the group consisting of

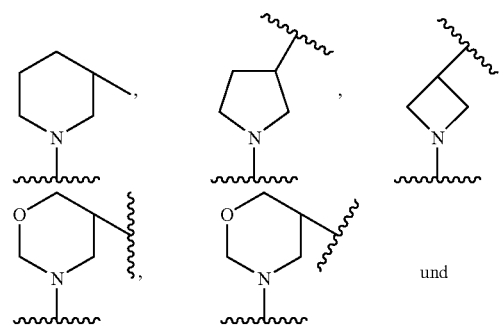

-continued

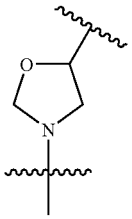

[und = and]

or R³ and R⁸ together with the —N—CH$_2$—CH$_2$—N group joining them form the following residue

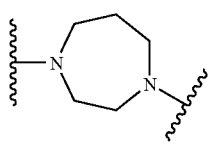

or R⁴ and R⁶ together with the —CH—CH group joining them form the following residue

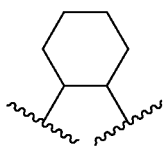

and R⁹ denotes a residue selected from the group consisting of pyrid-2-yl, pyrid-3-yl, pyrid-4-yl, phenyl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-chlorophenyl, 3-chlorophenyl, 3-chlorophenyl, 2-trifluoromethylphenyl, 3-trifluoro-methylphenyl, 4-trifluoromethylphenyl, 2-methoxyphenyl, 3-methoxyphenyl, 4-methoxyphenyl, (2,4)-difluorophenyl, (2,4)-dichlorophenyl, (3,5)-dichlorophenyl, (3,5)-difluorophenyl, 2-thiophenyl, 2-chloro-5-trifluoromethylphenyl, 3-fluoro-4-methylphenyl, 2-fluoro-3-methylphenyl, 2-difluoromethylphenyl, 3-difluoromethylphenyl, 4-difluoro-methylphenyl, 2-fluoromethylphenyl, 3-fluoromethylphenyl, 4-fluoromethylphenyl, 3-nitrophenyl, 3-ethenylphenyl, 3-ethynylphenyl, 3-allylphenyl, 3-bromophenyl, 2-trifluoro-methoxyphenyl, 3-trifluoromethoxyphenyl and 4-trifluoromethoxyphenyl;

in each case optionally in the form of one of the pure stereoisomers thereof, the racemate thereof or in the form of a mixture of stereoisomers in any desired mixing ratio, or in each case in the form of a corresponding salt.

26. A compound according to claim 1 selected from the group consisting of

[1] 3-phenyl-N-(1-(thiazol-2-yl)pyrrolidin-3-yl)propiolamide,

[2] N-methyl-3-phenyl-N-(1-(thiazol-2-yl)pyrrolidin-3-yl)propiolamide hydrochloride,

[3] 1-thiazol-2-yl-4-(3-phenylpropiolyl)-1,4-diazepane,

[4] N-Methyl-N-(2-(methyl(thiazol-2-yl)amino)ethyl)-3-phenylpropiolamide,

[5] N-(2-((thiazol-2-yl)amino)ethyl)-3-phenylpropiolamide,

[6] 3-phenyl-N-(2-(thiazol-2-ylamino)cyclohexyl)propiolamide,

[7] N-methyl-N-(2-(methyl(thiazol-2-yl)amino)ethyl)-3-(3-methylphenyl)-propiolamide,

[8] 3-phenyl-N-(1-(thiazol-2-yl)azetidin-3-yl)propiolamide,

[9] N-(2-(methyl(thiazol-2-yl)amino)ethyl)-3-phenylpropiolamide,

[10] N-methyl-N-(2-(thiazol-2-yl)amino)ethyl-3-phenyl-propiolamide,

[11] 3-(thiazol-2-yl-amino)-1-(3-phenylpropiolyl)pyrrolidine,

[12] N-methyl-N-(2-(methyl(thiazol-2-yl)amino)cyclohexyl)-3-phenylpropiolamide,

[13] N-methyl-N-(2-(methyl(thiazol-2-yl)amino)ethyl)-3-(3-cyanophenyl)-propiolamide,

[14] N-methyl-N-(2-(methyl(thiazol-2-yl)amino)-2-oxo-ethyl)-3-phenylpropiolamide,

[15] 3-phenyl-N-(1-(thiazol-2-yl)piperidin-3-yl)propiolamide,

[16] N-methyl-N-(1-(thiazol-2-yl)piperidin-3-yl)-3-phenylpropiolamide,

[17] N-methyl-N-(2-(methyl(thiazol-2-yl)amino)ethyl)-3-(pyrid-2-yl)-propiolamide,

[18] N-methyl-N-(2-(methyl(thiazol-2-yl)amino)ethyl)-3-(3-chlorophenyl)-propiolamide,

[19] N-(2-(methyl(thiazol-2-yl)amino)ethyl)-3-(3-chlorophenyl)-propiolamide,

[20] N-methyl-N-(1-(thiazol-2-yl)azetidin-3-yl)-3-phenylpropiolamide,

[21] N-(2-(methyl(thiazol-2-yl)amino)ethyl)-3-(tol-3-yl)-propiolamide,

[22] 3-methyl(thiazol-2-yl)amino)-1-(3-phenylpropiolyl)pyrrolidine,

[23] N-(2-(methyl(thiazol-2-yl)-amino)ethyl)-3-(3-chlorophenyl)-propiolamide hydrochloride,

[24] N-(2-(benzo[d]thiazol-2-yl(methyl)amino)ethyl)-3-(3-chlorophenyl)propiolamide,

[25] N-(2-methyl(5-ethoxycarbonylthiazol-2-yl)amino)ethyl)-3-(3-chlorophenyl)-propiolamide,

[26] N-(2-methyl(4-ethoxycarbonylthiazol-2-yl)amino)ethyl)-3-(3-chlorophenyl)-propiolamide,

[27] 3-(thiazol-2-yl-amino)-1-(3-phenylpropiolyl)piperidine,

[28] 3-(methyl-(thiazol-2-yl)-amino)-1-(3-phenylpropiolyl)piperidine,

[29] N-(2-(methyl-(4-methylthiazol-2-yl)amino)ethyl)-3-(3-chlorophenyl)-propiolamide,

[30] 3-(3-chlorophenyl)-N-(2-(methyl(5-methylthiazol-2-yl)amino)ethyl)propiolamide

[31] N-(2-((5-bromothiazol-2-yl)(methyl)amino)ethyl)-3-(3-chlorophenyl)-propiolamide,

[32] 3-(3-chlorophenyl)-N-(1-(thiazol-2-yl)piperidin-3-yl)propiolamide,

[33] N-(2-((4-bromothiazol-2-yl)(methyl)amino)ethyl)-3-(3-chlorophenyl)-propiolamide,

[34] methyl 2-((2-(3-(3-chlorophenyl)propiolamido)ethyl)(methyl)amino)thiazole-5-carboxylate,

[35] 1-(3-(3-chlorophenyl)propiolyl)-3-(methyl(thiazol-2-yl)amino)azetidine,

[36] 3-(3-chlorophenyl)-N-methyl-N-(1-(thiazol-2-yl)piperidin-3-yl)propiolamide,

[37] 3-(3-chlorophenyl)-N-(2-((4-chlorothiazol-2-yl)(methyl)amino)ethyl)-propiolamide,

[38] 3-(3-chlorophenyl)-N-(2-((5-chlorothiazol-2-yl)(methyl)amino)ethyl)-propiolamide,
[39] 3-(3-chlorophenyl)-N-(1-(thiazol-2-yl)azetidin-3-yl)propiolamide,
[40] 3-(3-chlorophenyl)-N-methyl-N-(1-(thiazol-2-yl)azetidin-3-yl)propiolamide,
[41] 3-(3-chlorophenyl)-N-(2-(ethyl(thiazol-2-yl)amino)ethyl)propiolamide,
[42] 3-(3-chlorophenyl)-N-(2-((5-cyanothiazol-2-yl)(methyl)amino)ethyl)propiolamide,
[43] 1-(3-(3-chlorophenyl)propiolyl)-3-(methyl(5-fluorothiazol-2-yl)amino)azetidine,
[44] 1-(3-(3-chlorophenyl)propiolyl)-3-(methyl(5-fluorothiazol-2-yl)amino)pyrrolidine,
[45] N-(1-(4-methylthiazol-2-yl)pyrrolidin-3-yl)-3-phenylpropiolamide,
[46] 3-(3-methoxyphenyl)-N-(1-(4-methylthiazol-2-yl)pyrrolidin-3-yl)propiolamide,
[47] 3-(2-methoxyphenyl)-N-(1-(4-methylthiazol-2-yl)pyrrolidin-3-yl)propiolamide,
[48] 3-(4-methoxyphenyl)-N-(1-(4-methylthiazol-2-yl)pyrrolidin-3-yl)propiolamide,
[49] 3-(4-fluorophenyl)-N-(1-(4-methylthiazol-2-yl)pyrrolidin-3-yl)propiolamide,
[50] N-(1-(4-methylthiazol-2-yl)pyrrolidin-3-yl)-3-p-tolylpropiolamide,
[51] N-(1-(4,5-dimethylthiazol-2-yl)pyrrolidin-3-yl)-3-phenylpropiolamide,
[52] N-(1-(4,5-dimethylthiazol-2-yl)pyrrolidin-3-yl)-3-(4-methoxyphenyl)-propiolamide,
[53] N-(1-(4,5-dimethylthiazol-2-yl)pyrrolidin-3-yl)-3-(4-fluorophenyl)propiolamide,
[54] N-(1-(4,5-dimethylthiazol-2-yl)pyrrolidin-3-yl)-3-(2-methoxyphenyl)-propiolamide,
[55] N-(1-(4-tert.-butylthiazol-2-yl)pyrrolidin-3-yl)-3-(4-methoxyphenyl)propiolamide,
[56] N-(1-(4-tert.-butylthiazol-2-yl)pyrrolidin-3-yl)-3-p-tolylpropiolamide,
[57] N-(1-(4-tert.-butylthiazol-2-yl)pyrrolidin-3-yl)-3-(4-fluorophenyl)propiolamide,
[58] N-(1-(4-tert.-butylthiazol-2-yl)pyrrolidin-3-yl)-3-o-tolylpropiolamide,
[59] N-(1-(4-tert.-butylthiazol-2-yl)pyrrolidin-3-yl)-3-(3-fluorophenyl)propiolamide,
[60] N-(1-(4-tert.-butylthiazol-2-yl)pyrrolidin-3-yl)-3-phenylpropiolamide,
[61] N-(1-(4-tert.-butylthiazol-2-yl)pyrrolidin-3-yl)-3-(2-fluorophenyl)propiolamide,
[62] N-(1-(4-tert.-butylthiazol-2-yl)pyrrolidin-3-yl)-3-(3-methoxyphenyl)propiolamide,
[63] N-(1-(4-tert.-butylthiazol-2-yl)pyrrolidin-3-yl)-3-(3-fluoro-4-methylphenyl)-propiolamide,
[64] N-(1-(4-tert.-butylthiazol-2-yl)pyrrolidin-3-yl)-3-(2-methoxyphenyl)propiolamide,
[65] N-(1-(4-methylthiazol-2-yl)pyrrolidin-3-yl)-3-(4-(trifluoromethyl)phenyl)-propiolamide,
[66] N-(1-(4-methylthiazol-2-yl)pyrrolidin-3-yl)-3-o-tolylpropiolamide,
[67] 3-(3-fluorophenyl)-N-(1-(4-methylthiazol-2-yl)pyrrolidin-3-yl)propiolamide,
[68] 3-(3-fluoro-4-methylphenyl)-N-(1-(4-methylthiazol-2-yl)pyrrolidin-3-yl)-propiolamide,
[69] 3-(2,4-difluorophenyl)-N-(1-(4-methylthiazol-2-yl)pyrrolidin-3-yl)propiolamide,
[70] 3-(2-fluorophenyl)-N-(1-(4-methylthiazol-2-yl)pyrrolidin-3-yl)propiolamide,
[71] N-(1-(4-methylthiazol-2-yl)pyrrolidin-3-yl)-3-(3-(trifluoromethyl)phenyl)-propiolamide,
[72] N-(1-(4-methylthiazol-2-yl)pyrrolidin-3-yl)-3-m-tolylpropiolamide,
[73] N-(1-(5-methylthiazol-2-yl)pyrrolidin-3-yl)-3-p-tolylpropiolamide,
[74] N-(1-(5-methylthiazol-2-yl)pyrrolidin-3-yl)-3-m-tolylpropiolamide,
[75] 3-(2-methoxyphenyl)-N-(1-(5-methylthiazol-2-yl)pyrrolidin-3-yl)propiolamide,
[76] N-(1-(5-methylthiazol-2-yl)pyrrolidin-3-yl)-3-phenylpropiolamide,
[77] 3-(2-fluorophenyl)-N-(1-(5-methylthiazol-2-yl)pyrrolidin-3-yl)propiolamide,
[78] 3-(3-methoxyphenyl)-N-(1-(5-methylthiazol-2-yl)pyrrolidin-3-yl)propiolamide,
[79] N-(1-(4,5-dimethylthiazol-2-yl)pyrrolidin-3-yl)-3-(3-fluoro-4-methylphenyl)-propiolamide,
[80] N-(1-(4,5-dimethylthiazol-2-yl)pyrrolidin-3-yl)-3-o-tolylpropiolamide,
[81] 3-(3-fluorophenyl)-N-(1-(5-methylthiazol-2-yl)pyrrolidin-3-yl)propiolamide,
[82] N-(1-(4,5-dimethylthiazol-2-yl)pyrrolidin-3-yl)-3-m-tolylpropiolamide,
[83] N-(1-(5-methylthiazol-2-yl)pyrrolidin-3-yl)-3-o-tolylpropiolamide,
[84] N-(1-(5-methylthiazol-2-yl)pyrrolidin-3-yl)-3-p-tolylpropiolamide,
[85] N-(1-(4,5-dimethylthiazol-2-yl)pyrrolidin-3-yl)-3-(3-(trifluoromethyl)phenyl)-propiolamide,
[86] 3-(4-methoxyphenyl)-N-(1-(5-methylthiazol-2-yl)pyrrolidin-3-yl)propiolamide,
[87] N-(1-(5-methylthiazol-2-yl)pyrrolidin-3-yl)-3-(3-(trifluoromethyl)phenyl)-propiolamide,
[88] N-(1-(4,5-dimethylthiazol-2-yl)pyrrolidin-3-yl)-3-(4-(trifluoromethyl)phenyl)-propiolamide,
[89] 3-(4-fluorophenyl)-N-(1-(5-methylthiazol-2-yl)pyrrolidin-3-yl)propiolamide,
[90] N-(1-(4,5-dimethylthiazol-2-yl)pyrrolidin-3-yl)-3-(3-methoxyphenyl)-propiolamide,
[91] 3-(2,4-difluorophenyl)-N-(1-(4,5-dimethylthiazol-2-yl)pyrrolidin-3-yl)-propiolamide,
[92] N-(1-(4,5-dimethylthiazol-2-yl)pyrrolidin-3-yl)-3-(2-fluorophenyl)propiolamide,
[93] N-(1-(5-methylthiazol-2-yl)pyrrolidin-3-yl)-3-(4-(trifluoromethyl)phenyl)-propiolamide,
[94] 3-(3-fluoro-4-methylphenyl)-N-(1-(5-methylthiazol-2-yl)pyrrolidin-3-yl)-propiolamide,
[95] 3-(2,4-difluorophenyl)-N-(1-(5-methylthiazol-2-yl)pyrrolidin-3-yl)propiolamide,
[96] N-(1-(4-tert.-butylthiazol-2-yl)pyrrolidin-3-yl)-3-(2,4-difluorophenyl)-propiolamide,
[97] N-(1-(4-tert.-butylthiazol-2-yl)pyrrolidin-3-yl)-3-(4-(trifluoromethyl)phenyl)-propiolamide,
[98] N-(1-(4-tert.-butylthiazol-2-yl)pyrrolidin-3-yl)-3-(3-(trifluoromethyl)phenyl)-propiolamide,
[99] N-(1-(4-tert.-butylthiazol-2-yl)pyrrolidin-3-yl)-3-m-tolylpropiolamide,
[100] N-(1-(4-tert.-butylthiazol-2-yl)pyrrolidin-3-yl)-3-(3-chlorophenyl)propiolamide,
[101] N-(1-(4-tert.-butylthiazol-2-yl)pyrrolidin-3-yl)-3-(thiophen-2-yl)propiolamide,
[102] N-(1-(4-tert.-butylthiazol-2-yl)pyrrolidin-3-yl)-3-(2,4-dichlorophenyl)-propiolamide,
[103] N-(1-(4-tert.-butylthiazol-2-yl)pyrrolidin-3-yl)-3-(2-chloro-5-(trifluoromethyl)-phenyl)propiolamide,

[104] N-(1-(4-tert.-butylthiazol-2-yl)pyrrolidin-3-yl)-3-(3,5-dichlorophenyl)-propiolamide,
[105] 3-(3-chlorophenyl)-N-(1-(4-methylthiazol-2-yl)pyrrolidin-3-yl)propiolamide,
[106] N-(1-(4-methylthiazol-2-yl)pyrrolidin-3-yl)-3-(thiophen-2-yl)propiolamide,
[107] 3-(2,4-dichlorophenyl)-N-(1-(4-methylthiazol-2-yl)pyrrolidin-3-yl)propiolamide,
[108] 3-(2-chloro-5-(trifluoromethyl)phenyl)-N-(1-(4-methylthiazol-2-yl)pyrrolidin-3-yl)propiolamide,
[109] 3-(3,5-dichlorophenyl)-N-(1-(4-methylthiazol-2-yl)pyrrolidin-3-yl)propiolamide,
[110] 3-(3-chlorophenyl)-N-(1-(4,5-dimethylthiazol-2-yl)pyrrolidin-3-yl)propiolamide,
[111] 3-(2,4-dichlorophenyl)-N-(1-(4,5-dimethylthiazol-2-yl)pyrrolidin-3-yl)-propiolamide,
[112] 3-(3-chlorophenyl)-N-(1-(5-methylthiazol-2-yl)pyrrolidin-3-yl)propiolamide,
[113] N-(1-(5-methylthiazol-2-yl)pyrrolidin-3-yl)-3-(thiophen-2-yl)propiolamide,
[114] 3-(2,4-dichlorophenyl)-N-(1-(5-methylthiazol-2-yl)pyrrolidin-3-yl)propiolamide,
[115] 3-(2-chloro-5-(trifluoromethyl)phenyl)-N-(1-(5-methylthiazol-2-yl)pyrrolidin-3-yl)propiolamide,
[116] 3-(3,5-dichlorophenyl)-N-(1-(5-methylthiazol-2-yl)pyrrolidin-3-yl)propiolamide,
[117] N-(1-(4,5-dimethylthiazol-2-yl)pyrrolidin-3-yl)-3-(thiophen-2-yl)propiolamide,
[118] 3-(2-chloro-5-(trifluoromethyl)phenyl)-N-(1-(4,5-dimethylthiazol-2-yl)pyrrolidin-3-yl)propiolamide,
[119] N-(1-(5-methylthiazol-2-yl)pyrrolidin-3-yl)-3-(pyridin-2-yl)propiolamide,
[120] N-(1-(5-methylthiazol-2-yl)pyrrolidin-3-yl)-3-(pyridin-3-yl)propiolamide,
[121] N-(1-(5-methylthiazol-2-yl)pyrrolidin-3-yl)-3-(pyridin-4-yl)propiolamide,
[122] N-(1-(4-tert.-butylthiazol-2-yl)pyrrolidin-3-yl)-3-(pyridin-2-yl)propiolamide,
[123] N-(1-(4-tert.-butylthiazol-2-yl)pyrrolidin-3-yl)-3-(pyridin-3-yl)propiolamide, and
[126] 3-(3-chlorophenyl)-N-(2-((5-fluorothiazol-2-yl)(methyl)amino)ethyl)-propiolamide;

in each case optionally in the form of one of the pure stereoisomers thereof, the racemate thereof or in the form of a mixture of stereoisomers in any desired mixing ratio, or in each case in the form of a corresponding salt.

27. A compound according to claim 1, which, after 60 minutes' incubation in 450 µg of protein from pig brain homogenate at a temperature of between 20° C. and 25° C. in a concentration of less than 2000 nM, brings about a 50 percent displacement of [$^3$H]-2-methyl-6-(3-methoxyphenyl)-ethynylpyridine, which is present in a concentration of 5 nM.

28. A pharmaceutical composition comprising at least one compound according to claim 1 and optionally one or more physiologically acceptable auxiliary substances.

29. A method for inhibiting the mGluR5 receptor, said method comprising administering to a patient in need of such regulating an effective amount therefor of at least one compound according to claim 1.

30. A method for treating a disorder or disease that is mediated at least in part by mGluR5 receptors, wherein the disorder or disease is pain selected from the group consisting of neuropathic pain and visceral pain, said method comprising administering to a patient in need of such treating an effective amount therefor of at least one compound according to claim 1.

* * * * *

UNITED STATES PATENT AND TRADEMARK OFFICE
CERTIFICATE OF CORRECTION

| | | |
|---|---|---|
| PATENT NO. | : 7,871,999 B2 | Page 1 of 1 |
| APPLICATION NO. | : 12/147121 | |
| DATED | : January 18, 2011 | |
| INVENTOR(S) | : Haurand et al. | |

It is certified that error appears in the above-identified patent and that said Letters Patent is hereby corrected as shown below:

In the Specification:

Column 105, line 32, "compound 273" -- should read -- compound 27 3 --.

Column 105, line 35, "compound 283" -- should read -- compound 28 3 --.

Column 119, line 34, "23N-(2-" -- should read -- 23 N-(2- --.

In the Claims:

Column 138, line 25, "R18" -- should read -- R16 --.

Column 139, line 53, "R20" -- should read -- R18 --.

Column 139, line 53, "R21" -- should read -- R19 --.

Column 154, line 52, "R44" -- should read -- R42 --.

Column 154, line 52, "R45" -- should read -- R43 --.

Column 154, line 52, "R44" -- should read -- R43 --.

Column 154, line 52, "R45" -- should read -- R42 --.

Column 158, line 5, "R7" -- should read -- R5 --.

Signed and Sealed this
Twenty-ninth Day of April, 2014

Michelle K. Lee
*Deputy Director of the United States Patent and Trademark Office*